United States Patent
Spivak et al.

(10) Patent No.: US 10,106,855 B2
(45) Date of Patent: Oct. 23, 2018

(54) GENETIC ASSAY TO DETERMINE PROGNOSIS IN POLYCYTHEMIA VERA PATIENTS

(71) Applicant: THE JOHNS HOPKINS UNIVERSITY, Baltimore, MD (US)

(72) Inventors: Jerry L Spivak, Baltimore, MD (US); Michael Ochs, Oreland, PA (US); Michael Considine, Bel Air, MD (US); Donna Rowley, Beltsville, MD (US); Alison R Moliterno, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 211 days.

(21) Appl. No.: 14/441,721

(22) PCT Filed: Nov. 8, 2013

(86) PCT No.: PCT/US2013/069192
§ 371 (c)(1),
(2) Date: May 8, 2015

(87) PCT Pub. No.: WO2014/074847
PCT Pub. Date: May 15, 2014

(65) Prior Publication Data
US 2015/0292028 A1    Oct. 15, 2015

Related U.S. Application Data

(60) Provisional application No. 61/724,707, filed on Nov. 9, 2012.

(51) Int. Cl.
| | |
|---|---|
| *C12Q 1/68* | (2018.01) |
| *G06F 19/00* | (2018.01) |
| *C12Q 1/6886* | (2018.01) |
| *C12Q 1/6883* | (2018.01) |
| *G01N 33/80* | (2006.01) |
| *G16H 50/30* | (2018.01) |

(52) U.S. Cl.
CPC ......... *C12Q 1/6886* (2013.01); *C12Q 1/6883* (2013.01); *G01N 33/80* (2013.01); *G16H 50/30* (2018.01); *C12Q 2600/118* (2013.01); *C12Q 2600/158* (2013.01); *C12Q 2600/16* (2013.01); *G01N 2800/226* (2013.01); *G01N 2800/52* (2013.01)

(58) Field of Classification Search
None
See application file for complete search history.

(56) References Cited

U.S. PATENT DOCUMENTS

| 6,027,902 A | 2/2000 | Spivak |
| 6,150,120 A | 11/2000 | Spivak et al. |
| 7,429,456 B2 | 9/2008 | Vainchenker |
| 7,514,229 B2 | 4/2009 | Jamieson et al. |

FOREIGN PATENT DOCUMENTS

| WO | 1998053318 A1 | 11/1993 |
| WO | 2003009816 A2 | 2/2003 |
| WO | 2009079587 A2 | 6/2009 |
| WO | 2009104001 A2 | 8/2009 |
| WO | 2011056688 A2 | 5/2011 |

OTHER PUBLICATIONS

Seaman et al (Int. J. Environ. Res. Public Health Jul. 2010, 1139-1152).*
Raedler (Am Health Drug Benefits. Oct. 2014; 7(7 suppl3): S36-S47).*
Radich JP, Dai H, Mao M et al. Gene expression changes associated with progression and response in chronic myeloid leukemia. Proc. Natl. Acad. Sci. U.S.A. 2006; 103(8):2794-2799.
Ranjan A Penninga E, Jelsig AM, Hasselbalch HC, Bjerrum OW. Inheritance of the chronic myeloproliferative neoplasms. A systematic review. Clin. Genet. 2013;83(2):99-107.
Ridell B, Carneskog J, Wedel H et al. Incidence of chronic myeloproliferative disorders in the city of Goteborg, Sweden 1983-1992. Eur. J. Haematol. 2000;65(4):267-271.
Ridnour LA, Barasch KM, Windhausen AN et al. Nitric oxide synthase and breast cancer: role of TIMP-1 in NO-mediated Akt activation. PLoS One 2012;7(9):e44081.
Rosario M, Paterson HF, Marshall CJ. Activation of the Raf/MAP kinase cascade by the Ras-related protein TC21 is required for the TC21-mediated transformation ofNIH 3T3 cells. EMBO J. 1999; 18(5): 1270-1279.
Rosario M, Paterson HF, Marshall CJ. Activation of the Ral and phosphatidylinositol 3' kinase signaling pathways by the ras-related protein TC21. Mol. Cell. Biol. 2001 ;21(1 1):3750-3762.
Scharer CD, McCabe CD, Ali-Seyed M, Berger MF, Bulyk ML, Moreno CS. Genome-wide promoter analysis of the SOX4 transcriptional network in prostate cancer cells. Cancer Res. 2009;69(2):709-717.
Schepers K, Pietras EM, Reynaud D et al. Myeloproliferative Neoplasia Remodels the Endosteal Bone Marrow Niche into a Self-Reinforcing Leukemic Niche. Cell Stem Cell 2013.

(Continued)

*Primary Examiner* — Brian Gangle
*Assistant Examiner* — Andrea K McCollum
(74) *Attorney, Agent, or Firm* — Johns Hopkins Technology Ventures

(57) ABSTRACT

The presently disclosed subject matter provides a genetic assay to determine the prognosis in Polycythemia Vera (PV) patients with an indolent form of PV. This assay involves measuring certain messenger RNAs (mRNAs) in blood cells, such as white blood cells. In some embodiments, the cells are CD34+ cells. These mRNA levels are inserted into an algorithm that yields a predictive score of the risk of PV in the patient transforming from an indolent form to an aggressive form.

15 Claims, 12 Drawing Sheets

Specification includes a Sequence Listing.

(56) References Cited

OTHER PUBLICATIONS

Segal JB, Moliterno AR. Platelet counts differ by sex, ethnicity, and age in the United States. Ann. Epidemiol. 2006; 16(2): 123-130.
Shibata S, Ishiyama J. Secreted protein acidic and rich in cysteine (SPARC) is upregulated by transforming growth factor (TGF)-beta and is required for TGF-beta-induced hydrogen peroxide production in fibroblasts. Fibrogenesis Tissue Repair 2013;6(1):6.
Silverstein MN. Postpolycythemia myeloid metaplasia. Arch. Intern. Med. 1974; 134(1): 1 13-1 17.
Slezak S, Jin P, Caruccio L et al. Gene and microRNA analysis of neutrophils from patients with polycythemia vera and essential thrombocytosis: down-regulation of micro RNA-1 and -133a. J. Transl. Med. 2009;7:39.
Smalberg JH, Arends LR, Valla DC, Kiladjian JJ, Janssen HL, Leebeek FW. Myeloproliferative neoplasms in Budd-Chiari syndrome and portal vein thrombosis: a meta-analysis. Blood 2012; 120(25):4921-4928.
Song S, Mazurek N, Liu C et al. Galectin-3 mediates nuclear beta-catenin accumulation and Wnt signaling in human colon cancer cells by regulation of glycogen synthase kinase-3beta activity. Cancer Res. 2009;69(4): 1343-1349.
Spivak JL. Polycythemia vera:myths, mechanisms, and management. Blood 2002; 100:4272-4290.
Spivak JL. Narrative review: Thrombocytosis, polycythemia vera, and JAK2 mutations: The phenotypic mimicry of chronic myeloproliferation. Ann. Intern. Med. 2010; 152:300-306.
Spivak JL, Hasselbalch H. Hydroxycarbamide: a user's guide for chronic myeloproliferative disorders. Expert. Rev. Anticancer Ther. 2011 ; 11 :403-414.
Stein BL, Rademaker A, Spivak JL, Moliterno AR. Gender and Vascular Complications in the JAK2 V617F-Positive Myeloproliferative Neoplasms. Thrombosis 201 1;201 1 :874146.
Stein BL, Williams DM, O'Keefe C et al. Disruption of the ASXL1 gene is frequent in primary, post-essential thrombocytosis and post-polycythemia vera myelofibrosis, but not essential thrombocytosis or polycythemia vera: analysis of molecular genetics and clinical phenotypes. Haematologica 201 1;96(10): 1462-1469.
Stein BL, Williams DM, Rogers O, Isaacs MA, Spivak JL, Moliterno AR. Disease burden at the progenitor level is a feature of primary myelofibrosis: a multivariable analysis of 164 JAK2 V617F-positive myeloproliferative neoplasm patients. Exp. Hematol. 201 1;39(1):95-101.
Stein BL, Williams DM, Wang NY et al. Sex differences in the JAK2 V617F allele burden in chronic myeloproliferative disorders. Haematologica 2010;95(7): 1090-1097.
Sugita M, Haney JL, Gemmill RM, Franklin WA. One-step duplex reverse transcription-polymerase chain reaction for quantitative assessment of RNA degradation. Anal. Biochem. 2001 ;295(1): 1 13-1 16.
Tan AC, Naiman DQ, Xu L, Winslow RL, Geman D. Simple decision rules for classifying human cancers from gene expression profiles. Bioinformatics 2005;21(20):3896-3904.
Tripodo C, Sangaletti S, Guarnotta C et al. Stromal SPARC contributes to the detrimental fibrotic changes associated with myeloproliferation whereas its deficiency favors myeloid cell expansion. Blood 2012; 120(17):3541-3554.
Verstovsek S, Kantarjian H, Mesa RA et al. Safety and efficacy of INCBO 18424, a JAKI and JAK2 inhibitor, in myelofibrosis. N. Engl. J. Med. 2010;363(12): 1 117-1 127.
Videbaek A. Polycythemia Vera. Course and Prognosis. Acta Med. Scand. 1950; 138: 179-187.
Wall DS, Mears AJ, McNeill B et al. Progenitor cell proliferation in the retina is dependent on Notch-independent Sonic hedgehog/Hesl activity. J. Cell. Biol. 2009; 184(1): 101-1 12.
Wang J, Leclercq I, Brymora JM et al. Kupffer cells mediate leptin-induced liver fibrosis. Gastroenterology 2009; 137(2):713-723.
Wasserman L. The Management of Polycythemia Vera. British Journal of Hematology 1971;21 :371-376.
Williams DM, Kim AH, Rogers O, Spivak JL, Moliterno AR. Phenotypic variations and new mutations in JAK2 V617F-negative polycythemia vera, erythrocytosis, and idiopathic myelofibrosis. Exp. Hematol. 2007;35(11): 1641-1646.
Yamamoto-Sugitani M, Kuroda J, Ashihara E et al. Galectin-3 (Gal-3) induced by leukemia microenvironment promotes drug resistance and bone marrow lodgment in chronic myelogenous leukemia. Proc. Natl. Acad. Sci. U.S.A. 2011 ; 108(42): 17468-17473.
Yuwaraj S, Ding J, Liu M, Marsden PA, Levy GA. Genomic characterization, localization, and functional expression of FGL2, the human gene encoding fibroleukin: a novel human procoagulant. Genomics 2001 ;71(3):330-338.
International Search Report dated Feb. 6, 2014 from PCT International Application No. PCT/US2013/069192.
Mirza et al., "Transformation of Polycythemia Vera to Chronic Myelogenous Leukemia," Archives of Pathology and Laboratory Medicine, vol. 131, No. 11, pp. 1719-1724 (Nov. 2007).
Tefferi et al., "TET2 Mutations and Their Clinical Correlates in Polycythemia Vera Essential Thrombocythennia and Myelofibrosis," Leukemia, vol. 23, No. 5, pp. 905-911 (Mar. 5, 2009).
Berkofsy-Fesser W, Buzzai M Kim, M K-H et al. Transcriptional Profiling of Polycythemia Vera Identifies Gene Expression Patterns Both Dependent and Independent from the Action of JAK2V617F. Clinical Cancer Research 16: 4339,2010.
Rice KL. et al. Analysis of genomic aberrations and gene expression profiling identifies novel lesions and pathways in myeloproliferative neoplasms. Blood Cancer J. Nov. 2011;1(11):e40. doi: 10.1038/bcj. 2011.39. Epub Nov. 11, 2011.
Skov V. et al. Gene expression profiling with principal component analysis depicts the biological continuum from essential thrombocythemia over polycythemia vera to myelofibrosis. Experimental Hematology. 2012.
Hobbs RF, Wahl RL, Frey EC, Kasamon Y, Song H, Huang P, Jones RJ, Sgouros G.Radiobiologic optimization of combination radiopharmaceutical therapy applied to myeloablative treatment of non-Hodgkin lymphoma. J Nucl Med. Sep. 2013;54(9):1535-42.
Adamson JW, Fialkow PJ, Murphy S, Prchal JF, Steinmann L. Polycythemia vera: stem-cell and probable clonal origin of the disease. N. Engl. J. Med. 1976;295:913-916.
Anand S, Stedham F, Gudgin E et al. Increased basal intracellular signaling patterns do not correlate with JAK2 genotype in human myeloproliferative neoplasms. Blood 201 1 ; 118(6) : 1610-1621.
Andreasson B, Swolin B, Kutti J. Increase of CD34 positive cells in polycythaemia vera. Eur. J. Haematol. 1997;59(3): 171-176.
Barbui T, Barosi G, Birgegard G et al. Philadelphia-negative classical myeloproliferative neoplasms:critical concepts and management recommendations from European LeukemiaNet. J. Clin. Oncol. 2011 ;29:761-770.
Baricos WH, Cortez SL, Deboisblanc M, Xin S. Transforming growth factor—beta is a potent inhibitor of extracellular matrix degradation by cultured human mesangial cells. J. Am. Soc. Nephrol. 1999; 10(4):790-795.
Barosi G, Viarengo G, Pecci A et al. Diagnostic and clinical relevance of the number of circulating CD34+ cells in myelofibrosis and myeloid metaplasia. Blood 2001 ;98(12):3249-3255.
Beer PA, Delhommeau F, Le Couedic JP et al. Two routes to leukemic transformation following a JAK2 mutation-positive myeloproliferative neoplasm. Blood 2009; 1 15:2891-2900.
Bergamaschi A, Tagliabue E, Sorlie T et al. Extracellular matrix signature identifies breast cancer subgroups with different clinical outcome. J. Pathol. 2008;214(3):357-367.
Berk PD, Goldberg JD, Silverstein MN et al. Increased incidence of acute leukemia in polycythemia vera associated with chlorambucil therapy. N. Engl. J. Med. 1981 ;304:441-447.
Zheng C, Li L, Haak M et al. Gene expression profiling of CD34+ cells identifies a molecular signature of chronic myeloid leukemia blast crisis. Leukemia 2006;20(6): 1028-1034.
Bonnefoy A, Hoylaerts MF. Thrombospondin-1 in von Willebrand factor function. Curr Drug Targets 2008;9(10):822-832.
Bruns I, Czibere A, Fischer JC et al. The hematopoietic stem cell in chronic phase CML is characterized by a transcriptional profile

(56) References Cited

OTHER PUBLICATIONS resembling normal myeloid progenitor cells and reflecting loss of quiescence. Leukemia 2009;23(5):892-899.

Catani L, Zini R, Sollazzo D et al. Molecular profile of CD34+ stem/progenitor cells according to JAK2V617F mutation status in essential thrombocythemia. Leukemia 2009;23(5):997-1000.

Daniel C, Wiede J, Krutzsch HC et al. Thrombospondin-1 is a major activator of TGF-beta in fibrotic renal disease in the rat in vivo. Kidney Int 2004;65(2):459-468.

Diaz-Bianco E, Bruns I, Neumann F et al. Molecular signature of CD34(+) hematopoietic stem and progenitor cells of patients with CML in chronic phase. Leukemia 2007;21(3):494-504.

Edgar R, Domrachev M, Lash AE. Gene Expression Omnibus: NCBI gene expression and hybridization array data repository. Nucleic Acids Res. 2002;30(1):207-210.

Espinosa L, Cathelin S, D'Altri T et al. The Notch/Hes I pathway sustains NF-kappaB activation through CYLD repression in T cell leukemia. Cancer Cell 2010; 18(3):268-281.

Gaidano G, Pastore C, Santini V et al. Genetic lesions associated with blastic transformation of polycythemia vera and essential thrombocythemia. Genes Chromosomes. Cancer 1997; 19:250-255.

Gangat N, Strand J, Lasho TL et al. Cytogenetic studies at diagnosis in polycythemia vera: clinical and JAK2V617F allele burden correlates. Eur J. Haematol. 2008;80(3): 197-200.

Graham SM, Vass JK, Holyoake TL, Graham GJ. Transcriptional analysis of quiescent and proliferating CD34+ human hemopoietic cells from normal and chronic myeloid leukemia sources. Stem Cells 2007;25(12):311 1-3120.

Gruppo Italiano Studio Policitemia. Polycythemia vera: the natural history of 1213 patients followed for 20 years. Ann. Intern. Med. 1995; 123 :656-664.

Hantschel O, Warsch W, Eckelhart E et al. BCR-ABL uncouples canonical JAK2-STAT5 signaling in chronic myeloid leukemia. Nat. Chem. Biol. 2012;8(3):285-293.

Harrison CN, Campbell PJ, Buck G et al. Hydroxyurea compared with anagrelide in high-risk essential thrombocythemia. N. Engl. J. Med. 2005;353(1):33-45.

Horita M, Andreu EJ, Benito A et al. Blockade of the Bcr-Abl kinase activity induces apoptosis of chronic myelogenous leukemia cells by suppressing signal transducer and activator of transcription 5-dependent expression of Bcl-xL. J. Exp. Med. 2000; 191(6):977-984.

Huang Y, Sitwala K, Bronstein J et al. Identification and characterization of Hoxa9 binding sites in hematopoietic cells. Blood 2012; 119(2):388-398.

Ikushima H, Todo T, Ino Y, Takahashi M, Miyazawa K, Miyazono K. Autocrine TGF-beta signaling maintains tumorigenicity of glioma-initiating cells through Sly-related HMG-box factors. Cell Stem Cell 2009;5(5):504-514.

Isenberg JS, Ridnour LA, Perruccio EM, Espey MG, Wink DA, Roberts DD. Thrombospondin-1 inhibits endothelial cell responses to nitric oxide in a cGMP-dependent manner. Proc. Natl. Acad. Sci. U.S.A. 2005; 102(37): 13141-13146.

James C, Ugo V, Le Couedic JP et al. A unique clonal JAK2 mutation leading to constitutive signaling causes polycythaemia vera. Nature 2005;434(7037): 1 144-1148.

Jones AV, Kreil S, Zoi K et al. Widespread occurrence of the JAK2 V617F mutation in chronic myeloproliferative disorders. Blood 2005; 106:2162-2168.

Kamakura S, Oishi K, Yoshimatsu T, Nakafuku M, Masuyama N, Gotoh Y. Hes binding to STAT3 mediates crosstalk between Notch and JAK-STAT signaling. Nat. Cell. Biol. 2004;6(6):547-554.

Kerbauy DM, Gooley TA, Sale GE et al. Hematopoietic cell transplantation as curative therapy for idiopathic myelofibrosis, advanced polycythemia vera, and essential thrombocythemia. Biol. Blood Marrow Transplant. 2007; 13 :355-365.

Kiladjian JJ, Chevret S, Dosquet C, Chomienne C, Rain JD. Treatment of polycythemia vera with hydroxyurea and pipobroman: final results of a randomized trial initiated in 1980. J. Clin. Oncol. 2011 ;29:3907-3913.

Koli K, Ryynanen MJ, Keski-Oja J. Latent TGF-beta binding proteins (LTBPs)-I and -3 coordinate proliferation and osteogenic differentiation of human mesenchymal stem cells. Bone 2008;43(4):679-688.

Lamy T, Devillers A, Bernard M et al. Inapparent polycythemia vera: an unrecognized diagnosis. Am. J. Med. 1997;102(1): 14-20.

Lee JH, Suk J, Park J et al. Notch signal activates hypoxia pathway through HES 1-dependent SRC/signal transducers and activators of transcription 3 pathway. Mol. Cancer Res. 2009;7(10): 1663-1671.

Lenz G, Wright G, Dave SS et al. Stromal gene signatures in large-B-cell lymphomas. N. Engl. J. Med. 2008;359(22):2313-2323.

Lenz G, Wright GW, Emre NC et al. Molecular subtypes of diffuse large B-cell lymphoma arise by distinct genetic pathways. Proc. Natl. Acad. Sci. U.S.A. 2008; 105: 13520-13525.

Mackinnon AC, Gibbons MA, Farnworth SL et al. Regulation of transforming growth factor-beta 1-driven lung fibrosis by galectin-3. Am. J. Respir. Crit. Care Med. 2012; 185(5):537-546.

McNally RJ, Rowland D, Roman E, Cartwright RA. Age and sex distributions of hematological malignancies in the U.K. Hematol. Oncol. 1997; 15: 173-189.

Moliterno AR, Williams DM, Rogers O, Isaacs MA, Spivak JL. Phenotypic variability within the JAK2 V617F-positive MPD: Roles of progenitor cell and neutrophil allele burdens. Exp. Hematol. 2008;36(11): 1480-1486.

Najean Y, Rain J. Treatment of Polycythemia Vera: The use of Hydroxyurea and Pipobroman in 292 Patients Under the Age of 65 Years. Blood 1997;90:3370-3377.

Nakahara F, Sakata-Yanagimoto M, Komeno Y et al. Hes1 immortalizes committed progenitors and plays a role in blast crisis transition in chronic myelogenous leukemia. Blood 2010; 115(14):2872-2881.

Nowicki MO, Pawlowski P, Fischer T, Hess G, Pawlowski T, Skorski T. Chronic myelogenous leukemia molecular signature. Oncogene 2003;22(25):3952-3963.

Nussenzveig RH, Swierczek SI, Jelinek J et al. Polycythemia vera is not initiated by JAK2V617F mutation. Exp. Hematol. 2007;35(I):32-38.

Passamonti F, Rumi E, Caramella M et al. A dynamic prognostic model to predict survival in post-polycythemia vera myelofibrosis. Blood 2008; 11 1(7):3383-3387.

Patel V, Noureddine L. MicroRNAs and fibrosis. Curr. Opin. Nephrol. Hypertens. 2012;21(4):410-416.

* cited by examiner

SEQUENCE LISTING

<160> NUMBER OF SEQ ID NOS: 20

<210> SEQ ID NO 1
<211> LENGTH: 25
<212> TYPE: DNA
<213> ORGANISM: Artificial Sequence
<220> FEATURE:
<223> OTHER INFORMATION: Probe for proliferating cell nuclear antigen

<400> SEQUENCE: 1
aaagaggagg aagctgttac catag                25

<210> SEQ ID NO 2
<211> LENGTH: 25
<212> TYPE: DNA
<213> ORGANISM: Artificial Sequence
<220> FEATURE:
<223> OTHER INFORMATION: Probe for translin

<400> SEQUENCE: 2
gccagtgaac tgtcgaggct gtctg                25

<210> SEQ ID NO 3
<211> LENGTH: 25
<212> TYPE: DNA
<213> ORGANISM: Artificial Sequence
<220> FEATURE:
<223> OTHER INFORMATION: Probe for cyclin-dependent kinase inhibitor 1A

```
<400> SEQUENCE: 3
gcagaccagc atgacagatt tctac                                           25

<210> SEQ ID NO 4
<211> LENGTH: 25
<212> TYPE: DNA
<213> ORGANISM: Artificial Sequence
<220> FEATURE:
<223> OTHER INFORMATION: Probe for myosin, light chain 9

<400> SEQUENCE: 4
tggcctcgct gggtttcatc catga                                           25

<210> SEQ ID NO 5
<211> LENGTH: 25
<212> TYPE: DNA
<213> ORGANISM: Artificial Sequence
<220> FEATURE:
<223> OTHER INFORMATION: Probe for interferon, gamma-inducible protein
      30

<400> SEQUENCE: 5
ctgccagttg taccagggca agaag                                           25

<210> SEQ ID NO 6
<211> LENGTH: 25
<212> TYPE: DNA
<213> ORGANISM: Artificial Sequence
<220> FEATURE:
<223> OTHER INFORMATION: Probe ofr cortactin

<400> SEQUENCE: 6
cagaagatgg aggtgcagcg ccggc                                           25

<210> SEQ ID NO 7
<211> LENGTH: 25
<212> TYPE: DNA
<213> ORGANISM: Artificial Sequence
<220> FEATURE:
<223> OTHER INFORMATION: Probe for structural maintenance of chromosomes
      4

<400> SEQUENCE: 7
aaaagaagga agaattgtat ttgca                                           25

<210> SEQ ID NO 8
<211> LENGTH: 25
<212> TYPE: DNA
<213> ORGANISM: Artificial Sequence
<220> FEATURE:
<223> OTHER INFORMATION: Probe for cortactin

<400> SEQUENCE: 8
ctaccaggct gcgggcgatg atgag                                           25

<210> SEQ ID NO 9
<211> LENGTH: 25
<212> TYPE: DNA
<213> ORGANISM: Artificial Sequence
<220> FEATURE:
<223> OTHER INFORMATION: Probe for SON DNA binding protein

<400> SEQUENCE: 9
caaacatttt ctctttaggg tattg                                           25
```

<210> SEQ ID NO 10
<211> LENGTH: 25
<212> TYPE: DNA
<213> ORGANISM: Artificial Sequence
<220> FEATURE:
<223> OTHER INFORMATION: Probe for TIA1 cytotoxic granule-associated RNA
      binding protein

<400> SEQUENCE: 10
cccgtgcaac agcagaatca aattg                                       25

<210> SEQ ID NO 11
<211> LENGTH: 25
<212> TYPE: DNA
<213> ORGANISM: Homo sapiens

<400> SEQUENCE: 11
aaagaggagg aagctgttac catag                                       25

<210> SEQ ID NO 12
<211> LENGTH: 25
<212> TYPE: DNA
<213> ORGANISM: Homo sapiens

<400> SEQUENCE: 12
gccagtgaac tgtcgaggct gtctg                                       25

<210> SEQ ID NO 13
<211> LENGTH: 25
<212> TYPE: DNA
<213> ORGANISM: Homo sapiens

<400> SEQUENCE: 13
gcagaccagc atgacagatt tctac                                       25

<210> SEQ ID NO 14
<211> LENGTH: 25
<212> TYPE: DNA
<213> ORGANISM: Homo sapiens

<400> SEQUENCE: 14
tggcctcgct gggtttcatc catga                                       25

<210> SEQ ID NO 15
<211> LENGTH: 25
<212> TYPE: DNA
<213> ORGANISM: Homo sapiens

<400> SEQUENCE: 15
ctgccagttg taccagggca agaag                                       25

<210> SEQ ID NO 16
<211> LENGTH: 25
<212> TYPE: DNA
<213> ORGANISM: Homo sapiens

<400> SEQUENCE: 16
cagaagatgg aggtgcagcg ccggc                                       25

<210> SEQ ID NO 17
<211> LENGTH: 25
<212> TYPE: DNA
<213> ORGANISM: Homo sapiens

```
<400> SEQUENCE: 17
aaaagaagga agaattgtat ttgca                                          25

<210> SEQ ID NO 18
<211> LENGTH: 25
<212> TYPE: DNA
<213> ORGANISM: Homo sapiens

<400> SEQUENCE: 18
ctaccaggct gcgggcgatg atgag                                          25

<210> SEQ ID NO 19
<211> LENGTH: 25
<212> TYPE: DNA
<213> ORGANISM: Homo sapiens

<400> SEQUENCE: 19
caaacatttt ctctttaggg tattg                                          25

<210> SEQ ID NO 20
<211> LENGTH: 25
<212> TYPE: DNA
<213> ORGANISM: Homo sapiens

<400> SEQUENCE: 20
cccgtgcaac agcagaatca aattg                                          25
```

GENETIC ASSAY TO DETERMINE PROGNOSIS IN POLYCYTHEMIA VERA PATIENTS

CROSS REFERENCE TO RELATED APPLICATIONS

This application is a 35 U.S.C. § 371 National Stage Entry of International Application No. PCT/US2013/069192 having an international filing date of Nov. 8, 2013, which claims the benefit of U.S. Provisional Application No. 61/724,707, filed Nov. 9, 2012, which is incorporated herein by reference in its entirety.

FEDERALLY SPONSORED RESEARCH OR DEVELOPMENT

This invention was made with United States government support under P01CA108671 awarded by the National Institutes of Health (NIH) and W81XWH-05-1-0347 awarded by the Department of Defense (DOD). The U.S. government has certain rights in the invention.

BACKGROUND

Polycythemia vera (PV) is a hematopoietic stem cell disorder characterized by the increased production of red cells, white cells and platelets and complicated by thrombotic and hemorrhagic events, extramedullary hematopoiesis, and transformation to myelofibrosis or acute leukemia (AML), albeit at variable frequencies (FIG. 1) (Spivak, 2002), and many of these clinical features are shared in common with its companion myeloproliferative disorder, primary myelofibrosis (PMF). PV is unique since with phlebotomy alone its natural history can be measured in decades. However, not all PV patients enjoy substantial longevity or freedom from significant complications but, in contrast to PMF, no satisfactory clinical criteria exist for stratification with respect to the risk of disease transformation, and usually no cytogenetic or molecular markers predictive of disease transformation are present before the event (Gaidano et al., 1997). Although JAK2 V617F is expressed in both PV and PMF, these are stem cell disorders and hematopoietic stem cells are not dependent on this tyrosine kinase for either survival or proliferation (Spivak, 2010), nor has the extent of JAK2 V617F expression been useful for prognostic purposes (Barbui et al., 2011). Bone marrow transplantation is the only curative therapy for PV (Kerbauy et al., 2007) and pegylated interferon is the only drug that can induce a molecular remission, although not in all patients (Kiladjian et al., 2008). Both have significant toxicities, while all chemotherapeutic drugs employed to suppress marrow and extramedullary hematopoiesis as supportive therapy can increase the rate of leukemic transformation ten-fold (Najean and Rain, 1997; Berk et al., 1981).

For many malignancies, gene expression profiling (GEP) has been a useful approach for risk stratifying cancer patients with a shared clinical or histologic phenotype (Radich et al., 2006), and for developing predictors of disease behavior irrespective of the clinical phenotype (Lenz et al., 2008).

SUMMARY

The presently disclosed subject matter provides a genetic assay and kits to determine the prognosis in Polycythemia Vera (PV) patients with an indolent form of PV. The presently disclosed assay involves measuring certain messenger RNAs (mRNAs) in blood cells. These mRNA levels are inserted into an algorithm that yields a predictive score of the risk of PV in the patient transforming from an indolent form to an aggressive form.

In one aspect, the presently disclosed subject matter provides a method for determining the likelihood of an indolent form of Polycythemia Vera (PV) transforming to an aggressive form of PV in a subject, the method comprising: (a) measuring the gene products of PCNA, IFI30, TSN, CTSA, SMC4, CDKN1A, CTTN, SON, TIA1, and MYL9 in a biological sample comprising blood cells obtained from the subject; (b) making the following comparisons of the gene product levels measured in (a) and recording a score of 1 for a true result and a score of 0 for a false result: PCNA>IFI30; TSN>CTSA; SMC4>CDKN1A; PCNA>CTTN; SON>CTTN; TIA1>MYL9; (c) adding the scores together to obtain an added score and calculating a ratio of the added score/6 to calculate a total score; and (d) using the total score to predict if the indolent form of PV in the subject is likely to transform to an aggressive form of PV in the subject. In some embodiments, the blood cells are white blood cells. In other embodiments, the blood cells are CD34+ cells.

Accordingly, in some aspects, a total score of 5/6 or 6/6 predicts that the indolent form of PV in a subject is likely to transform to an aggressive form of PV in a subject. In other aspects, a total score of less than 5/6 predicts that the indolent form of PV in a subject is not likely to transform to an aggressive form of PV in the subject.

In another aspect, the presently disclosed subject matter provides a diagnostic kit for determining whether an indolent form of PV in a subject is likely to transform to an aggressive form of PV, the kit comprising a means for measuring the gene product levels of PCNA, IFI30, TSN, CTSA, SMC4, CDKN1A, CTTN, SON, TIA1, and MYL9 and a set of instructions comprising an algorithm for predicting if the indolent form of PV in the subject is likely to transform to an aggressive form of PV.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
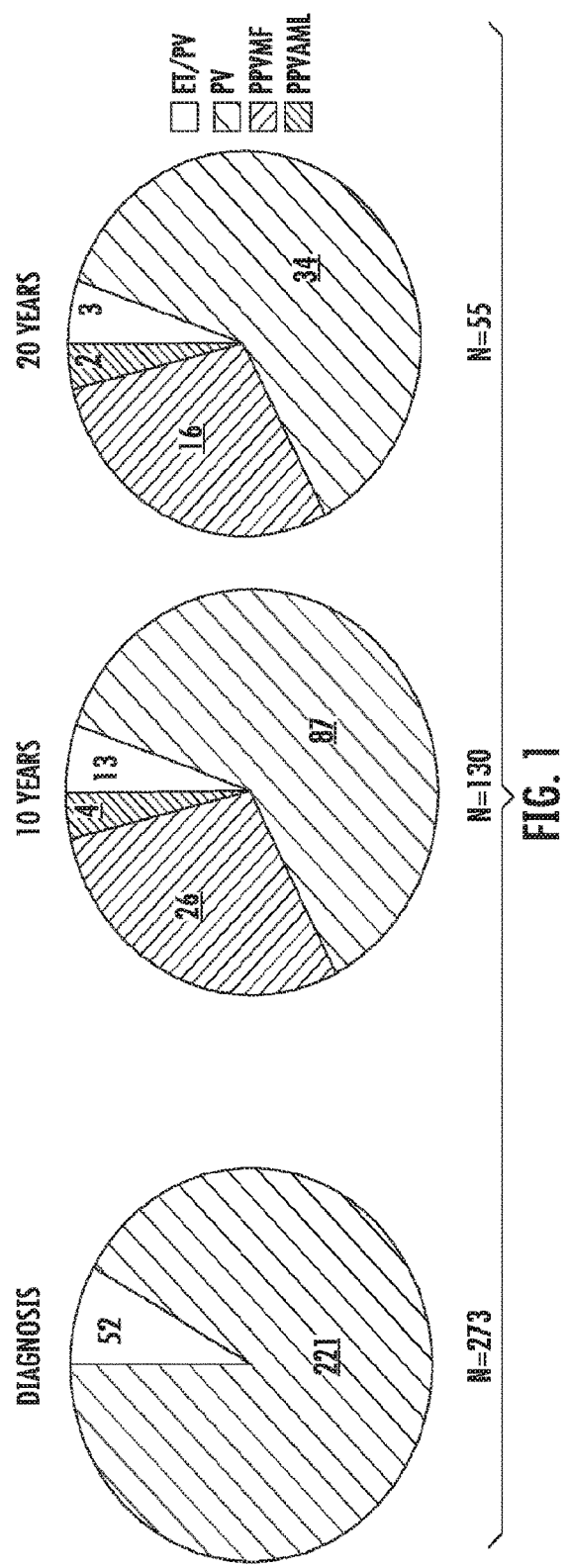
Figure 2:
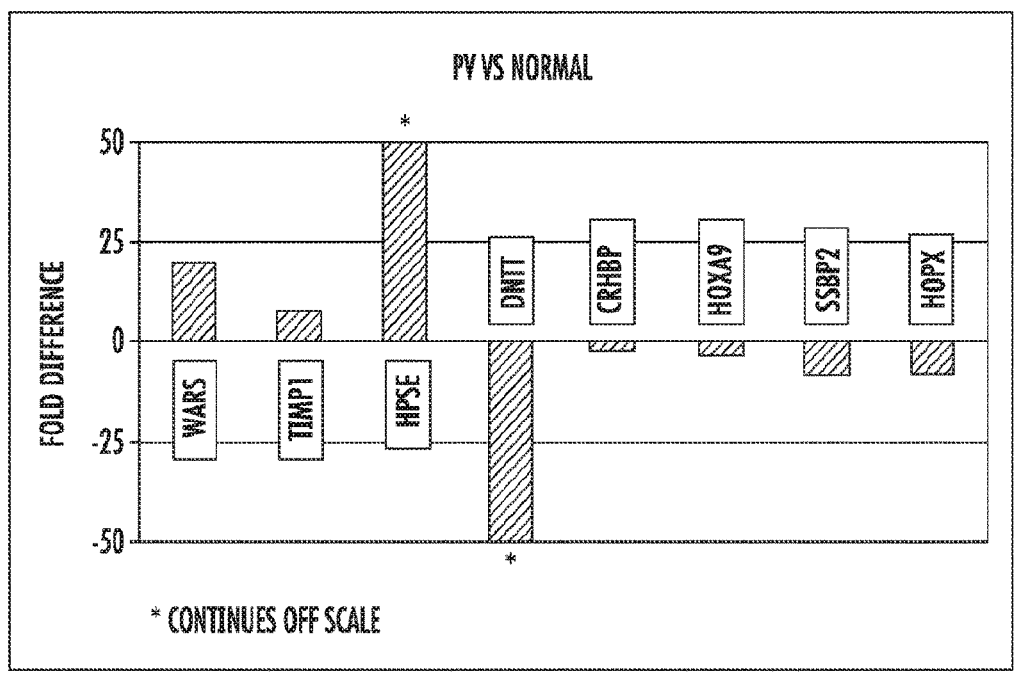
Figure 3A:
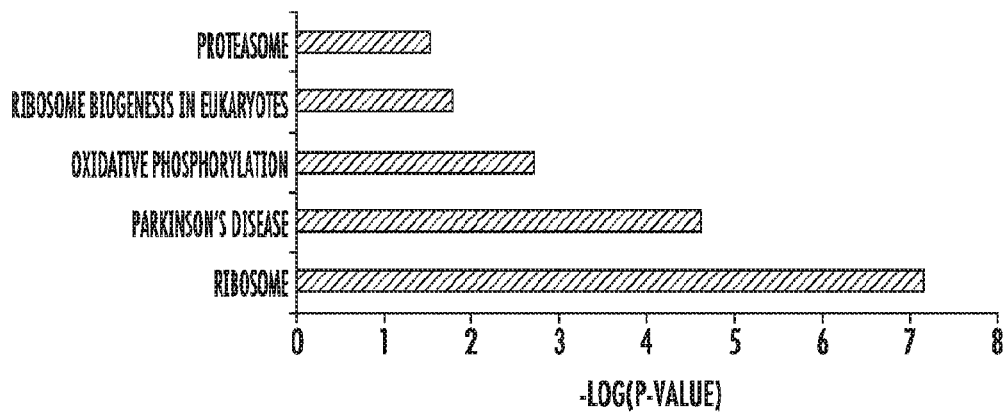
Figure 3B:
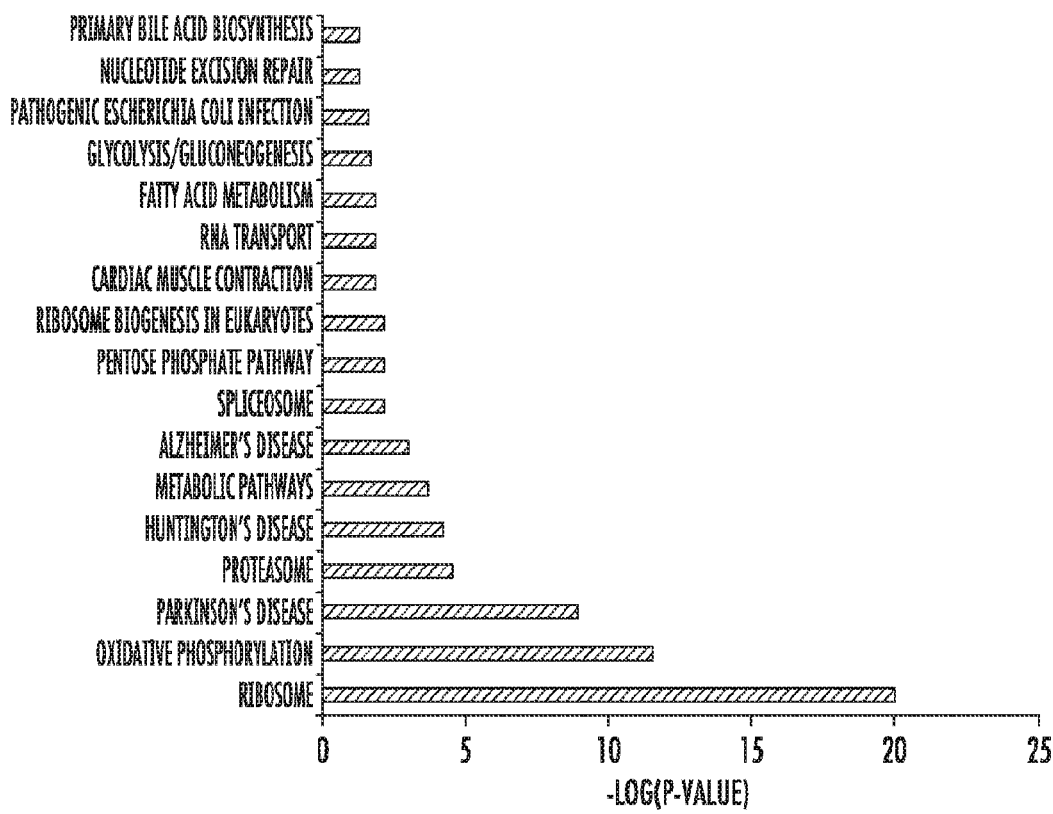
Figure 4:
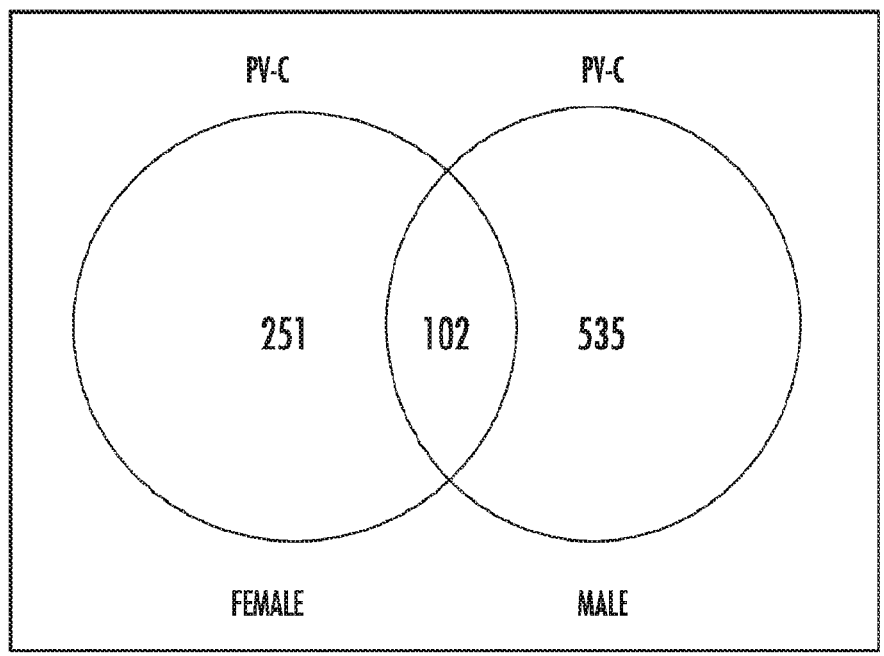
Figure 5:
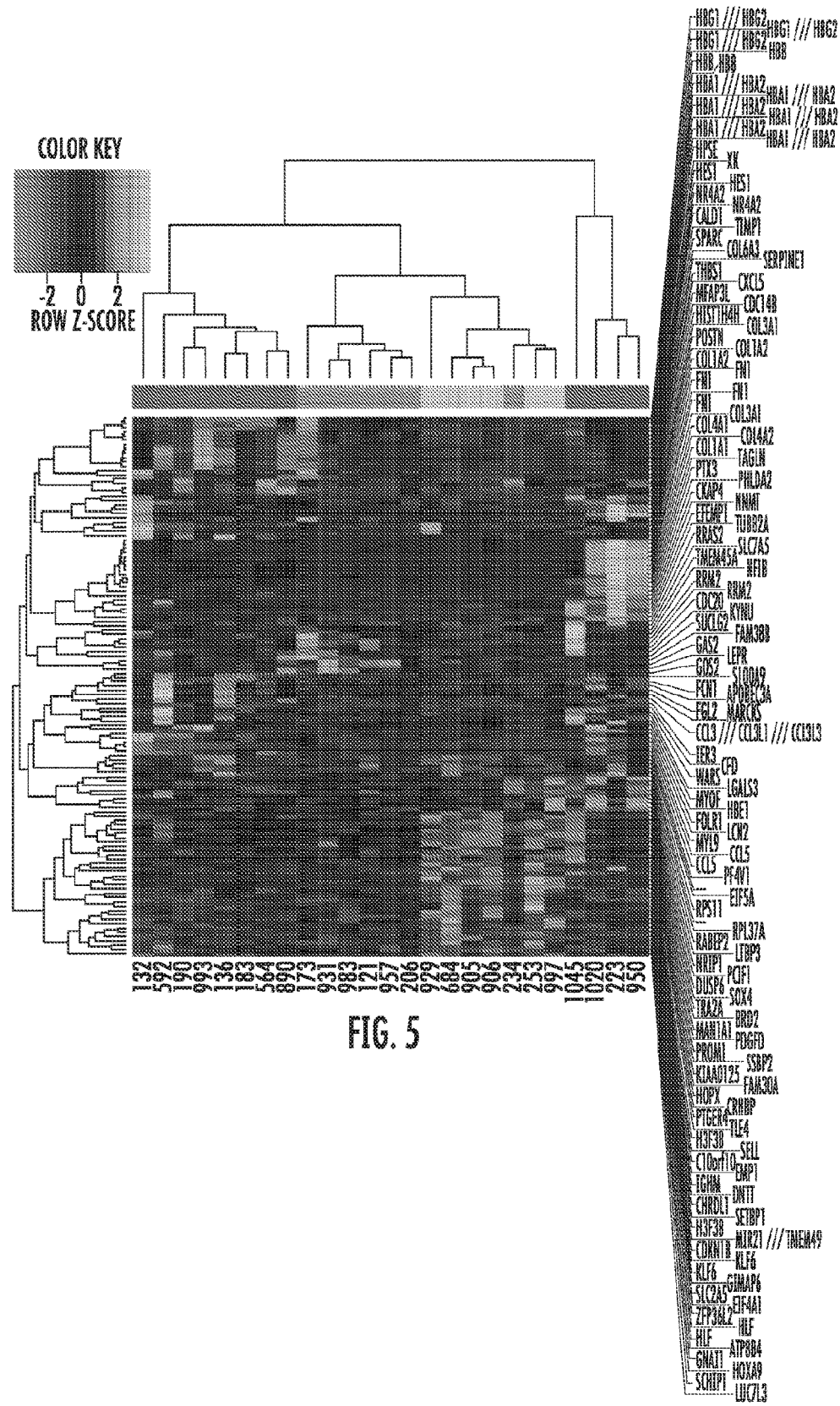
Figure 6:
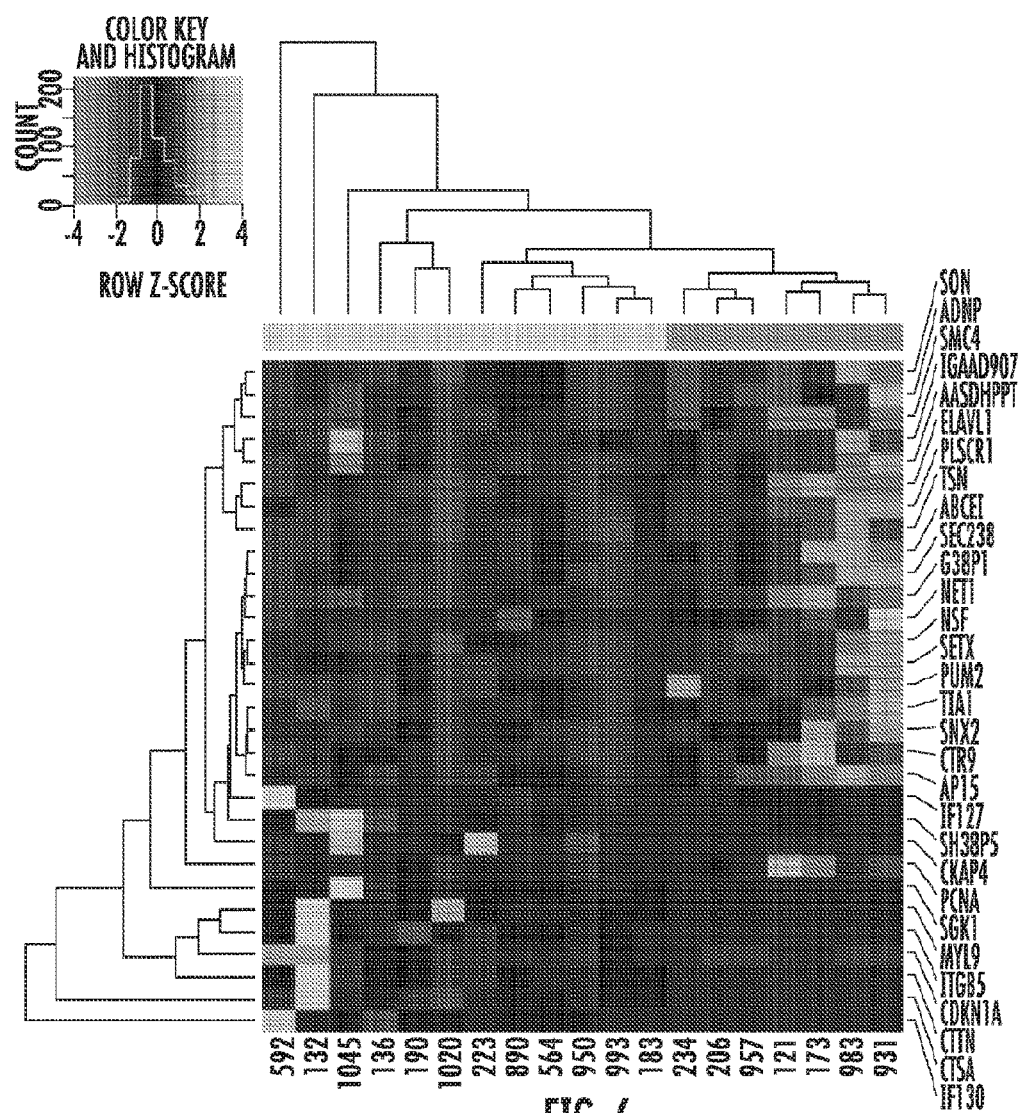
Figure 7:
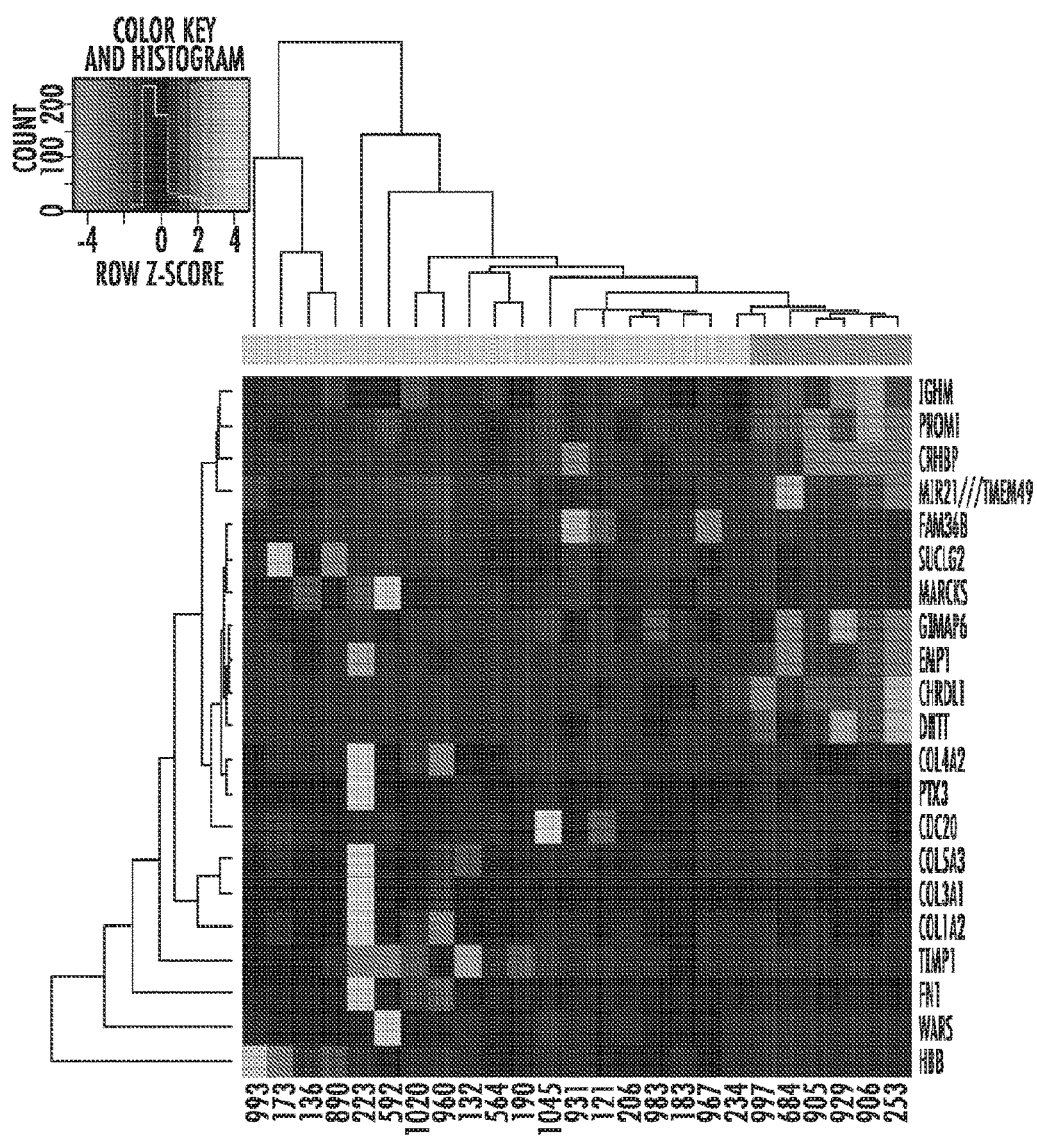
Figure 8:
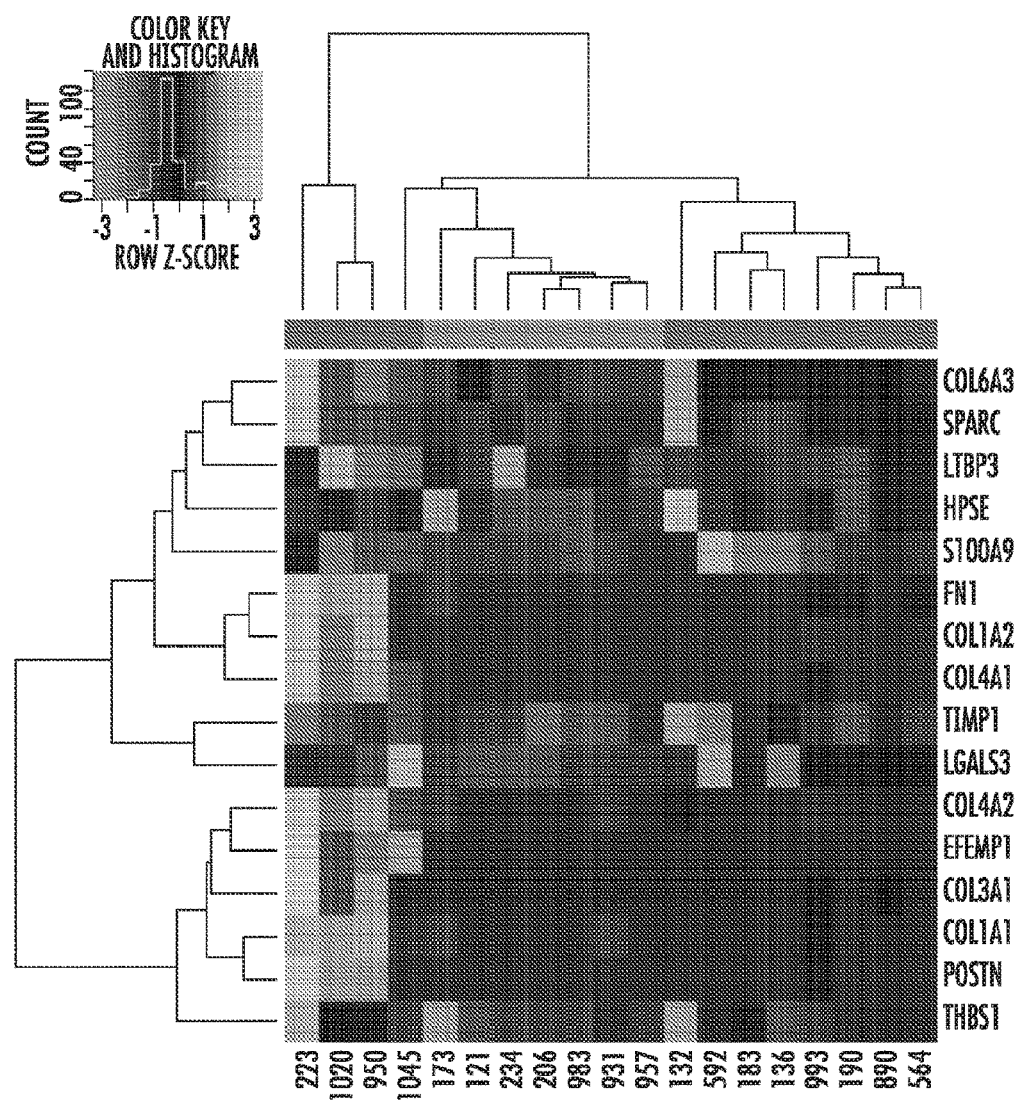
Figure 9A:
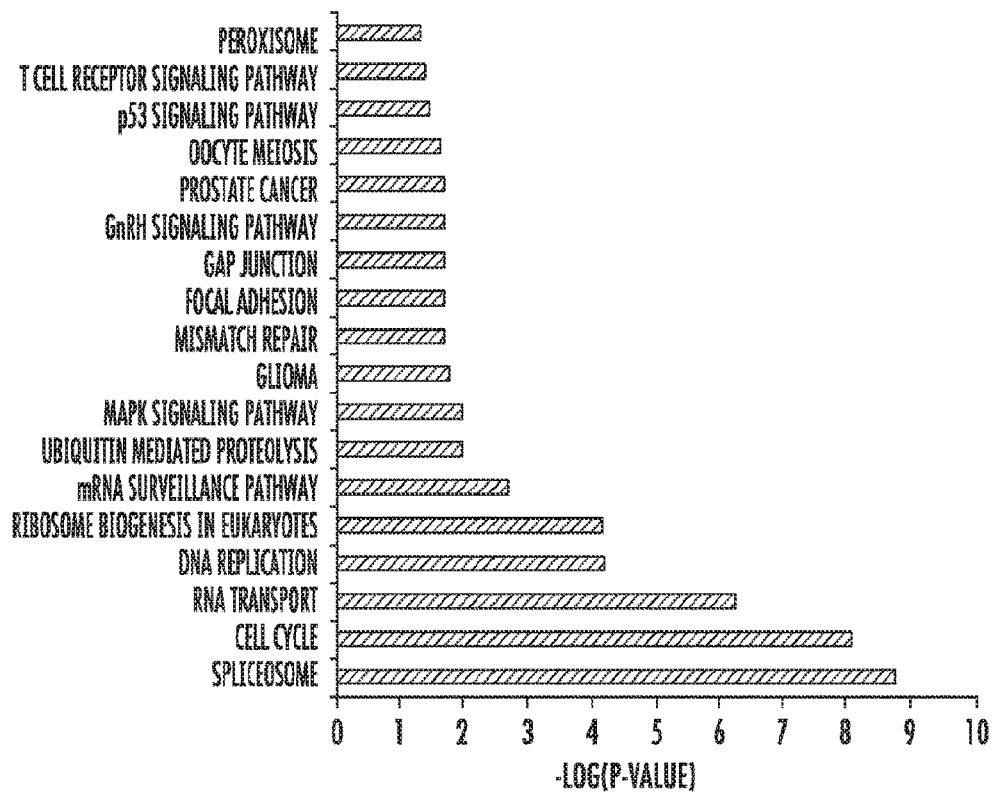
Figure 9B:
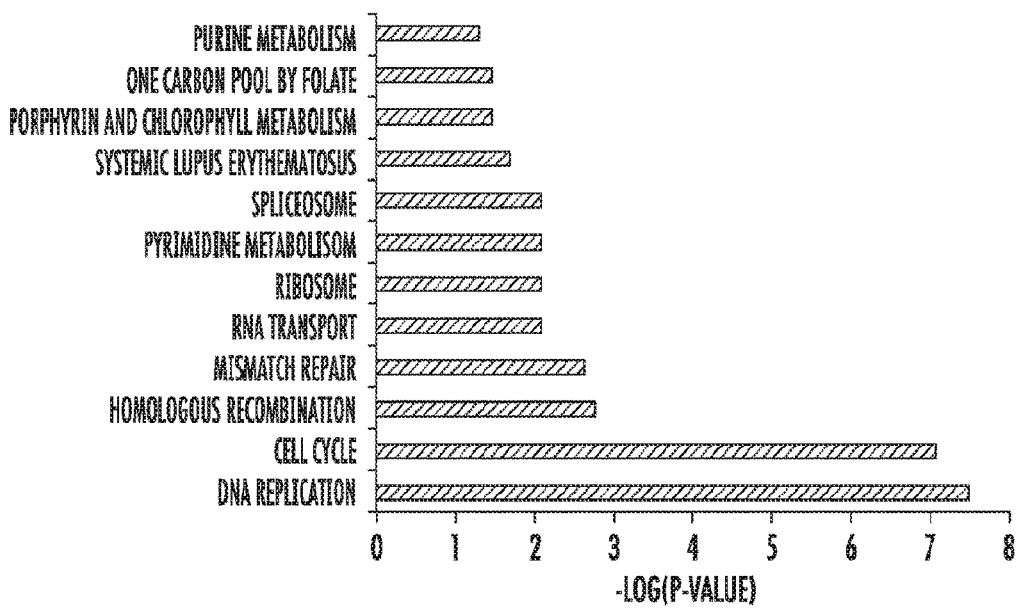
Figure 10:
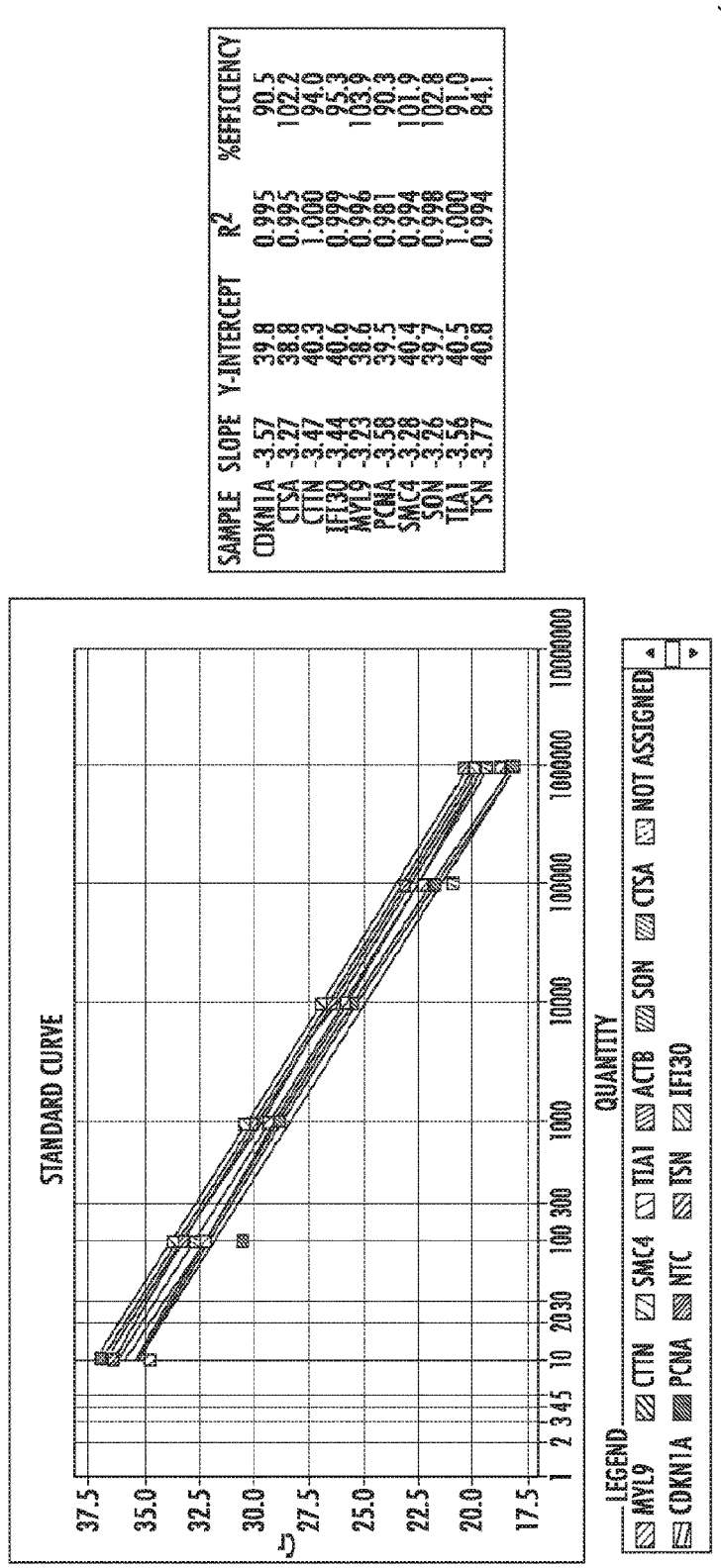
Figure 11B:
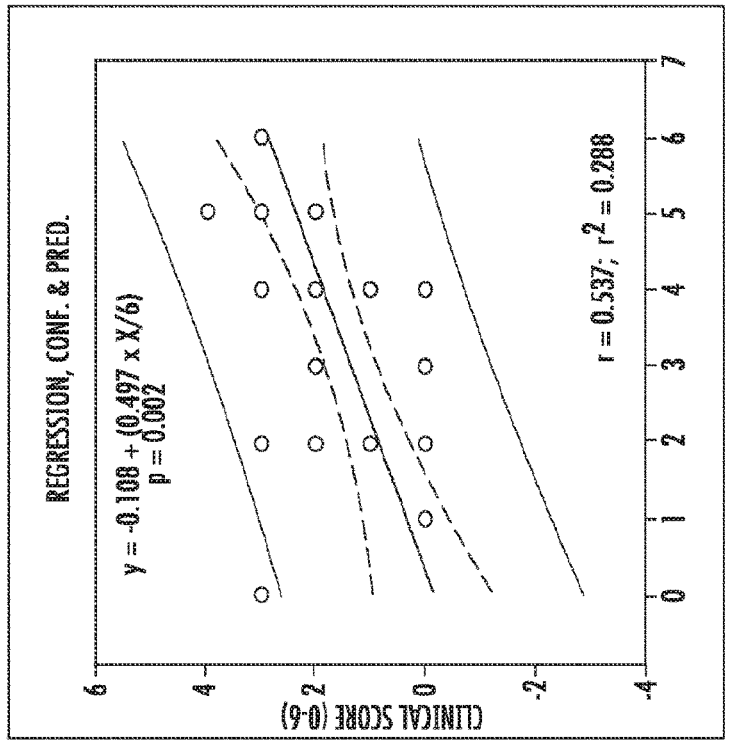
Figure 11A:
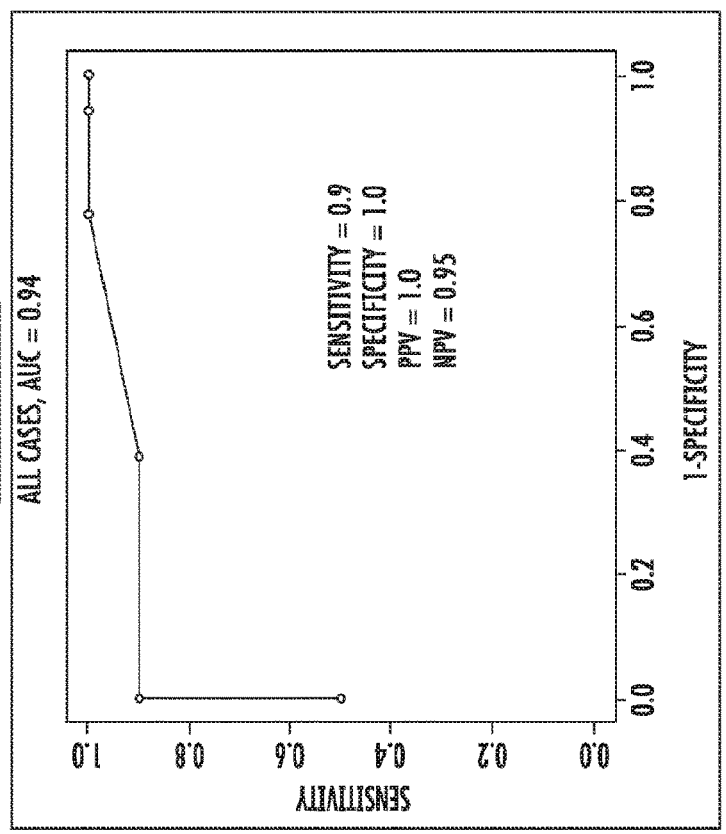
Figure 12B:
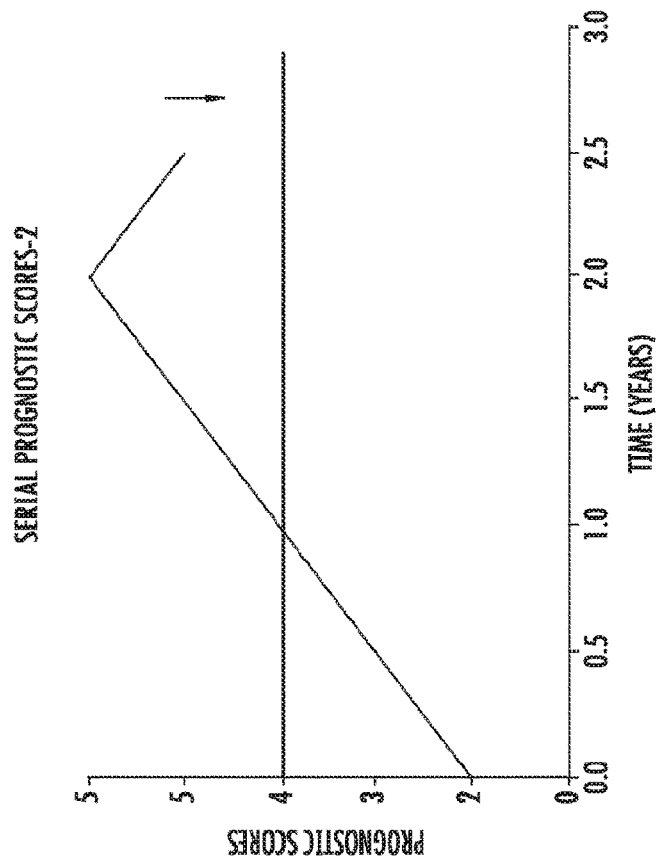
Figure 12A:
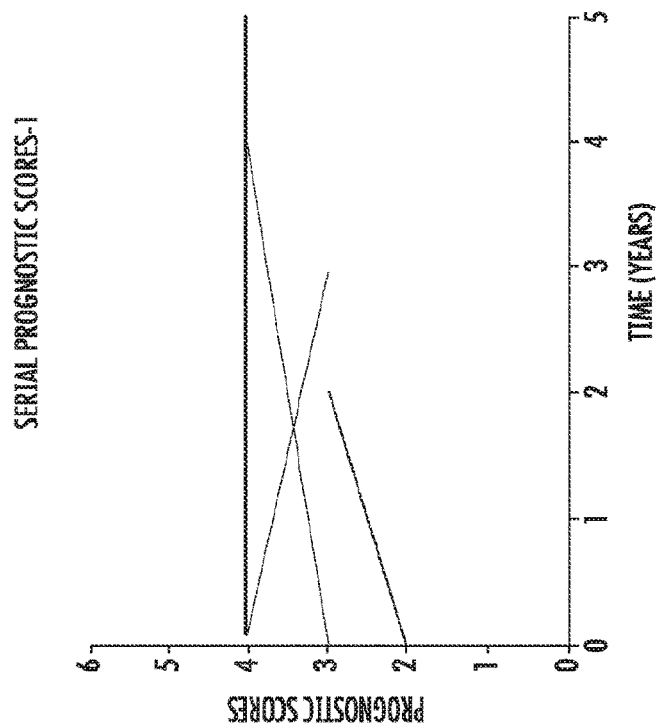

Having thus described the presently disclosed subject matter in general terms, reference will now be made to the accompanying Figures, which are not necessarily drawn to scale, and wherein:

FIG. 1 shows the natural history of PV as shown by the evolution of PV over time with transformation to myelofibrosis and acute leukemia in 273 PV patients;

FIG. 2 shows quantitative real-time polymerase chain reaction (Q-RT-PCR) confirmation of PV CD34+ cell gene expression using the primers described in Table 1;

FIGS. 3A-3B show representative KEGG pathway analysis for: A) male and B) female patient groups;

FIG. 4 shows a representative Venn diagram of the genes differentially expressed by the 8 men and 11 women PV patients illustrating the number of genes concordantly differentially regulated by both sexes;

FIG. 5 shows a representative dendrogram and heat map for the unsupervised hierarchical clustering of the 19 PV patients using the 102 genes concordantly deregulated by both sexes. The green color bar indicates the normal controls; the blue and red color bars indicate the PV patients. For the heat map, red indicates decreased gene expression and green increased gene expression;

FIG. 6 shows a representative dendrogram and heat map for the supervised clustering of the 19 PV patients using 30 genes identified by top scoring pair analysis. The blue color bar indicates the 12 PV patients with indolent disease and the red color bar the 7 PV patients with aggressive disease. For the heat map, red indicates decreased gene expression and green increased gene expression;

FIG. 7 shows a representative dendrogram and heat map for supervised clustering of the 19 PV patients in blue and the normal controls in red using 21 genes identified by top scoring pair analysis from the 102 core gene set; with the 21 genes the PV patients could be separated almost completely from the normal controls. For the heat map, red indicates decreased gene expression and green increased gene expression;

FIG. 8 shows a representative dendrogram and heat map for the unsupervised hierarchical clustering of the 19 PV patients using the 16 gene "stromal signature." The blue color bar indicates the indolent patient group and the red color bar aggressive patient group. For the heat map, red indicates decreased gene expression and green increased gene expression;

FIGS. 9A-9B show a representative KEGG pathway analysis for: A) indolent and B) aggressive patient groups;

FIG. 10 shows a representative test using standards for copy number calculations (absolute quantitation). Standard curves were based on log dilutions ($10^6$–$10^1$) of plasmids containing targeted regions of known length of each gene. Copy numbers were determined using calculations based upon the assumption that the average weight of a base pair (bp) is 650 Daltons (g/mol). By utilizing Avogadro's number and converting grams to nanograms, the number of copies of plasmid per weight in ng was calculated by the equation: number of copies=(amount*$6.022 \times 10^{23}$)/(length*$1 \times 10^9$*650);

FIGS. 11A-11B show: A) ROC curve for the probability score assay using the test set and B) regression and correlation for the probability and clinical scores for the 30 PV patient test set; and FIGS. 12A-12B show: A) serial probability scores over time in 5 PV patients, with none changing from an indolent to aggressive score; and B) serial probability scores over time in 2 PV patients with an indolent score, with progression to an aggressive score over time in association with leukocytosis and increasing splenomegaly in one, and transformation to acute leukemia in the other without any other clinical change.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Predictive Methods for PV Transformation

PV is complicated by extramedullary hematopoiesis, myelofibrosis and acute leukemia. An explanation for this clinical phenotype was provided by the discovery of an activating mutation (V617F) in JAK2 (James et al., 2005), a tyrosine kinase utilized for signal transduction by the receptors for erythropoietin, granulocyte colony-stimulating factor, granulocyte-macrophage colony-stimulating factor and thrombopoietin. However, the same mutation occurs in essential thrombocytosis (ET) and primary myelofibrosis (PMF), diseases with overlapping phenotypes but distinctly different natural histories (Jones et al., 2005). While it is undisputed that JAK2 V617F can produce a myeloproliferative phenotype, how this mutation could be responsible for the pathogenesis of three different diseases is a conundrum not explainable by the JAK2 V617F allele burden since it overlaps substantially amongst them (Stein et al., 2010). Several lines of evidence suggest that additional genetic and epigenetic events are involved. For example, in PV and ET, gene expression in CD34+ marrow cells was not different in JAK2 V617F-positive and JAK2 V617F-negative patients (Berkofsky-Fessler et al., 2010; Catani et al., 2009), while PV clonal granulocytes do not always express JAK2 V617F (Nussenzveig et al., 2007). Furthermore, JAK2 V617F expression, regardless of its allelic burden, did not influence signal transduction in circulating PV CD34+ cells (Anand et al., 2011). Finally, PV is more common in women (Stein et al., 2010; Ridell et al., 2000) in whom it presents earlier (Ranjan et al., 2013), more often with splenomegaly (Videbaek, 1950), masked erythrocytosis (Lamy et al., 1997), hepatic vein thrombosis (Stein et al., 2011; Smalberg et al., 2012) and a lower JAK2 V617F neutrophil allele burden than men (Stein et al., 2010).

None of the observations should be surprising since myeloproliferative disorders (MPD) are hematopoietic stem cell disorders and animal studies indicate that, unlike committed erythroid and megakaryocytic progenitor cells, primitive hematopoietic stem cells do not require JAK2 or its primary substrate, STAT5, for either survival or self renewal. Further, clonal dominance is a characteristic feature of the MPD, but expansion of the involved JAK2 V617 CD34+ cell population occurs more slowly than that of committed hematopoietic progenitor cell populations, at a different rate in each of the MPD, and independently of JAK2 V617F homozygosity. Importantly in this regard, clonal dominance at the CD34+ cell level correlated better with splenomegaly, leukocytosis and anemia than did the neutrophil JAK2 V17F allele burden and was disease-specific. Finally, gene expression studies of JAK2 V617F-positive PV CD34+ marrow cells indicated dysregulation of JAK2-independent genes, while in ET, gene expression in CD34+ marrow cells did not differ between JAK2 V617F-positive and JAK2 V617F-negative ET patients.

Accordingly, to further define the molecular abnormalities in PV at the stem cell level, gene expression in circulating CD34+ cells from nineteen JAK2 V617F-positive PV patients controlling for gender as a possible confounder was examined. It was observed that CD34+ cell gene expression not only differed between the PV patients and the controls, but also differed between men and women patients. Based on these differences, 102 genes were identified that concordantly differentially regulated by both men and women, which likely represent a core set of genes involved in the pathogenesis of PV.

Using this gene set and several clustering algorithms, the nineteen patients could be separated into two groups that differed significantly with respect to hemoglobin level, thrombosis frequency, splenomegaly, splenectomy, chemotherapy exposure, leukemic transformation and survival. One group had a more aggressive disease with a lower hemoglobin level, more thromboembolic events, larger spleens, a greater frequency of chemotherapy and splenectomy and a higher mortality rate despite having a JAK2 V617F allelic burden similar to the other group. Using a supervised approach, a 19 gene profile was defined, which also segregated the PV patients with aggressive disease from those with a more indolent phenotype with 100% accuracy.

Based on these 19 genes, a smaller gene panel was derived consisting of the 10 genes (PCNA, IF130, TSN, CTSA, SMC4, CDKN1A, CTTN, SON, TIA1 and MYL9) for establishing the probability that a PV patient has an aggressive or indolent form of the disease using Q-RT-PCR and scoring 1 for true and 0 for false. If PCNA>IF130; TSN>CTSA; SMC4>CDKN1A; PCNA>CTTN; SON>CTTN; and TIA1>MYL9, the probability that the disease is aggressive is the total score/6. After developing absolute copy number standard Ct curves for the 10 genes, the behavior of this screen on the training set PV patients was verified.

Further, the predictability of the screen was tested using CD34+ cell RNA from twenty-three PV patients. The presently disclosed subject matter provides a molecular method for risk stratification in PV that reflects clinical phenotype and anticipates disease transformation with a high degree of certainty. The data herein indicate that it is now possible to use gene expression to identify those PV patients most likely to benefit from early institution of definitive therapy.

Accordingly, in some embodiments, the presently disclosed subject matter provides a method for determining the likelihood of an indolent form of Polycythemia Vera (PV) transforming to an aggressive form of PV in a subject, the method comprising: (a) measuring the gene products of PCNA, IFI30, TSN, CTSA, SMC4, CDKN1A, CTTN, SON, TIA1, and MYL9 in a biological sample comprising blood cells obtained from the subject; (b) making the following comparisons of the gene product levels measured in (a) and recording a score of 1 for a true result and a score of 0 for a false result: PCNA>IFI30; TSN>CTSA; SMC4>CDKN1A; PCNA>CTTN; SON>CTTN; TIA1>MYL9; (c) adding the scores together to obtain an added score and calculating a ratio of the added score/6 to calculate a total score; and (d) using the total score to predict if the indolent form of PV in the subject is likely to transform to an aggressive form of PV in the subject.

In such embodiments, a total score of 5/6 or 6/6 predicts that the indolent form of PV in a subject is likely to transform to an aggressive form of PV in the subject. A total score of less than 5/6 predicts that the indolent form of PV in a subject is not likely to transform to an aggressive form of PV in the subject.

The presently disclosed subject matter provides a 10 gene screening panel comprised of PCNA (proliferating cell nuclear antigen), TSN (translin), CDKN1A (cyclin-dependent kinase inhibitor 1A (p21, Cip1)), MYL9 (myosin, light chain 9, regulatory), IFI30 (interferon, gamma-inducible protein 30), CTSA (cathepsin A), SMC4 (structural maintenance of chromosomes 4), CTTN (cortactin), SON (SON DNA binding protein), and TIA1 (TIA1 cytotoxic granule-associated RNA binding protein).

The biomarkers of the presently disclosed subject matter can be used in diagnostic tests to assess or determine whether an indolent form of PV in a patient will transform to an aggressive form of PV. In other embodiments, the biomarkers may be used to determine if a patient has PV.

The indolent form of PV is characterized by the unregulated production of red cells, white cells and platelets. PV patients afflicted with the indolent form of PV may be asymptomatic or may show milder symptoms of the disease. In contrast, patients with the aggressive form show more severe symptoms, such as thrombotic and hemorrhagic events, extramedullary hematopoiesis, myelofibrosis and acute leukemia, albeit at varying frequencies.

The blood cells can be obtained from different sources in a subject. In some embodiments, the biological sample comprises peripheral blood or bone marrow. In some embodiments, the blood cells are white blood cells. In other embodiments, the blood cells are CD34+ cells.

In some embodiments, the subject is mammalian. In other embodiments, the subject is human.

In further embodiments, the expression products of PCNA, IFI30, TSN, CTSA, SMC4, CDKN1A, CTTN, SON, TIA1, and MYL9 are measured. In other embodiments, one or more of these expression products are substituted with other expression products that have both correlated expression and the same category of biological function.

In some embodiments, the expression products of the relevant genes are measured by determining RNA levels. In further embodiments, the expression products are measured by determining mRNA expression levels. Generally, in a first step, the total RNA is isolated from a biological sample. The methods for RNA extraction are well known in the art.

Methods for measuring mRNA levels include methods based on hybridization analysis of polynucleotides as well as methods based on sequencing of polynucleotides. These methods include, but are not limited to, northern blotting, in situ hybridization, RNase protection assays, reverse transcription polymerase chain reaction (RT-PCR), real-time PCR (QPCR), antibodies that can recognize specific duplexes (DNA duplexes, RNA duplexes, DNA-RNA hybrid duplexes, DNA-protein duplexes, for example), sequence-based gene expression analysis including Serial Analysis of Gene Expression (SAGE), and gene expression analysis by massively parallel signature sequencing (MPSS).

In some embodiments, the mRNA expression levels are measured by using reverse transcription PCR (RT-PCR). Commonly used reverse transcriptases are avilo myeloblastosis virus reverse transcriptase (AMV-RT) and Moloney murine leukemia virus reverse transcriptase (MLV-RT). The reverse transcription step is typically primed using specific primers, random hexamers, or oligo-dT primers. The RT-PCR reaction reverse transcribes the RNA template into cDNA.

In still further embodiments, the mRNA expression levels are measured by using reverse transcription PCR (RT-PCR) followed by real-time PCR (Q-PCR). In the Q-PCR reaction, the cDNA produced from the RT-PCR is amplified and simultaneously quantified. The PCR step can use a variety of thermostable DNA-dependent DNA polymerases, such as Taq DNA polymerase, which has a 5'-3' nuclease activity but lacks a 3'-5' proofreading endonuclease activity. Two oligonucleotide primers are used to generate a PCR product. A third oligonucleotide, or probe, is designed to detect the PCR product.

Generally, primer design or determining which sequences to use for making a primer is well known in the art. Computer programs are available to determine if a set of nucleotides in a polynucleotide is optimal for initiating a PCR reaction. Therefore, different primers can be used to initiate a PCR reaction and to detect a specific gene product. As such, the expression products of the presently disclosed subject matter can be detected using different primers and the presently disclosed subject matter is not limited to a specific set of primers.

In other embodiments, the expression products of PCNA, IFI30, TSN, CTSA, SMC4, CDKN1A, CTTN, SON, TIA1, and MYL9 are measured by determining protein expression levels. Examples of detection methods for proteins include, but are not limited to, immunohistochemical assays, Western blot analyses, ELISAs, polyacrylamide gels, and protein activity assays. Other detection methods are well known in the art and include methods that are not and need not be stated here.

In some embodiments, the expression products are expression products of variants or fragments of PCNA, IFI30, TSN, CTSA, SMC4, CDKN1A, CTTN, SON, TIA1, or MYL9. Therefore, a gene or gene product comprising variants of polynucleotides according to the presently disclosed subject matter include, but are not limited to, nucleotide sequences which are at least 70% identical, e.g., at least 75%, 80%, 85%, 90%, 91%, 92%, 93%, 94%, 95%, 96%, 97%, 98%, or 99% identical to the nucleotide sequence of PCNA, IFI30, TSN, CTSA, SMC4, CDKN1A, CTTN, SON, TIA1, or MYL9 may be substituted for PCNA, IFI30, TSN, CTSA, SMC4, CDKN1A, CTTN, SON, TIA1, or MYL9. In other embodiments, more than one gene may be substituted.

The biological samples used to obtain the RNA of the relevant genes can be any part of a subject that comprises blood cells. In some embodiments, the biological sample comprises peripheral blood or bone marrow. In other embodiments, the biological sample comprises blood cells that are white blood cells. In still other embodiments, the biological sample is comprised of unpurified white blood cells. In further embodiments, the biological sample is comprised of CD34+ cells isolated from unpurified circulating white blood cells. In still further embodiments, circulating CD34+ cells are quantitated clinically by flow cytometry in a pretest step.

In some embodiments, the RNA from a subject is not purified before being used in the presently disclosed methods. In other embodiments, total RNA, such as from unseparated peripheral blood mononuclear cells or from isolated neutrophils, is used in the presently disclosed assays without being purified. In the former case, with respect to the issue of sample dilution and assay sensitivity, the rate limiting step would still be the number of circulating CD34+ cells.

The indolent form of PV in a subject is characterized by many symptoms, both general and specific for the disease. A particular subject may have one or more than one of the symptoms. In some embodiments, the indolent form of PV is characterized by at least one of symptom selected from the group consisting of increased production of red cells, increased production of white cells, increased production of platelets, itching, gouty arthritis peptic ulcer disease, enlarged liver or spleen, elevated hemoglobin levels, and low erythropoietin levels in a subject.

The aggressive form of PV in a subject is generally characterized by more serious symptoms, some of which are life threatening. In some embodiments, the aggressive form of PV is characterized by at least one symptom selected from the group consisting of thrombosis, heart attack, stroke, Budd-Chiari syndrome, myelofibrosis and acute leukemia (AML) in a subject.

PV is chronic disorder, which has a very variable clinical course depending on the host response to the malignant clone (Spivak, 2002). In many patients, the disease remains indolent with only a requirement for phlebotomy therapy to control red cell mass expansion and prevent thrombotic events. In other patients, there is inexorable expansion of the malignant clone with massive splenomegaly for which the treatment options include bone marrow transplantation, interferon or potentially leukemogenic chemotherapy, of which the latter is at best palliative and may actually shorten survival (Berk et al., 1981; Gruppo, 1995). To date, there is no way to anticipate how the disease will evolve clinically. However, the presently disclosed methods can anticipate disease transformation and, based on this, are useful for determining which PV patients would most benefit from the institution of definitive therapy, such as interferon or bone marrow transplantation before clonal expansion is too far advanced. Currently the only curative therapy for PV is bone marrow transplantation and the only therapy capable of inducing molecular remission is pegylated interferon, both of which have significant toxicities. All chemotherapeutic drugs used to suppress marrow and extramedullary hematopoiesis increase the basal rate of leukemic transformation ten-fold or greater. For example, despite the lack of evidence-based data (Spivak, 2002; Spivak and Hasselbalch, 2011), hydroxyurea is considered to be the first-line drug of choice for PV management, particularly in patients older than 65 years of age (Barbui et al., 2011). Unfortunately, hydroxyurea is leukemogenic (Najean and Rain, 1997; Kiladjian et al., 2011) and both age over 60 (McNally et al., 1997) and PV predispose to acute leukemia (Berk et al., 1981), creating a triply dangerous situation for older PV patients since, in contrast to sickle cell disease, a nonclonal disorder in which hydroxyurea improves survival, hydroxyurea neither prevents major vessel arterial or venous thrombosis (Harrison et al., 2005) nor improves survival in PV (Najean and Rain, 1997). Therefore, the presently disclosed methods, which identify PV patients with nonaggressive disease can improve patient safety as well as reduce drug costs. In this regard, the presently disclosed methods can also be used to screen patients for the appropriate use of ruxolitinib when that drug is approved for therapy in PV. Thus, a method to predict transformation risk is very useful to avoid unnecessary exposure to toxic therapies. In some embodiments, the presently disclosed methods are used more than once with a patient to follow PV in the patient. For example, the assay can be used for the first time as a baseline test and then can be used longitudinally as clinically indicated by a rising leukocyte count or advancing splenomegaly, two signs of potentially aggressive behavior in PV. In other embodiments, the presently disclosed methods display a sensitivity of at least 80% and a specificity of at least 90%. In some embodiments, the method further comprises informing the subject or a treating physician of the likelihood of the indolent form of PV transforming to an aggressive form of PV in the subject. In other embodiments, the method is used to determine if a subject should undergo further therapy for PV. In still other embodiments, the method further comprises treating the patient with further therapy for PV. In further embodiments, the therapy is selected from the group consisting of bone marrow transplantation, pegylated interferon, chemotherapy, and ruxolitinib.

II. Kits for Predicting PV Transformation

The presently disclosed subject matter also relates to kits for determining if the indolent PV in a subject will transform to an aggressive form of PV. In general, a presently disclosed kit contains some or all of the components, reagents, supplies, and the like to practice a method according to the presently disclosed subject matter. In some embodiments, the term "kit" refers to any intended any article of manufacture (e.g., a package or a container) comprising a means for detecting the gene products of PCNA, IFI30, TSN, CTSA, SMC4, CDKN1A, CTTN, SON, TIA1, and MYL9 and a set of particular instructions for practicing the methods of the presently disclosed subject matter. In other embodiments, the set of particular instructions includes the algorithm for predicting whether the indolent PV in a subject will transform to aggressive PV. In some embodiments, the kit comprises components that detect the levels of RNA transcripts, such as mRNA transcripts. For example, the kit may comprise the primers necessary to detect the mRNA levels of PCNA, IFI30, TSN, CTSA, SMC4, CDKN1A, CTTN, SON, TIA1, and MYL9, the enzymes necessary to perform reverse transcription and PCR amplification, such as a polymerase and a reverse transcriptase, deoxynucleotides, and a buffer. In other embodiments, the kit comprises components that detect the protein expression levels of PCNA, IFI30, TSN, CTSA, SMC4, CDKN1A, CTTN, SON, TIA1, and MYL9. The kit provided may be an ELISA kit comprising antibodies to the biomarkers of the presently disclosed subject matter. In still other embodiments, the kit is a diagnostic kit that determines whether an indolent form of PV in a subject is likely to transform to an aggressive form of PV, the kit comprising a means for measuring the gene product levels of PCNA, IFI30, TSN, CTSA, SMC4, CDKN1A, CTTN, SON, TIA1, and MYL9 and a set of instructions comprising an algorithm for predicting if the indolent form of PV in the subject is likely to transform to an aggressive form of PV.

III. Definitions

Unless defined otherwise, all technical and scientific terms used herein have the meaning commonly understood by a person skilled in the art to which this invention belongs.

As used herein, the term "biomarker" refers to any gene, RNA or protein whose level of expression in a cell or tissue is altered in some way compared to that of a normal or healthy cell or tissue. In some embodiments, the amount of biomarker may be changed. In other embodiments, the biomarker may be differentially modified in some way. Biomarkers of the presently disclosed subject matter are selective for PV.

As used herein, the term "level of expression" of a biomarker refers to the amount of biomarker detected. Levels of biomarker can be detected at the transcriptional level, the translational level, and the post-translational level, for example. "mRNA expression levels" refers to the amount of mRNA detected in a sample and "protein expression levels" refers to the amount of protein detected in a sample.

As used herein, the term "microarray" refers to an ordered arrangement of hybridizable array elements, preferably polynucleotide probes, on a substrate.

As used herein, the term "polynucleotide" generally refers to any polyribonucleotide or polydeoxyribonucleotide, which may be unmodified RNA or DNA or modified RNA or DNA.

As used herein, the term "oligonucleotide" refers to a relatively short polynucleotide. This includes, without limitation, single-stranded deoxyribonucleotides, single- or double-stranded ribonucleotides, RNA:DNA hybrids and double-stranded DNAs.

As used herein, the term "gene product" refers to biochemical material, such as RNA or protein, resulting from expression of a gene. A measurement of the amount of gene product is sometimes used to infer how active a gene is at a particular time.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters, including default parameters for pairwise alignments. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the sequence analysis software described herein.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al. (1990) *J. Mol. Biol.* 215:403-410, and DNASTAR (DNASTAR, Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

The term "primer" denotes a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

The term "probe" denotes a defined nucleic acid segment which can be used to identify a specific polynucleotide sequence present in samples, wherein the nucleic acid segment comprises a nucleotide sequence complementary to the specific polynucleotide sequence to be identified.

The terms "complementary" or "complement thereof" are used herein to refer to the sequences of polynucleotides that are capable of forming Watson & Crick base pairing with another specified polynucleotide throughout the entirety of the complementary region. For the purpose of the presently disclosed subject matter, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide," "complementary nucleic acid" and "complementary nucleotide sequence". These terms are applied to pairs of polynucleotides based solely upon their sequences and not any particular set of conditions under which the two polynucleotides would actually bind.

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (See Berg et al. (2011) *Biochemistry*, $7^{th}$ revised international ed., ISBN-10:1429276355).

Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

A polynucleotide fragment refers to a nucleotide sequence of reduced length relative to the reference nucleic acid and comprising, over the common portion, a nucleotide sequence identical to the reference nucleic acid. Such a nucleic acid fragment according to the presently disclosed subject matter may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the presently disclosed subject matter.

Such fragments may be "free-standing," i.e. not part of or fused to other polynucleotides, or they may be comprised within a single larger polynucleotide of which they form a part or region. Indeed, several of these fragments may be present within a single larger polynucleotide.

The term "predictive" or "predictability" is used herein to refer to the likelihood that a patient will respond either favorably or unfavorably to therapy. Therapy includes, but is not limited to, drugs, surgical intervention, chemotherapy, radiation therapy, and bone marrow transplants.

As used herein, the terms "treat," "treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. It will be appreciated that, although not precluded, treating a disease, disorder or condition does not require that the disease, disorder, condition or symptoms associated therewith be completely eliminated.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition.

As used herein, the term "diagnosing" refers to the process of attempting to determine or identify a disease or disorder.

As used herein, the term "comparing" refers to making an assessment of how the proportion, level or cellular localization of one or more biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample. More specifically, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels that correspond to, for example, a patient having an indolent form of PV that is likely to transform to an aggressive form of PV, not having an indolent form of PV that is likely to transform to an aggressive form of PV, is responding to treatment for PV, is not responding to treatment for PV, is/is not likely to respond to a particular PV treatment, or having/not having another disease or condition. In a specific embodiment, the term "comparing" refers to assessing whether the level of one or more biomarkers of the presently disclosed subject matter in a sample from a patient is the same as, more or less than, different from other otherwise correspond (or not) to levels of the same biomarkers in a control sample (e.g., predefined levels that correlate to uninfected individuals, standard PV levels, and the like).

As used herein, the term "transform" means that the condition that is being transformed changes in some way. For example, the indolent form of PV can change to the aggressive form of PV.

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient has an indolent form of PV that is likely to transform to an aggressive form of PV. In specific embodiments, the parameter may comprise the level of one or more biomarkers of the presently disclosed subject matter. A particular set or pattern of the amounts of one or more biomarkers may indicate that a patient has an indolent form of PV that is likely to transform to an aggressive form of PV (i.e., an indolent form of PV that is likely to transform to an aggressive form of PV). In other embodiments, a particular set or pattern of the amounts of one or more biomarkers may be correlated to a patient being unaffected (i.e., indicates a patient does not have an indolent form of PV that is likely to transform to an aggressive form of PV). In certain embodiments, "indicating," or "correlating," as used according to the presently disclosed subject matter, may be by any linear or non-linear method of quantifying the relationship between levels of biomarkers to a standard, control or comparative value for the assessment of the diagnosis, prediction of PV progression or transformation, assessment of efficacy of clinical treatment, identification of a patient that may respond to a particular treatment regime or pharmaceutical agent, monitoring of the progress of treatment, and in the context of a screening assay, for the identification of an anti-PV therapeutic.

The terms "patient," "individual," or "subject" are used interchangeably herein, and refer to a mammal, particularly, a human. A "subject" can include a patient afflicted with or suspected of being afflicted with a condition or disease. The patient may have mild, intermediate or severe disease. The patient may be treatment naive, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects.

As used herein, the term "subject at risk" of getting a disease refers to estimating that a subject will have a disease or disorder in the future based on the subject's current symptoms, family history, lifestyle choices, and the like.

As used herein, the term "disease" refers to any condition, dysfunction or disorder that damages or interferes with the normal function of a cell, tissue, or organ.

The term "training set" refers to a group of patients that is used to develop the assay. The testing set is a different group of patients with the same disease used to validate the assay (i.e. reproduce the results).

The terms "measuring" and "determining" are used interchangeably throughout, and refer to methods which include obtaining a patient sample and/or detecting the level of a biomarker(s) in a sample. In one embodiment, the terms refer to obtaining a patient sample and detecting the level of one or more biomarkers in the sample. In another embodiment, the terms "measuring" and "determining" mean detecting the level of one or more biomarkers in a patient sample. Measuring can be accomplished by methods known in the art and those further described herein. The term "measuring" is also used interchangeably throughout with the term "detecting."

As used herein, the term "indicative" or "likely" means that the event referred to is probable. For example, if the methods of the presently disclosed subject matter result in a conclusion that the indolent form of PV in a subject is likely to transforming to an aggressive form of PV in the subject, then that means it is probable that the indolent form of PV in the subject will transform to an aggressive form of PV.

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of PV. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cerebrospinal fluid, urine, saliva, stool and synovial fluid), solid tissue samples such as a biopsy specimen or tissue cultures or cells derived therefrom and the progeny thereof. In a specific embodiment, a sample comprises a blood sample. In another embodiment, a serum sample is used. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, and the like, to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, and the like, determined in a cell, organ, or patient, e.g., a control or normal cell, organ, or patient, exhibiting, for example, normal traits. For example, the biomarkers of the presently disclosed subject matter may be assayed for levels in a sample from an unaffected individual (UI) or a normal control individual (NC) (both terms are used interchangeably herein). In another embodiment, a "suitable control" or "appropriate control" is a value, level, feature, characteristic, property, and the like, determined prior to performing a therapy (e.g., a PV treatment) on a patient. In yet another embodiment, a transcription rate, mRNA level, translation rate, protein level, biological activity, cellular characteristic or property, genotype, phenotype, and the like, can be determined prior to, during, or after administering a therapy into a cell, organ, or patient. In a further embodiment, a "suitable control" or "appropriate control" is a predefined value, level, feature, characteristic, property, and the like. A "suitable control" can be a profile or pattern of levels of one or more biomarkers of the presently disclosed subject matter that correlates to the presence of an indolent form of PV that is likely to transform to an aggressive form of PV, to which a patient sample can be compared. The patient sample can also be compared to a negative control, i.e., a profile that correlates to not having an indolent form of PV that is likely to transform to an aggressive form of PV.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Methods

The study protocol was approved by the Johns Hopkins University Institutional Review Board and written informed consent was obtained from each patient in accordance with the Helsinki Declaration. Patients were undergoing diagnostic or therapeutic phlebotomy. The diagnosis of PV was based on the Polycythemia Vera Study Group criteria (Wasserman, 1971). Patient accrual was solely predicated on obtaining sufficient peripheral blood CD34+ cells for analysis. Clinical data including cell counts, spleen size, history of thromboembolic events, chemotherapy and splenectomy were extracted from patient medical records at study entry and termination. Splenomegaly was considered present if the spleen was palpable on physical examination and is reported as centimeters (cm) below the left costal margin.

Neutrophil isolation and DNA preparation were performed as described previously (Williams et al., 2007). Peripheral blood CD34+ cells from PV patients were isolated from processed buffy coats (FICOLL-PAQUE®, G5 Healthcare, St. Louis, Mo.) with a purity of greater than 95% and a viability of 98% using immunomagnetic beads (Miltenyi, Auburn, Calif.) according to the manufacturer's instructions, and frozen at −80° C. in 10% DMSO and 90% FBS until studied.

The CD34+ cells were analyzed for CD34, CD38, CD33, CD41 and glycophorin expression using commercially available fluorescent-labeled antibodies. Fluorescence of at least 10,000 cells was measured on a FACS Caliber and analyzed with software (CELLQUEST™ and PAINT-A-GATE™, BD Biosciences, San Jose, Calif.). Similar to published reports of the peripheral blood CD34+ cell immunophenotype in normal individuals and MPD patients, CD34+ cells from both sources were greater than 98% CD38− positive and 85% CD33− positive; CD41 was expressed on less than 3% of CD34+ cells from both sources, while glycophorin was not expressed by either CD34+ cell population. Cell cycle analysis by flow cytometry using propidium iodide revealed that 91% of the PV and 90% of the mobilized normal CD34+ cells were in Go/$G_1$ (data not shown).

JAK2 V617F analysis was performed using an allele-specific, quantitative real-time PCR assay sensitive to 5% of either the wild-type or mutant allele (Stein et al., 2010).

For CD34+ cell isolation and analysis, peripheral blood CD34+ cells from PV patients were isolated from processed buffy coats (FICOLL-PAQUE®, G5 Healthcare, St. Louis, Mo.) with a purity of greater than 95% and a viability of 98% using immunomagnetic beads (Miltenyi, Auburn, Calif.) according to the manufacturer's instructions, and frozen at −80° C. in 10% DMSO and 90% fetal bovine serum until studied. As controls, G-CSF mobilized peripheral blood CD34+ cells from three normal men and three normal women were obtained from commercial sources (AllCell Technologies LLC, Chicago, Ill. and StemCell Technologies Inc, Vancouver, BC).

The CD34+ cells were analyzed for CD34, CD38, CD33, CD41 and glycophorin expression using commercially available fluorescent-labeled antibodies (Becton Dickinson, San Jose Calif.). Fluorescence of at least 10,000 cells was measured on a FACS Caliber and analyzed with software (CELLQUEST™ and PAINT-A-GATE™, BD Biosciences, San Jose, Calif.). Similar to published reports of the peripheral blood CD34+ cell immunophenotype in normal individuals and MPD patients (Barosi et al., 2001; Andreasson et al., 1997), CD34+ cells from both sources were greater than 98% CD38-positive and 85% CD33-positive; CD41 was expressed on less than 3% of CD34+ cells from both sources, while glycophorin was not expressed by either CD34+ cell population. Cell cycle analysis by flow cytometry using propidium iodide revealed that 91% of the PV and 90% of the mobilized normal CD34+ cells were in Go/$G_1$ (data not shown).

Total CD34+ cell RNA was isolated with an added DNAse step according to the manufacturer's instructions RNEASY® (Qiagen, Valencia, Calif.). To confirm sample quality, duplex RT-PCR was employed to assess RNA integrity (Sugita et al., 2001), and the Agilent Bioanalyzer Lab on a Chip (Agilent Technologies, Inc., Santa Clara, Calif.) was used to confirm that all samples had an optimal rRNA ratio (1:2, for 18S and 28S, respectively), and clean run patterns before microarray analysis.

For oligonucleotide microarray analysis, total RNA samples were processed using the Affymetrix two-round RNA amplification protocol (Affymetrix, Santa Clara, Calif.). Briefly, 100 ng of starting total RNA were used to synthesize first strand cDNA using oligonucleotide probes with 24 oligo-dT plus T7 promoter as primer (PROLIGO®, Proligo LLC, Boulder, Colo.), and the SUPERSCRIPT® Choice System (Invitrogen, Carlsbad, Calif.). Following the double stranded cDNA synthesis, the product was purified by Affymetrix sample clean up columns, and unlabeled ribonucleotides were used in a first round of in vitro transcription cRNA amplification (MEGASCRIPT®, Ambion, Austin, Tex.). The following cycle of cDNA synthesis was started with random primers, and the oligo-dT with T7 promoter was again used as primer at the second strand cDNA synthesis step. The ds cDNA product was again column purified. Subsequently, biotinylated anti-sense cRNA was generated through in vitro transcription using a RNA High Yield Transcript Labeling kit (BIOARRAY™, ENZO Life Sciences Inc, Plymouth Meeting, Pa.). 15 ug of the biotinylated labeled cRNA was fragmented at 94° C. for 35 min (100 mM Tris-acetate, pH 8.2, 500 mM KOAc, 150 mM MgOAC), and bug of total fragmented cRNA was hybridized to the Affymetrix human genome array U133A (GENECHIP®) for 16 hr at 45° C. with constant rotation (60 rpm). The Affymetrix Fluidics Station 450 was then used to wash and stain the chips, remove the non-hybridized target and incubate with a streptavidin-phycoerythrin conjugate to stain the biotinylated cRNA. The staining was amplified using goat IgG as blocking reagent and biotinylated goat streptavidin antibody, followed by a second staining step with a streptavidin-phycoerythrin conjugate.

Fluorescence was detected using the Affymetrix GS3000 GeneArray Scanner and image analysis of each GeneChip was done with the GeneChip Operating System software from Affymetrix (GCOS1.1.1), using the standard default settings. For comparison between different chips, global scaling was used, scaling all probe sets to a user-defined target intensity of 150. To assess the QC of the hybridization, chip image, and comparison between chips, the following parameters were studied: the scaling factor, related to the overall intensity of the chip, to confirm the similar signal intensity and staining throughout the samples; background estimation of nonspecific or cross-hybridization; percentage of transcripts that were considered significantly hybridized to the chip (present) by the algorithm; RNA integrity by measurement of the ratio of 3' to 5' regions for the housekeeping gene GAPDH, since its presence in the chip and a ratio close to 1 indicates good integrity of the target sample; spikes (BioB/BioC), to confirm the detection level and sensitivity after hybridization.

To assess quality control between replicates, the percentage of differential calls (up or down regulated) was analyzed between pair-wise comparisons, and scatter plot analyses from the different replicates was also conducted to demonstrate reproducibility amongst the experiments. Consistently, the Pearson's correlation coefficients obtained in these studies were between 0.80 and 0.95 for different comparative analyses, and between 0.97 and 0.99 for all duplicate samples. The differences in gene expression associated with RNA amplification as opposed to the analysis of unamplified RNA were also assessed because of the difficulty in obtaining sufficient CD34+ cell RNA for microarray analysis. The results of this analysis indicated that 72% of the present calls were conserved following amplification.

Using the default algorithms for image analysis provided by Affymetrix, approximately 30%-45% of genes represented in the chips were recorded as present in the RNA samples, indicating good quality data. To achieve gene expression signal intensity estimates with a higher precision and a lower false discovery rate (FDR) in differential gene expression analysis, RMA (Robust Multiarray Analysis) was used to improve the Affymetrix default algorithms. RMA also performs quantile normalization to reduce the obscuring variation between microarrays, which might be introduced during the processes of sample preparation, manufacture, fluorescence labeling, hybridization and scanning. With the expression signals estimated as above, a parametric empirical Bayes statistical modeling method, which uses a hierarchical mixture model to account for differences amongst genes in their average expression levels and measurement fluctuations, was employed for differential gene expression analysis between the PV samples and the normal controls. Based on this method, posterior probabilities were obtained, from which inferences regarding differential expression patterns could be made. Specifically, the standard rule of a posterior probability of >0.5 was taken to assert significance in differential gene expression and minimize the false discovery rate.

For Q-RT-PCR validation of the microarray results, additional CD34+ cell samples were analyzed from a subset of the patients by real-time PCR (Q-RT-PCR) without prior RNA amplification. For the mRNA transcripts, first-strand cDNA synthesis was carried out on RNA extracted from the cells with a Reverse Transcription Reagents kit (TAQ-MAN®, Applied Biosystems, Carlsbad, Calif.) using the oligo d $(T)_{16}$ RT primer following the manufacturer's suggested protocol. To quantitate miR-21 expression, CD34+ cell RNA was isolated using a miRNA Isolation Kit (MIR-VANA™, Applied Biosystems) following the manufacturer's procedure for total RNA isolation. The TAQMAN® MicroRNA Reverse Transcription Kit (Applied Biosystems) was used as directed to generate cDNA. Q-RT-PCR was carried out using the gene expression GEX or microRNA assays (Applied Biosystems) listed in Table 1. Duplicate 20.mu.l reactions were set up using the TAQMAN® Universal PCR Master Mix, No AMPERASE® UNG (2×), and performed on an Applied Biosystems 7500 sequence detection system using the default "standard 7500" PCR conditions (95° C. for 10 minutes followed by 40 cycles of 95° C. for 15 seconds and 60° C. for 1 minute). For each GEX primer/probe set, a standard curve with known relative concentrations of RNA from either a patient or normal control sample was used to calculate reaction efficiency and quantitate the reaction products. GAPDH reactions were run in parallel samples on the same assay plate. All the GEX Q-RT-PCR results were calculated using the "Standard Curve Assay" program of the 7500 SDS system (Applied Biosystems) and normalized to the GAPDH (glyceraldehyde-3-phosphate dehydrogenase) and the data are shown in FIG. 2. For the miR-21 primer/probe set, relative quantitation using the $\Delta\Delta C_T$ calculation method was utilized rather than a standard curve. U6 RNA was the reference RNA.

For supervised analysis, EBarrays analysis was performed for male and female patients separately. The 549 probes that showed a posterior probability greater than 0.5 of differential expression between aggressive and indolent phenotypes in both male and female patients were retained for further analysis. Further analysis of these 549 probes included both genders.

Top-scoring pair analysis (Tan et al., 2005) was run on the 549 probes and the top 30 top-scoring pairs (TSPs) were retained. As some genes had duplicate probes, the R limma package was used, an empirical Bayes test was applied to this data (now both genders), and the highest scoring probe for each gene was retained. The list of TSPs was sorted by the average difference between aggressive and indolent phenotype for that TSP and the six best TSPs were retained. The validation cohort was analyzed using Q-RT-PCR with probes designed to the genes in the retained TSPs. ROC analysis was performed. The AUC for all cases was 0.94, while the AUC excluding AML cases was 0.925. The best point for calls in both cases was setting the call of aggressive phenotype at 5 positive TSP calls, with sensitivity of 0.9 and 0.875 and specificity of 1.0 and 1.0, respectively. The PPV at this threshold was 1.0 in both cases, and the NPV was 0.95 in both cases. A similar approach was used for the supervised analysis of the 19 PV patients and the 6 normal controls.

Gene annotations were developed by collating data from the following data bases: OMIM, Gene, KEGG, AceView, GO Ontology and IPA (Ingenuity Systems, Redwood City, Calif.). The microarray data were deposited in the Gene Expression Omnibus MIAME compliant database (Series number GSE47018) (Edgar et al., 2002).

Example 2

Characteristics of Patients

The clinical features of the 19 patients are listed in Tables 2 and 3. Median age and disease duration were not different between the men and women. All patients expressed JAK2 V617F and the median neutrophil allele burdens in men (94%) and women (100%) were also similar; in 13, the median CD34+ cell JAK2 V617F allele burden was 82% (range 50-100%, data not shown), indicating clonal dominance at both the progenitor cell and neutrophil levels (Moliterno et al., 2008; Stein et al., 2011). The two groups differed significantly (p=0.016) only with respect to their platelet counts, with men having a lower median platelet count ($421,000 \times 10^3/\mu L$) than the women ($948,000 \times 10^3/\mu L$), which may reflect a gender-related difference (Segal and Moliterno, 2006).

Example 3

Gene Expression in Men and Women Patients

Given the differences in disease behavior between men and women PV patients, it was hypothesized that there could be gender-specific differences in gene expression independent of JAK2 V617F expression. Therefore, patient gene expression was compared with controls of the corresponding gender and it was found that there was differential gene expression in women patients compared to men, with 251 genes differentially regulated (126 up and 109 down) in women (Table 4) compared to 535 genes (486 up and 85 down) in the men (Table 5). Despite a smaller number of deregulated genes, KEGG analysis revealed that over three times as many molecular pathways were activated in the women patients, including one, the pentose phosphate pathway, which was not activated in any male patient (FIGS. 3A-3B).

Example 4

Identification of Concordantly Deregulated Genes by the Men and Women Patients

Subtracting genes whose expression was gender-specific left 102 genes (68 up regulated and 34 down regulated), whose differential expression was concordant in both men and women (FIG. 4), and could represent a core set of genes involved in the pathogenesis of PV. Gene expression was validated for 8 of the 102 genes by Q-RT-PCR (Table 1) using CD34+ cells from a subset of the patients, and there was good correlation between the observed microarray gene expression changes and the Q-RT-PCR measurements (FIG. 2).

Example 5

Unsupervised Hierarchical Clustering Using the 102 Concordantly Deregulated Genes Unsupervised hierarchical clustering was employed to determine if the 102 core gene set segregated the PV patients from the normal controls. As shown in FIG. 5, the PV patients clustered into two distinct groups, one of which clustered independently from the controls and demonstrated heterogeneity with respect to core gene expression, while the other was more homogeneous and overlapped with the controls. Table 6 lists the clinical features of the two patient groups, which did not differ with respect to age, JAK2 V617F neutrophil allele burden, leukocyte and platelet counts or clonal dominance. However, they did differ statistically with respect to disease duration, hemoglobin level, thromboembolic events, palpable splenomegaly, splenectomy, chemotherapy exposure, leukemic transformation and survival, indicating that disease behavior was aggressive in one group and indolent in the other.

To validate the unsupervised hierarchical clustering, a supervised approach based on top-scoring pairs was used (Tan et al., 2005). A 30 gene set was identified, none of which were in the 102 core gene set, which segregated the patients into the same aggressive and indolent clinical groups with 100% accuracy, validating the unsupervised hierarchical clustering results (FIG. 6).

Example 6

Annotation of the 102 Concordantly Deregulated Genes

Annotation of the 102 genes is provided in Table 7. Of note, there was differential regulation of the stem cell maintenance genes HES1, HOXA9, PTGER4 and NR4A2, the master transcription factor SOX4 and the oncogenes SETBP1 and miR-21. Eight antiapoptotic genes, LEPR, CKAP4, RRAS2, TIMP1, IER3, THSB1, POSTN, and LGALS3, were up regulated while five proapoptotic genes, EIF5A, EMP1, ZFP36L2, LUC7L3, HLF and HOPX and three tumor suppressor genes, SSBP2, TLE4 and KLF6 were down regulated.

Importantly, consistent with the propensity for myelofibrosis in PV, there was up regulation of 16 extracellular matrix genes, including six collagen genes (COL1A1, COL1A2, COL3A1, COL4A1, COL4A2 and COL6A3), and the matricellular genes SPARC, POSTN, TIMP1, THBS1, HSPE, FN1, S1OOA9, EFEMP1, LGALS3, and LTBP3, essentially comprising a "stromal gene signature". Furthermore, given the inflammatory milieu that characterizes the MPD (Slezak et al., 2009; Verstovsek et al., 2010), there was increased expression of 10 cytokine and inflammatory mediator genes, CCL3 (MIP1-α), CCL5 (RANTES), CXCL5, SERPINE1 (PAI-1), S100A9, LCN2, PTX3, PF4V1, FCN1 and CFD, similarly comprising a "cytokine gene signature".

Given the striking dysregulation of extracellular matrix protein genes, unsupervised hierarchical clustering was used to determine whether stromal gene expression segregated with a particular clinical phenotype. As shown in FIG. 8, the stromal gene set also separated the aggressive and indolent groups, with the latter showing the same heterogeneity seen using the 102 core gene classifier (FIG. 5).

Example 7

Gene Expression in the Aggressive and Indolent Patient Groups

Analysis of differential gene expression in the aggressive and indolent groups reinforced the importance of JAK2 V617F-independent expression of disease phenotype-modifying genes. For example, although there was no difference in the JAK2 V617F allelic burdens between the two groups (Table 6), gene expression differed markedly with 707 genes differently regulated (248 up and 459 down regulated) in the indolent group as compared to the controls (Table 8), while only 149 genes were differentially regulated (68 up and 81 down regulated) in the aggressive group (Table 9). Furthermore, the two groups also differed markedly with respect to expression of the 102 core genes (Tables 10 and 11). KEGG analysis (FIGS. 9A-9B) emphasized the predominance of deregulated molecular pathways involving DNA and RNA metabolism and function in both groups but histone gene deregulation predominated in the aggressive group.

Example 8

Expression of PV Core Genes in the Chronic and Blast Crisis Phases of Chronic Myelogenous Leukemia Finally, to determine if the gene expression changes in the 102 core genes were unique to PV or a nonspecific consequence of constitutive tyrosine kinase activation, the expression of these genes was examined in the chronic and blast crisis phases of chronic myelogenous leukemia (CML) (Bruns et al., 2009; Diaz-Blanco et al., 2007; Graham et al., 2007; Nowicki et al., 2003; Zheng et al., 2006; Yamamoto-Sugitani et al., 2011; Nakahara et al., 2010), a disease characterized by constitutive tyrosine kinase signaling in which STAT5 phosphorylation has a central role in disease pathogenesis (Horita et al., 2000; Hantschel et al., 2012). As shown in Table 12, there was concordant up regulation of 16 PV core genes in chronic phase CML, with concordant down regulation of 9. This pattern was reversed in CML blast crisis, with up regulation of 6 down regulated PV core genes, including the oncogene SETBP1, and down regulation of 11 up regulated PV core genes. Listed are 55 genes from the 102 core PV gene set showing their regulation in chronic phase and blast phase CML (Bruns et al., 2009; Diaz-Blanco et al., 2007; Graham et al., 2007; Nowicki et al., 2003; Zheng et al., 2006; Yamamoto-Sugitani et al., 2011; Nakahara et al., 2010). White background indicates concordant regulation in P and grey background indicates discordant regulation in PV.

Example 9

Discussion of Gene Expression Profiling in PV

PV has been scrutinized scientifically for decades but its molecular basis remains an enigma. In contrast to CML with its characteristic t(9; 22)(q34; q11) translocation and resulting BCR-ABL fusion tyrosine kinase gene, no genetic defect or protein marker specific for PV has yet been identified despite the use of high resolution techniques such as oligonucleotide array comparative genomic hybridization and high resolution single nucleotide polymorphism array karyotyping.

Central to the success of the strategy disclosed herein was the choice of an informative target cell population, a control cell population matched with respect to origin and phenotype, and avoidance of confounding effects on gene expression. Since PV is a stem cell disorder, CD34+ cells were studied. Because myelofibrosis is part of its natural history, to ensure inclusive patient representation, as well as easy access for the repeated harvests necessary to obtain sufficient cells for analysis, peripheral blood CD34+ cells were chosen rather than their marrow counterparts. At the same time, without being bound to any one particular theory, there is no reason to believe that there would be distinctly different gene expression patterns in blood and marrow CD34+ cells since this has not been the case for either acute myelogenous leukemia or CML.

The approach used herein was facilitated by the characteristic constitutive mobilization of CD34+ cells in PV, which represents an endogenous purification step with respect to residual nonclonal marrow CD34+ cells. Although the presence of circulating nonclonal CD34+ cells is still a potential confounder, clonal dominance is another feature of PV that results in suppression of polyclonal hematopoiesis and serves as an additional endogenous purification step.

As demonstrated by the quantitative JAK2 V617F neutrophil allelic burden in all 19 patients, and in CD34+ cells in thirteen, clonal dominance was present in all patients, reducing or eliminating contamination of patient CD34+ cells by normal CD34+ cells. Additionally, since only 6 patients (26%) were receiving chemotherapy at the time of study and five of these were taking hydroxyurea, which only affects dividing cells, it is unlikely that drug effects were a significant confounder with respect to CD34+ cell gene expression.

G-CSF mobilized peripheral blood CD34+ cells from normal subjects as the control study population were chosen because they have not been found to differ from their steady state peripheral blood counterparts with respect to cell cycle activity, immunophenotype and gene expression, while differing significantly from marrow CD34+ cells with regards to these and gene expression, as well. Both G-CSF mobilized normal CD34+ cells and PV peripheral blood CD34+ cells were similar with respect to immunophenotype and cell cycle activity, with both largely in $G_0/G_1$ in contrast to marrow CD34+ cells, which are actively cycling. Furthermore, and most importantly, G-CSF exposure was unlikely to be a confounder with respect to CD34+ cell gene expression because these cells do not express G-CSF receptors, PV neutrophils are also already constitutively activated by virtue of JAK2 V617F expression, and plasma G-CSF is also increased in this disorder.

Given the number of CD34+ cells required to obtain sufficient mRNA for analysis, no attempt was made to fractionate patient or control peripheral blood CD34+ cells on the basis of immunophenotype before microarray analysis. This has clinical relevance since the data herein establishes that unfractionated patient peripheral blood CD34+ cells can serve as an informative cell population for analyzing clinical risk assessment at the molecular level.

Because of the differences in disease frequency, disease manifestations, disease complications and JAK2 V617F expression between men and women PV patients, it was hypothesized that gender might also be a confounder with respect to gene expression and analyzed each patient individually with a gender-specific control. As shown in FIG. 4, sex was, indeed, an important confounder; women patients differentially up or down regulated only 251 genes compared to 535 genes for the men. The biological basis for this difference is unknown but it fits with the observed suppression of the myeloproliferative clone during pregnancy, and thus could have an epigenetic, hormonal or immunologic basis.

The importance of these genes in the disease process was substantiated by the fact that they could be used to segregate a disorder perceived to be monolithic into two groups with distinctly different clinical features and complication rates that were independent of sex as well as the JAK2 V617F allelic burden (Table 2). Although the study population was small, the aggressive group fits the clinical phenotype of the 10-15% of PV patients who develop the post-polycythemia myelofibrosis syndrome, and these are the same patients who are at risk of the spontaneous evolution of a JAK2 V617F-positive acute leukemia. In this regard, it is of interest that with gene expression profiling it was possible to identify those CML patients in the chronic phase of the disease who were at risk of early transformation, or who had already transformed at the molecular level despite a chronic phase clinical phenotype.

In contrast to primary myelofibrosis, for which there are well-validated prognostic factors for risk stratification at diagnosis and during disease progression, to date no such prognostic factors have been identified under either circumstance for PV and, as the data herein indicate, neither the JAK2 V617F allelic burden nor clonal dominance per se are useful in this regard. However, the data suggest that differential gene expression could be useful. Since gene expression appeared largely fixed from disease diagnosis for the indolent group, it is possible that acquisition of new genetic lesions in the aggressive group, whether spontaneous or treatment-related was responsible for disease transformation. The latter appeared to be the case in one indolent group patient, who developed therapy-related acute leukemia associated with the acquisition of a 5q-abnormality while taking hydroxyurea. Thus, the presently disclosed 30 gene classifier can be used to identify during the course of the disease, those patients who might benefit from early therapeutic intervention with pegylated interferon or allogeneic stem cell transplantation, while sparing other patients the side effects of unnecessary treatment.

Gene expression was examined in circulating PV CD34+ cells after removing gender as a potential confounder. This led to the identification of 102 genes whose importance in the disease process was substantiated by the fact that they could be used to segregate the PV patients into two groups with distinctly different clinical features independent of the JAK2 V617F allelic burden, leukocyte and platelet counts. The aggressive group fit the phenotype of PV patients who develop the post-polycythemia myelofibrosis syndrome (Silverstein, 1974; Passamonti et al., 2008), and are at risk of spontaneous leukemic transformation (Beer et al., 2009). In this regard, during chronic phase CML, it was possible using gene expression to identify patients who were at risk of early transformation, or who had already transformed at the molecular level (Radich et al., 2006). Thus, given the low frequency of cytogenetic abnormalities in PV before disease transformation (Gangat et al., 2008; Stein et al., 2011), gene expression profiling could have prognostic relevance in PV.

With respect to disease specificity, it was informative to examine the expression of the 102 PV core genes in chronic and blast phase CML CD34+ cells (Bruns et al., 2009; Diaz-Blanco et al., 2007; Graham et al., 2007; Nowicki et al., 2003; Zheng et al., 2006; Yamamoto-Sugitani et al., 2011; Nakahara et al., 2010). Fifty-five of the 102 PV core genes were dysregulated in CML, with concordant dysregulation of 25 in chronic phase CML.

However, with blast crisis, there was a reversal of the up or down regulation of 17 PV core genes, providing a window into the genetic mechanisms that govern the clinical behavior of these two disorders and the potential relevance of specific genes or pathways in maintaining normal differentiation or promoting leukemic transformation. Interestingly, the gene expression profile of the aggressive group, as in CML blast crisis patients, was closest to that of normal CD34+ cells (Radich et al., 2006).

The mechanisms driving differential gene deregulation in PV are unknown but rather than behaving like canaries in a mine shaft, gene expression appeared to be cell autonomous, a contention supported by the comparison with CML CD34+ cell gene expression (Table 12). The extent to which JAK2 V617F contributed to gene expression remains undefined but no significant differences in gene expression were observed in a study of PV CD34+ marrow cells from JAK2 V617F-positive and negative patients (Berkofsky-Fessler). In this study, the JAK2 V617F allelic burdens were not different between the aggressive and indolent groups even though their gene expression patterns differed both globally (Tables 8 and 9), as well as with respect to the 102 core gene set (Tables 10 and 11), supporting an important role for other signaling pathways in PV pathogenesis.

The 102 core gene list provides ample evidence for this contention and for synergistic interactions amongst these pathways as well. For example, HES1 up regulation suggests activation of either the Notch or Hedgehog pathways and couples these pathways with JAK2-STAT3 signaling, and NF-κB and HIF-1α activation (Kamakura et al., 2004; Wall et al., 2009; Lee et al., 2009; Espinosa et al., 2010). LEPR, LGALS3, LTBP3 and THBS1 activate TGF-β1 (Wang et al., 2009; Mackinnon et al., 2012; Koli et al., 2008; Daniel et al., 2004), whose target genes include SOX4, SPARC, SERPINE1 (PAI-1) and miR-21 (Scharer et al., 2009; Shibata and Ishiyama, 2013; Baricos et al., 1999; Patel and Noureddine, 2012). SOX4 is also associated with activation of the Wnt, Notch and Hedgehog pathways (Scharer et al., 2009) and up regulation of HOXA9 (Scharer et al., 2009; Ikushima et al., 2009); which in turn enhances the transcriptional activity of SOX4 and STAT5 (Huang et al., 2012). LGALS3 also enhances Wnt pathway activity (Song et al., 2009); TIMP1 and SOX4 activate the PI3-K/AKT pathway (Scharer et al., 2009; Ridnour et al., 2012), while RRAS2 activates the RAF/MAPK/ERK and PI-3K/AKT pathways (Rosario et al., 2001; Rosario et al., 1999).

Other striking abnormalities were the up regulation of 16 genes encoding important matricellular proteins, essentially comprising a stromal signature similar to that described in lymphomas and breast cancer (Lenz et al., 2008; Bergamaschi et al., 2008), and 10 inflammatory cytokine genes, comprising a cytokine signature. The stromal signature identified genes probably involved in PV myelofibrosis (Tripodo et al., 2012) as well as in CML myelofibrosis (Yamamoto-Sugitani et al., 2011), and confirms the importance of malignant CD34+ cells in marrow stem cell niche maintenance and remodeling (Schepers et al., 2013). The cytokine signature not only adds new members to those previously identified as involved in PV (Slezak et al., 2009; Verstovsek et al., 2010), but also identifies genes linking inflammation with coagulation such as the complement-activating genes, CFD, FCN1 and PTX3. In addition, the data suggest a potential prothrombotic role for PF4V1, SERPINE1 (PAI-1), HSPE and THSB1, which antagonizes both nitric oxide (Isenberg et al., 2005) and ADAMTS13 (Bonnefoy and Hoylaerts, 2008), and the prothrombinase, FGL2 (Yuwaraj et al., 2001), a gene not previously identified as up regulated in PV.

The CD34+ cell population is diverse, and, although for technical reasons the cells could not be further fractionated, the study disclosed herein confirms that analysis of unfractionated circulating CD34+ cells has clinical utility (Radich et al., 2006). Gene expression, of course, only represents one component of the complex process from gene transcription to protein product and is subject to epigenetic as well as genetic influences not controlled for in this study. Nevertheless, the data provide new insights into the molecular abnormalities of PV, establish a molecular basis for disease heterogeneity, identify genes and pathways for targeted therapy outside the canonical JAK2 signaling pathway, as well as previously unrecognized genes potentially involved in promoting myelofibrosis, inflammation and thrombosis.

This study has identified a number of important genes that may be worthy of consideration for targeted therapy. They include HES1, a transcriptional repressor that negatively regulates the tumor suppressor PTEN, SPARC a multifunctional, antiadhesive matricellular protein that regulates extracellular matrix organization and up regulates osteopontin, a protein responsible for stem cell niche maintenance, and LGALS3 and TIMP1, the cognate ligand for CD36, which promotes platelet aggregation, antagonizes nitric oxide and activates TGF-β. In addition to TIMP1, the up regulation of a number of previously recognized coagulation genes that may contribute to the thrombotic diathesis that complicates PV were also identified. These include the fibrinolysis inhibitor PAI-1 and the prothrombinase FGL2, as well as the gene PTX3.

Hematopoietic stem cells do not require JAK2 for either survival or proliferation and no difference was found between the size of the hematopoietic stem cell compartment between PV, ET and normal controls in vivo or their behavior in vitro. This is not surprising since JAK2 expression and activation in a JAK2-naive cell line did not appear to alter global gene transcript above that observed with unactivated JAK2 expression. Furthermore, no significant changes in gene expression were observed in a study of PV CD34+ marrow cells from JAK2 V617F-positive and negative patients, nor was a significant difference observed when the gene expression in PV CD34+ marrow cells was compared with that following overexpression of wild type JAK2 in normal CD34+ cells. Similar observations have been made with CD34+ marrow cells from JAK2 V617F-positive and negative ET patients. At the same time, it is well documented that in the nucleus, JAK2 directly modifies gene transcription and enhances mitotic recombination and promotes genetic instability by altering histone phosphorylation and methylation and damaging DNA by generating reactive oxygen species, which may be its most important contributions to PV stem cell behavior. In addition to the influence of JAK2 V617F, our data indicate activation of a number of other signal transduction pathways. For example, HES1 expression is dependent on either the Notch or Hedgehog pathways and HES1 itself activates STAT3 through either SRC or JAK2 signaling.

A striking abnormality was up regulation of genes encoding matricellular proteins and inflammatory cytokines. Whether such signals are the consequence of constitutive JAK2 activation involving stem cell cytokine receptors is unclear but with respect to the genes whose expression is normally influenced by JAK2, only two genes, SPARC and PTX, the latter a gene normally down regulated by JAK2, were up regulated in the PV CD34+ cells, suggesting that gene expression in these cells was driven by signal pathways primarily unrelated to JAK2. This contention is supported by the upregulation of genes involved in Notch or Hh signaling such as HES1, genes involved in NFK-β signaling such as NR4A2, IER3, and RRAS2, genes involved in Wnt signaling such as LGALS3, GAS2, SPARC and S100A9, and genes involved in TGF-β signaling such as LGALS3, TIMP1, THSB1 and LEPR.

With respect to the specificity of gene expression associated with JAK2 signaling in PV CD34+ cells, it was informative to compare their gene expression profiles with those of chronic phase CML CD34+ cells, since constitutive tyrosine kinase signaling involving STAT5 is a central feature of both disorders and both share a similar clinical phenotype with respect to leukocytosis, thrombocytosis, extramedullary hematopoiesis, myelofibrosis and transformation to acute leukemia, although at differing frequencies, possibly because BCR-ABL signaling is ectopic while signaling by JAK2 V617F occurs through physiologic pathways.

As shown in Table 12, there was concordant dysregulation of 28 of the PV 105 core gene set in chronic phase CML, which is compatible with the observation that STAT5 is activated by BCR-ABL signaling. By contrast, however, in CML blast crisis, there was a reversal in the up or down regulation of 17 PV core set genes, providing a window into the genetic mechanisms that govern the different clinical courses of these two disorders and the potential relevance of specific genes or pathways in maintaining normal differentiation or promoting leukemic transformation. In this regard, it is interesting to note that the gene expression profile of both the aggressive patient group and those CML patients who developed blast crisis was not only different from the indolent group or chronic phase CML patients respectively, but also closer to that of normal CD34+ cells.

This study provides a snap shot of gene expression in a heterogenous stem cell population of a chronic disorder characterized by phenotypic variability over time. The data provide insight into the molecular abnormalities of PV, identify new candidate genes for targeted therapy outside the canonical JAK2 signaling pathway and as well as previously unrecognized genes that may be involved in promoting thrombosis in PV patients.

The molecular behavior of PV CD34+ cells has been exposed in this study. The data indicate that PV can no longer be considered a monolithic disorder with bone marrow failure as an inevitable event, that patients with an aggressive form of the disorder can be identified early in the course of their disease and that, as has been previously argued, women PV patients cannot be treated as small men, and this should be true both in clinical trials and in pregnancy. Whether controlling for sex as a potential confounder is applicable to gene expression analysis in other hematologic malignancies is worthy of evaluation given the remarkable insights described here.

Recent studies have suggested that in PV, as well as in CML, the disease may arise in a later stage progenitor cell, and, in particular, one with a predilection for erythroid differentiation. While the data herein do not directly speak to this contention, in keeping with it, six globin genes were upregulated in PV CD34+ cells. However, it is noteworthy that in chronic phase CML there was up regulation of the $\alpha_2$, $\beta$, $\delta$ and $\gamma_2$ globin genes as well as an increase in the MEP population despite the fact that CML is phenotypically myeloid-restricted, while PV is not. Therefore, without wishing to be bound to any one particular theory, it is believed that as opposed to being associated with CD34+ maturation status, these gene expression changes may merely reflect nonspecific up regulation of gene expression by JAK2 activation in both disorders, or aberrant activation of multiple genetic pathways in a transformed pluripotent stem cell as can be seen in biphenotypic leukemias. The up regulation of both embryonic and fetal globin genes supports this latter contention, as does the observation that in vivo, the balance between erythroid and myeloid progenitor cell pools in PV was not different from normal.

Example 10

10 Gene Screening Panel for Predicting Aggressive Forms of PV

Since PV is a stem cell disorder, PV CD34+ cells were examined for constructing a gene
screening panel for PV. Specifically, to avoid repeated marrow aspirations to collect these cells, circulating CD34+ cells were studied. This was also technically advantageous because an increase in the number of circulating CD34+ cells is a feature of PV, and because of clonal dominance, which is also a feature of PV, the bulk of the circulating CD34+ cells were likely to be from the malignant clone (Adamson et al., 1976). Mobilized normal circulating CD34+ cells, which are immunophenotypically similar and have the same cell cycle status, were used as the control cell population, and, because female PV patients have different clinical features than male patients (Stein et al., 2010; Stein et al., 2011; Videbaek, 1950), each patient was compared with a gender-specific control. Using oligonucleotide microarray technology, it was found that women differentially regulated 251 genes and men 535 genes, but both concordantly differentially regulated 102 genes (FIG. 4). Using this 102 core gene set and unsupervised hierarchical clustering, PV patients were able to be segregated into two groups (FIG. 5), with one group having a more aggressive disease with lower hemoglobin levels, more thromboembolic events, a higher frequency of splenomegaly, larger spleens, a greater frequency of chemotherapy and splenectomy, more leukemic transformation and a higher mortality rate, despite having a JAK2 V617F allelic burden similar to the other group (Table 6). Using a supervised approach, top scoring pairs, a 29 gene profile was defined, which also segregated the PV patients with aggressive disease from those with a more indolent phenotype with 100% accuracy (FIG. 6).

Based on these 19 genes, a smaller gene panel was derived consisting of 10 genes (PCNA, IF130, TSN, CTSA, SMC4, CDKN1A, CTTN, SON, TIA1 and MYL9) for establishing the probability that a PV patient has an aggressive or indolent form of the disease. Using qRT-PCR and scoring 1 for true and 0 for false. If PCNA>IF30; TSN>CTSA; SMC4>CDKN1A; PCNA>CTTN; SON>CTTN; and TIA1>MYL9, the probability that the disease is aggressive is the total score/6. After developing absolute copy number standard curves for the 10 genes (FIG. 10), the behavior of this screen on seven patients was verified in the initial training set and its predictability examined in a blinded fashion using CD34+ cell RNA from 30 additional PV patients as described herein below.

For biomarker association with clinical measures, patient probability scores were correlated with the presence or absence of clinical complications as defined from the training set aggressive PV group and calculated as a clinical score (0-6). These clinical complications were: anemia, palpable splenomegaly or history of splenectomy, spleen size, major vessel thrombosis, chemotherapy or immunomodulatory therapy and leukemic transformation. Of the 30 patients, 8 had clinical features compatible with the aggressive form of PV with a median clinical score of 3.0 (range, 2-4) and a median probability score of 5/6 (range, 5-6) using the 10 gene panel. In these 8 patients, each of the clinical complications occurred at a significantly higher frequency than in the indolent group. Of the 22 patients who did not have an aggressive clinical phenotype, the median clinical score was 1 (range 0-3) and the median probability score was 3/6 (range 0-4) (Table 13). The difference in clinical scores between the two groups was statistically significant ($p<0.001$), and the probability score was also significantly different between the groups at $p<0.001$ with a ROC curve with an AUC of 0.94 (FIG. 11A). There was good correlation between the probability score and the clinical score in this group of patients ($p=0.002$; FIG. 11B). Median disease duration was 15.5 years (range, 9-39) in the aggressive group and 7.0 years (range, 1-27; $p=0.011$) in the indolent group ($p=0.003$), while the median JAK2 V617F allelic burden was not different in the aggressive group compared to the indolent group (94% vs 81%), though 5 of the indolent group, but none of the aggressive group, had allele burdens of 50% or less. In 7 patients, it was possible to obtain repeat measurements over a period of 3-5 years and in 5, the probability score remained constant at 4/6 or less with similar JAK2 V617F allelic burdens and clinical scores (FIG. 12A). In one patient with a probability score of 1-2/6, the probability score increased to 5/6 in advance of AML transformation in one (FIG. 12B).

Table 14 discloses the genes and context sequences (probe sequences; Applied Biosystems primer/probe kits) comprising the 10 gene screening panel for the presently disclosed methods. Table 15 shows representative NCBI Accession numbers for each gene and Table 16 discloses the probes (Life Technologies, Carlsbad, Calif.) used to detect each gene.

After cloning the appropriate probes and developing absolute copy number standard Ct curves for the 10 genes, the behavior of this screen on PV patients in the training set was verified. The predictability of this screen was examined using CD34+ cell RNA from a test set of 23 PV patients (Tables 18 and 19). Patient probability scores were correlated with the presence or absence of clinical features defined by the training set aggressive PV group and calculated as a clinical score. Of the 23 patients, 7 had clinical features compatible with the aggressive form of PV with a median clinical score of 3.0 (range, 1-6) and a median probability score of 6/6 (range, 3-6), with one patient having a score of 3/6. Of the 16 patients who did not have an aggressive clinical phenotype, the median clinical score was 0 (range 0-1) and the median probability score was 3/6 (range 1-4). The difference in clinical scores between the two groups was statistically significant (p<0.001) and the probability score was also significantly different between the groups at p=0.001. Median disease duration was 13.0 years (range, 9-39) in the aggressive group and 6.0 years (range, 1-17) in the indolent group (p=0.003), while the median JAK2 V617F allelic burden was greater in the aggressive group (95% vs 82.5%; p=0.04) with 5 of the indolent group, but none of the aggressive group, having allele burdens of 50% or less. In 2 patients, it was possible to obtain repeat measurements over a period of 3-5 years and in both the probability score remained constant at 4/6 with similar Jak2 V617F allelic burdens and clinical scores. In one patient with a probability score of 3/6, the score increased to 6/6 in advance of AML transformation. ROC (Receiver Operating Characteristic) analysis revealed that the AUC for all cases was 0.94, while the AUC excluding AML cases was 0.925. The best point for calls in both cases was setting the call of aggressive phenotype at 5 positive TSP calls, with sensitivity of 0.9 and 0.875 and specificity of 1.0 and 1.0, respectively. The PPV at this threshold was 1.0 in both cases, and the NPV was 0.95 in both cases. (AUC=area under the curve; FN=falsely negative; FP=falsely positive; TP=total positives; TN=total negatives).

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. A ROC curve provides the sensitivity of a test as a function of 1-specificity. The greater the area under the ROC curve, the more powerful the predictive value of the test. Positive predictive value is the percentage of people who test positive that are actually positive. Negative predictive value is the percentage of people who test negative that are actually negative.

Relevant equations are defined below:

Sensitivity=$TP/(TP+FN)$

Specificity=$TN/(TN+FP)$ $PPV$(positive predictive value)=$TP/(TP+FP)$ $NPV$(negative predictive value)=$TN/(TN+FN)$ The positive predictive value is often reported as it gives the probability that a patient who tests positive is truly positive for a phenotype, and therefore is an indication of how much the test can be trusted clinically to reflect the phenotype. The sensitivity gives the probability that a patient who is positive actually tests positive.

In summary, a molecular method for risk stratification in PV that reflects clinical phenotype but also anticipates disease transformation has been identified. The presently disclosed subject matter provides a clinical assay that uses gene expression (Table 14) and a specific algorithm (Table 17) to identify those PV patients most likely to benefit from early institution of definitive therapy.

Example 11

Embodiment of a 10 Gene Panel Assay

The starting tissue can be either peripheral blood collected in standard EDTA vacutainer tubes or buffy coat cells isolated from a unit of whole blood.

For CD34+ cell isolation, peripheral blood mononuclear cells (PBMCs) are isolated from fresh samples by FICOLL-PAQUE® (GE Healthcare Cat. No. 17-1440-03) density gradient centrifugation. CD34+ cells are isolated from the PBMCs using the Miltenyi Biotech CD34 Microbead Kit (Cat. No. 130-097-047) following the manufacturer's instructions. In an embodiment, the required amount of CD34+ cells is approximately 1-4.times.10.sup.6.

For optional CD34+ cell storage, purified CD34+ cells can be resuspended in freezing media (10% DMSO (Sigma Cat. No. D2650) 90% Fetal Bovine Serum (Gibco Cat. No. 26140)) and stored frozen at −80° C. using a slow cooling freezing unit (Thermo Scientific Cat. No. 5100-0001). Cells can also be transferred to liquid nitrogen for long term storage. Before RNA isolation, the cells are washed in Phosphate Buffered Saline pH 7.4 (Gibco Cat No. 10010-023) to remove all media.

For RNA isolation, RNA is extracted using the Qiagen RNEASY® mini kit (Cat. No. 74104) with the QIA shredder (Cat. No. 79654) and on-column DNase treatment (Cat. No. 79254) following the manufacturer's instructions. Beta Actin levels (ACTB endogenous control; Applied Biosystems, Cat. No. 4333762F) for each sample are measured to determine if the concentration and quality was acceptable for further analysis. This assay is based upon a 10 gene signature and an algorithm (Table 17) which stratifies PV patients into indolent and aggressive forms of the disease. A qRT-PCR probability score of 5 or 6 indicates an aggressive form of PV. Each of the six described ratios must always be >2 to be scored as positive. Scores of 5/6 or 6/6 are considered indicative of an aggressive PV phenotype based on the supervised analysis of our initial gene expressing profiling results using top scoring pairs. Transcript expression levels are measured (in absolute copy numbers). The assay can be performed with a plurality of samples using a high throughput qRT-PCR platform.

Because this assay compares different genes within a single patient sample, absolute quantitation calculations are performed rather than compare relative expression levels. Therefore, plasmids containing either full length or partial cDNA of the targeted region for each gene are cloned and used to generate standard curves (FIG. 10). Once optimized, three standard dilutions can be chosen to use in the assay based upon the observed expression range of each gene. Copy numbers are calculated based on the known size and concentration of each plasmid. In addition to the standard curves and no template control, at least one patient sample with a previously determined qRT-PCR probability score is included in each run as a quality control.

Intra-assay precision is assessed by running all samples in duplicate. Replicate Ct values with standard deviations of greater than 0.5 are re-evaluated. Inter-assay precision is assessed by performing replicate assays on different days with fresh template cDNA from the same RNA sample of separate patients. In an example, the applied algorithm on samples from 8 patients generated the same call, either >4/6 or <5/6. In another example, four sets of patient samples using RNA extracted from CD34+ samples isolated from separate blood draws within the same twelve month period were run with no reported disease progression. Again, in each case there was no difference in the stratification of the patients using the methods of the presently disclosed subject matter.

In an example, the clinical sensitivity of the assay using 5-6/6 as indicative of an aggressive phenotype was 0.9. The clinical specificity of the assay using 5-6/6 as indicative of an aggressive phenotype was 1.0. The PPV at this threshold was 1.0 and the NPV was 0.95.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Adamson J W, Fialkow P J, Murphy S, Prchal J F, Steinmann L. Polycythemia vera: stem-cell and probable clonal origin of the disease. N. Engl. J. Med. 1976; 295:913-916.

Anand S, Stedham F, Gudgin E et al. Increased basal intracellular signaling patterns do not correlate with JAK2 genotype in human myeloproliferative neoplasms. Blood 2011; 118(6):1610-1621.

Andreasson B, Swolin B, Kutti J. Increase of CD34 positive cells in polycythaemia vera. Eur. J. Haematol. 1997; 59(3):171-176.

Barbui T, Barosi G, Birgegard G et al. Philadelphia-negative classical myeloproliferative neoplasms:critical concepts and management recommendations from European LeukemiaNet. J. Clin. Oncol. 2011; 29:761-770.

Baricos W H, Cortez S L, Deboisblanc M, Xin S. Transforming growth factor-beta is a potent inhibitor of extracellular matrix degradation by cultured human mesangial cells. J. Am. Soc. Nephrol. 1999; 10(4):790-795.

Barosi G, Viarengo G, Pecci A et al. Diagnostic and clinical relevance of the number of circulating CD34+ cells in myelofibrosis and myeloid metaplasia. Blood 2001; 98(12):3249-3255.

Beer P A, Delhommeau F, Le Couedic J P et al. Two routes to leukemic transformation following a JAK2 mutation-positive myeloproliferative neoplasm. Blood 2009; 115:2891-2900.

Bergamaschi A, Tagliabue E, Sorlie T et al. Extracellular matrix signature identifies breast cancer subgroups with different clinical outcome. J. Pathol. 2008; 214(3):357-367.

Berk P D, Goldberg J D, Silverstein M N et al. Increased incidence of acute leukemia in polycythemia vera associated with chlorambucil therapy. N. Engl. J. Med. 1981; 304:441-447.

Berkofsky-Fessler W, Buzzai M, Kim M K et al. Transcriptional profiling of polycythemia vera identifies gene expression patterns both dependent and independent from the action of JAK2V617F. Clin. Cancer Res. 2010; 16(17):4339-4352.

Bonnefoy A, Hoylaerts M F. Thrombospondin-1 in von Willebrand factor function. Curr Drug Targets 2008; 9(10):822-832.

Bruns I, Czibere A, Fischer J C et al. The hematopoietic stem cell in chronic phase CML is characterized by a transcriptional profile resembling normal myeloid progenitor cells and reflecting loss of quiescence. Leukemia 2009; 23(5):892-899.

Catani L, Zini R, Sollazzo D et al. Molecular profile of CD34+ stem/progenitor cells according to JAK2V617F mutation status in essential thrombocythemia. Leukemia 2009; 23(5):997-1000.

Daniel C, Wiede J, Krutzsch H C et al. Thrombospondin-1 is a major activator of TGF-beta in fibrotic renal disease in the rat in vivo. Kidney Int 2004; 65(2):459-468.

Diaz-Blanco E, Bruns I, Neumann F et al. Molecular signature of CD34(+) hematopoietic stem and progenitor cells of patients with CML in chronic phase. Leukemia 2007; 21(3):494-504.

Edgar R, Domrachev M, Lash A E. Gene Expression Omnibus: NCBI gene expression and hybridization array data repository. Nucleic Acids Res. 2002; 30(1):207-210.

Espinosa L, Cathelin S, D'Altri T et al. The Notch/Hes1 pathway sustains NF-kappaB activation through CYLD repression in T cell leukemia. Cancer Cell 2010; 18(3):268-281.

Gaidano G, Pastore C, Santini V et al. Genetic lesions associated with blastic transformation of polycythemia vera and essential thrombocythemia. Genes Chromosomes. Cancer 1997; 19:250-255.

Gangat N, Strand J, Lasho T L et al. Cytogenetic studies at diagnosis in polycythemia vera: clinical and JAK2V617F allele burden correlates. Eur. J. Haematol. 2008; 80(3):197-200.

Graham S M, Vass J K, Holyoake T L, Graham G J. Transcriptional analysis of quiescent and proliferating CD34+ human hemopoietic cells from normal and chronic myeloid leukemia sources. Stem Cells 2007; 25(12):3111-3120.

Gruppo Italiano Studio Policitemia. Polycythemia vera: the natural history of 1213 patients followed for 20 years. Ann. Intern. Med. 1995; 123:656-664.

Hantschel O, Warsch W, Eckelhart E et al. BCR-ABL uncouples canonical JAK2-STAT5 signaling in chronic myeloid leukemia. Nat. Chem. Biol. 2012; 8(3):285-293.

Harrison C N, Campbell P J, Buck G et al. Hydroxyurea compared with anagrelide in high-risk essential thrombocythemia. N. Engl. J. Med. 2005; 353(1):33-45.

Horita M, Andreu E J, Benito A et al. Blockade of the Bcr-Abl kinase activity induces apoptosis of chronic myelogenous leukemia cells by suppressing signal transducer and activator of transcription 5-dependent expression of Bcl-xL. J. Exp. Med. 2000; 191(6):977-984.

Huang Y, Sitwala K, Bronstein J et al. Identification and characterization of Hoxa9 binding sites in hematopoietic cells. Blood 2012; 119(2):388-398.

Ikushima H, Todo T, Ino Y, Takahashi M, Miyazawa K, Miyazono K. Autocrine TGF-beta signaling maintains tumorigenicity of glioma-initiating cells through Sry-related HMG-box factors. Cell Stem Cell 2009; 5(5):504-514.

Isenberg J S, Ridnour L A, Perruccio E M, Espey M G, Wink D A, Roberts D D. Thrombospondin-1 inhibits endothelial cell responses to nitric oxide in a cGMP-dependent manner. Proc. Natl. Acad. Sci. U.S.A. 2005; 102(37):13141-13146.

James C, Ugo V, Le Couedic J P et al. A unique clonal JAK2 mutation leading to constitutive signaling causes polycythaemia vera. Nature 2005; 434(7037):1144-1148.

Jones A V, Kreil S, Zoi K et al. Widespread occurrence of the JAK2 V617F mutation in chronic myeloproliferative disorders. Blood 2005; 106:2162-2168.

Kamakura S, Oishi K, Yoshimatsu T, Nakafuku M, Masuyama N, Gotoh Y. Hes binding to STAT3 mediates crosstalk between Notch and JAK-STAT signaling. Nat. Cell. Biol. 2004; 6(6):547-554.

Kerbauy D M, Gooley T A, Sale G E et al. Hematopoietic cell transplantation as curative therapy for idiopathic myelofibrosis, advanced polycythemia vera, and essential thrombocythemia. Biol. Blood Marrow Transplant. 2007; 13:355-365.

Kiladjian J J, Cassinat B, Chevret S et al. Pegylated interferon-alfa-2a induces complete hematologic and molecular responses with low toxicity in polycythemia vera. Blood 2008; 112:3065-3072.

Kiladjian J J, Chevret S, Dosquet C, Chomienne C, Rain J D. Treatment of polycythemia vera with hydroxyurea and pipobroman: final results of a randomized trial initiated in 1980. J. Clin. Oncol. 2011; 29:3907-3913.

Koli K, Ryynanen M J, Keski-Oja J. Latent TGF-beta binding proteins (LTBPs)-1 and -3 coordinate proliferation and osteogenic differentiation of human mesenchymal stem cells. Bone 2008; 43(4):679-688.

Lamy T, Devillers A, Bernard M et al. Inapparent polycythemia vera: an unrecognized diagnosis. Am. J. Med. 1997; 102(1):14-20.

Lee J H, Suk J, Park J et al. Notch signal activates hypoxia pathway through HES1-dependent SRC/signal transducers and activators of transcription 3 pathway. Mol. Cancer Res. 2009; 7(10):1663-1671.

Lenz G, Wright G, Dave S S et al. Stromal gene signatures in large-B-cell lymphomas. N. Engl. J. Med. 2008; 359(22):2313-2323.

Lenz G, Wright G W, Emre N C et al. Molecular subtypes of diffuse large B-cell lymphoma arise by distinct genetic pathways. Proc. Natl. Acad. Sci. U.S.A. 2008; 105:13520-13525.

Mackinnon A C, Gibbons M A, Farnworth S L et al. Regulation of transforming growth factor-beta1-driven lung fibrosis by galectin-3. Am. J. Respir. Crit. Care Med. 2012; 185(5):537-546.

McNally R J, Rowland D, Roman E, Cartwright R A. Age and sex distributions of hematological malignancies in the U.K. Hematol. Oncol. 1997; 15:173-189.

Moliterno A R, Williams D M, Rogers 0, Isaacs M A, Spivak J L. Phenotypic variability within the JAK2 V617F-positive MPD: Roles of progenitor cell and neutrophil allele burdens. Exp. Hematol. 2008; 36(11):1480-1486.

Najean Y, Rain J. Treatment of Polycythemia Vera: The use of Hydroxyurea and Pipobroman in 292 Patients Under the Age of 65 Years. Blood 1997; 90:3370-3377.

Nakahara F, Sakata-Yanagimoto M, Komeno Y et al. Hes1 immortalizes committed progenitors and plays a role in blast crisis transition in chronic myelogenous leukemia. Blood 2010; 115(14):2872-2881.

Nowicki M O, Pawlowski P, Fischer T, Hess G, Pawlowski T, Skorski T. Chronic myelogenous leukemia molecular signature. Oncogene 2003; 22(25):3952-3963.

Nussenzveig R H, Swierczek S I, Jelinek J et al. Polycythemia vera is not initiated by JAK2V617F mutation. Exp. Hematol. 2007; 35(1):32-38.

Passamonti F, Rumi E, Caramella M et al. A dynamic prognostic model to predict survival in post-polycythemia vera myelofibrosis. Blood 2008; 111(7):3383-3387.

Patel V, Noureddine L. MicroRNAs and fibrosis. Curr. Opin. Nephrol. Hypertens. 2012; 21(4):410-416.

Radich J P, Dai H, Mao M et al. Gene expression changes associated with progression and response in chronic myeloid leukemia. Proc. Natl. Acad. Sci. U.S.A. 2006; 103(8):2794-2799.

Ranjan A, Penninga E, Jelsig A M, Hasselbalch H C, Bjerrum O W. Inheritance of the chronic myeloproliferative neoplasms. A systematic review. Clin. Genet. 2013; 83(2):99-107.

Ridell B, Carneskog J, Wedel H et al. Incidence of chronic myeloproliferative disorders in the city of Goteborg, Sweden 1983-1992. Eur. J. Haematol. 2000; 65(4):267-271.

Ridnour L A, Barasch K M, Windhausen A N et al. Nitric oxide synthase and breast cancer: role of TIMP-1 in NO-mediated Akt activation. PLoS ONE 2012; 7(9): e44081.

Rosario M, Paterson H F, Marshall C J. Activation of the Raf/MAP kinase cascade by the Ras-related protein TC21 is required for the TC21-mediated transformation of NIH 3T3 cells. EMBO J. 1999; 18(5):1270-1279.

Rosario M, Paterson H F, Marshall C J. Activation of the Ra1 and phosphatidylinositol 3' kinase signaling pathways by the ras-related protein TC21. Mol. Cell. Biol. 2001; 21(11):3750-3762.

Scharer C D, McCabe C D, Ali-Seyed M, Berger M F, Bulyk M L, Moreno C S. Genome-wide promoter analysis of the SOX4 transcriptional network in prostate cancer cells. Cancer Res. 2009; 69(2):709-717.

Schepers K, Pietras E M, Reynaud D et al. Myeloproliferative Neoplasia Remodels the Endosteal Bone Marrow Niche into a Self-Reinforcing Leukemic Niche. Cell Stem Cell 2013.

Segal J B, Moliterno A R. Platelet counts differ by sex, ethnicity, and age in the United States. Ann. Epidemiol. 2006; 16(2):123-130.

Shibata S, Ishiyama J. Secreted protein acidic and rich in cysteine (SPARC) is upregulated by transforming growth factor (TGF)-beta and is required for TGF-beta-induced hydrogen peroxide production in fibroblasts. Fibrogenesis Tissue Repair 2013; 6(1):6.

Silverstein M N. Postpolycythemia myeloid metaplasia. Arch. Intern. Med. 1974; 134(1):113-117.

Slezak S, Jin P, Caruccio L et al. Gene and microRNA analysis of neutrophils from patients with polycythemia vera and essential thrombocytosis: down-regulation of micro RNA-1 and -133a. J. Transl. Med. 2009; 7:39.

Smalberg J H, Arends L R, Valla D C, Kiladjian J J, Janssen H L, Leebeek F W. Myeloproliferative neoplasms in Budd-Chiari syndrome and portal vein thrombosis: a meta-analysis. Blood 2012; 120(25):4921-4928.

Song S, Mazurek N, Liu C et al. Galectin-3 mediates nuclear beta-catenin accumulation and Wnt signaling in human colon cancer cells by regulation of glycogen synthase kinase-3beta activity. Cancer Res. 2009; 69(4):1343-1349.

Spivak J L. Polycythemia vera:myths, mechanisms, and management. Blood 2002; 100:4272-4290.

Spivak J L. Narrative review: Thrombocytosis, polycythemia vera, and JAK2 mutations: The phenotypic mimicry of chronic myeloproliferation. Ann. Intern. Med. 2010; 152:300-306.

Spivak J L, Hasselbalch H. Hydroxycarbamide: a user's guide for chronic myeloproliferative disorders. Expert. Rev. Anticancer Ther. 2011; 11:403-414.

Stein B L, Rademaker A, Spivak J L, Moliterno A R. Gender and Vascular Complications in the JAK2 V617F-Positive Myeloproliferative Neoplasms. Thrombosis 2011; 2011: 874146.

Stein B L, Williams D M, O'Keefe C et al. Disruption of the ASXL1 gene is frequent in primary, post-essential thrombocytosis and post-polycythemia vera myelofibrosis, but not essential thrombocytosis or polycythemia vera: analysis of molecular genetics and clinical phenotypes. Haematologica 2011; 96(10):1462-1469.

Stein B L, Williams D M, Rogers O, Isaacs M A, Spivak J L, Moliterno A R. Disease burden at the progenitor level is a feature of primary myelofibrosis: a multivariable analysis of 164 JAK2 V617F-positive myeloproliferative neoplasm patients. Exp. Hematol. 2011; 39(1):95-101.

Stein B L, Williams D M, Wang N Y et al. Sex differences in the JAK2 V617F allele burden in chronic myeloproliferative disorders. Haematologica 2010; 95(7):1090-1097.

Sugita M, Haney J L, Gemmill R M, Franklin W A. One-step duplex reverse transcription-polymerase chain reaction for quantitative assessment of RNA degradation. Anal. Biochem. 2001; 295(1):113-116.

Tan A C, Naiman D Q, Xu L, Winslow R L, Geman D. Simple decision rules for classifying human cancers from gene expression profiles. Bioinformatics 2005; 21(20): 3896-3904.

Tripodo C, Sangaletti S, Guarnotta C et al. Stromal SPARC contributes to the detrimental fibrotic changes associated with myeloproliferation whereas its deficiency favors myeloid cell expansion. Blood 2012; 120(17):3541-3554.

Verstovsek S, Kantarjian H, Mesa R A et al. Safety and efficacy of INCB018424, a JAK1 and JAK2 inhibitor, in myelofibrosis. N. Engl. J. Med. 2010; 363(12):1117-1127.

Videbaek A. Polycythemia Vera. Course and Prognosis. Acta Med. Scand. 1950; 138:179-187.

Wall D S, Mears A J, McNeill B et al. Progenitor cell proliferation in the retina is dependent on Notch-independent Sonic hedgehog/Hes1 activity. J. Cell. Biol. 2009; 184(1):101-112.

Wang J, Leclercq I, Brymora J M et al. Kupffer cells mediate leptin-induced liver fibrosis. Gastroenterology 2009; 137 (2):713-723.

Wasserman L. The Management of Polycythemia Vera. British Journal of Hematology 1971; 21:371-376.

Williams D M, Kim A H, Rogers O, Spivak J L, Moliterno A R. Phenotypic variations and new mutations in JAK2 V617F-negative polycythemia vera, erythrocytosis, and idiopathic myelofibrosis. Exp. Hematol. 2007; 35(11): 1641-1646.

Yamamoto-Sugitani M, Kuroda J, Ashihara E et al. Galectin-3 (Gal-3) induced by leukemia microenvironment promotes drug resistance and bone marrow lodgment in chronic myelogenous leukemia. Proc. Natl. Acad. Sci. U.S.A. 2011; 108(42):17468-17473.

Yuwaraj S, Ding J, Liu M, Marsden P A, Levy G A. Genomic characterization, localization, and functional expression of FGL2, the human gene encoding fibroleukin: a novel human procoagulant. Genomics 2001; 71(3):330-338.

Zheng C, Li L, Haak M et al. Gene expression profiling of CD34+ cells identifies a molecular signature of chronic myeloid leukemia blast crisis. Leukemia 2006; 20(6): 1028-1034.

Although the foregoing subject matter has been described in some detail by way of illustration and example for purposes of clarity of understanding, it will be understood by those skilled in the art that certain changes and modifications can be practiced within the scope of the appended claims.

Tables

TABLE 1

QPCR using the Gene Expression GEX Assays

| ABI GEX Assay ID | Gene Symbol | Gene Name | GEX Target Exon Boundaries |
|---|---|---|---|
| Hs00188259_m1 | WARS | tryptophanyl-tRNA synthetase | 9-10 |
| Hs99999139_m1 | TIMP1 | TIMP metallopeptidase inhibitor 1 | 2-3 |
| Hs00180737_m1 | HPSE | heparanase | 8-9 |
| Hs00172743_m1 | DNTT | deoxynucleotidyltransferase, terminal | 10-11 |
| Hs00181810_m1 | CRHBP | corticotropin releasing hormone binding protein | 6-7 |
| Hs00365956_m1 | HOXA9 | homeobox A9 | 1-2 |
| Hs00202825_m1 | SSBP2 | single-stranded DNA binding protein 2 | 7-8 |
| Hs00261238_m1 | HOPX | HOP homeobox | 2-3 |
| Hs99999905_m1 | GAPDH | glyceraldehyde-3-phosphate dehydrogenase | 3-3 |
| 000397 | miR-21 | Human microRNA-21 (hsa-miR-21-5p) | N/A |
| 001093 | RNU6B | U6 small nuclear 2, small nuclear RNA | N/A |

TABLE 2

Polycythemia Vera Study Population Demographics

| | Men (8) | Women (11) |
|---|---|---|
| Median Age (years; range) | 69 (57-82)* | 60 (46-76) |
| Median Disease Duration (years; range) | 11.5 (1-28)* | 9 (1-18) |
| Median JAK2 V617F Neutrophil Allele Burden (%; range) | 94 (55-100)* | 100 (60-100) |
| Median Hemoglobin (gm %; range) | 13.2 (8.3-15.9)* | 11.7 (10.4-14.7) |
| Median Leukocyte Count ($10^3/\mu L$; range) | 16,690* (4430-177,190) | 19,970 (5080-50,070) |
| Median Platelet Count ($10^3/\mu L$; range) | 421,000** (151,000-810,000) | 948,000 (191,100-1,480,000) |
| Median Spleen size (cm; range) | 10.2 (0-32)* | 5.0 (0-20) |

*Not significantly different
**p = 0.016

TABLE 3

Demographics and Clinical Features of the 19 Polycythemia Vera Patients at Study Entry

| Gender | Age In Years | Disease Duration In Years | Hemoglobin (gm %) | Leukocyte count ($10^6/\mu L$) | Platelet count ($10^6/\mu L$) | Spleen size (cm below the left costal margin) | Splenectomy | JAK2 V617F Neutro-phil allele burden (%) | Thrombosis/ TIA | Therapy |
|---|---|---|---|---|---|---|---|---|---|---|
| M | 74 | 7 | 12.9 | 17,620 | 388,000 | 32 | No | 100 | No | Phlebotomy, Anagrelide, Hydroxyurea, Busulfan |
| M | 66 | 20 | 8.3 | 177,190 | 454,000 | 25 | Yes | 100 | Arterial | Phlebotomy, Thalidomide, Cytoxan |
| F | 55 | 13 | 11.1 | 33,110 | 802,000 | 20 | Yes | 100 | Portal and hepatic veins; TIA | Phlebotomy, Hydroxyurea, Cytoxan, Anagrelide |
| F | 74 | 8 | 11.7 | 10,720 | 366,000 | 8 | No | 68 | Hepatic vein | Anagrelide, Hydroxyurea |
| M | 63 | 16 | 9.3 | 10,020 | 171,000 | 8 | Yes | 86 | No | Phlebotomy, Hydroxyurea |
| F | 48 | 18 | 10.4 | 50,070 | 1,017,000 | 5 | Yes | 100 | Arterial and venous | Phlebotomy, Hydroxyurea, Busulfan, Imatinib |
| M | 72 | 1 | 13.7 | 16,490 | 712,000 | 0 | No | 68 | No | Phlebotomy |
| F | 68 | 11 | 13.0 | 11,980 | 865,000 | 5 | No | 67 | No | Phlebotomy |
| M | 73 | 4 | 14.3 | 16,610 | 151,000 | 12.5 | No | 95 | No | Phlebotomy |
| M | 82 | 25 | 15.9 | 4,430 | 197,000 | 0 | No | 50 | Arterial | Phlebotomy, Hydroxyurea |
| F | 76 | 10 | 11.5 | 5,080 | 948,000 | 0 | No | 52 | TIA | Phlebotomy, Hydroxyurea |
| M | 57 | 4 | 13.6 | 19,970 | 810,000 | 0 | No | 88 | No | Phlebotomy |
| F | 57 | 12 | 13.0 | 19,530 | 1,119,000 | 8 | No | 60 | No | Phlebotomy, Hydroxyurea |
| F | 51 | 5 | 10.7 | 19,130 | 1,052,000 | 5 | No | 100 | No | Phlebotomy |
| F | 46 | 4 | 11.1 | 20,520 | 1,480,000 | 0 | No | 82 | No | Phlebotomy |
| F | 67 | 7 | 14.5 | 27,270 | 191,000 | 14 | No | 100 | No | Phlebotomy |
| F | 60 | 9 | 12.5 | 13,870 | 1,176,000 | 4 | No | 49 | No | Phlebotomy |
| M | 71 | 33 | 12.5 | 16,770 | 491,000 | 20 | Yes | 100 | No | Phlebotomy, Hydroxyurea |

TABLE 4

Gene Expression in Women Patients

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 204805_s_at | H1FX | H1 histone family, member X | 8971 | 1.91935 | 0.00114 | 0.1019 |
| 202888_s_at | ANPEP | alanyl (membrane) aminopeptidase | 290 | 1.43197 | 0.001209 | 0.1019 |
| 213326_at | VAMP1 | vesicle-associated membrane protein 1 (synaptobrevin 1) | 6843 | 1.380311 | 0.001564 | 0.1019 |
| 212543_at | AIM1 | absent in melanoma 1 | 202 | 1.689059 | 0.002053 | 0.1019 |
| 201427_s_at | SEPP1 | selenoprotein P, plasma, 1 | 6414 | 1.427475 | 0.003366 | 0.125981 |
| 206674_at | FLT3 | fms-related tyrosine kinase 3 | 2322 | 1.701119 | 0.003846 | 0.125981 |
| 206385_s_at | ANK3 | ankyrin 3, node of Ranvier (ankyrin G) | 288 | 1.257882 | 0.004488 | 0.125981 |
| 209487_at | RBPMS | RNA binding protein with multiple splicing | 11030 | 1.23478 | 0.00567 | 0.125981 |
| 219871_at | FLJ13197 | uncharacterized FLJ13197 | 79667 | 1.301817 | 0.005704 | 0.125981 |
| 209488_s_at | RBPMS | RNA binding protein with multiple splicing | 11030 | 1.275396 | 0.006845 | 0.125981 |
| 221645_s_at | ZNF83 | zinc finger protein 83 | 55769 | 1.200283 | 0.007674 | 0.125981 |
| 213005_s_at | KANK1 | KN motif and ankyrin repeat domains 1 | 23189 | 1.707475 | 0.008166 | 0.125981 |
| 213817_at | IRAK3 | interleukin-1 receptor-associated kinase 3 | 11213 | 1.218239 | 0.010346 | 0.125981 |
| 202039_at | MYO18A | myosin XVIIIA | 399687 | 1.175294 | 0.011058 | 0.125981 |
| 210644_s_at | LAIR1 | leukocyte-associated immunoglobulin-like receptor 1 | 3903 | 1.348313 | 0.011154 | 0.125981 |
| 204352_at | TRAF5 | TNF receptor-associated factor 5 | 7188 | 1.125428 | 0.012268 | 0.125981 |
| 214290_s_at | HIST2H2AA4 | histone cluster 2, H2aa4 | 723790 | 1.879605 | 0.013116 | 0.125981 |
| 222146_s_at | TCF4 | transcription factor 4 | 6925 | 1.385756 | 0.013155 | 0.125981 |
| 59375_at | MYO15B | myosin XVB pseudogene | 80022 | 1.108123 | 0.013372 | 0.125981 |
| 206486_at | LAG3 | lymphocyte-activation gene 3 | 3902 | 0.994363 | 0.014533 | 0.125981 |

TABLE 4-continued

Gene Expression in Women Patients

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 212794_s_at | KIAA1033 | KIAA1033 | 23325 | 1.287389 | 0.014972 | 0.125981 |
| 218086_at | NPDC1 | neural proliferation, differentiation and control, 1 | 56654 | 1.013593 | 0.015204 | 0.125981 |
| 218280_x_at | HIST2H2AA4 | histone cluster 2, H2aa4 | 723790 | 1.830191 | 0.01535 | 0.125981 |
| 213655_at | YWHAE | tyrosine 3-monooxygenase/tryptophan 5-monooxygenase activation protein, epsilon polypeptide | 7531 | −1.40323 | 0.015549 | 0.125981 |
| 219173_at | MYO15B | myosin XVB pseudogene | 80022 | 1.147267 | 0.016111 | 0.127919 |
| 212587_s_at | PTPRC | protein tyrosine phosphatase, receptor type, C | 5788 | 1.942028 | 0.016627 | 0.128539 |
| 218312_s_at | ZSCAN18 | zinc finger and SCAN domain containing 18 | 65982 | 1.539329 | 0.017836 | 0.128539 |
| 207836_s_at | RBPMS | RNA binding protein with multiple splicing | 11030 | 1.091491 | 0.018254 | 0.128539 |
| 207426_s_at | TNFSF4 | tumor necrosis factor (ligand) superfamily, member 4 | 7292 | 1.381424 | 0.019204 | 0.129221 |
| 212762_s_at | TCF7L2 | transcription factor 7-like 2 (T-cell specific, HMG-box) | 6934 | 1.046634 | 0.019813 | 0.129892 |
| 209398_at | HIST1H1C | histone cluster 1, H1c | 3006 | 1.60555 | 0.020228 | 0.129892 |
| 211675_s_at | MDFIC | MyoD family inhibitor domain containing | 29969 | 1.155886 | 0.020685 | 0.129892 |
| 206133_at | XAF1 | XIAP associated factor 1 | 54739 | 1.158372 | 0.020857 | 0.129892 |
| 218966_at | MYO5C | myosin VC | 55930 | 1.536923 | 0.02094 | 0.129892 |
| 214455_at | HIST1H2BC | histone cluster 1, H2bc | 8347 | 1.482403 | 0.023205 | 0.131273 |
| 205471_s_at | DACH1 | dachshund homolog 1 (Drosophila) | 1602 | 0.95962 | 0.023854 | 0.131273 |
| 218346_s_at | SESN1 | sestrin 1 | 27244 | 1.057229 | 0.024057 | 0.131273 |
| 209993_at | ABCB1 | ATP-binding cassette, sub-family B (MDR/TAP), member 1 | 5243 | 1.012543 | 0.024783 | 0.131273 |
| 206710_s_at | EPB41L3 | erythrocyte membrane protein band 4.1-like 3 | 23136 | 0.977202 | 0.024885 | 0.131273 |
| 202708_s_at | HIST2H2BE | histone cluster 2, H2be | 8349 | 1.769114 | 0.02667 | 0.131273 |
| 200986_at | SERPING1 | serpin peptidase inhibitor, clade G (C1 inhibitor), member 1 | 710 | 1.048714 | 0.026758 | 0.131273 |
| 207111_at | EMR1 | egf-like module containing, mucin-like, hormone receptor-like 1 | 2015 | 1.04867 | 0.026977 | 0.131273 |
| 219355_at | CXorf57 | chromosome X open reading frame 57 | 55086 | 0.956366 | 0.027482 | 0.131273 |
| 201196_s_at | AMD1 | adenosylmethionine decarboxylase 1 | 262 | 1.127364 | 0.02763 | 0.131273 |
| 207564_x_at | OGT | O-linked N-acetylglucosamine (GlcNAc) transferase | 8473 | 1.180955 | 0.027642 | 0.131273 |
| 202686_s_at | AXL | AXL receptor tyrosine kinase | 558 | −1.17476 | 0.027808 | 0.131273 |
| 208268_at | ADAM28 | ADAM metallopeptidase domain 28 | 10863 | 1.222576 | 0.028106 | 0.131273 |
| 215307_at | ZNF529 | zinc finger protein 529 | 57711 | 1.029099 | 0.028782 | 0.132865 |
| 219571_s_at | ZNF12 | zinc finger protein 12 | 7559 | 1.033403 | 0.030225 | 0.136525 |
| 209994_s_at | ABCB1 | ATP-binding cassette, sub-family B (MDR/TAP), member 1 | 5243 | 0.988532 | 0.030956 | 0.136933 |
| 212560_at | SORL1 | sortilin-related receptor, L(DLR class) A repeats containing | 6653 | 1.232375 | 0.031193 | 0.136933 |
| 205767_at | EREG | epiregulin | 2069 | 1.576209 | 0.032309 | 0.137923 |
| 221718_s_at | AKAP13 | A kinase (PRKA) anchor protein 13 | 11214 | 0.990575 | 0.033371 | 0.139481 |
| 214472_at | HIST1H2AD | histone cluster 1, H2ad | 3013 | 1.221696 | 0.034306 | 0.139481 |
| 209447_at | SYNE1 | spectrin repeat containing, nuclear envelope 1 | 23345 | 1.026492 | 0.034672 | 0.139481 |
| 207571_x_at | THEMIS2 | thymocyte selection associated family member 2 | 9473 | 1.23688 | 0.035236 | 0.139481 |
| 210785_s_at | THEMIS2 | thymocyte selection associated family member 2 | 9473 | 1.258674 | 0.035631 | 0.139481 |
| 209543_s_at | CD34 | CD34 molecule | 947 | 1.31764 | 0.037479 | 0.144458 |
| 220952_s_at | PLEKHA5 | pleckstrin homology domain containing, family A member 5 | 54477 | 1.059186 | 0.039091 | 0.147854 |
| 201448_at | TIA1 | TIA1 cytotoxic granule-associated RNA binding protein | 7072 | 1.289342 | 0.039105 | 0.147854 |
| 221543_s_at | ERLIN2 | ER lipid raft associated 2 | 11160 | 1.019463 | 0.040859 | 0.150196 |
| 206715_at | TFEC | transcription factor EC | 22797 | 1.291151 | 0.042627 | 0.153844 |
| 220122_at | MCTP1 | multiple C2 domains, transmembrane 1 | 79772 | 1.025269 | 0.043486 | 0.155532 |

TABLE 4-continued

Gene Expression in Women Patients

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 209318_x_at | PLAGL1 | pleiomorphic adenoma gene-like 1 | 5325 | 1.315505 | 0.046285 | 0.160061 |
| 208056_s_at | CBFA2T3 | core-binding factor, runt domain, alpha subunit 2; translocated to, 3 | 863 | 1.116738 | 0.04637 | 0.160061 |
| 204972_at | OAS2 | 2'-5'-oligoadenylate synthetase 2, 69/71 kDa | 4939 | 1.090829 | 0.046707 | 0.160061 |
| 201236_s_at | BTG2 | BTG family, member 2 | 7832 | 1.091134 | 0.046768 | 0.160061 |
| 214218_s_at | XIST | X inactive specific transcript (non-protein coding) | 7503 | 1.3244 | 0.04853 | 0.163276 |
| 220940_at | ANKRD36B | ankyrin repeat domain 36B | 57730 | 1.168735 | 0.049352 | 0.163699 |
| 209930_s_at | NFE2 | nuclear factor (erythroid-derived 2), 45 kDa | 4778 | 1.331755 | 0.050315 | 0.163699 |
| 205239_at | AREG | amphiregulin | 374 | 1.205571 | 0.051692 | 0.163838 |
| 217593_at | ZSCAN18 | zinc finger and SCAN domain containing 18 | 65982 | 0.840704 | 0.054078 | 0.167551 |
| 222067_x_at | HIST1H2BD | histone cluster 1, H2bd | 3017 | 1.198697 | 0.063984 | 0.189566 |
| 213094_at | GPR126 | G protein-coupled receptor 126 | 57211 | 1.17747 | 0.06522 | 0.191029 |
| 212775_at | OBSL1 | obscurin-like 1 | 23363 | 1.331391 | 0.065586 | 0.191029 |
| 221249_s_at | FAM117A | family with sequence similarity 117, member A | 81558 | 1.637593 | 0.066403 | 0.191029 |
| 210172_at | SF1 | splicing factor 1 | 7536 | 0.997588 | 0.067011 | 0.191391 |
| 207496_at | MS4A2 | membrane-spanning 4-domains, subfamily A, member 2 | 2206 | 0.772601 | 0.069284 | 0.193702 |
| 218589_at | LPAR6 | lysophosphatidic acid receptor 6 | 10161 | 1.080018 | 0.071983 | 0.199841 |
| 204749_at | NAP1L3 | nucleosome assembly protein 1-like 3 | 4675 | 1.296406 | 0.073554 | 0.202786 |
| 211302_s_at | PDE4B | phosphodiesterase 4B, cAMP-specific | 5142 | 0.858839 | 0.076239 | 0.207306 |
| 215779_s_at | HIST1H2BG | histone cluster 1, H2bg | 8339 | 0.902184 | 0.076987 | 0.207917 |
| 213293_s_at | TRIM22 | tripartite motif containing 22 | 10346 | 1.468514 | 0.077535 | 0.207984 |
| 218352_at | RCBTB1 | regulator of chromosome condensation (RCC1) and BTB (POZ) domain containing protein 1 | 55213 | 1.08448 | 0.082823 | 0.214891 |
| 220918_at | RUNX1-IT1 | RUNX1 intronic transcript 1 (non-protein coding) | 80215 | 1.110688 | 0.083008 | 0.214891 |
| 204116_at | IL2RG | interleukin 2 receptor, gamma | 3561 | 0.892953 | 0.085322 | 0.217134 |
| 210254_at | MS4A3 | membrane-spanning 4-domains, subfamily A, member 3 (hematopoietic cell-specific) | 932 | 1.032003 | 0.088393 | 0.223517 |
| 213998_s_at | DDX17 | DEAD (Asp-Glu-Ala-Asp) box helicase 17 | 10521 | 1.29709 | 0.090384 | 0.225675 |
| 206631_at | PTGER2 | prostaglandin E receptor 2 (subtype EP2), 53 kDa | 5732 | 0.863461 | 0.094568 | 0.233189 |
| 219737_s_at | PCDH9 | protocadherin 9 | 5101 | 1.423384 | 0.095952 | 0.235143 |
| 206067_s_at | WT1 | Wilms tumor 1 | 7490 | −0.97509 | 0.097098 | 0.235189 |
| 212813_at | JAM3 | junctional adhesion molecule 3 | 83700 | 0.851683 | 0.097156 | 0.235189 |
| 203708_at | PDE4B | phosphodiesterase 4B, cAMP-specific | 5142 | 1.258787 | 0.098941 | 0.236778 |
| 213734_at | WSB2 | WD repeat and SOCS box containing 2 | 55884 | −1.03595 | 0.103178 | 0.243147 |
| 212382_at | TCF4 | transcription factor 4 | 6925 | 1.222721 | 0.103506 | 0.243147 |
| 212044_s_at | RPL27A | ribosomal protein L27a | 6157 | −1.30359 | 0.11014 | 0.255203 |
| 209774_x_at | CXCL2 | chemokine (C-X-C motif) ligand 2 | 2920 | −1.35733 | 0.111447 | 0.255748 |
| 204420_at | FOSL1 | FOS-like antigen 1 | 8061 | 0.777712 | 0.125065 | 0.28372 |
| 219352_at | HERC6 | HECT and RLD domain containing E3 ubiquitin protein ligase family member 6 | 55008 | 0.731325 | 0.126978 | 0.286421 |
| 219371_s_at | KLF2 | Kruppel-like factor 2 (lung) | 10365 | 0.952494 | 0.133808 | 0.29512 |
| 208436_s_at | IRF7 | interferon regulatory factor 7 | 3665 | 0.817301 | 0.142117 | 0.308309 |
| 208490_x_at | HIST1H2BF | histone cluster 1, H2bf | 8343 | 0.823714 | 0.153384 | 0.325493 |
| 217168_s_at | HERPUD1 | homocysteine-inducible, endoplasmic reticulum stress-inducible, ubiquitin-like domain member 1 | 9709 | −1.02032 | 0.153554 | 0.325493 |
| 218723_s_at | RGCC | regulator of cell cycle | 28984 | 1.178353 | 0.16831 | 0.347202 |
| 221943_x_at | RPL38 | ribosomal protein L38 | 6169 | −0.87537 | 0.169666 | 0.347202 |
| 202912_at | ADM | adrenomedullin | 133 | −0.90139 | 0.175228 | 0.356746 |
| 202086_at | MX1 | myxovirus (influenza virus) resistance 1, interferon-inducible protein p78 (mouse) | 4599 | 1.082812 | 0.179388 | 0.362009 |

TABLE 4-continued

Gene Expression in Women Patients

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 204794_at | DUSP2 | dual specificity phosphatase 2 | 1844 | −1.05607 | 0.185851 | 0.370769 |
| 200878_at | EPAS1 | endothelial PAS domain protein 1 | 2034 | −0.94127 | 0.187138 | 0.371469 |
| 214395_x_at | EEF1D | eukaryotic translation elongation factor 1 delta (guanine nucleotide exchange protein) | 1936 | −0.75421 | 0.221404 | 0.418581 |
| 39248_at | AQP3 | aquaporin 3 (Gill blood group) | 360 | −1.0387 | 0.221416 | 0.418581 |
| 201590_x_at | ANXA2 | annexin A2 | 302 | −0.83364 | 0.224539 | 0.422475 |
| 202087_s_at | CTSL1 | cathepsin L1 | 1514 | −0.72277 | 0.227535 | 0.426091 |
| 201897_s_at | CKS1B | CDC28 protein kinase regulatory subunit 1B | 1163 | −0.75777 | 0.23559 | 0.436077 |
| 202869_at | OAS1 | 2′-5′-oligoadenylate synthetase 1, 40/46 kDa | 4938 | 0.645604 | 0.239395 | 0.44 |
| 204351_at | S100P | S100 calcium binding protein P | 6286 | −1.19041 | 0.248298 | 0.447645 |
| 205220_at | HCAR3 | hydroxycarboxylic acid receptor 3 | 8843 | −0.75269 | 0.248929 | 0.447645 |
| 201289_at | CYR61 | cysteine-rich, angiogenic inducer, 61 | 3491 | −0.94996 | 0.249241 | 0.447645 |
| 213943_at | TWIST1 | twist basic helix-loop-helix transcription factor 1 | 7291 | −0.76051 | 0.251394 | 0.447645 |
| 201566_x_at | ID2 | inhibitor of DNA binding 2, dominant negative helix-loop-helix protein | 3398 | 0.738645 | 0.252916 | 0.448249 |
| 204286_s_at | PMAIP1 | phorbol-12-myristate-13-acetate-induced protein 1 | 5366 | 0.658217 | 0.254968 | 0.449876 |
| 203038_at | PTPRK | protein tyrosine phosphatase, receptor type, K | 5796 | −0.89732 | 0.259282 | 0.450102 |
| 212097_at | CAV1 | caveolin 1, caveolae protein, 22 kDa | 857 | −0.8953 | 0.259704 | 0.450102 |
| 202733_at | P4HA2 | prolyl 4-hydroxylase, alpha polypeptide II | 8974 | −0.88547 | 0.260765 | 0.450102 |
| 203917_at | CXADR | coxsackie virus and adenovirus receptor | 1525 | −0.70323 | 0.261975 | 0.450233 |
| 204103_at | CCL4 | chemokine (C-C motif) ligand 4 | 6351 | −0.93799 | 0.264919 | 0.453331 |
| 202458_at | PRSS23 | protease, serine, 23 | 11098 | −0.75062 | 0.266945 | 0.454838 |
| 213539_at | CD3D | CD3d molecule, delta (CD3-TCR complex) | 915 | −0.74368 | 0.268679 | 0.455836 |
| 210321_at | GZMH | granzyme H (cathepsin G-like 2, protein h-CCPX) | 2999 | −0.6763 | 0.279967 | 0.472525 |
| 214453_s_at | IFI44 | interferon-induced protein 44 | 10561 | 0.80743 | 0.280897 | 0.472525 |
| 211560_s_at | ALAS2 | aminolevulinate, delta-, synthase 2 | 212 | −0.96058 | 0.293731 | 0.486931 |
| 201744_s_at | LUM | lumican | 4060 | −0.72481 | 0.298238 | 0.491288 |
| 211340_s_at | MCAM | melanoma cell adhesion molecule | 4162 | −0.77567 | 0.306814 | 0.499201 |
| 204959_at | MNDA | myeloid cell nuclear differentiation antigen | 4332 | −0.90022 | 0.316701 | 0.504456 |
| 202587_s_at | AK1 | adenylate kinase 1 | 203 | −0.63641 | 0.317949 | 0.504456 |
| 218959_at | HOXC10 | homeobox C10 | 3226 | −0.61573 | 0.319085 | 0.504456 |
| 205495_s_at | GNLY | granulysin | 10578 | −0.68517 | 0.320209 | 0.504456 |
| 221958_s_at | WLS | wntless homolog (Drosophila) | 79971 | −0.70884 | 0.324929 | 0.50696 |
| 202688_at | TNFSF10 | tumor necrosis factor (ligand) superfamily, member 10 | 8743 | 0.618043 | 0.325629 | 0.50696 |
| 209087_x_at | MCAM | melanoma cell adhesion molecule | 4162 | −0.81432 | 0.326954 | 0.507034 |
| 209210_s_at | FERMT2 | fermitin family member 2 | 10979 | −1.11824 | 0.329723 | 0.50854 |
| 205488_at | GZMA | granzyme A (granzyme 1, cytotoxic T-lymphocyte-associated serine esterase 3) | 3001 | −0.59006 | 0.330487 | 0.50854 |
| 201739_at | SGK1 | serum/glucocorticoid regulated kinase 1 | 6446 | −1.0293 | 0.335357 | 0.508988 |
| 211506_s_at | IL8 | interleukin 8 | 3576 | −0.69682 | 0.336251 | 0.508988 |
| 204962_s_at | CENPA | centromere protein A | 1058 | −0.67424 | 0.336317 | 0.508988 |
| 212698_s_at | 10-Sep | septin 10 | 151011 | −0.74724 | 0.337188 | 0.508988 |
| 33322_i_at | SFN | stratifin | 2810 | −0.75401 | 0.341463 | 0.509458 |
| 218705_s_at | SNX24 | sorting nexin 24 | 28966 | −0.57987 | 0.342374 | 0.509458 |
| 205552_s_at | OAS1 | 2′-5′-oligoadenylate synthetase 1, 40/46 kDa | 4938 | 0.50836 | 0.344124 | 0.509458 |
| 201506_at | TGFBI | transforming growth factor, beta-induced, 68 kDa | 7045 | −0.66233 | 0.345804 | 0.509458 |
| 202011_at | TJP1 | tight junction protein 1 | 7082 | −0.64431 | 0.347774 | 0.509458 |
| 204517_at | PPIC | peptidylprolyl isomerase C (cyclophilin C) | 5480 | −0.59936 | 0.349374 | 0.509458 |

TABLE 4-continued

Gene Expression in Women Patients

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 209230_s_at | NUPR1 | nuclear protein, transcriptional regulator, 1 | 26471 | −0.65323 | 0.350449 | 0.509458 |
| 219073_s_at | OSBPL10 | oxysterol binding protein-like 10 | 114884 | −0.59261 | 0.351262 | 0.509458 |
| 205476_at | CCL20 | chemokine (C-C motif) ligand 20 | 6364 | −0.6399 | 0.357651 | 0.512993 |
| 221577_x_at | GDF15 | growth differentiation factor 15 | 9518 | −0.65491 | 0.364519 | 0.516042 |
| 202718_at | IGFBP2 | insulin-like growth factor binding protein 2, 36 kDa | 3485 | −0.57195 | 0.365259 | 0.516042 |
| 207039_at | CDKN2A | cyclin-dependent kinase inhibitor 2A | 1029 | −0.71306 | 0.36807 | 0.517873 |
| 204920_at | CPS1 | carbamoyl-phosphate synthase 1, mitochondrial | 1373 | −0.81774 | 0.369164 | 0.517873 |
| 200771_at | LAMC1 | laminin, gamma 1 (formerly LAMB2) | 3915 | −0.65676 | 0.37062 | 0.518085 |
| 219454_at | EGFL6 | EGF-like-domain, multiple 6 | 25975 | −0.56974 | 0.374512 | 0.518966 |
| 212328_at | LIMCH1 | LIM and calponin homology domains 1 | 22998 | −0.72538 | 0.37555 | 0.518966 |
| 207076_s_at | ASS1 | argininosuccinate synthase 1 | 445 | −0.96506 | 0.376479 | 0.518966 |
| 201983_s_at | EGFR | epidermal growth factor receptor | 1956 | −0.56631 | 0.379717 | 0.519326 |
| 203438_at | STC2 | stanniocalcin 2 | 8614 | −0.54868 | 0.385726 | 0.520981 |
| 212012_at | PXDN | peroxidasin homolog (Drosophila) | 7837 | −0.69905 | 0.3859 | 0.520981 |
| 203153_at | IFIT1 | interferon-induced protein with tetratricopeptide repeats 1 | 3434 | 0.55537 | 0.389138 | 0.520981 |
| 206785_s_at | KLRC1 | killer cell lectin-like receptor subfamily C, member 1 | 3821 | −0.5784 | 0.393476 | 0.520981 |
| 217564_s_at | CPS1 | carbamoyl-phosphate synthase 1, mitochondrial | 1373 | −0.79731 | 0.394672 | 0.520981 |
| 202052_s_at | RAI14 | retinoic acid induced 14 | 26064 | −0.5724 | 0.3967 | 0.520981 |
| 204992_s_at | PFN2 | profilin 2 | 5217 | −0.772 | 0.396957 | 0.520981 |
| 204007_at | FCGR3B | Fc fragment of IgG, low affinity IIIb, receptor (CD16b) | 2215 | −0.64158 | 0.397187 | 0.520981 |
| 210095_s_at | IGFBP3 | insulin-like growth factor binding protein 3 | 3486 | −0.60033 | 0.397625 | 0.520981 |
| 200798_x_at | MCL1 | myeloid cell leukemia sequence 1 (BCL2-related) | 4170 | 0.540947 | 0.39956 | 0.521124 |
| 212364_at | MYO1B | myosin IB | 4430 | −0.55526 | 0.401476 | 0.521124 |
| 212765_at | CAMSAP2 | calmodulin regulated spectrin-associated protein family, member 2 | 23271 | −0.56269 | 0.401672 | 0.521124 |
| 204284_at | PPP1R3C | protein phosphatase 1, regulatory subunit 3C | 5507 | −0.54464 | 0.406184 | 0.523753 |
| 201976_s_at | MYO10 | myosin X | 4651 | −0.55951 | 0.406337 | 0.523753 |
| 208079_s_at | AURKA | aurora kinase A | 6790 | −0.65513 | 0.408025 | 0.524226 |
| 219959_at | MOCOS | molybdenum cofactor sulfurase | 55034 | −0.85667 | 0.410521 | 0.525731 |
| 213139_at | SNAI2 | snail homolog 2 (Drosophila) | 6591 | −0.55315 | 0.414603 | 0.526676 |
| 201292_at | TOP2A | topoisomerase (DNA) II alpha 170 kDa | 7153 | −0.61773 | 0.41473 | 0.526676 |
| 209101_at | CTGF | connective tissue growth factor | 1490 | −0.63969 | 0.416358 | 0.526676 |
| 210587_at | INHBE | inhibin, beta E | 83729 | −0.61908 | 0.419791 | 0.526676 |
| 202768_at | FOSB | FBJ murine osteosarcoma viral oncogene homolog B | 2354 | 0.785327 | 0.421407 | 0.526676 |
| 219148_at | PBK | PDZ binding kinase | 55872 | −0.62389 | 0.422616 | 0.526676 |
| 201505_at | LAMB1 | laminin, beta 1 | 3912 | −0.59203 | 0.422812 | 0.526676 |
| 204439_at | IFI44L | interferon-induced protein 44-like | 10964 | 0.779572 | 0.423198 | 0.526676 |
| 204688_at | SGCE | sarcoglycan, epsilon | 8910 | −0.53807 | 0.427632 | 0.530004 |
| 210274_at | MAGEA8 | melanoma antigen family A, 8 | 4107 | −0.55437 | 0.440077 | 0.53411 |
| 218400_at | OAS3 | 2'-5'-oligoadenylate synthetase 3, 100 kDa | 4940 | 0.401878 | 0.441825 | 0.53411 |
| 204033_at | TRIP13 | thyroid hormone receptor interactor 13 | 9319 | −0.53242 | 0.443536 | 0.53411 |
| 205033_s_at | DEFA1 | defensin, alpha 1 | 1667 | −0.68446 | 0.443688 | 0.53411 |
| 209921_at | SLC7A11 | solute carrier family 7 (anionic amino acid transporter light chain, xc- system), member 11 | 23657 | −0.67363 | 0.443971 | 0.53411 |
| 204415_at | IFI6 | interferon, alpha-inducible protein 6 | 2537 | 0.448113 | 0.446822 | 0.53412 |
| 203510_at | MET | met proto-oncogene (hepatocyte growth factor receptor) | 4233 | −0.59266 | 0.449267 | 0.53412 |

TABLE 4-continued

Gene Expression in Women Patients

| ProbesetID | Symbol (Na32 consensus Mar13) | Gene Title (Na32 consensus Mar-13) | Entrez GeneID (consensus Mar-13) | Log2(FC) | P-Value | Adjusted P-Value |
|---|---|---|---|---|---|---|
| 33323_r_at | SFN | stratifin | 2810 | −0.63466 | 0.450623 | 0.53412 |
| 212671_s_at | HLA-DQA1 | major histocompatibility complex, class II, DQ alpha 1 | 3117 | −0.73617 | 0.45086 | 0.53412 |
| 205047_s_at | ASNS | asparagine synthetase (glutamine-hydrolyzing) | 440 | −0.62208 | 0.454871 | 0.534967 |
| 200606_at | DSP | desmoplakin | 1832 | −0.6615 | 0.455463 | 0.534967 |
| 205573_s_at | SNX7 | sorting nexin 7 | 51375 | −0.50744 | 0.460196 | 0.538931 |
| 204684_at | NPTX1 | neuronal pentraxin I | 4884 | −0.48978 | 0.463571 | 0.540181 |
| 204483_at | ENO3 | enolase 3 (beta, muscle) | 2027 | −0.57582 | 0.463984 | 0.540181 |
| 221008_s_at | AGXT2L1 | alanine-glyoxylate aminotransferase 2-like 1 | 64850 | −0.59789 | 0.471814 | 0.545637 |
| 200795_at | SPARCL1 | SPARC-like 1 (hevin) | 8404 | −0.50481 | 0.475562 | 0.546517 |
| 211618_s_at | ALPI | alkaline phosphatase, intestinal | 248 | −0.48827 | 0.477352 | 0.546517 |
| 207140_at | ALPI | alkaline phosphatase, intestinal | 248 | −0.90959 | 0.477868 | 0.546517 |
| 204288_s_at | SORBS2 | sorbin and SH3 domain containing 2 | 8470 | −0.52462 | 0.481567 | 0.546517 |
| 201681_s_at | DLG5 | discs, large homolog 5 (*Drosophila*) | 9231 | −0.47202 | 0.48294 | 0.546517 |
| 203881_s_at | DMD | dystrophin | 1756 | −0.49504 | 0.483193 | 0.546517 |
| 219599_at | EIF4B | eukaryotic translation initiation factor 4B | 1975 | −0.53684 | 0.487369 | 0.548489 |
| 203636_at | MID1 | midline 1 (Opitz/BBB syndrome) | 4281 | −0.45754 | 0.488315 | 0.548489 |
| 214240_at | GAL | galanin/GMAP prepropeptide | 51083 | −0.50116 | 0.489081 | 0.548489 |
| 209094_at | DDAH1 | dimethylarginine dimethylaminohydrolase 1 | 23576 | −0.51772 | 0.495452 | 0.554068 |
| 218631_at | AVPI1 | arginine vasopressin-induced 1 | 60370 | −0.49809 | 0.500208 | 0.556142 |
| 204540_at | EEF1A2 | eukaryotic translation elongation factor 1 alpha 2 | 1917 | −0.42637 | 0.500471 | 0.556142 |
| 210016_at | MYT1L | myelin transcription factor 1-like | 23040 | −0.55739 | 0.502376 | 0.556142 |
| 205289_at | BMP2 | bone morphogenetic protein 2 | 650 | −0.51385 | 0.50342 | 0.556142 |
| 205751_at | SH3GL2 | SH3-domain GRB2-like 2 | 6456 | −0.43617 | 0.50431 | 0.556142 |
| 218541_s_at | C8orf4 | chromosome 8 open reading frame 4 | 56892 | −0.52893 | 0.509174 | 0.559951 |
| 214247_s_at | DKK3 | dickkopf 3 homolog (*Xenopus laevis*) | 27122 | −0.51465 | 0.511216 | 0.560643 |
| 214212_x_at | FERMT2 | fermitin family member 2 | 10979 | −0.44903 | 0.514141 | 0.562297 |
| 208209_s_at | C4BPB | complement component 4 binding protein, beta | 725 | −0.49739 | 0.518251 | 0.565235 |
| 208396_s_at | PDE1A | phosphodiesterase 1A, calmodulin-dependent | 5136 | −0.46854 | 0.526142 | 0.571827 |
| 209942_x_at | MAGEA3 | melanoma antigen family A, 3 | 4102 | −0.58148 | 0.5289 | 0.572135 |
| 214612_x_at | MAGEA6 | melanoma antigen family A, 6 | 4105 | −0.60458 | 0.532798 | 0.57304 |
| 201660_at | ACSL3 | acyl-CoA synthetase long-chain family member 3 | 2181 | −0.42544 | 0.533497 | 0.57304 |
| 204975_at | EMP2 | epithelial membrane protein 2 | 2013 | −0.47324 | 0.536232 | 0.57304 |
| 201667_at | GJA1 | gap junction protein, alpha 1, 43 kDa | 2697 | −0.55978 | 0.536604 | 0.57304 |
| 201291_s_at | TOP2A | topoisomerase (DNA) II alpha 170 kDa | 7153 | −0.51625 | 0.536954 | 0.57304 |
| 204653_at | TFAP2A | transcription factor AP-2 alpha (activating enhancer binding protein 2 alpha) | 7020 | −0.43406 | 0.544838 | 0.579895 |
| 205132_at | ACTC1 | actin, alpha, cardiac muscle 1 | 70 | −0.38632 | 0.55232 | 0.584901 |
| 217127_at | CTH | cystathionase (cystathionine gamma-lyase) | 1491 | −0.44229 | 0.552489 | 0.584901 |
| 205381_at | LRRC17 | leucine rich repeat containing 17 | 10234 | −0.39955 | 0.554073 | 0.585019 |
| 209967_s_at | CREM | cAMP responsive element modulator | 1390 | −0.45103 | 0.557616 | 0.587198 |
| 202672_s_at | ATF3 | activating transcription factor 3 | 467 | 0.490404 | 0.560082 | 0.587586 |
| 209631_s_at | GPR37 | G protein-coupled receptor 37 (endothelin receptor type B-like) | 2861 | −0.44217 | 0.560945 | 0.587586 |
| 221730_at | COL5A2 | collagen, type V, alpha 2 | 1290 | −0.40443 | 0.562469 | 0.587632 |
| 210467_x_at | MAGEA12 | melanoma antigen family A, 12 | 4111 | −0.46503 | 0.566943 | 0.590752 |
| 203083_at | THBS2 | thrombospondin 2 | 7058 | −0.37936 | 0.569007 | 0.59135 |
| 215034_s_at | TM4SF1 | transmembrane 4 L six family member 1 | 4071 | −0.4484 | 0.571318 | 0.592202 |
| 206377_at | FOXF2 | forkhead box F2 | 2295 | −0.36443 | 0.585328 | 0.605143 |
| 213131_at | OLFM1 | olfactomedin 1 | 10439 | −0.35953 | 0.610643 | 0.629676 |
| 202976_s_at | RHOBTB3 | Rho-related BTB domain containing 3 | 22836 | −0.3467 | 0.614674 | 0.63219 |
| 202887_s_at | DDIT4 | DNA-damage-inducible transcript 4 | 54541 | −0.45548 | 0.618537 | 0.63452 |

TABLE 4-continued

Gene Expression in Women Patients

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 203984_s_at | CASP9 | caspase 9, apoptosis-related cysteine peptidase | 842 | −0.35376 | 0.632586 | 0.647259 |
| 205290_s_at | BMP2 | bone morphogenetic protein 2 | 650 | −0.47882 | 0.640799 | 0.653977 |
| 204337_at | RGS4 | regulator of G-protein signaling 4 | 5999 | −0.26477 | 0.708833 | 0.717874 |
| 217867_x_at | BACE2 | beta-site APP-cleaving enzyme 2 | 25825 | −0.2906 | 0.71423 | 0.721499 |
| 212327_at | LIMCH1 | LIM and calponin homology domains 1 | 22998 | −0.28139 | 0.723086 | 0.728591 |
| 202391_at | BASP1 | brain abundant, membrane attached signal protein 1 | 10409 | 0.338672 | 0.73503 | 0.738752 |

TABLE 5

Gene Expression in Men Patients

| Probe set ID | Symbol (Na32 consensus Mar13) | Gene Title (Na32 consensus Mar13) | Entrez Gene ID (consensus Mar-13) | Log2 (FC) | P-Value | Adjusted p-Value |
|---|---|---|---|---|---|---|
| 208730_x_at | RAB2A | RAB2A, member RAS oncogene family | 5862 | −2.23913 | 0.00173 | 0.22461 |
| 201242_s_at | ATP1B1 | ATPase, Na+/K+ transporting, beta 1 polypeptide | 481 | −2.30995 | 0.001936 | 0.22461 |
| 206857_s_at | FKBP1B | FK506 binding protein 1B, 12.6 kDa | 2281 | −2.18904 | 0.003742 | 0.22461 |
| 208636_at | ACTN1 | actinin, alpha 1 | 87 | −1.91968 | 0.005679 | 0.22461 |
| 206493_at | ITGA2B | integrin, alpha 2b (platelet glycoprotein IIb of IIb/IIIa complex, antigen CD41) | 3674 | −2.94275 | 0.006689 | 0.22461 |
| 211986_at | AHNAK | AHNAK nucleoprotein | 79026 | 1.54422 | 0.00875 | 0.22461 |
| 203509_at | SORL1 | sortilin-related receptor, L(DLR class) A repeats containing | 6653 | 1.561462 | 0.009157 | 0.22461 |
| 206494_s_at | ITGA2B | integrin, alpha 2b (platelet glycoprotein IIb of IIb/IIIa complex, antigen CD41) | 3674 | −3.20741 | 0.009481 | 0.22461 |
| 201846_s_at | RYBP | RING1 and YY1 binding protein | 23429 | −1.62523 | 0.009701 | 0.22461 |
| 213229_at | DICER1 | dicer 1, ribonuclease type III | 23405 | −1.70923 | 0.010255 | 0.22461 |
| 202620_s_at | PLOD2 | procollagen-lysine, 2-oxoglutarate 5-dioxygenase 2 | 5352 | −1.86792 | 0.010535 | 0.22461 |
| 202760_s_at | AKAP2 | A kinase (PRKA) anchor protein 2 | 11217 | −1.66558 | 0.010984 | 0.22461 |
| 215813_s_at | PTGS1 | prostaglandin-endoperoxide synthase 1 (prostaglandin G/H synthase and cyclooxygenase) | 5742 | −2.12304 | 0.011371 | 0.22461 |
| 219054_at | NPR3 | natriuretic peptide receptor C/guanylate cyclase C (atrionatriuretic peptide receptor C) | 4883 | 1.815762 | 0.012117 | 0.22461 |
| 37462_i_at | SF3A2 | splicing factor 3a, subunit 2, 66 kDa | 8175 | −1.73475 | 0.01271 | 0.22461 |
| 212266_s_at | SRSF5 | serine/arginine-rich splicing factor 5 | 6430 | 1.814328 | 0.012914 | 0.22461 |
| 201489_at | PPIF | peptidylprolyl isomerase F | 10105 | −1.57807 | 0.013197 | 0.22461 |
| 203096_s_at | RAPGEF2 | Rap guanine nucleotide exchange factor (GEF) 2 | 9693 | −1.90184 | 0.013308 | 0.22461 |
| 205128_x_at | PTGS1 | prostaglandin-endoperoxide synthase 1 (prostaglandin G/H synthase and cyclooxygenase) | 5742 | −1.98263 | 0.013941 | 0.22461 |
| 221059_s_at | COTL1 | coactosin-like 1 (Dictyostelium) | 23406 | −2.38475 | 0.014419 | 0.22461 |
| 212268_at | SERPINB1 | serpin peptidase inhibitor, clade B (ovalbumin), member 1 | 1992 | 1.576065 | 0.015209 | 0.22461 |
| 201012_at | ANXA1 | annexin A1 | 301 | 1.431866 | 0.015821 | 0.22461 |
| 207808_s_at | PROS1 | protein S (alpha) | 5627 | −2.54684 | 0.01834 | 0.22461 |
| 206302_s_at | NUDT4 | nudix (nucleoside diphosphate linked moiety X)-type motif 4 | 11163 | −1.35819 | 0.01853 | 0.22461 |
| 203320_at | SH2B3 | SH2B adaptor protein 3 | 10019 | −1.48125 | 0.019452 | 0.22461 |
| 205647_at | RAD52 | RAD52 homolog (S. cerevisiae) | 5893 | 1.244884 | 0.019524 | 0.22461 |
| 210105_s_at | FYN | FYN oncogene related to SRC, FGR, YES | 2534 | −1.57809 | 0.020057 | 0.22461 |

TABLE 5-continued

Gene Expression in Men Patients

| Probe set ID | Symbol (Na32 consensus Mar13) | Gene Title (Na32 consensus Mar13) | Entrez Gene ID (consensus Mar-13) | Log2 (FC) | P-Value | Adjusted p-Value |
|---|---|---|---|---|---|---|
| 200598_s_at | HSP90B1 | heat shock protein 90 kDa beta (Grp94), member 1 | 7184 | −1.77815 | 0.020317 | 0.22461 |
| 200964_at | UBA1 | ubiquitin-like modifier activating enzyme 1 | 7317 | −1.39778 | 0.020397 | 0.22461 |
| 221493_at | TSPYL1 | TSPY-like 1 | 7259 | 1.744517 | 0.021178 | 0.22461 |
| 206174_s_at | PPP6C | protein phosphatase 6, catalytic subunit | 5537 | −1.35248 | 0.021364 | 0.22461 |
| 202284_s_at | CDKN1A | cyclin-dependent kinase inhibitor 1A (p21, Cip1) | 1026 | −2.00033 | 0.023319 | 0.22461 |
| 206207_at | CLC | Charcot-Leyden crystal protein | 1178 | −1.88811 | 0.023511 | 0.22461 |
| 206655_s_at | GP1BB | glycoprotein Ib (platelet), beta polypeptide | 2812 | −2.92989 | 0.023514 | 0.22461 |
| 206571_s_at | MAP4K4 | mitogen-activated protein kinase kinase kinase kinase 4 | 9448 | −1.25865 | 0.02388 | 0.22461 |
| 209651_at | TGFB1I1 | transforming growth factor beta 1 induced transcript 1 | 7041 | −2.18243 | 0.024567 | 0.22461 |
| 204689_at | HHEX | hematopoietically expressed homeobox | 3087 | 1.462027 | 0.024863 | 0.22461 |
| 205067_at | IL1B | interleukin 1, beta | 3553 | 1.255404 | 0.025653 | 0.22461 |
| 203380_x_at | SRSF5 | serine/arginine-rich splicing factor 5 | 6430 | 1.503237 | 0.025756 | 0.22461 |
| 200923_at | LGALS3BP | lectin, galactoside-binding, soluble, 3 binding protein | 3959 | −1.56076 | 0.025836 | 0.22461 |
| 202949_s_at | FHL2 | four and a half LIM domains 2 | 2274 | −1.37209 | 0.026399 | 0.22461 |
| 201695_s_at | PNP | purine nucleoside phosphorylase | 4860 | −1.41068 | 0.026458 | 0.22461 |
| 220748_s_at | ZNF580 | zinc finger protein 580 | 51157 | −1.34215 | 0.028123 | 0.22461 |
| 217901_at | DSG2 | desmoglein 2 | 1829 | 1.320976 | 0.028803 | 0.22461 |
| 219798_s_at | MEPCE | methylphosphate capping enzyme | 56257 | −1.33001 | 0.029245 | 0.22461 |
| 209381_x_at | SF3A2 | splicing factor 3a, subunit 2, 66 kDa | 8175 | −1.41034 | 0.029259 | 0.22461 |
| 204222_s_at | GLIPR1 | GLI pathogenesis-related 1 | 11010 | 1.439903 | 0.030437 | 0.22461 |
| 221004_s_at | ITM2C | integral membrane protein 2C | 81618 | 1.219859 | 0.030753 | 0.22461 |
| 206049_at | SELP | selectin P (granule membrane protein 140 kDa, antigen CD62) | 6403 | −2.17111 | 0.031111 | 0.22461 |
| 37966_at | PARVB | parvin, beta | 29780 | −2.06542 | 0.031383 | 0.22461 |
| 219681_s_at | RAB11FIP1 | RAB11 family interacting protein 1 (class I) | 80223 | −1.35248 | 0.031529 | 0.22461 |
| 212242_at | TUBA4A | tubulin, alpha 4a | 7277 | −2.39641 | 0.03153 | 0.22461 |
| 218237_s_at | SLC38A1 | solute carrier family 38, member 1 | 81539 | 1.547237 | 0.032294 | 0.22461 |
| 213726_x_at | TUBB4B | tubulin, beta 4B class IVb | 10383 | −1.30164 | 0.032486 | 0.22461 |
| 39402_at | IL1B | interleukin 1, beta | 3553 | 1.235287 | 0.032639 | 0.22461 |
| 209820_s_at | TBL3 | transducin (beta)-like 3 | 10607 | −1.20712 | 0.032649 | 0.22461 |
| 212312_at | BCL2L1 | BCL2-like 1 | 598 | −1.39562 | 0.033632 | 0.22461 |
| 211600_at | PTPRO | protein tyrosine phosphatase, receptor type, O | 5800 | −1.45225 | 0.03416 | 0.22461 |
| 214783_s_at | ANXA11 | annexin A11 | 311 | −1.22688 | 0.034175 | 0.22461 |
| 200616_s_at | MLEC | malectin | 9761 | −1.20495 | 0.034386 | 0.22461 |
| 211926_s_at | MYH9 | myosin, heavy chain 9, non-muscle | 4627 | −1.2641 | 0.034926 | 0.22461 |
| 202059_s_at | KPNA1 | karyopherin alpha 1 (importin alpha 5) | 3836 | −1.12248 | 0.034962 | 0.22461 |
| 221899_at | N4BP2L2 | NEDD4 binding protein 2-like 2 | 10443 | 1.316587 | 0.035008 | 0.22461 |
| 210347_s_at | BCL11A | B-cell CLL/lymphoma 11A (zinc finger protein) | 53335 | 1.273905 | 0.035019 | 0.22461 |
| 221748_s_at | TNS1 | tensin 1 | 7145 | −1.4894 | 0.035747 | 0.22461 |
| 203940_s_at | VASH1 | vasohibin 1 | 22846 | −1.35628 | 0.037032 | 0.22461 |
| 204610_s_at | CCDC85B | coiled-coil domain containing 85B | 11007 | −1.5951 | 0.037663 | 0.22461 |
| 222231_s_at | LRRC59 | leucine rich repeat containing 59 | 55379 | −1.11855 | 0.038092 | 0.22461 |
| 212177_at | PNISR | PNN-interacting serine/arginine-rich protein | 25957 | 1.175547 | 0.038211 | 0.22461 |
| 201692_at | SIGMAR1 | sigma non-opioid intracellular receptor 1 | 10280 | −1.06876 | 0.038307 | 0.22461 |
| 202112_at | VWF | von Willebrand factor | 7450 | −1.36382 | 0.039327 | 0.22461 |
| 206310_at | SPINK2 | serine peptidase inhibitor, Kazal type 2 (acrosin-trypsin inhibitor) | 6691 | 1.568851 | 0.039466 | 0.22461 |
| 218899_s_at | BAALC | brain and acute leukemia, cytoplasmic | 79870 | 1.51143 | 0.039771 | 0.22461 |
| 208308_s_at | GPI | glucose-6-phosphate isomerase | 2821 | −1.24247 | 0.040139 | 0.22461 |
| 221834_at | LONP2 | lon peptidase 2, peroxisomal | 83752 | 1.261036 | 0.040303 | 0.22461 |
| 210719_s_at | HMG20B | high mobility group 20B | 10362 | −1.39762 | 0.040525 | 0.22461 |
| 200808_s_at | ZYX | zyxin | 7791 | −1.54764 | 0.041293 | 0.22461 |

TABLE 5-continued

Gene Expression in Men Patients

| Probe set ID | Symbol (Na32 consensus Mar13) | Gene Title (Na32 consensus Mar13) | Entrez Gene ID (consensus Mar-13) | Log2 (FC) | P-Value | Adjusted p-Value |
|---|---|---|---|---|---|---|
| 209945_s_at | GSK3B | glycogen synthase kinase 3 beta | 2932 | −1.28118 | 0.041713 | 0.22461 |
| 208637_x_at | ACTN1 | actinin, alpha 1 | 87 | −1.74284 | 0.041994 | 0.22461 |
| 209088_s_at | UBN1 | ubinuclein 1 | 29855 | −1.14187 | 0.042143 | 0.22461 |
| 211005_at | LAT | linker for activation of T cells | 27040 | −1.83145 | 0.042364 | 0.22461 |
| 218131_s_at | GATAD2A | GATA zinc finger domain containing 2A | 54815 | −1.22531 | 0.042653 | 0.22461 |
| 202729_s_at | LTBP1 | latent transforming growth factor beta binding protein 1 | 4052 | −1.87245 | 0.042694 | 0.22461 |
| 219357_at | GTPBP1 | GTP binding protein 1 | 9567 | −1.11964 | 0.042776 | 0.22461 |
| 201980_s_at | RSU1 | Ras suppressor protein 1 | 6251 | −1.33636 | 0.043967 | 0.22461 |
| 211671_s_at | NR3C1 | nuclear receptor subfamily 3, group C, member 1 (glucocorticoid receptor) | 2908 | 1.257541 | 0.044183 | 0.22461 |
| 203007_x_at | LYPLA1 | lysophospholipase I | 10434 | −1.24485 | 0.04487 | 0.22461 |
| 210299_s_at | FHL1 | four and a half LIM domains 1 | 2273 | 1.459962 | 0.045279 | 0.22461 |
| 210783_x_at | CLEC11A | C-type lectin domain family 11, member A | 6320 | −1.14617 | 0.045531 | 0.22461 |
| 209154_at | TAX1BP3 | Tax1 (human T-cell leukemia virus type I) binding protein 3 | 30851 | −1.80171 | 0.045558 | 0.22461 |
| 212279_at | TMEM97 | transmembrane protein 97 | 27346 | −1.20825 | 0.046373 | 0.22461 |
| 202102_s_at | BRD4 | bromodomain containing 4 | 23476 | −1.31832 | 0.046377 | 0.22461 |
| 200719_at | SKP1 | S-phase kinase-associated protein 1 | 6500 | −1.18511 | 0.046416 | 0.22461 |
| 213416_at | ITGA4 | integrin, alpha 4 (antigen CD49D, alpha 4 subunit of VLA-4 receptor) | 3676 | 1.500306 | 0.046971 | 0.22461 |
| 201251_at | PKM | pyruvate kinase, muscle | 5315 | −1.61415 | 0.04732 | 0.22461 |
| 220094_s_at | CCDC90A | coiled-coil domain containing 90A | 63933 | −1.33066 | 0.048464 | 0.22461 |
| 202275_at | G6PD | glucose-6-phosphate dehydrogenase | 2539 | −1.46785 | 0.04883 | 0.22461 |
| 214146_s_at | PPBP | pro-platelet basic protein (chemokine (C-X-C motif) ligand 7) | 5473 | −2.44242 | 0.049566 | 0.22461 |
| 204081_at | NRGN | neurogranin (protein kinase C substrate, RC3) | 4900 | −2.56374 | 0.049579 | 0.22461 |
| 209868_s_at | RBMS1 | RNA binding motif, single stranded interacting protein 1 | 5937 | 1.165728 | 0.050155 | 0.22461 |
| 211922_s_at | CAT | catalase | 847 | 1.232958 | 0.051088 | 0.22461 |
| 222310_at | SCAF4 | SR-related CTD-associated factor 4 | 57466 | 1.077534 | 0.05119 | 0.22461 |
| 200697_at | HK1 | hexokinase 1 | 3098 | −1.1627 | 0.051949 | 0.22461 |
| 200706_s_at | LITAF | lipopolysaccharide-induced TNF factor | 9516 | 1.091394 | 0.052104 | 0.22461 |
| 220964_s_at | RAB1B | RAB1B, member RAS oncogene family | 81876 | −1.24067 | 0.052429 | 0.22461 |
| 210215_at | TFR2 | transferrin receptor 2 | 7036 | −1.65926 | 0.052589 | 0.22461 |
| 201260_s_at | SYPL1 | synaptophysin-like 1 | 6856 | 1.519931 | 0.052716 | 0.22461 |
| 221771_s_at | MPHOSPH8 | M-phase phosphoprotein 8 | 54737 | 1.277564 | 0.053033 | 0.22461 |
| 210986_s_at | TPM1 | tropomyosin 1 (alpha) | 7168 | −1.54226 | 0.053308 | 0.22461 |
| 203674_at | HELZ | helicase with zinc finger | 9931 | 1.115528 | 0.053318 | 0.22461 |
| 207238_s_at | PTPRC | protein tyrosine phosphatase, receptor type, C | 5788 | 1.189131 | 0.053365 | 0.22461 |
| 201864_at | GDI1 | GDP dissociation inhibitor 1 | 2664 | −1.17328 | 0.053513 | 0.22461 |
| 212036_s_at | PNN | pinin, desmosome associated protein | 5411 | 1.514285 | 0.053837 | 0.22461 |
| 213521_at | PTPN18 | protein tyrosine phosphatase, non-receptor type 18 (brain-derived) | 26469 | −1.32436 | 0.05412 | 0.22461 |
| 202644_s_at | TNFAIP3 | tumor necrosis factor, alpha-induced protein 3 | 7128 | −1.72075 | 0.054213 | 0.22461 |
| 219090_at | SLC24A3 | solute carrier family 24 (sodium/potassium/calcium exchanger), member 3 | 57419 | −1.33752 | 0.054392 | 0.22461 |
| 209117_at | WBP2 | WW domain binding protein 2 | 23558 | −1.30969 | 0.054585 | 0.22461 |
| 209160_at | AKR1C3 | aldo-keto reductase family 1, member C3 | 8644 | 1.332339 | 0.054731 | 0.22461 |
| 203085_s_at | TGFB1 | transforming growth factor, beta 1 | 7040 | −1.75422 | 0.055437 | 0.22461 |
| 200613_at | AP2M1 | adaptor-related protein complex 2, mu 1 subunit | 1173 | −1.26768 | 0.05634 | 0.22461 |
| 212406_s_at | PCMTD2 | protein-L-isoaspartate (D-aspartate) O-methyltransferase domain containing 2 | 55251 | 1.40919 | 0.057779 | 0.22461 |

TABLE 5-continued

Gene Expression in Men Patients

| Probe set ID | Symbol (Na32 consensus Mar13) | Gene Title (Na32 consensus Mar13) | Entrez Gene ID (consensus Mar-13) | Log2 (FC) | P-Value | Adjusted p-Value |
|---|---|---|---|---|---|---|
| 212281_s_at | TMEM97 | transmembrane protein 97 | 27346 | −1.25212 | 0.058007 | 0.22461 |
| 222113_s_at | EPS15L1 | epidermal growth factor receptor pathway substrate 15-like 1 | 58513 | −1.22321 | 0.058228 | 0.22461 |
| 41047_at | C9orf16 | chromosome 9 open reading frame 16 | 79095 | −1.3784 | 0.058369 | 0.22461 |
| 202083_s_at | SEC14L1 | SEC14-like 1 (S. cerevisiae) | 6397 | −1.60251 | 0.058462 | 0.22461 |
| 43544_at | MED16 | mediator complex subunit 16 | 10025 | −1.37264 | 0.059358 | 0.22461 |
| 208398_s_at | TBPL1 | TBP-like 1 | 9519 | −1.09285 | 0.060353 | 0.22461 |
| 200001_at | CAPNS1 | calpain, small subunit 1 | 826 | −1.38469 | 0.060708 | 0.22461 |
| 203321_s_at | ADNP2 | ADNP homeobox 2 | 22850 | −1.14224 | 0.060952 | 0.22461 |
| 214752_x_at | FLNA | filamin A, alpha | 2316 | −1.51816 | 0.061564 | 0.22461 |
| 221539_at | EIF4EBP1 | eukaryotic translation initiation factor 4E binding protein 1 | 1978 | −1.09846 | 0.062496 | 0.22461 |
| 208860_s_at | ATRX | alpha thalassemia/mental retardation syndrome X-linked | 546 | 1.305128 | 0.06313 | 0.22461 |
| 215933_s_at | HHEX | hematopoietically expressed homeobox | 3087 | 1.399528 | 0.063251 | 0.22461 |
| 214753_at | N4BP2L2 | NEDD4 binding protein 2-like 2 | 10443 | 1.043575 | 0.063268 | 0.22461 |
| 208284_x_at | GGT1 | gamma-glutamyltransferase 1 | 2678 | −1.13931 | 0.063281 | 0.22461 |
| 203163_at | KATNB1 | katanin p80 (WD repeat containing) subunit B 1 | 10300 | −1.04468 | 0.06434 | 0.22461 |
| 209301_at | CA2 | carbonic anhydrase II | 760 | −1.80993 | 0.064349 | 0.22461 |
| 204480_s_at | C9orf16 | chromosome 9 open reading frame 16 | 79095 | −1.50337 | 0.064729 | 0.22461 |
| 205668_at | LY75 | lymphocyte antigen 75 | 4065 | 1.143917 | 0.064806 | 0.22461 |
| 211047_x_at | AP2S1 | adaptor-related protein complex 2, sigma 1 subunit | 1175 | −1.1541 | 0.065359 | 0.22461 |
| 201563_at | SORD | sorbitol dehydrogenase | 6652 | −1.02865 | 0.066229 | 0.225836 |
| 214246_x_at | MINK1 | misshapen-like kinase 1 | 50488 | −1.37631 | 0.066383 | 0.225836 |
| 212563_at | BOP1 | block of proliferation 1 | 23246 | −1.07647 | 0.067055 | 0.226454 |
| 215706_x_at | ZYX | zyxin | 7791 | −1.14429 | 0.067478 | 0.226454 |
| 215116_s_at | DNM1 | dynamin 1 | 1759 | −1.02496 | 0.067568 | 0.226454 |
| 209044_x_at | SF3B4 | splicing factor 3b, subunit 4, 49 kDa | 10262 | −1.14403 | 0.069176 | 0.227703 |
| 208977_x_at | TUBB4B | tubulin, beta 4B class IVb | 10383 | −1.06783 | 0.069385 | 0.227703 |
| 203175_at | RHOG | ras homolog family member G | 391 | −1.12466 | 0.07026 | 0.227703 |
| 212739_s_at | NME4 | NME/NM23 nucleoside diphosphate kinase 4 | 4833 | −1.18 | 0.070482 | 0.227703 |
| 200734_s_at | ARF3 | ADP-ribosylation factor 3 | 377 | −1.10487 | 0.070887 | 0.227703 |
| 213036_x_at | ATP2A3 | ATPase, Ca++ transporting, ubiquitous | 489 | −1.21253 | 0.07161 | 0.227703 |
| 210428_s_at | HGS | hepatocyte growth factor-regulated tyrosine kinase substrate | 9146 | −1.08114 | 0.071709 | 0.227703 |
| 206272_at | SPHAR | S-phase response (cyclin related) | 10638 | −1.37986 | 0.071711 | 0.227703 |
| 200742_s_at | TPP1 | tripeptidyl peptidase I | 1200 | −1.44492 | 0.071977 | 0.227703 |
| 202944_at | NAGA | N-acetylgalactosaminidase, alpha- | 4668 | −1.0861 | 0.073258 | 0.229457 |
| 216841_s_at | SOD2 | superoxide dismutase 2, mitochondrial | 6648 | −1.07023 | 0.073344 | 0.229457 |
| 203414_at | MMD | monocyte to macrophage differentiation-associated | 23531 | −1.57415 | 0.073626 | 0.229457 |
| 215438_x_at | GSPT1 | G1 to S phase transition 1 | 2935 | −1.03476 | 0.074204 | 0.229457 |
| 217918_at | DYNLRB1 | dynein, light chain, roadblock-type 1 | 83658 | −1.21177 | 0.07474 | 0.229995 |
| 204628_s_at | ITGB3 | integrin, beta 3 (platelet glycoprotein IIIa, antigen CD61) | 3690 | −1.70942 | 0.076434 | 0.233122 |
| 214450_at | CTSW | cathepsin W | 1521 | −1.09904 | 0.076703 | 0.233122 |
| 203262_s_at | FAM50A | family with sequence similarity 50, member A | 9130 | −1.05318 | 0.077683 | 0.233565 |
| 216956_s_at | ITGA2B | integrin, alpha 2b (platelet glycoprotein IIb of IIb/IIIa complex, antigen CD41) | 3674 | −2.02417 | 0.07797 | 0.233565 |
| 201639_s_at | CPSF1 | cleavage and polyadenylation specific factor 1, 160 kDa | 29894 | −1.05345 | 0.079365 | 0.234598 |
| 36711_at | MAFF | v-maf musculoaponeurotic fibrosarcoma oncogene homolog F (avian) | 23764 | −2.66779 | 0.079702 | 0.234598 |
| 210910_s_at | POMZP3 | POM121 and ZP3 fusion | 22932 | −0.98043 | 0.080921 | 0.234598 |
| 206390_x_at | PF4 | platelet factor 4 | 5196 | −2.17632 | 0.081141 | 0.234598 |
| 218443_s_at | DAZAP1 | DAZ associated protein 1 | 26528 | −0.99013 | 0.081405 | 0.234598 |

TABLE 5-continued

| Gene Expression in Men Patients | | | | | | |
|---|---|---|---|---|---|---|
| Probe set ID | Symbol (Na32 consensus Mar13) | Gene Title (Na32 consensus Mar13) | Entrez Gene ID (consensus Mar-13) | Log2 (FC) | P-Value | Adjusted p-Value |
| 201052_s_at | PSMF1 | proteasome (prosome, macropain) inhibitor subunit 1 (PI31) | 9491 | −1.17083 | 0.081493 | 0.234598 |
| 211716_x_at | ARHGDIA | Rho GDP dissociation inhibitor (GDI) alpha | 396 | −1.05994 | 0.081516 | 0.234598 |
| 200839_s_at | CTSB | cathepsin B | 1508 | −1.23855 | 0.081791 | 0.234598 |
| 203561_at | FCGR2A | Fc fragment of IgG, low affinity IIa, receptor (CD32) | 2212 | −1.50392 | 0.082039 | 0.234598 |
| 218611_at | IER5 | immediate early response 5 | 51278 | −1.41626 | 0.082127 | 0.234598 |
| 202619_s_at | PLOD2 | procollagen-lysine, 2-oxoglutarate 5-dioxygenase 2 | 5352 | −1.06567 | 0.082911 | 0.234625 |
| 204627_s_at | ITGB3 | integrin, beta 3 (platelet glycoprotein IIIa, antigen CD61) | 3690 | −2.11954 | 0.083412 | 0.234625 |
| 201224_s_at | SRRM1 | serine/arginine repetitive matrix 1 | 10250 | −1.23842 | 0.08352 | 0.234625 |
| 217736_s_at | EIF2AK1 | eukaryotic translation initiation factor 2-alpha kinase 1 | 27102 | −1.07432 | 0.083557 | 0.234625 |
| 200649_at | NUCB1 | nucleobindin 1 | 4924 | −1.0434 | 0.085339 | 0.23596 |
| 209555_s_at | CD36 | CD36 molecule (thrombospondin receptor) | 948 | −1.82889 | 0.086873 | 0.23596 |
| 212520_at | SMARCA4 | SWI/SNF related, matrix associated, actin dependent regulator of chromatin, subfamily a, member 4 | 6597 | −1.12786 | 0.086976 | 0.23596 |
| 209367_at | STXBP2 | syntaxin binding protein 2 | 6813 | −1.12693 | 0.087289 | 0.23596 |
| 53071_s_at | OGFOD3 | 2-oxoglutarate and iron-dependent oxygenase domain containing 3 | 79701 | −1.02384 | 0.087372 | 0.23596 |
| 221953_s_at | MMP24 | matrix metallopeptidase 24 (membrane-inserted) | 10893 | −1.14292 | 0.087422 | 0.23596 |
| 212640_at | PTPLB | protein tyrosine phosphatase-like (proline instead of catalytic arginine), member b | 201562 | 1.184144 | 0.087703 | 0.23596 |
| 201797_s_at | VARS | valyl-tRNA synthetase | 7407 | −0.95792 | 0.087831 | 0.23596 |
| 204232_at | FCER1G | Fc fragment of IgE, high affinity I, receptor for; gamma polypeptide | 2207 | −1.72735 | 0.088324 | 0.236346 |
| 202201_at | BLVRB | biliverdin reductase B (flavin reductase (NADPH)) | 645 | −1.03625 | 0.088981 | 0.236552 |
| 203192_at | ABCB6 | ATP-binding cassette, sub-family B (MDR/TAP), member 6 | 10058 | −1.03424 | 0.090022 | 0.237141 |
| 221829_s_at | TNPO1 | transportin 1 | 3842 | −1.16481 | 0.090459 | 0.237366 |
| 213016_at | BBX | bobby sox homolog (Drosophila) | 56987 | −1.01796 | 0.091007 | 0.237691 |
| 207574_s_at | GADD45B | growth arrest and DNA-damage-inducible, beta | 4616 | −1.53642 | 0.091507 | 0.237691 |
| 207134_x_at | TPSB2 | tryptase beta 2 (gene/pseudogene) | 64499 | −1.2023 | 0.092025 | 0.237791 |
| 211962_s_at | ZFP36L1 | ZFP36 ring finger protein-like 1 | 677 | −1.08806 | 0.094727 | 0.239603 |
| 201412_at | LRP10 | low density lipoprotein receptor-related protein 10 | 26020 | −1.16907 | 0.095687 | 0.239603 |
| 200859_x_at | FLNA | filamin A, alpha | 2316 | −1.28906 | 0.09598 | 0.239603 |
| 201760_s_at | WSB2 | WD repeat and SOCS box containing 2 | 55884 | −0.9579 | 0.097393 | 0.239603 |
| 212256_at | GALNT10 | UDP-N-acetyl-alpha-D-galactosamine: polypeptide N-acetylgalactosaminyltransferase 10 (GalNAc-T10) | 55568 | −0.9355 | 0.097486 | 0.239603 |
| 202411_at | IFI27 | interferon, alpha-inducible protein 27 | 3429 | −1.2038 | 0.097807 | 0.239603 |
| 209190_s_at | DIAPH1 | diaphanous homolog 1 (Drosophila) | 1729 | −1.03246 | 0.097812 | 0.239603 |
| 212886_at | CCDC69 | coiled-coil domain containing 69 | 26112 | −1.0779 | 0.098162 | 0.239603 |
| 215087_at | C15orf39 | chromosome 15 open reading frame 39 | 56905 | −1.19136 | 0.09937 | 0.239603 |
| 211417_x_at | GGT1 | gamma-glutamyltransferase 1 | 2678 | −0.97792 | 0.09942 | 0.239603 |
| 218039_at | NUSAP1 | nucleolar and spindle associated protein 1 | 51203 | −1.16811 | 0.100201 | 0.239603 |
| 215535_s_at | AGPAT1 | 1-acylglycerol-3-phosphate O-acyltransferase 1 | 10554 | −1.14266 | 0.10071 | 0.239603 |
| 219938_s_at | PSTPIP2 | proline-serine-threonine phosphatase interacting protein 2 | 9050 | −1.02201 | 0.100884 | 0.239603 |
| 213746_s_at | FLNA | filamin A, alpha | 2316 | −1.37828 | 0.100915 | 0.239603 |

TABLE 5-continued

Gene Expression in Men Patients

| Probe set ID | Symbol (Na32 consensus Mar13) | Gene Title (Na32 consensus Mar13) | Entrez Gene ID (consensus Mar-13) | Log2 (FC) | P-Value | Adjusted p-Value |
|---|---|---|---|---|---|---|
| 200611_s_at | WDR1 | WD repeat domain 1 | 9948 | −1.08654 | 0.101143 | 0.239603 |
| 208615_s_at | PTP4A2 | protein tyrosine phosphatase type IVA, member 2 | 8073 | −1.16457 | 0.101287 | 0.239603 |
| 208002_s_at | ACOT7 | acyl-CoA thioesterase 7 | 11332 | −0.98943 | 0.101855 | 0.239603 |
| 201280_s_at | DAB2 | Dab, mitogen-responsive phosphoprotein, homolog 2 (Drosophila) | 1601 | −1.47352 | 0.10199 | 0.239603 |
| 217529_at | ORAI2 | ORAI calcium release-activated calcium modulator 2 | 80228 | −0.94855 | 0.102013 | 0.239603 |
| 214054_at | DOK2 | docking protein 2, 56 kDa | 9046 | −1.44148 | 0.102476 | 0.239603 |
| 222043_at | CLU | clusterin | 1191 | −1.34754 | 0.102489 | 0.239603 |
| 201059_at | CTTN | cortactin | 2017 | −1.75221 | 0.102546 | 0.239603 |
| 220239_at | KLHL7 | kelch-like family member 7 | 55975 | −1.04556 | 0.102824 | 0.239603 |
| 201950_x_at | CAPZB | capping protein (actin filament) muscle Z-line, beta | 832 | −0.9793 | 0.10316 | 0.239603 |
| 207196_s_at | TNIP1 | TNFAIP3 interacting protein 1 | 10318 | −1.00708 | 0.103374 | 0.239603 |
| 211160_x_at | ACTN1 | actinin, alpha 1 | 87 | −1.26927 | 0.103783 | 0.239603 |
| 209350_s_at | GPS2 | G protein pathway suppressor 2 | 2874 | −1.10209 | 0.103921 | 0.239603 |
| 219667_s_at | BANK1 | B-cell scaffold protein with ankyrin repeats 1 | 55024 | −1.00308 | 0.104821 | 0.239603 |
| 210075_at | MARCH2 | membrane-associated ring finger (C3HC4) 2, E3 ubiquitin protein ligase | 51257 | −1.43742 | 0.104896 | 0.239603 |
| 201170_s_at | BHLHE40 | basic helix-loop-helix family, member e40 | 8553 | −1.52602 | 0.105204 | 0.239603 |
| 204254_s_at | VDR | vitamin D (1,25-dihydroxyvitamin D3) receptor | 7421 | −1.04354 | 0.10546 | 0.239603 |
| 210128_s_at | LTB4R | leukotriene B4 receptor | 1241 | −0.92553 | 0.105789 | 0.239603 |
| 221210_s_at | NPL | N-acetylneuraminate pyruvate lyase (dihydrodipicolinate synthase) | 80896 | −1.20989 | 0.105822 | 0.239603 |
| 210512_s_at | VEGFA | vascular endothelial growth factor A | 7422 | −1.15461 | 0.10674 | 0.240343 |
| 202499_s_at | SLC2A3 | solute carrier family 2 (facilitated glucose transporter), member 3 | 6515 | −1.58321 | 0.106858 | 0.240343 |
| 201125_s_at | ITGB5 | integrin, beta 5 | 3693 | −1.33107 | 0.107555 | 0.24035 |
| 206414_s_at | ASAP2 | ArfGAP with SH3 domain, ankyrin repeat and PH domain 2 | 8853 | −1.34473 | 0.107572 | 0.24035 |
| 201360_at | CST3 | cystatin C | 1471 | −1.68937 | 0.108964 | 0.242661 |
| 215047_at | TRIM58 | tripartite motif containing 58 | 25893 | −0.99092 | 0.11023 | 0.243627 |
| 204493_at | BID | BH3 interacting domain death agonist | 637 | −0.9825 | 0.110478 | 0.243627 |
| 202728_s_at | LTBP1 | latent transforming growth factor beta binding protein 1 | 4052 | −1.27115 | 0.113678 | 0.246714 |
| 209969_s_at | STAT1 | signal transducer and activator of transcription 1, 91 kDa | 6772 | −1.15673 | 0.113691 | 0.246714 |
| 205241_at | SCO2 | SCO2 cytochrome c oxidase assembly protein | 9997 | −1.4845 | 0.114175 | 0.246714 |
| 203017_s_at | SSX2IP | synovial sarcoma, X breakpoint 2 interacting protein | 117178 | −0.94238 | 0.114827 | 0.246714 |
| 203833_s_at | TGOLN2 | trans-golgi network protein 2 | 10618 | −0.93445 | 0.115059 | 0.246714 |
| 205269_at | LCP2 | lymphocyte cytosolic protein 2 (SH2 domain containing leukocyte protein of 76 kDa) | 3937 | −0.97027 | 0.115226 | 0.246714 |
| 209522_s_at | CRAT | carnitine O-acetyltransferase | 1384 | −1.01234 | 0.116038 | 0.246714 |
| 204629_at | PARVB | parvin, beta | 29780 | −1.33625 | 0.116976 | 0.246714 |
| 200609_s_at | WDR1 | WD repeat domain 1 | 9948 | −0.99605 | 0.11718 | 0.246714 |
| 203680_at | PRKAR2B | protein kinase, cAMP-dependent, regulatory, type II, beta | 5577 | −1.23212 | 0.117344 | 0.246714 |
| 208918_s_at | NADK | NAD kinase | 65220 | −1.16887 | 0.119342 | 0.248598 |
| 213716_s_at | SECTM1 | secreted and transmembrane 1 | 6398 | −1.08088 | 0.119767 | 0.248718 |
| 221269_s_at | SH3BGRL3 | SH3 domain binding glutamic acid-rich protein like 3 | 83442 | −1.35229 | 0.120323 | 0.24911 |
| 212492_s_at | KDM4B | lysine (K)-specific demethylase 4B | 23030 | −0.91067 | 0.121784 | 0.251366 |
| 209729_at | GAS2L1 | growth arrest-specific 2 like 1 | 10634 | −1.27348 | 0.12433 | 0.255074 |
| 204928_s_at | SLC10A3 | solute carrier family 10 (sodium/bile acid cotransporter family), member 3 | 8273 | −1.17192 | 0.124419 | 0.255074 |
| 205390_s_at | ANK1 | ankyrin 1, erythrocytic | 286 | −0.88253 | 0.124711 | 0.255074 |
| 211795_s_at | FYB | FYN binding protein | 2533 | −1.18122 | 0.125242 | 0.255154 |
| 31845_at | ELF4 | E74-like factor 4 (ets domain transcription factor) | 2000 | −0.94729 | 0.125919 | 0.255154 |

TABLE 5-continued

Gene Expression in Men Patients

| Probe set ID | Symbol (Na32 consensus Mar13) | Gene Title (Na32 consensus Mar13) | Entrez Gene ID (consensus Mar-13) | Log2 (FC) | P-Value | Adjusted p-Value |
|---|---|---|---|---|---|---|
| 212573_at | ENDOD1 | endonuclease domain containing 1 | 23052 | −1.40577 | 0.126395 | 0.255154 |
| 209560_s_at | DLK1 | delta-like 1 homolog (Drosophila) | 8788 | −1.19672 | 0.126533 | 0.255154 |
| 201095_at | DAP | death-associated protein | 1611 | −1.11419 | 0.126929 | 0.255154 |
| 212840_at | UBXN7 | UBX domain protein 7 | 26043 | −1.01058 | 0.127011 | 0.255154 |
| 221267_s_at | FAM108A1 | family with sequence similarity 108, member A1 | 81926 | −1.01634 | 0.128163 | 0.256705 |
| 208074_s_at | AP2S1 | adaptor-related protein complex 2, sigma 1 subunit | 1175 | −0.99964 | 0.128569 | 0.256758 |
| 200990_at | TRIM28 | tripartite motif containing 28 | 10155 | −1.00558 | 0.129664 | 0.257321 |
| 209839_at | DNM3 | dynamin 3 | 26052 | −1.34338 | 0.130264 | 0.257321 |
| 201714_at | TUBG1 | tubulin, gamma 1 | 7283 | −0.88297 | 0.130361 | 0.257321 |
| 200752_s_at | CAPN1 | calpain 1, (mu/I) large subunit | 823 | −0.92096 | 0.131139 | 0.258085 |
| 220751_s_at | FAXDC2 | fatty acid hydroxylase domain containing 2 | 10826 | −1.32403 | 0.132172 | 0.258731 |
| 210357_s_at | SMOX | spermine oxidase | 54498 | −1.03467 | 0.132612 | 0.258731 |
| 218175_at | CCDC92 | coiled-coil domain containing 92 | 80212 | −1.09884 | 0.132796 | 0.258731 |
| 204000_at | GNB5 | guanine nucleotide binding protein (G protein), beta 5 | 10681 | −1.19778 | 0.133164 | 0.258731 |
| 217748_at | ADIPOR1 | adiponectin receptor 1 | 51094 | −0.93144 | 0.13362 | 0.258731 |
| 207389_at | GP1BA | glycoprotein Ib (platelet), alpha polypeptide | 2811 | −1.24025 | 0.134051 | 0.258731 |
| 217992_s_at | EFHD2 | EF-hand domain family, member D2 | 79180 | −1.0245 | 0.134143 | 0.258731 |
| 200884_at | CKB | creatine kinase, brain | 1152 | −0.88314 | 0.13483 | 0.259317 |
| 206145_at | RHAG | Rh-associated glycoprotein | 6005 | −1.17935 | 0.13531 | 0.259504 |
| 220757_s_at | UBXN6 | UBX domain protein 6 | 80700 | −0.88851 | 0.136128 | 0.259746 |
| 213274_s_at | CTSB | cathepsin B | 1508 | −0.90565 | 0.136204 | 0.259746 |
| 202464_s_at | PFKFB3 | 6-phosphofructo-2-kinase/fructose-2,6-biphosphatase 3 | 5209 | −1.06242 | 0.137167 | 0.26039 |
| 202665_s_at | WIPF1 | WAS/WASL interacting protein family, member 1 | 7456 | −1.08477 | 0.13731 | 0.26039 |
| 206488_s_at | CD36 | CD36 molecule (thrombospondin receptor) | 948 | −1.53958 | 0.138985 | 0.260645 |
| 212089_at | LMNA | lamin A/C | 4000 | −0.92285 | 0.140733 | 0.261597 |
| 205436_s_at | H2AFX | H2A histone family, member X | 3014 | −1.00358 | 0.140821 | 0.261597 |
| 206834_at | HBD | hemoglobin, delta | 3045 | −1.42844 | 0.141235 | 0.261597 |
| 209919_x_at | GGT1 | gamma-glutamyltransferase 1 | 2678 | −0.89741 | 0.141427 | 0.261597 |
| 207741_x_at | TPSAB1 | tryptase alpha/beta 1 | 7177 | −1.06406 | 0.142116 | 0.261597 |
| 31874_at | GAS2L1 | growth arrest-specific 2 like 1 | 10634 | −1.54272 | 0.142456 | 0.261597 |
| 201700_at | CCND3 | cyclin D3 | 896 | −0.99741 | 0.142709 | 0.261597 |
| 205683_x_at | TPSAB1 | tryptase alpha/beta 1 | 7177 | −1.01525 | 0.142713 | 0.261597 |
| 201061_s_at | STOM | stomatin | 2040 | −1.01078 | 0.14297 | 0.261597 |
| 203016_s_at | SSX2IP | synovial sarcoma, X breakpoint 2 interacting protein | 117178 | −0.95396 | 0.143425 | 0.261722 |
| 220496_at | CLEC1B | C-type lectin domain family 1, member B | 51266 | −1.54811 | 0.14406 | 0.262175 |
| 209929_s_at | IKBKG | inhibitor of kappa light polypeptide gene enhancer in B-cells, kinase gamma | 8517 | −0.89402 | 0.145589 | 0.262942 |
| 37028_at | PPP1R15A | protein phosphatase 1, regulatory subunit 15A | 23645 | −1.05228 | 0.14582 | 0.262942 |
| 212769_at | TLE3 | transducin-like enhancer of split 3 (E(sp1) homolog, Drosophila) | 7090 | −0.90676 | 0.14604 | 0.262942 |
| 203581_at | RAB4A | RAB4A, member RAS oncogene family | 5867 | −1.01651 | 0.146743 | 0.262942 |
| 213956_at | CEP350 | centrosomal protein 350 kDa | 9857 | −0.85883 | 0.146813 | 0.262942 |
| 215382_x_at | TPSB2 | tryptase beta 2 (gene/pseudogene) | 64499 | −0.977 | 0.148064 | 0.263547 |
| 201830_s_at | NET1 | neuroepithelial cell transforming 1 | 10276 | −0.9677 | 0.148301 | 0.263547 |
| 201693_s_at | EGR1 | early growth response 1 | 1958 | −1.15545 | 0.148318 | 0.263547 |
| 215498_s_at | MAP2K3 | mitogen-activated protein kinase kinase 3 | 5606 | −1.08177 | 0.149281 | 0.264012 |
| 204026_s_at | ZWINT | ZW10 interactor, kinetochore protein | 11130 | −1.12549 | 0.149413 | 0.264012 |
| 209170_s_at | GPM6B | glycoprotein M6B | 2824 | 0.976338 | 0.14975 | 0.264012 |
| 221211_s_at | MAP3K7CL | MAP3K7 C-terminal like | 56911 | −1.30326 | 0.150281 | 0.264261 |
| 203045_at | NINJ1 | ninjurin 1 | 4814 | −1.13628 | 0.15069 | 0.264293 |
| 210084_x_at | TPSAB1 | tryptase alpha/beta 1 | 7177 | −0.99706 | 0.151879 | 0.264649 |
| 207945_s_at | CSNK1D | casein kinase 1, delta | 1453 | −0.90784 | 0.152234 | 0.264649 |

TABLE 5-continued

Gene Expression in Men Patients

| Probe set ID | Symbol (Na32 consensus Mar13) | Gene Title (Na32 consensus Mar13) | Entrez Gene ID (consensus Mar-13) | Log2 (FC) | P-Value | Adjusted p-Value |
|---|---|---|---|---|---|---|
| 204158_s_at | TCIRG1 | T-cell, immune regulator 1, ATPase, H+ transporting, lysosomal V0 subunit A3 | 10312 | −1.17593 | 0.152276 | 0.264649 |
| 200766_at | CTSD | cathepsin D | 1509 | −0.93104 | 0.153066 | 0.265027 |
| 215819_s_at | RHCE | Rh blood group, CcEe antigens | 6006 | −0.9917 | 0.154157 | 0.266177 |
| 203485_at | RTN1 | reticulon 1 | 6252 | −1.21235 | 0.154517 | 0.266177 |
| 215240_at | ITGB3 | integrin, beta 3 (platelet glycoprotein IIIa, antigen CD61) | 3690 | −1.44118 | 0.156 | 0.267603 |
| 201761_at | MTHFD2 | methylenetetrahydrofolate dehydrogenase (NADP+ dependent) 2, methenyltetrahydrofolate cyclohydrolase | 10797 | −0.98494 | 0.156692 | 0.267603 |
| 201904_s_at | CTDSPL | CTD (carboxy-terminal domain, RNA polymerase II, polypeptide A) small phosphatase-like | 10217 | −0.91323 | 0.156796 | 0.267603 |
| 201906_s_at | CTDSPL | CTD (carboxy-terminal domain, RNA polymerase II, polypeptide A) small phosphatase-like | 10217 | −0.94383 | 0.156925 | 0.267603 |
| 203854_at | CFI | complement factor I | 3426 | 0.869863 | 0.158526 | 0.268092 |
| 204925_at | CTNS | cystinosin, lysosomal cystine transporter | 1497 | −0.97532 | 0.158632 | 0.268092 |
| 204306_s_at | CD151 | CD151 molecule (Raph blood group) | 977 | −0.94181 | 0.158669 | 0.268092 |
| 206380_s_at | CFP | complement factor properdin | 5199 | −1.1026 | 0.158939 | 0.268092 |
| 204961_s_at | NCF1 | neutrophil cytosolic factor 1 | 653361 | −1.43048 | 0.159385 | 0.268092 |
| 201810_s_at | SH3BP5 | SH3-domain binding protein 5 (BTK-associated) | 9467 | −1.02141 | 0.159588 | 0.268092 |
| 204192_at | CD37 | CD37 molecule | 951 | −1.01901 | 0.162409 | 0.270814 |
| 202082_s_at | SEC14L1 | SEC14-like 1 (S. cerevisiae) | 6397 | −0.89139 | 0.163106 | 0.271309 |
| 218009_s_at | PRC1 | protein regulator of cytokinesis 1 | 9055 | −1.11022 | 0.16572 | 0.274981 |
| 218522_s_at | MAP1S | microtubule-associated protein 1S | 55201 | −0.95913 | 0.166988 | 0.275781 |
| 214369_s_at | RASGRP2 | RAS guanyl releasing protein 2 (calcium and DAG-regulated) | 10235 | −0.91512 | 0.167017 | 0.275781 |
| 218243_at | RUFY1 | RUN and FYVE domain containing 1 | 80230 | −1.00705 | 0.168966 | 0.278235 |
| 214965_at | SPATA2L | spermatogenesis associated 2-like | 124044 | −0.97367 | 0.169324 | 0.278235 |
| 212027_at | RBM25 | RNA binding motif protein 25 | 58517 | −1.0829 | 0.17147 | 0.279943 |
| 218148_at | CENPT | centromere protein T | 80152 | −0.88627 | 0.171898 | 0.279943 |
| 203234_at | UPP1 | uridine phosphorylase 1 | 7378 | −1.02931 | 0.172377 | 0.279943 |
| 200661_at | CTSA | cathepsin A | 5476 | −1.40173 | 0.172629 | 0.279943 |
| 210793_s_at | NUP98 | nucleoporin 98 kDa | 4928 | −1.01125 | 0.173817 | 0.279943 |
| 215464_s_at | TAX1BP3 | Tax1 (human T-cell leukemia virus type I) binding protein 3 | 30851 | −1.07322 | 0.174266 | 0.279943 |
| 204482_at | CLDN5 | claudin 5 | 7122 | −1.19654 | 0.174447 | 0.279943 |
| 204198_s_at | RUNX3 | runt-related transcription factor 3 | 864 | −0.98615 | 0.174457 | 0.279943 |
| 212195_at | IL6ST | interleukin 6 signal transducer (gp130, oncostatin M receptor) | 3572 | −0.93935 | 0.174626 | 0.279943 |
| 209304_x_at | GADD45B | growth arrest and DNA-damage-inducible, beta | 4616 | −0.99482 | 0.174913 | 0.279943 |
| 204079_at | TPST2 | tyrosylprotein sulfotransferase 2 | 8459 | −1.11621 | 0.177613 | 0.283594 |
| 206167_s_at | ARHGAP6 | Rho GTPase activating protein 6 | 395 | −1.27531 | 0.178208 | 0.283875 |
| 220336_s_at | GP6 | glycoprotein VI (platelet) | 51206 | −1.06098 | 0.183391 | 0.290763 |
| 214464_at | CDC42BPA | CDC42 binding protein kinase alpha (DMPK-like) | 8476 | −0.96701 | 0.186028 | 0.292695 |
| 213887_s_at | POLR2E | polymerase (RNA) II (DNA directed) polypeptide E, 25 kDa | 5434 | −0.91232 | 0.186513 | 0.292695 |
| 216261_at | ITGB3 | integrin, beta 3 (platelet glycoprotein IIIa, antigen CD61) | 3690 | −1.19784 | 0.187072 | 0.292695 |
| 213836_s_at | WIPI1 | WD repeat domain, phosphoinositide interacting 1 | 55062 | −1.00273 | 0.187347 | 0.292695 |
| 218032_at | SNN | stannin | 8303 | −1.21538 | 0.189158 | 0.293378 |
| 200931_s_at | VCL | vinculin | 7414 | −0.92232 | 0.190234 | 0.294037 |
| 220110_s_at | NXF3 | nuclear RNA export factor 3 | 56000 | −0.84883 | 0.194112 | 0.298064 |
| 219998_at | LGALSL | lectin, galactoside-binding-like | 29094 | −0.88669 | 0.19416 | 0.298064 |
| 200648_s_at | GLUL | glutamate-ammonia ligase | 2752 | −0.885 | 0.196266 | 0.300615 |
| 207075_at | NLRP3 | NLR family, pyrin domain containing 3 | 114548 | −1.04141 | 0.196978 | 0.300727 |
| 202814_s_at | HEXIM1 | hexamethylene bis-acetamide inducible 1 | 10614 | −0.86963 | 0.197227 | 0.300727 |

TABLE 5-continued

Gene Expression in Men Patients

| Probe set ID | Symbol (Na32 consensus Mar13) | Gene Title (Na32 consensus Mar13) | Entrez Gene ID (consensus Mar-13) | Log2 (FC) | P-Value | Adjusted p-Value |
|---|---|---|---|---|---|---|
| 211582_x_at | LST1 | leukocyte specific transcript 1 | 7940 | −0.89977 | 0.198407 | 0.301846 |
| 57588_at | SLC24A3 | solute carrier family 24 (sodium/potassium/calcium exchanger), member 3 | 57419 | −0.8268 | 0.199252 | 0.301985 |
| 209881_s_at | LAT | linker for activation of T cells | 27040 | −0.84958 | 0.199391 | 0.301985 |
| 213537_at | HLA-DPA1 | major histocompatibility complex, class II, DP alpha 1 | 3113 | −1.00128 | 0.200355 | 0.302768 |
| 214084_x_at | NCF1C | neutrophil cytosolic factor 1C pseudogene | 654817 | −1.32671 | 0.201691 | 0.303721 |
| 202555_s_at | MYLK | myosin light chain kinase | 4638 | −1.35821 | 0.201883 | 0.303721 |
| 222024_s_at | AKAP13 | A kinase (PRKA) anchor protein 13 | 11214 | −0.9453 | 0.20348 | 0.305445 |
| 207522_s_at | ATP2A3 | ATPase, Ca++ transporting, ubiquitous | 489 | −0.86192 | 0.204597 | 0.305832 |
| 202228_s_at | NPTN | neuroplastin | 27020 | −0.94477 | 0.204641 | 0.305832 |
| 204396_s_at | GRK5 | G protein-coupled receptor kinase 5 | 2869 | −1.18973 | 0.205515 | 0.306089 |
| 214073_at | CTTN | cortactin | 2017 | −1.42385 | 0.205717 | 0.306089 |
| 217764_s_at | RAB31 | RAB31, member RAS oncogene family | 11031 | −1.28868 | 0.206889 | 0.306253 |
| 208792_s_at | CLU | clusterin | 1191 | −1.32868 | 0.207424 | 0.306253 |
| 218945_at | METTL22 | methyltransferase like 22 | 79091 | −0.81822 | 0.207478 | 0.306253 |
| 209166_s_at | MAN2B1 | mannosidase, alpha, class 2B, member 1 | 4125 | −0.87235 | 0.207908 | 0.306253 |
| 221856_s_at | FAM63A | family with sequence similarity 63, member A | 55793 | −0.90737 | 0.208242 | 0.306253 |
| 200622_x_at | CALM3 | calmodulin 3 (phosphorylase kinase, delta) | 808 | −1.05371 | 0.208541 | 0.306253 |
| 216834_at | RGS1 | regulator of G-protein signaling 1 | 5996 | −1.58039 | 0.209603 | 0.307146 |
| 201234_at | ILK | integrin-linked kinase | 3611 | −0.893 | 0.210231 | 0.307401 |
| 212016_s_at | PTBP1 | polypyrimidine tract binding protein 1 | 5725 | −0.82271 | 0.214043 | 0.311628 |
| 203196_at | ABCC4 | ATP-binding cassette, sub-family C (CFTR/MRP), member 4 | 10257 | −0.94809 | 0.215339 | 0.312842 |
| 204838_s_at | MLH3 | mutL homolog 3 (E. coli) | 27030 | −1.17819 | 0.217494 | 0.314178 |
| 210314_x_at | TNFSF13 | tumor necrosis factor (ligand) superfamily, member 13 | 8741 | −0.85424 | 0.217651 | 0.314178 |
| 221027_s_at | PLA2G12A | phospholipase A2, group XIIA | 81579 | −1.0047 | 0.219833 | 0.31622 |
| 207206_s_at | ALOX12 | arachidonate 12-lipoxygenase | 239 | −1.20411 | 0.221481 | 0.316376 |
| 336_at | TBXA2R | thromboxane A2 receptor | 6915 | −0.9854 | 0.221852 | 0.316376 |
| 208924_at | RNF11 | ring finger protein 11 | 26994 | −0.85227 | 0.222362 | 0.316376 |
| 204440_at | CD83 | CD83 molecule | 9308 | −0.86406 | 0.222738 | 0.316376 |
| 216033_s_at | FYN | FYN oncogene related to SRC, FGR, YES | 2534 | −0.86181 | 0.222912 | 0.316376 |
| 207414_s_at | PCSK6 | proprotein convertase subtilisin/kexin type 6 | 5046 | −1.24651 | 0.224243 | 0.317072 |
| 202014_at | PPP1R15A | protein phosphatase 1, regulatory subunit 15A | 23645 | −0.9299 | 0.224339 | 0.317072 |
| 204256_at | ELOVL6 | ELOVL fatty acid elongase 6 | 79071 | −0.916 | 0.225463 | 0.317997 |
| 216474_x_at | TPSB2 | tryptase beta 2 (gene/pseudogene) | 64499 | −0.84525 | 0.227141 | 0.319076 |
| 200696_s_at | GSN | gelsolin | 2934 | −0.94992 | 0.227466 | 0.319076 |
| 206632_s_at | APOBEC3B | apolipoprotein B mRNA editing enzyme, catalytic polypeptide-like 3B | 9582 | −1.04605 | 0.228843 | 0.320097 |
| 221496_s_at | TOB2 | transducer of ERBB2, 2 | 10766 | −0.78204 | 0.231572 | 0.323245 |
| 219630_at | PDZK1IP1 | PDZK1 interacting protein 1 | 10158 | −1.15529 | 0.234788 | 0.326336 |
| 214696_at | MIR22HG | MIR22 host gene (non-protein coding) | 84981 | −0.82752 | 0.235232 | 0.326336 |
| 213275_x_at | CTSB | cathepsin B | 1508 | −0.98223 | 0.235914 | 0.326614 |
| 215343_at | CCDC88C | coiled-coil domain containing 88C | 440193 | −0.83997 | 0.23881 | 0.328606 |
| 205347_s_at | TMSB15A | thymosin beta 15a | 11013 | −0.82645 | 0.241173 | 0.329982 |
| 213093_at | PRKCA | protein kinase C, alpha | 5578 | −0.92248 | 0.241407 | 0.329982 |
| 218217_at | SCPEP1 | serine carboxypeptidase 1 | 59342 | −0.82069 | 0.2415 | 0.329982 |
| 201490_s_at | PPIF | peptidylprolyl isomerase F | 10105 | −0.81917 | 0.242498 | 0.329982 |
| 204187_at | GMPR | guanosine monophosphate reductase | 2766 | −0.83239 | 0.248436 | 0.336382 |
| 217762_s_at | RAB31 | RAB31, member RAS oncogene family | 11031 | −1.02517 | 0.252078 | 0.339954 |
| 204790_at | SMAD7 | SMAD family member 7 | 4092 | −0.76543 | 0.253693 | 0.341452 |
| 209813_x_at | TARP | TCR gamma alternate reading frame protein | 445347 | −0.85554 | 0.256336 | 0.344324 |

TABLE 5-continued

Gene Expression in Men Patients

| Probe set ID | Symbol (Na32 consensus Mar13) | Gene Title (Na32 consensus Mar13) | Entrez Gene ID (consensus Mar-13) | Log2 (FC) | P-Value | Adjusted p-Value |
|---|---|---|---|---|---|---|
| 212636_at | QKI | QKI, KH domain containing, RNA binding | 9444 | −0.79642 | 0.257784 | 0.344583 |
| 211429_s_at | SERPINA1 | serpin peptidase inhibitor, clade A (alpha-1 antiproteinase, antitrypsin), member 1 | 5265 | −1.37823 | 0.258343 | 0.344583 |
| 205253_at | PBX1 | pre-B-cell leukemia homeobox 1 | 5087 | −0.76555 | 0.258565 | 0.344583 |
| 201735_s_at | CLCN3 | chloride channel, voltage-sensitive 3 | 1182 | −0.94043 | 0.260503 | 0.346484 |
| 205950_s_at | CA1 | carbonic anhydrase I | 759 | −0.96583 | 0.262137 | 0.347974 |
| 201334_s_at | ARHGEF12 | Rho guanine nucleotide exchange factor (GEF) 12 | 23365 | −0.77329 | 0.264462 | 0.350312 |
| 210987_x_at | TPM1 | tropomyosin 1 (alpha) | 7168 | −0.82871 | 0.265224 | 0.350312 |
| 209806_at | HIST1H2BK | histone cluster 1, H2bk | 85236 | −0.86055 | 0.266486 | 0.350312 |
| 215492_x_at | PTCRA | pre T-cell antigen receptor alpha | 171558 | −0.904 | 0.271153 | 0.355069 |
| 205099_s_at | CCR1 | chemokine (C-C motif) receptor 1 | 1230 | −0.80241 | 0.275833 | 0.359113 |
| 202007_at | NID1 | nidogen 1 | 4811 | −0.78832 | 0.278249 | 0.361563 |
| 210845_s_at | PLAUR | plasminogen activator, urokinase receptor | 5329 | −0.82653 | 0.280926 | 0.364343 |
| 218662_s_at | NCAPG | non-SMC condensin I complex, subunit G | 64151 | −0.73805 | 0.281927 | 0.364942 |
| 209459_s_at | ABAT | 4-aminobutyrate aminotransferase | 18 | −0.83695 | 0.28286 | 0.365451 |
| 208161_s_at | ABCC3 | ATP-binding cassette, sub-family C (CFTR/MRP), member 3 | 8714 | −0.87352 | 0.283451 | 0.365517 |
| 210429_at | RHD | Rh blood group, D antigen | 6007 | −1.02292 | 0.285289 | 0.365856 |
| 208791_at | CLU | clusterin | 1191 | −1.10749 | 0.285331 | 0.365856 |
| 36566_at | CTNS | cystinosin, lysosomal cystine transporter | 1497 | −0.72179 | 0.285335 | 0.365856 |
| 218711_s_at | SDPR | serum deprivation response | 8436 | −0.86687 | 0.285908 | 0.365897 |
| 201732_s_at | CLCN3 | chloride channel, voltage-sensitive 3 | 1182 | −0.82971 | 0.287865 | 0.367365 |
| 212570_at | ENDOD1 | endonuclease domain containing 1 | 23052 | −0.73257 | 0.289756 | 0.368708 |
| 203411_s_at | LMNA | lamin A/C | 4000 | −0.7781 | 0.290282 | 0.368708 |
| 211252_x_at | PTCRA | pre T-cell antigen receptor alpha | 171558 | −0.8545 | 0.291611 | 0.369032 |
| 204908_s_at | BCL3 | B-cell CLL/lymphoma 3 | 602 | −0.87358 | 0.292902 | 0.369953 |
| 218935_at | EHD3 | EH-domain containing 3 | 30845 | −0.93363 | 0.293563 | 0.370097 |
| 219983_at | HRASLS | HRAS-like suppressor | 57110 | −0.72599 | 0.298402 | 0.374935 |
| 220091_at | SLC2A6 | solute carrier family 2 (facilitated glucose transporter), member 6 | 11182 | −0.7439 | 0.298508 | 0.374935 |
| 212657_s_at | IL1RN | interleukin 1 receptor antagonist | 3557 | −0.78633 | 0.300604 | 0.376172 |
| 210240_s_at | CDKN2D | cyclin-dependent kinase inhibitor 2D (p19, inhibits CDK4) | 1032 | −0.7304 | 0.304949 | 0.380904 |
| 213338_at | TMEM158 | transmembrane protein 158 (gene/pseudogene) | 25907 | −0.83724 | 0.308131 | 0.382561 |
| 218559_s_at | MAFB | v-maf musculoaponeurotic fibrosarcoma oncogene homolog B (avian) | 9935 | −1.05359 | 0.308532 | 0.382561 |
| 221050_s_at | GTPBP2 | GTP binding protein 2 | 54676 | −0.69663 | 0.308832 | 0.382561 |
| 201131_s_at | CDH1 | cadherin 1, type 1, E-cadherin (epithelial) | 999 | −0.70327 | 0.3091 | 0.382561 |
| 216253_s_at | PARVB | parvin, beta | 29780 | −0.85494 | 0.309748 | 0.382663 |
| 202988_s_at | RGS1 | regulator of G-protein signaling 1 | 5996 | −1.01339 | 0.312601 | 0.385484 |
| 205786_s_at | ITGAM | integrin, alpha M (complement component 3 receptor 3 subunit) | 3684 | −0.83414 | 0.314385 | 0.386979 |
| 210757_x_at | DAB2 | Dab, mitogen-responsive phosphoprotein, homolog 2 (*Drosophila*) | 1601 | −0.74514 | 0.315103 | 0.387159 |
| 212723_at | JMJD6 | jumonji domain containing 6 | 23210 | −0.75129 | 0.319118 | 0.391333 |
| 211743_s_at | PRG2 | proteoglycan 2, bone marrow (natural killer cell activator, eosinophil granule major basic protein) | 5553 | −0.78462 | 0.319656 | 0.391333 |
| 222108_at | AMIGO2 | adhesion molecule with Ig-like domain 2 | 347902 | −0.67947 | 0.320818 | 0.392046 |
| 204240_s_at | SMC2 | structural maintenance of chromosomes 2 | 10592 | −0.70057 | 0.322141 | 0.392954 |

TABLE 5-continued

Gene Expression in Men Patients

| Probe set ID | Symbol (Na32 consensus Mar13) | Gene Title (Na32 consensus Mar13) | Entrez Gene ID (consensus Mar-13) | Log2 (FC) | P-Value | Adjusted p-Value |
|---|---|---|---|---|---|---|
| 217763_s_at | RAB31 | RAB31, member RAS oncogene family | 11031 | −0.86003 | 0.327317 | 0.397715 |
| 204467_s_at | SNCA | synuclein, alpha (non A4 component of amyloid precursor) | 6622 | −0.70464 | 0.327807 | 0.397715 |
| 216063_at | HBBP1 | hemoglobin, beta pseudogene 1 | 3044 | −0.94717 | 0.329519 | 0.399078 |
| 202581_at | HSPA1A | heat shock 70 kDa protein 1 A | 3303 | −0.98594 | 0.331291 | 0.40042 |
| 210169_at | SEC14L5 | SEC14-like 5 (S. cerevisiae) | 9717 | −0.74193 | 0.33181 | 0.40042 |
| 57082_at | LDLRAP1 | low density lipoprotein receptor adaptor protein 1 | 26119 | −0.8255 | 0.333963 | 0.402301 |
| 217022_s_at | IGH | immunoglobulin heavy locus | 3492 | −0.84526 | 0.336016 | 0.404055 |
| 210734_x_at | MAX | MYC associated factor X | 4149 | −0.69037 | 0.337578 | 0.405064 |
| 204099_at | SMARCD3 | SWI/SNF related, matrix associated, actin dependent regulator of chromatin, subfamily d, member 3 | 6604 | −0.66865 | 0.338052 | 0.405064 |
| 218585_s_at | DTL | denticleless E3 ubiquitin protein ligase homolog (Drosophila) | 51514 | −0.76574 | 0.338678 | 0.405098 |
| 220968_s_at | TSPAN9 | tetraspanin 9 | 10867 | −0.64905 | 0.342149 | 0.408528 |
| 204993_at | GNAZ | guanine nucleotide binding protein (G protein), alpha z polypeptide | 2781 | −0.77214 | 0.343386 | 0.409282 |
| 210992_x_at | FCGR2C | Fc fragment of IgG, low affinity IIc, receptor for (CD32) (gene/pseudogene) | 9103 | −0.70674 | 0.344048 | 0.409351 |
| 219412_at | RAB38 | RAB38, member RAS oncogene family | 23682 | −0.70456 | 0.345526 | 0.410051 |
| 219892_at | TM6SF1 | transmembrane 6 superfamily member 1 | 53346 | −0.67737 | 0.345848 | 0.410051 |
| 205098_at | CCR1 | chemokine (C-C motif) receptor 1 | 1230 | −0.67251 | 0.348407 | 0.411654 |
| 206883_x_at | GP9 | glycoprotein IX (platelet) | 2815 | −0.93388 | 0.348416 | 0.411654 |
| 204546_at | KIAA0513 | KIAA0513 | 9764 | −0.6776 | 0.354075 | 0.416884 |
| 211984_at | CALM1 | calmodulin 1 (phosphorylase kinase, delta) | 801 | −0.67903 | 0.356016 | 0.418443 |
| 212681_at | EPB41L3 | erythrocyte membrane protein band 4.1-like 3 | 23136 | −0.74882 | 0.363256 | 0.426212 |
| 209586_s_at | PRUNE | prune homolog (Drosophila) | 58497 | −0.71365 | 0.365133 | 0.427673 |
| 204122_at | TYROBP | TYRO protein tyrosine kinase binding protein | 7305 | −0.98164 | 0.368409 | 0.429921 |
| 221698_s_at | CLEC7A | C-type lectin domain family 7, member A | 64581 | −0.72388 | 0.368957 | 0.429921 |
| 202269_x_at | GBP1 | guanylate binding protein 1, interferon-inducible | 2633 | −0.72489 | 0.374443 | 0.434817 |
| 37965_at | PARVB | parvin, beta | 29780 | −0.73203 | 0.378544 | 0.438076 |
| 20693 7_at | SPTA1 | spectrin, alpha, erythrocytic 1 (elliptocytosis 2) | 6708 | −0.63911 | 0.379343 | 0.438252 |
| 205863_at | S100A12 | S100 calcium binding protein A12 | 6283 | −0.76877 | 0.385662 | 0.443766 |
| 206465_at | ACSBG1 | acyl-CoA synthetase bubblegum family member 1 | 23205 | −0.69391 | 0.386083 | 0.443766 |
| 208601_s_at | TUBB1 | tubulin, beta 1 class VI | 81027 | −0.7751 | 0.38836 | 0.445627 |
| 208501_at | GFI1B | growth factor independent 1B transcription repressor | 8328 | −0.69445 | 0.391518 | 0.44802 |
| 204319_s_at | RGS10 | regulator of G-protein signaling 10 | 6001 | −0.66481 | 0.391769 | 0.44802 |
| 204115_at | GNG11 | guanine nucleotide binding protein (G protein), gamma 11 | 2791 | −0.85973 | 0.396611 | 0.450473 |
| 222204_s_at | RRN3 | RRN3 RNA polymerase I transcription factor homolog (S. cerevisiae) | 54700 | −0.6018 | 0.396615 | 0.450473 |
| 204446_s_at | ALOX5 | arachidonate 5-lipoxygenase | 240 | −0.88998 | 0.397241 | 0.450473 |
| 203508_at | TNFRSF1B | tumor necrosis factor receptor superfamily, member 1B | 7133 | −0.6867 | 0.398463 | 0.451103 |
| 203305_at | F13A1 | coagulation factor XIII, A1 polypeptide | 2162 | −0.84164 | 0.401077 | 0.453304 |
| 208438_s_at | FGR | Gardner-Rasheed feline sarcoma viral (v-fgr) oncogene homolog | 2268 | −0.62594 | 0.406618 | 0.458801 |
| 205463_s_at | PDGFA | platelet-derived growth factor alpha polypeptide | 5154 | −0.67628 | 0.408281 | 0.459911 |
| 202917_s_at | S100A8 | S100 calcium binding protein A8 | 6279 | −1.20152 | 0.411847 | 0.463156 |
| 207156_at | HIST1H2AG | histone cluster 1, H2ag | 8969 | −0.70408 | 0.413233 | 0.463944 |

TABLE 5-continued

Gene Expression in Men Patients

| Probe set ID | Symbol (Na32 consensus Mar13) | Gene Title (Na32 consensus Mar13) | Entrez Gene ID (consensus Mar-13) | Log2 (FC) | P-Value | Adjusted p-Value |
|---|---|---|---|---|---|---|
| 202833_s_at | SERPINA1 | serpin peptidase inhibitor, clade A (alpha-1 antiproteinase, antitrypsin), member 1 | 5265 | −0.91706 | 0.413994 | 0.46403 |
| 207315_at | CD226 | CD226 molecule | 10666 | −0.62666 | 0.418074 | 0.466595 |
| 204971_at | CSTA | cystatin A (stefin A) | 1475 | −0.89766 | 0.418207 | 0.466595 |
| 201954_at | ARPC1B | actin related protein 2/3 complex, subunit 1B, 41 kDa | 10095 | −0.64277 | 0.41835 | 0.466595 |
| 206254_at | EGF | epidermal growth factor | 1950 | −0.61118 | 0.425271 | 0.472756 |
| 204475_at | MMP1 | matrix metallopeptidase 1 (interstitial collagenase) | 4312 | −0.79765 | 0.427481 | 0.474434 |
| 205229_s_at | COCH | coagulation factor C homolog, cochlin (Limulus polyphemus) | 1690 | −0.53396 | 0.432368 | 0.479072 |
| 205127_at | PTGS1 | prostaglandin-endoperoxide synthase 1 (prostaglandin G/H synthase and cyclooxygenase) | 5742 | −0.54531 | 0.44234 | 0.488522 |
| 203087_s_at | KIF2A | kinesin heavy chain member 2A | 3796 | −0.59853 | 0.443634 | 0.488965 |
| 202953_at | C1QB | complement component 1, q subcomponent, B chain | 713 | −0.82302 | 0.444186 | 0.488965 |
| 218656_s_at | LHFP | lipoma HMGIC fusion partner | 10186 | −0.56539 | 0.445989 | 0.489822 |
| 214511_x_at | FCGR1B | Fc fragment of IgG, high affinity Ib, receptor (CD64) | 2210 | −0.69072 | 0.446411 | 0.489822 |
| 208406_s_at | GRAP2 | GRB2-related adaptor protein 2 | 9402 | −0.68765 | 0.451229 | 0.492736 |
| 56256_at | SIDT2 | SID1 transmembrane family, member 2 | 51092 | −0.74229 | 0.451977 | 0.492736 |
| 209204_at | LMO4 | LIM domain only 4 | 8543 | −0.52105 | 0.454155 | 0.494314 |
| 205612_at | MMRN1 | multimerin 1 | 22915 | −0.58072 | 0.457551 | 0.496919 |
| 206116_s_at | TPM1 | tropomyosin 1 (alpha) | 7168 | −0.61863 | 0.458017 | 0.496919 |
| 204858_s_at | TYMP | thymidine phosphorylase | 1890 | −0.62323 | 0.459985 | 0.497869 |
| 204308_s_at | TECPR2 | tectonin beta-propeller repeat containing 2 | 9895 | −0.56607 | 0.460363 | 0.497869 |
| 204466_s_at | SNCA | synuclein, alpha (non A4 component of amyloid precursor) | 6622 | −0.60596 | 0.461512 | 0.498316 |
| 202270_at | GBP1 | guanylate binding protein 1, interferon-inducible | 2633 | −0.55471 | 0.469505 | 0.505333 |
| 218223_s_at | PLEKHO1 | pleckstrin homology domain containing, family O member 1 | 51177 | −0.63829 | 0.474253 | 0.509634 |
| 206881_s_at | LILRA3 | leukocyte immunoglobulin-like receptor, subfamily A (without TM domain), member 3 | 11026 | −0.61236 | 0.483816 | 0.518375 |
| 222218_s_at | PILRA | paired immunoglobin-like type 2 receptor alpha | 29992 | −0.60956 | 0.483919 | 0.518375 |
| 213566_at | RNASE6 | ribonuclease, RNase A family, k6 | 6039 | −0.53861 | 0.485481 | 0.519227 |
| 221160_s_at | CABP5 | calcium binding protein 5 | 56344 | −0.52004 | 0.487926 | 0.521019 |
| 206964_at | NAT8B | N-acetyltransferase 8B (GCN5-related, putative, gene/pseudogene) | 51471 | −0.52553 | 0.491589 | 0.523279 |
| 206420_at | IGSF6 | immunoglobulin superfamily, member 6 | 10261 | −0.58815 | 0.495872 | 0.52701 |
| 219386_s_at | SLAMF8 | SLAM family member 8 | 56833 | −0.64079 | 0.500574 | 0.531173 |
| 209949_at | NCF2 | neutrophil cytosolic factor 2 | 4688 | −0.64425 | 0.501391 | 0.531207 |
| 206110_at | HIST1H3H | histone cluster 1, H3h | 8357 | −0.78197 | 0.502267 | 0.531304 |
| 210660_at | LILRA1 | leukocyte immunoglobulin-like receptor, subfamily A (with TM domain), member 1 | 11024 | −0.51819 | 0.518847 | 0.547986 |
| 203560_at | GGH | gamma-glutamyl hydrolase (conjugase, folylpolygammaglutamyl hydrolase) | 8836 | −0.53164 | 0.520075 | 0.548428 |
| 214677_x_at | CYAT1 | immunoglobulin lambda light chain-like | 100290481 | −0.49954 | 0.537027 | 0.564546 |
| 211985_s_at | CALM1 | calmodulin 1 (phosphorylase kinase, delta) | 801 | −0.5249 | 0.539781 | 0.566561 |
| 200660_at | S100A11 | S100 calcium binding protein A11 | 6282 | −0.57564 | 0.542655 | 0.568696 |
| 201279_s_at | DAB2 | Dab, mitogen-responsive phosphoprotein, homolog 2 (Drosophila) | 1601 | −0.47879 | 0.546344 | 0.571676 |
| 203585_at | ZNF185 | zinc finger protein 185 (LIM domain) | 7739 | −0.5405 | 0.548693 | 0.573249 |
| 203140_at | BCL6 | B-cell CLL/lymphoma 6 | 604 | −0.48632 | 0.5566 | 0.580552 |
| 202295_s_at | CTSH | cathepsin H | 1512 | −0.54025 | 0.557399 | 0.580552 |

TABLE 5-continued

Gene Expression in Men Patients

| Probe set ID | Symbol (Na32 consensus Mar13) | Gene Title (Na32 consensus Mar13) | Entrez Gene ID (consensus Mar-13) | Log2 (FC) | P-Value | Adjusted p-Value |
|---|---|---|---|---|---|---|
| 210146_x_at | LILRB2 | leukocyte immunoglobulin-like receptor, subfamily B (with TM and ITIM domains), member 2 | 10288 | −0.42185 | 0.572195 | 0.593923 |
| 212188_at | KCTD12 | potassium channel tetramerisation domain containing 12 | 115207 | −0.40898 | 0.572868 | 0.593923 |
| 203973_s_at | CEBPD | CCAAT/enhancer binding protein (C/EBP), delta | 1052 | −0.50468 | 0.574596 | 0.594804 |
| 204588_s_at | SLC7A7 | solute carrier family 7 (amino acid transporter light chain, y + L system), member 7 | 9056 | −0.52401 | 0.57568 | 0.595016 |
| 218232_at | C1QA | complement component 1, q subcomponent, A chain | 712 | −0.45679 | 0.578484 | 0.597002 |
| 219159_s_at | SLAMF7 | SLAM family member 7 | 57823 | −0.41122 | 0.581677 | 0.599384 |
| 209448_at | HTATIP2 | HIV-1 Tat interactive protein 2, 30 kDa | 10553 | −0.4519 | 0.584526 | 0.601404 |
| 208450_at | LGALS2 | lectin, galactoside-binding, soluble, 2 | 3957 | −0.61288 | 0.591141 | 0.607288 |
| 207857_at | LILRA2 | leukocyte immunoglobulin-like receptor, subfamily A (with TM domain), member 2 | 11027 | −0.38829 | 0.612701 | 0.626584 |
| 220088_at | C5AR1 | complement component 5a receptor 1 | 728 | −0.41369 | 0.614585 | 0.627563 |
| 204912_at | IL10RA | interleukin 10 receptor, alpha | 3587 | −0.36301 | 0.677582 | 0.688773 |
| 201005_at | CD9 | CD9 molecule | 928 | −0.46299 | 0.696997 | 0.707447 |
| 205119_s_at | FPR1 | formyl peptide receptor 1 | 2357 | −0.34184 | 0.703731 | 0.713213 |
| 213831_at | HLA-DQA1 | major histocompatibility complex, class II, DQ alpha 1 | 3117 | −0.41115 | 0.757666 | 0.766726 |
| 205898_at | CX3CR1 | chemokine (C-X3-C motif) receptor 1 | 1524 | −0.2373 | 0.789441 | 0.797689 |
| 201422_at | IFI30 | interferon, gamma-inducible protein 30 | 10437 | −0.26145 | 0.793548 | 0.800643 |
| 208579_x_at | H2BFS | H2B histone family, member S (pseudogene) | 54145 | −0.20818 | 0.82651 | 0.83266 |
| 212192_at | KCTD12 | potassium channel tetramerisation domain containing 12 | 115207 | −0.19775 | 0.828056 | 0.832977 |
| 219505_at | CECR1 | cat eye syndrome chromosome region, candidate 1 | 51816 | −0.18017 | 0.84442 | 0.848178 |
| 215071_s_at | HIST1H2AC | histone cluster 1, H2ac | 8334 | −0.16128 | 0.864886 | 0.867448 |

TABLE 6

Clinical Features of the Polycythemia Vera Patients Segregated by Unsupervised Hierarchical Clustering

| Clinical Phenotype | Aggressive | Indolent | p |
|---|---|---|---|
| Gender (M/F) | 4/3 | 4/8 | |
| Age (median, years) | 66 | 67.5 | ns |
| (range) | (48-74) | (46-82) | |
| Disease duration (median, years) | 16 | 6 | 0.040* |
| (range) | (7-28) | (1-25) | |
| JAK2 V617F Neutrophil Allele Burden (median, %) | 100 | 85 | ns |
| (range) | (64-100) | (55-100) | |
| Hemoglobin (median, gm %) | 11.1 | 13.3 | 0.007* |
| (range) | (8.3-12.9) | (10.7-15.9) | |
| Leukocyte count (median, 10³/μL) | 17,620 | 17,870 | ns |
| (range) | (10,020-171,190) | (4,430-27,270) | |
| Platelet count (median, 10³/μL) | 454,000 | 837,000 | ns |
| (range) | (171,000-1,017,000) | (151,000-1,480,000) | |
| Thrombosis (n) | 4/7 | 1/12 | 0.037** |
| Palpable splenomegaly (n) | 7/7 | 6/12 | 0.034** |
| Spleen size (median, cm below costal margin) | 20 | 2 | 0.005** |
| (range) | (5-32) | (0-14) | |
| Splenectomy (n) | 4/7 | 0/12 | 0.007** |
| Chemotherapy (n) | 5/7 | 2/12 | 0.029** |
| Transformation to acute leukemia (n) | 4/7 | 1/12 | 0.037** |
| Surviving (n) | 1/7 | 11/12 | 0.001** |

*Student t test

**Fisher exact probability test

TABLE 7

Annotation of the 102 Concordantly Deregulated Genes

| Probe set ID | Symbol (Na32 consensus Mar13) | Gene Title (Na32 consensus Mar13) | GeneID (consensus1 Mar-13) | Log2(FC) | P-Value | Adjusted p-Value |
|---|---|---|---|---|---|---|
| 202627_s_at | SERPINE1 | serpin peptidase inhibitor, clade E (nexin, plasminogen activator inhibitor type 1), member 1 | 5054 | 1.668478 | 0.005041 | 0.454117 |
| 201324_at | EMP1 | epithelial membrane protein 1 | 2012 | 1.16186 | 0.00771 | 0.454117 |
| 212667_at | SPARC | secreted protein, acidic, cysteine-rich (osteonectin) | 6678 | 1.45459 | 0.014744 | 0.454117 |
| 201438_at | COL6A3 | collagen, type VI, alpha 3 | 1293 | 1.278559 | 0.025847 | 0.454117 |
| 211161_s_at | COL3A1 | collagen, type III, alpha 1 | 1281 | 1.254327 | 0.029648 | 0.454117 |
| 215076_s_at | COL3A1 | collagen, type III, alpha 1 | 1281 | 1.488017 | 0.029998 | 0.454117 |
| 210809_s_at | POSTN | periostin, osteoblast specific factor | 10631 | 1.804584 | 0.035776 | 0.454117 |
| 212464_s_at | FN1 | fibronectin 1 | 2335 | 1.813392 | 0.036784 | 0.454117 |
| 202404_s_at | COL1A2 | collagen, type III, alpha 1 | 1281 | 1.791759 | 0.037999 | 0.454117 |
| 202403_s_at | COL1A2 | collagen, type III, alpha 1 | 1281 | 1.442683 | 0.042962 | 0.454117 |
| 211719_x_at | FN1 | fibronectin 1 | 2335 | 1.960598 | 0.043407 | 0.454117 |
| 216442_x_at | FN1 | fibronectin 1 | 2335 | 1.658895 | 0.047165 | 0.454117 |
| 210495_x_at | FN1 | fibronectin 1 | 2335 | 1.692178 | 0.047228 | 0.454117 |
| 211964_at | COL4A2 | collagen, type IV, alpha 2 | 1284 | 1.078275 | 0.053744 | 0.46673 |
| 202310_s_at | COL1A1 | collagen, type I, alpha 1 | 1277 | 1.496322 | 0.056008 | 0.46673 |
| 217388_s_at | KYNU | kynureninase | 8942 | −1.22118 | 0.072655 | 0.470938 |
| 217232_x_at | HBB | hemoglobin, beta | 3043 | −1.35066 | 0.073386 | 0.470938 |
| 205547_s_at | TAGLN | transgelin | 6876 | 1.275409 | 0.075803 | 0.470938 |
| 204848_x_at | HBG1 /// HBG2 | hemoglobin, gamma A | 3047 | −1.4219 | 0.077286 | 0.470938 |
| 211980_at | COL4A1 | collagen, type IV, alpha 1 | 1282 | 1.083935 | 0.081985 | 0.470938 |
| 209116_x_at | HBB | hemoglobin, beta | 3043 | −1.47367 | 0.087602 | 0.470938 |
| 213515_x_at | HBG1 /// HBG2 | hemoglobin, gamma A | 3047 | −1.72304 | 0.089471 | 0.470938 |
| 201842_s_at | EFEMP1 | EGF containing fibulin-like extracellular matrix protein 1 | 2202 | 1.153114 | 0.09001 | 0.470938 |
| 204897_at | PTGER4 | prostaglandin E receptor 4 (subtype EP4) | 5734 | 0.979697 | 0.094157 | 0.470938 |
| 209183_s_at | C10orf10 | chromosome 10 open reading frame 10 | 11067 | 0.631696 | 0.094188 | 0.470938 |
| 204419_x_at | HBG1 /// HBG2 | hemoglobin, gamma A | 3047 | −1.4151 | 0.105888 | 0.509076 |
| 211696_x_at | HBB | hemoglobin, beta | 3043 | −1.18995 | 0.11201 | 0.513618 |
| 204141_at | TUBB2A | tubulin, beta 2A class IIa | 7280 | 1.288228 | 0.115961 | 0.513618 |
| 211699_x_at | HBA1 /// HBA2 | hemoglobin, alpha 1 | 3039 | −1.21697 | 0.122356 | 0.513618 |
| 209458_x_at | HBA1 /// HBA2 | hemoglobin, alpha 1 | 3039 | −1.38137 | 0.130596 | 0.513618 |
| 221760_at | MAN1A1 | mannosidase, alpha, class 1A, member 1 | 4121 | 0.85605 | 0.130744 | 0.513618 |
| 204018_x_at | HBA1 /// HBA2 | hemoglobin, alpha 1 | 3039 | −1.23966 | 0.131486 | 0.513618 |
| 213350_at | RPS11 | ribosomal protein S11 | 6205 | 0.933771 | 0.136499 | 0.515634 |
| 215772_x_at | SUCLG2 | succinate-CoA ligase, GDP-forming, beta subunit | 8801 | −0.64738 | 0.145938 | 0.515634 |
| 217414_x_at | HBA1 /// HBA2 | hemoglobin, alpha 1 | 3039 | −1.27841 | 0.149825 | 0.515634 |
| 205382_s_at | CFD | complement factor D (adipsin) | 1675 | −0.8048 | 0.157142 | 0.515634 |
| 201890_at | RRM2 | ribonucleotide reductase M2 | 6241 | −0.95289 | 0.158408 | 0.515634 |
| 208960_s_at | KLF6 | Kruppel-like factor 6 | 1316 | 0.571081 | 0.15952 | 0.515634 |
| 206157_at | PTX3 | pentraxin 3, long | 5806 | 0.825089 | 0.160878 | 0.515634 |
| 205237_at | FCN1 | ficolin (collagen/fibrinogen domain containing) 1 | 2219 | −1.15146 | 0.170172 | 0.516857 |
| 204834_at | FGL2 | fibrinogen-like 2 | 10875 | −0.90858 | 0.17194 | 0.516857 |
| 211745_x_at | HBA1 /// HBA2 | hemoglobin, alpha 1 | 3039 | −1.33507 | 0.173664 | 0.516857 |
| 209803_s_at | PHLDA2 | pleckstrin homology-like domain, family A, member 2 | 7262 | 0.879169 | 0.180046 | 0.520921 |
| 200629_at | WARS | tryptophanyl-tRNA synthetase | 7453 | −0.69785 | 0.183988 | 0.520921 |
| 219602_s_at | PIEZO2 | piezo-type mechanosensitive ion channel component 2 | 63895 | −0.56733 | 0.187531 | 0.520921 |
| 205848_at | GAS2 | growth arrest-specific 2 | 2620 | −0.77375 | 0.196517 | 0.527987 |
| 210487_at | DNTT | deoxynucleotidyltransferase, terminal | 1791 | 0.622562 | 0.198523 | 0.527987 |
| 214414_x_at | HBA1 /// HBA2 | hemoglobin, alpha 1 | 3039 | −1.40997 | 0.215516 | 0.561241 |

TABLE 7-continued

Annotation of the 102 Concordantly Deregulated Genes

| Probe set ID | Symbol (Na32 consensus Mar13) | Gene Title (Na32 consensus Mar13) | GeneID (consensus1 Mar-13) | Log2(FC) | P-Value | Adjusted p-Value |
|---|---|---|---|---|---|---|
| 209374_s_at | IGHM | immunoglobulin heavy constant mu | 3507 | 0.614952 | 0.226098 | 0.576781 |
| 201110_s_at | THBS1 | thrombospondin 1 | 7057 | 0.617073 | 0.251014 | 0.58604 |
| 220377_at | KIAA0125 | KIAA0125 | 9834 | 0.553273 | 0.25106 | 0.58604 |
| 213524_s_at | G0S2 | G0/G1 switch 2 | 50486 | −0.85706 | 0.265596 | 0.58604 |
| 204304_s_at | PROM1 | prominin 1 | 8842 | 0.705885 | 0.270019 | 0.58604 |
| 208961_s_at | KLF6 | Kruppel-like factor 6 | 1316 | 0.50248 | 0.272895 | 0.58604 |
| 203787_at | SSBP2 | single-stranded DNA binding protein 2 | 23635 | 0.483855 | 0.27435 | 0.58604 |
| 212952_at | LOC100507328 | hypothetical LOC100507328 | 100507328 | 0.637258 | 0.276535 | 0.58604 |
| 209763_at | CHRDL1 | chordin-like 1 | 91851 | 0.393371 | 0.278706 | 0.58604 |
| 202600_s_at | NRIP1 | nuclear receptor interacting protein 1 | 8204 | 0.586587 | 0.279182 | 0.58604 |
| 209290_s_at | NFIB | nuclear factor I/B | 4781 | −0.55308 | 0.280861 | 0.58604 |
| 214041_x_at | RPL37A | ribosomal protein L37a | 6168 | 0.490226 | 0.283497 | 0.58604 |
| 202237_at | NNMT | nicotinamide N-methyltransferase | 4837 | 0.748218 | 0.285987 | 0.58604 |
| 211074_at | FOLR1 | folate receptor 1 (adult) | 2348 | 0.905935 | 0.306067 | 0.617071 |
| 204872_at | TLE4 | transducin-like enhancer of split 4 (E(sp1) homolog, *Drosophila*) | 7091 | 0.422998 | 0.331335 | 0.65741 |
| 217683_at | HBE1 | hemoglobin, epsilon 1 | 3046 | −0.47414 | 0.366576 | 0.687129 |
| 205933_at | SETBP1 | SET binding protein 1 | 26040 | 0.325978 | 0.36816 | 0.687129 |
| 204430_s_at | SLC2A5 | solute carrier family 2 (facilitated glucose/fructose transporter), member 5 | 6518 | 0.430164 | 0.378886 | 0.687129 |
| 209894_at | LEPR | leptin receptor | 3953 | −0.51789 | 0.379001 | 0.687129 |
| 221556_at | CDC14B | cell division cycle 14B | 8555 | 0.488325 | 0.379135 | 0.687129 |
| 202870_s_at | CDC20 | cell division cycle 20 | 991 | −0.50504 | 0.379295 | 0.687129 |
| 204755_x_at | HLF | hepatic leukemia factor | 3131 | 0.315735 | 0.425921 | 0.750089 |
| 209576_at | GNAI1 | guanine nucleotide binding protein (G protein), alpha inhibiting activity polypeptide 1 | 2770 | 0.312521 | 0.442731 | 0.750089 |
| 204030_s_at | IQCJ-SCHIP1 | IQCJ-SCHIP1 readthrough | 100505385 | 0.349599 | 0.447391 | 0.750089 |
| 213979_s_at | — | — | — | 0.43757 | 0.448237 | 0.750089 |
| 203535_at | S100A9 | S100 calcium binding protein A9 | 6280 | −0.55271 | 0.46106 | 0.750089 |
| 216248_s_at | NR4A2 | nuclear receptor subfamily 4, group A, member 2 | 4929 | −0.44972 | 0.465048 | 0.750089 |
| 211597_s_at | HOPX | HOP homeobox | 84525 | 0.403732 | 0.466948 | 0.750089 |
| 204622_x_at | NR4A2 | nuclear receptor subfamily 4, group A, member 2 | 4929 | −0.37372 | 0.468699 | 0.750089 |
| 220990_s_at | MIR21 | microRNA 21 | 406991 | 0.336172 | 0.469644 | 0.750089 |
| 213668_s_at | SOX4 | SRY (sex determining region Y)-box 4 | 6659 | 0.449329 | 0.474056 | 0.750089 |
| 205984_at | CRHBP | corticotropin releasing hormone binding protein | 1393 | 0.377363 | 0.518506 | 0.807842 |
| 209773_s_at | RRM2 | ribonucleotide reductase M2 | 6241 | −0.42832 | 0.528182 | 0.807842 |
| 201058_s_at | MYL9 | myosin, light chain 9, regulatory | 10398 | 0.492397 | 0.538149 | 0.807842 |
| 201631_s_at | IER3 | immediate early response 3 | 8870 | 0.438819 | 0.542829 | 0.807842 |
| 219777_at | GIMAP6 | GTPase, IMAP family member 6 | 474344 | 0.266496 | 0.54879 | 0.807842 |
| 212077_at | CALD1 | caldesmon 1 | 800 | 0.443992 | 0.549332 | 0.807842 |
| 210873_x_at | APOBEC3A | apolipoprotein B mRNA editing enzyme, catalytic polypeptide-like 3A | 200315 | −0.3463 | 0.599089 | 0.852599 |
| 201669_s_at | MARCKS | myristoylated alanine-rich protein kinase C substrate | 4082 | −0.26494 | 0.60049 | 0.852599 |
| 206478_at | KIAA0125 | KIAA0125 | 9834 | 0.32879 | 0.609726 | 0.852599 |
| 201666_at | TIMP1 | TIMP metallopeptidase inhibitor 1 | 7076 | 0.267758 | 0.619744 | 0.852599 |
| 219304_s_at | PDGFD | platelet derived growth factor D | 80310 | 0.204115 | 0.624045 | 0.852599 |
| 212531_at | LCN2 | lipocalin 2 | 3934 | 0.323764 | 0.624556 | 0.852599 |
| 212589_at | RRAS2 | related RAS viral (r-ras) oncogene homolog 2 | 22800 | −0.24032 | 0.62995 | 0.852599 |
| 206698_at | XK | X-linked Kx blood group (McLeod syndrome) | 7504 | −0.27856 | 0.634334 | 0.852599 |
| 209069_s_at | H3F3B | H3 histone, family 3B (H3.3B) | 3021 | 0.19436 | 0.64152 | 0.853085 |

TABLE 7-continued

Annotation of the 102 Concordantly Deregulated Genes

| Probe set ID | Symbol (Na32 consensus Mar13) | Gene Title (Na32 consensus Mar13) | GeneID (consensus1 Mar-13) | Log2(FC) | P-Value | Adjusted p-Value |
|---|---|---|---|---|---|---|
| 213593_s_at | TRA2A | transformer 2 alpha homolog (Drosophila) | 29896 | 0.256365 | 0.650412 | 0.855806 |
| 222044_at | PCIF1 | PDX1 C-terminal inhibiting factor 1 | 63935 | 0.1951 | 0.667828 | 0.861405 |
| 201798_s_at | MYOF | myoferlin | 26509 | 0.273459 | 0.66845 | 0.861405 |
| 201369_s_at | ZFP36L2 | ZFP36 ring finger protein-like 2 | 678 | 0.230642 | 0.684623 | 0.869074 |
| 211998_at | H3F3B | H3 histone, family 3B (H3.3B) | 3021 | 0.193469 | 0.693161 | 0.869074 |
| 214974_x_at | CXCL5 | chemokine (C-X-C motif) ligand 5 | 6374 | −0.26165 | 0.695259 | 0.869074 |
| 200999_s_at | CKAP4 | cytoskeleton-associated protein 4 | 10970 | 0.213798 | 0.708966 | 0.876694 |
| 208180_s_at | HIST1H4H | histone cluster 1, H4h | 8365 | 0.215184 | 0.725551 | 0.876694 |
| 214651_s_at | HOXA9 | homeobox A9 | 3205 | 0.201432 | 0.727565 | 0.876694 |
| 204563_at | SELL | selectin L | 6402 | 0.218847 | 0.72941 | 0.876694 |
| 74694_s_at | RABEP2 | rabaptin, RAB GTPase binding effector protein 2 | 79874 | 0.156251 | 0.74234 | 0.879603 |
| 209112_at | CDKN1B | cyclin-dependent kinase inhibitor 1B (p27, Kip1) | 1027 | −0.16341 | 0.746336 | 0.879603 |
| 220416_at | ATP8B4 | ATPase, class I, type 8B, member 4 | 79895 | 0.16502 | 0.75294 | 0.879603 |
| 1405_i_at | CCL5 | chemokine (C-C motif) ligand 5 | 6352 | −0.25823 | 0.790224 | 0.895478 |
| 201195_s_at | SLC7A5 | solute carrier family 7 (amino acid transporter light chain, L system), member 5 | 8140 | −0.13019 | 0.797734 | 0.895478 |
| 205442_at | MFAP3L | microfibrillar-associated protein 3-like | 9848 | 0.165446 | 0.798221 | 0.895478 |
| 214911_s_at | BRD2 | bromodomain containing 2 | 6046 | 0.126061 | 0.802554 | 0.895478 |
| 203395_s_at | HES1 | hairy and enhancer of split 1, (Drosophila) | 3280 | −0.15322 | 0.808284 | 0.895478 |
| 213757_at | EIF5A | eukaryotic translation initiation factor 5A | 1984 | 0.139559 | 0.810552 | 0.895478 |
| 204655_at | CCL5 | chemokine (C-C motif) ligand 5 | 6352 | −0.23378 | 0.816676 | 0.895478 |
| 208892_s_at | DUSP6 | dual specificity phosphatase 6 | 1848 | 0.125339 | 0.839353 | 0.91234 |
| 214805_at | EIF4A1 | eukaryotic translation initiation factor 4A1 | 1973 | 0.086848 | 0.847057 | 0.912777 |
| 208835_s_at | LUC7L3 | LUC7-like 3 (S. cerevisiae) | 51747 | 0.092821 | 0.854388 | 0.912807 |
| 205114_s_at | CCL3 /// CCL3L1 /// CCL3L3 | chemokine (C-C motif) ligand 3-like 3 | 414062 | 0.116024 | 0.882607 | 0.934965 |
| 219922_s_at | LTBP3 | latent transforming growth factor beta binding protein 3 | 4054 | −0.06412 | 0.893898 | 0.936218 |
| 207815_at | PF4V1 | platelet factor 4 variant 1 | 5197 | −0.10475 | 0.898769 | 0.936218 |
| 208949_at | LGALS3 | lectin, galactoside-binding, soluble, 3 | 3958 | −0.06541 | 0.917534 | 0.941056 |
| 203394_s_at | HES1 | hairy and enhancer of split 1, (Drosophila) | 3280 | −0.06134 | 0.922933 | 0.941056 |
| 204753_s_at | HLF | hepatic leukemia factor | 3131 | 0.037675 | 0.933009 | 0.941056 |
| 219410_at | TMEM45A | transmembrane protein 45A | 55076 | 0.044462 | 0.933528 | 0.941056 |
| 219403_s_at | HPSE | heparanase | 10855 | −0.01752 | 0.978683 | 0.978683 |

TABLE 8

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 208949_s_at | LGALS3 | lectin, galactoside-binding, soluble, 3 | 3958 | −2.46116 | 4.71E−07 | 0.000871 |
| 202284_s_at | CDKN1A | cyclin-dependent kinase inhibitor 1A (p21, Cip1) | 1026 | −1.98698 | 2.11E−06 | 0.002134 |
| 201059_at | CTTN | cortactin | 2017 | −2.72585 | 6.06E−06 | 0.002867 |
| 211458_s_at | GABARAPL1 | GABA(A) receptor-associated protein like 1 | 23710 | −1.79927 | 1.03E−05 | 0.003369 |
| 210592_s_at | SAT1 | spermidine/spermine N1-acetyltransferase 1 | 6303 | −1.22693 | 1.17E−05 | 0.003384 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 201666_at | TIMP1 | TIMP metallopeptidase inhibitor 1 | 7076 | −1.63942 | 2.35E−05 | 0.004281 |
| 203045_at | NINJ1 | ninjurin 1 | 4814 | −1.5136 | 2.55E−05 | 0.004462 |
| 203455_s_at | SAT1 | spermidine/spermine N1-acetyltransferase 1 | 6303 | −1.25184 | 2.78E−05 | 0.004519 |
| 202912_at | ADM | adrenomedullin | 133 | −1.55855 | 3.02E−05 | 0.004672 |
| 201058_s_at | MYL9 | myosin, light chain 9, regulatory | 10398 | −2.74637 | 3.07E−05 | 0.004672 |
| 207815_at | PF4V1 | platelet factor 4 variant 1 | 5197 | −2.82239 | 5.35E−05 | 0.005828 |
| 1405_i_at | CCL5 | chemokine (C-C motif) ligand 5 | 6352 | −3.32637 | 5.85E−05 | 0.006036 |
| 214211_at | FTH1 | ferritin, heavy polypeptide 1 | 2495 | −1.47129 | 8.74E−05 | 0.006826 |
| 201422_at | IFI30 | interferon, gamma-inducible protein 30 | 10437 | −2.1056 | 0.000104 | 0.00745 |
| 210845_s_at | PLAUR | plasminogen activator, urokinase receptor | 5329 | −1.48981 | 0.000116 | 0.007613 |
| 214020_x_at | ITGB5 | integrin, beta 5 | 3693 | −1.08903 | 0.000121 | 0.007815 |
| 204115_at | GNG11 | guanine nucleotide binding protein (G protein), gamma 11 | 2791 | −2.43614 | 0.000123 | 0.007906 |
| 213524_s_at | G0S2 | G0/G1 switch 2 | 50486 | −2.65615 | 0.000126 | 0.007998 |
| 201125_s_at | ITGB5 | integrin, beta 5 | 3693 | −1.67473 | 0.000134 | 0.008224 |
| 209154_at | TAX1BP3 | Tax1 (human T-cell leukemia virus type I) binding protein 3 | 30851 | −1.71214 | 0.000155 | 0.008862 |
| 201631_s_at | IER3 | immediate early response 3 | 8870 | −2.29781 | 0.000169 | 0.009257 |
| 213988_s_at | SAT1 | spermidine/spermine N1-acetyltransferase 1 | 6303 | −1.26095 | 0.000171 | 0.009309 |
| 200871_s_at | PSAP | prosaposin | 5660 | −1.0306 | 0.000195 | 0.009761 |
| 200661_at | CTSA | cathepsin A | 5476 | −1.96591 | 0.000218 | 0.010227 |
| 204440_at | CD83 | CD83 molecule | 9308 | −1.34989 | 0.000228 | 0.010503 |
| 214073_at | CTTN | cortactin | 2017 | −2.15431 | 0.000231 | 0.010534 |
| 204655_at | CCL5 | chemokine (C-C motif) ligand 5 | 6352 | −3.23424 | 0.000234 | 0.010534 |
| 219622_at | RAB20 | RAB20, member RAS oncogene family | 55647 | −1.10241 | 0.000283 | 0.011722 |
| 204546_at | KIAA0513 | KIAA0513 | 9764 | −1.19275 | 0.000321 | 0.012541 |
| 209304_x_at | GADD45B | growth arrest and DNA-damage-inducible, beta | 4616 | −1.51931 | 0.000364 | 0.013369 |
| 203535_at | S100A9 | S100 calcium binding protein A9 | 6280 | −2.4352 | 0.00037 | 0.013372 |
| 210075_at | MARCH2 | membrane-associated ring finger (C3HC4) 2, E3 ubiquitin protein ligase | 51257 | −1.72415 | 0.00043 | 0.014432 |
| 213716_s_at | SECTM1 | secreted and transmembrane 1 | 6398 | −1.05168 | 0.000482 | 0.015364 |
| 209398_at | HIST1H1C | histone cluster 1, H1c | 3006 | −1.53845 | 0.000487 | 0.015374 |
| 214246_x_at | MINK1 | misshapen-like kinase 1 | 50488 | −1.16871 | 0.000487 | 0.015374 |
| 204482_at | CLDN5 | claudin 5 | 7122 | −1.62602 | 0.000494 | 0.015531 |
| 206110_at | HIST1H3H | histone cluster 1, H3h | 8357 | −2.52014 | 0.000496 | 0.015566 |
| 200736_s_at | GPX1 | glutathione peroxidase 1 | 2876 | −1.14943 | 0.000508 | 0.015789 |
| 31874_at | GAS2L1 | growth arrest-specific 2 like 1 | 10634 | −1.87076 | 0.00052 | 0.016031 |
| 217764_s_at | RAB31 | RAB31, member RAS oncogene family | 11031 | −2.01066 | 0.000564 | 0.016422 |
| AFFX-HUMISGF3A/M97935_MA_at | STAT1 | signal transducer and activator of transcription 1, 91 kDa | 6772 | −1.37938 | 0.000621 | 0.016996 |
| 212501_at | CEBPB | CCAAT/enhancer binding protein (C/EBP), beta | 1051 | −1.54731 | 0.000671 | 0.017573 |
| 212077_at | CALD1 | caldesmon 1 | 800 | −2.04255 | 0.000688 | 0.017825 |
| 201108_s_at | THBS1 | thrombospondin 1 | 7057 | −2.12731 | 0.000718 | 0.018258 |
| 212647_at | RRAS | related RAS viral (r-ras) oncogene homolog | 6237 | −1.08906 | 0.000785 | 0.019036 |
| 205463_s_at | PDGFA | platelet-derived growth factor alpha polypeptide | 5154 | −1.5857 | 0.000872 | 0.020261 |
| 202083_s_at | SEC14L1 | SEC14-like 1 (S. cerevisiae) | 6397 | −1.38339 | 0.000926 | 0.020823 |
| 221211_s_at | MAP3K7CL | MAP3K7 C-terminal like | 56911 | −1.90471 | 0.000937 | 0.020912 |
| 221059_s_at | COTL1 | coactosin-like 1 (Dictyostelium) | 23406 | −1.53392 | 0.000965 | 0.021237 |
| 201743_at | CD14 | CD14 molecule | 929 | −2.10963 | 0.00106 | 0.022456 |
| 218999_at | TMEM140 | transmembrane protein 140 | 55281 | −1.58682 | 0.001078 | 0.022646 |
| 218032_at | SNN | stannin | 8303 | −1.79738 | 0.001083 | 0.022694 |
| 201739_at | SGK1 | serum/glucocorticoid regulated kinase 1 | 6446 | −2.23217 | 0.001109 | 0.02284 |
| 203234_at | UPP1 | uridine phosphorylase 1 | 7378 | −1.24029 | 0.001155 | 0.023122 |
| 215071_s_at | HIST1H2AC | histone cluster 1, H2ac | 8334 | −2.0219 | 0.001169 | 0.02321 |
| 202497_x_at | SLC2A3 | solute carrier family 2 (facilitated glucose transporter), member 3 | 6515 | −1.11253 | 0.001169 | 0.02321 |
| 207574_s_at | GADD45B | growth arrest and DNA-damage-inducible, beta | 4616 | −1.91282 | 0.001288 | 0.024289 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| AFFX-HUMISGF3A/ M97935_MB_at | STAT1 | signal transducer and activator of transcription 1, 91 kDa | 6772 | −1.22837 | 0.001313 | 0.024575 |
| 203414_at | MMD | monocyte to macrophage differentiation-associated | 23531 | −1.96502 | 0.001341 | 0.024732 |
| 204081_at | NRGN | neurogranin (protein kinase C substrate, RC3) | 4900 | −2.55869 | 0.001354 | 0.024788 |
| 212242_at | TUBA4A | tubulin, alpha 4a | 7277 | −1.98963 | 0.001384 | 0.025003 |
| 211600_at | PTPRO | protein tyrosine phosphatase, receptor type, O | 5800 | −1.25519 | 0.001385 | 0.025003 |
| 211252_x_at | PTCRA | pre T-cell antigen receptor alpha | 171558 | −1.20925 | 0.001454 | 0.025618 |
| 210357_s_at | SMOX | spermine oxidase | 54498 | −1.0824 | 0.00148 | 0.025958 |
| 214696_at | MIR22HG | MIR22 host gene (non-protein coding) | 84981 | −1.24889 | 0.001532 | 0.026408 |
| 201506_at | TGFBI | transforming growth factor, beta-induced, 68 kDa | 7045 | −1.47238 | 0.001571 | 0.026812 |
| 215464_s_at | TAX1BP3 | Tax1 (human T-cell leukemia virus type I) binding protein 3 | 30851 | −1.19481 | 0.001588 | 0.026937 |
| 203585_at | ZNF185 | zinc finger protein 185 (LIM domain) | 7739 | −1.63846 | 0.001619 | 0.027302 |
| 214752_x_at | FLNA | filamin A, alpha | 2316 | −1.19726 | 0.001669 | 0.027658 |
| 216261_at | ITGB3 | integrin, beta 3 (platelet glycoprotein IIIa, antigen CD61) | 3690 | −1.42557 | 0.001715 | 0.028036 |
| 209729_at | GAS2L1 | growth arrest-specific 2 like 1 | 10634 | −1.29217 | 0.001761 | 0.02833 |
| 217763_s_at | RAB31 | RAB31, member RAS oncogene family | 11031 | −1.57464 | 0.001927 | 0.029492 |
| 201565_s_at | ID2 | inhibitor of DNA binding 2, dominant negative helix-loop-helix protein | 3398 | −2.05847 | 0.001931 | 0.029494 |
| 202499_s_at | SLC2A3 | solute carrier family 2 (facilitated glucose transporter), member 3 | 6515 | −1.76034 | 0.001995 | 0.030069 |
| 200859_x_at | FLNA | filamin A, alpha | 2316 | −1.14829 | 0.001998 | 0.030073 |
| 214054_at | DOK2 | docking protein 2, 56 kDa | 9046 | −1.44762 | 0.002111 | 0.030716 |
| 209959_at | NR4A3 | nuclear receptor subfamily 4, group A, member 3 | 8013 | −1.06248 | 0.002113 | 0.030716 |
| 222043_at | CLU | clusterin | 1191 | −1.24582 | 0.002133 | 0.030796 |
| 204057_at | IRF8 | interferon regulatory factor 8 | 3394 | −1.20508 | 0.002179 | 0.031039 |
| 210873_x_at | APOBEC3A | apolipoprotein B mRNA editing enzyme, catalytic polypeptide-like 3A | 200315 | −1.7692 | 0.002336 | 0.032102 |
| 204794_at | DUSP2 | dual specificity phosphatase 2 | 1844 | −1.69252 | 0.002377 | 0.032376 |
| 204232_at | FCER1G | Fc fragment of IgE, high affinity I, receptor for; gamma polypeptide | 2207 | −1.80094 | 0.002409 | 0.032561 |
| 208792_s_at | CLU | clusterin | 1191 | −1.89367 | 0.002436 | 0.032794 |
| 207414_s_at | PCSK6 | proprotein convertase subtilisin/kexin type 6 | 5046 | −1.66589 | 0.00258 | 0.034033 |
| 202295_s_at | CTSH | cathepsin H | 1512 | −1.47757 | 0.002604 | 0.034228 |
| 208078_s_at | SIK1 | salt-inducible kinase 1 | 150094 | −1.38923 | 0.002612 | 0.034234 |
| 204446_s_at | ALOX5 | arachidonate 5-lipoxygenase | 240 | −1.78576 | 0.002664 | 0.034597 |
| 205863_at | S100A12 | S100 calcium binding protein A12 | 6283 | −1.44064 | 0.002691 | 0.034786 |
| 212531_at | LCN2 | lipocalin 2 | 3934 | −1.74945 | 0.002916 | 0.036334 |
| 204698_at | ISG20 | interferon stimulated exonuclease gene 20 kDa | 3669 | −1.01523 | 0.003089 | 0.037574 |
| 213338_at | TMEM158 | transmembrane protein 158 (gene/pseudogene) | 25907 | −1.19059 | 0.00326 | 0.038684 |
| 215492_x_at | PTCRA | pre T-cell antigen receptor alpha | 171558 | −1.15689 | 0.003318 | 0.038883 |
| 204838_s_at | MLH3 | mutL homolog 3 (E. coli) | 27030 | −1.4825 | 0.00334 | 0.039 |
| 336_at | TBXA2R | thromboxane A2 receptor | 6915 | −1.13899 | 0.003359 | 0.039168 |
| 203140_at | BCL6 | B-cell CLL/lymphoma 6 | 604 | −1.30948 | 0.003569 | 0.040549 |
| 220751_s_at | FAXDC2 | fatty acid hydroxylase domain containing 2 | 10826 | −1.36 | 0.003658 | 0.041081 |
| 205495_s_at | GNLY | granulysin | 10578 | −1.10567 | 0.003705 | 0.041271 |
| 200660_at | S100A11 | S100 calcium binding protein A11 | 6282 | −1.62087 | 0.003733 | 0.041423 |
| 211429_s_at | SERPINA1 | serpin peptidase inhibitor, clade A (alpha-1 antiproteinase, antitrypsin), member 1 | 5265 | −1.9862 | 0.003781 | 0.041543 |
| 202917_s_at | S100A8 | S100 calcium binding protein A8 | 6279 | −2.98812 | 0.003874 | 0.041998 |
| 205114_s_at | CCL3L3 | chemokine (C-C motif) ligand 3-like 3 | 414062 | −2.11268 | 0.003894 | 0.041998 |
| 212509_s_at | MXRA7 | matrix-remodeling associated 7 | 439921 | −1.13262 | 0.003902 | 0.042016 |
| 204627_s_at | ITGB3 | integrin, beta 3 (platelet glycoprotein IIIa, antigen CD61) | 3690 | −2.30401 | 0.003953 | 0.042268 |
| 203922_s_at | CYBB | cytochrome b-245, beta polypeptide | 1536 | −1.0925 | 0.004058 | 0.043079 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 208180_s_at | HIST1H4H | histone cluster 1, H4h | 8365 | −1.58615 | 0.004083 | 0.043185 |
| 205237_at | FCN1 | ficolin (collagen/fibrinogen domain containing) 1 | 2219 | −2.31794 | 0.004143 | 0.043449 |
| 204628_at | ITGB3 | integrin, beta 3 (platelet glycoprotein IIIa, antigen CD61) | 3690 | −1.63546 | 0.004208 | 0.043687 |
| 201810_s_at | SH3BP5 | SH3-domain binding protein 5 (BTK-associated) | 9467 | −1.35593 | 0.004294 | 0.044285 |
| 204621_s_at | NR4A2 | nuclear receptor subfamily 4, group A, member 2 | 4929 | −1.13205 | 0.004407 | 0.044874 |
| 214414_x_at | HBA1 | hemoglobin, alpha 1 | 3039 | −2.92562 | 0.004429 | 0.044949 |
| 203305_at | F13A1 | coagulation factor XIII, A1 polypeptide | 2162 | −2.17585 | 0.004493 | 0.045292 |
| 209803_s_at | PHLDA2 | pleckstrin homology-like domain, family A, member 2 | 7262 | −1.71861 | 0.00466 | 0.046283 |
| 208161_s_at | ABCC3 | ATP-binding cassette, sub-family C (CFTR/MRP), member 3 | 8714 | −1.21045 | 0.004758 | 0.046709 |
| 208406_s_at | GRAP2 | GRB2-related adaptor protein 2 | 9402 | −1.26529 | 0.004845 | 0.047046 |
| 209806_at | HIST1H2BK | histone cluster 1, H2bk | 85236 | −1.21587 | 0.004905 | 0.047465 |
| 217028_at | CXCR4 | chemokine (C-X-C motif) receptor 4 | 7852 | −1.25222 | 0.005221 | 0.04911 |
| 218454_at | PLBD1 | phospholipase B domain containing 1 | 79887 | −1.3316 | 0.005298 | 0.049397 |
| 202833_s_at | SERPINA1 | serpin peptidase inhibitor, clade A (alpha-1 antiproteinase, antitrypsin), member 1 | 5265 | −1.72053 | 0.005347 | 0.049661 |
| 205220_at | HCAR3 | hydroxycarboxylic acid receptor 3 | 8843 | −1.11127 | 0.005534 | 0.050489 |
| 201438_at | COL6A3 | collagen, type VI, alpha 3 | 1293 | −1.45596 | 0.005536 | 0.050489 |
| 221731_x_at | VCAN | versican | 1462 | −2.02316 | 0.005573 | 0.050668 |
| 201360_at | CST3 | cystatin C | 1471 | −1.47347 | 0.005761 | 0.051649 |
| AFFX-HUMISGF3A/M97935_5_at | STAT1 | signal transducer and activator of transcription 1, 91 kDa | 6772 | −1.22821 | 0.005786 | 0.051736 |
| 204858_s_at | TYMP | thymidine phosphorylase | 1890 | −1.19053 | 0.005857 | 0.052078 |
| 205547_s_at | TAGLN | transgelin | 6876 | −1.89687 | 0.006205 | 0.053812 |
| 208791_at | CLU | clusterin | 1191 | −1.6535 | 0.006231 | 0.053824 |
| 209383_at | DDIT3 | DNA-damage-inducible transcript 3 | 1649 | −1.19919 | 0.00626 | 0.053842 |
| 217022_s_at | IGH | immunoglobulin heavy locus | 3492 | −1.26043 | 0.006498 | 0.054967 |
| 201280_s_at | DAB2 | Dab, mitogen-responsive phosphoprotein, homolog 2 (Drosophila) | 1601 | −1.35685 | 0.006817 | 0.056659 |
| AFFX-DapX-M_at | — | — |  | −1.10207 | 0.007018 | 0.057621 |
| 211074_at | FOLR1 | folate receptor 1 (adult) | 2348 | −2.335 | 0.007106 | 0.057921 |
| 221556_s_at | CDC14B | cell division cycle 14B | 8555 | −1.35463 | 0.007226 | 0.058222 |
| 212723_at | JMJD6 | jumonji domain containing 6 | 23210 | −1.10344 | 0.007325 | 0.058511 |
| 211745_x_at | HBA1 | hemoglobin, alpha 1 | 3039 | −2.39195 | 0.007372 | 0.058683 |
| 204141_at | TUBB2A | tubulin, beta 2A class IIa | 7280 | −2.1393 | 0.007748 | 0.060237 |
| 208579_x_at | H2BFS | H2B histone family, member S (pseudogene) | 54145 | −1.4314 | 0.008655 | 0.063919 |
| 203973_s_at | CEBPD | CCAAT/enhancer binding protein (C/EBP), delta | 1052 | −1.24524 | 0.008766 | 0.064315 |
| 201170_s_at | BHLHE40 | basic helix-loop-helix family, member e40 | 8553 | −1.48301 | 0.008896 | 0.064843 |
| 205119_s_at | FPR1 | formyl peptide receptor 1 | 2357 | −1.27582 | 0.009081 | 0.065557 |
| 204961_s_at | NCF1 | neutrophil cytosolic factor 1 | 653361 | −1.3618 | 0.009093 | 0.06559 |
| 201616_s_at | CALD1 | caldesmon 1 | 800 | −1.10576 | 0.009118 | 0.065687 |
| 204018_x_at | HBA1 | hemoglobin, alpha 1 | 3039 | −1.98013 | 0.009214 | 0.066107 |
| 213539_at | CD3D | CD3d molecule, delta (CD3-TCR complex) | 915 | −1.04108 | 0.009761 | 0.067714 |
| 202388_at | RGS2 | regulator of G-protein signaling 2, 24 kDa | 5997 | −1.46404 | 0.009794 | 0.06779 |
| 201798_s_at | MYOF | myoferlin | 26509 | −1.51466 | 0.009894 | 0.068217 |
| 203708_at | PDE4B | phosphodiesterase 4B, cAMP-specific | 5142 | −1.38481 | 0.01 | 0.068731 |
| 214084_x_at | NCF1C | neutrophil cytosolic factor 1C pseudogene | 654817 | −1.39567 | 0.010409 | 0.070394 |
| 209458_x_at | HBA1 | hemoglobin, alpha 1 | 3039 | −2.13257 | 0.010802 | 0.071832 |
| 217762_s_at | RAB31 | RAB31, member RAS oncogene family | 11031 | −1.34439 | 0.010983 | 0.072433 |
| 208022_s_at | CDC14B | cell division cycle 14B | 8555 | −1.06029 | 0.011035 | 0.072627 |
| 204790_at | SMAD7 | SMAD family member 7 | 4092 | −1.18892 | 0.011176 | 0.072876 |
| 217414_x_at | HBA1 | hemoglobin, alpha 1 | 3039 | −2.04967 | 0.011779 | 0.075213 |
| 204480_s_at | C9orf16 | chromosome 9 open reading frame 16 | 79095 | −1.0583 | 0.01178 | 0.075213 |
| 204908_s_at | BCL3 | B-cell CLL/lymphoma 3 | 602 | −1.12158 | 0.011802 | 0.075244 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 206883_x_at | GP9 | glycoprotein IX (platelet) | 2815 | −1.39492 | 0.012283 | 0.076763 |
| 211964_at | COL4A2 | collagen, type IV, alpha 2 | 1284 | −1.30407 | 0.012296 | 0.076763 |
| AFFX-HUMGAPDH/M33197_5_at | GAPDH | glyceraldehyde-3-phosphate dehydrogenase | 2597 | −1.07979 | 0.012327 | 0.076822 |
| 202887_s_at | DDIT4 | DNA-damage-inducible transcript 4 | 54541 | −1.42927 | 0.012333 | 0.076822 |
| AFFX-HUMGAPDH/M33197_M_at | GAPDH | glyceraldehyde-3-phosphate dehydrogenase | 2597 | −1.25641 | 0.012335 | 0.076822 |
| 204588_s_at | SLC7A7 | solute carrier family 7 (amino acid transporter light chain, y + L system), member 7 | 9056 | −1.19903 | 0.012402 | 0.077024 |
| 206655_s_at | GP1BB | glycoprotein Ib (platelet), beta polypeptide | 2812 | −2.09441 | 0.0128 | 0.078521 |
| 221841_s_at | KLF4 | Kruppel-like factor 4 (gut) | 9314 | −1.65198 | 0.012861 | 0.078835 |
| 212657_s_at | IL1RN | interleukin 1 receptor antagonist | 3557 | −1.14627 | 0.013221 | 0.080181 |
| 204620_s_at | VCAN | versican | 1462 | −1.51568 | 0.013307 | 0.080358 |
| 205442_at | MFAP3L | microfibrillar-associated protein 3-like | 9848 | −1.52051 | 0.013437 | 0.080854 |
| 200665_s_at | SPARC | secreted protein, acidic, cysteine-rich (osteonectin) | 6678 | −1.75861 | 0.01347 | 0.080865 |
| 204396_s_at | GRK5 | G protein-coupled receptor kinase 5 | 2869 | −1.28375 | 0.013822 | 0.082085 |
| 202207_at | ARL4C | ADP-ribosylation factor-like 4C | 10123 | −1.06368 | 0.014043 | 0.082963 |
| AFFX-HSAC07/X00351_3_at | ACTB | actin, beta | 60 | −1.37822 | 0.014382 | 0.0839 |
| 214974_x_at | CXCL5 | chemokine (C-X-C motif) ligand 5 | 6374 | −1.55942 | 0.014408 | 0.083963 |
| 213275_x_at | CTSB | cathepsin B | 1508 | −1.09109 | 0.014496 | 0.084285 |
| 214677_x_at | CYAT1 | immunoglobulin lambda light chain-like | 100290481 | −1.19702 | 0.014517 | 0.084316 |
| 218559_s_at | MAFB | v-maf musculoaponeurotic fibrosarcoma oncogene homolog B (avian) | 9935 | −1.60023 | 0.014906 | 0.085665 |
| 208527_x_at | HIST1H2BE | histone cluster 1, H2be | 8344 | −1.0534 | 0.015738 | 0.08838 |
| 202310_s_at | COL1A1 | collagen, type I, alpha 1 | 1277 | −1.87619 | 0.016831 | 0.091891 |
| 208601_s_at | TUBB1 | tubulin, beta 1 class VI | 81027 | −1.17222 | 0.017934 | 0.095324 |
| 219403_s_at | HPSE | heparanase | 10855 | −1.31934 | 0.018497 | 0.096806 |
| 200622_x_at | CALM3 | calmodulin 3 (phosphorylase kinase, delta) | 808 | −1.04785 | 0.018549 | 0.096942 |
| 212667_at | SPARC | secreted protein, acidic, cysteine-rich (osteonectin) | 6678 | −1.34731 | 0.018812 | 0.097654 |
| 209949_at | NCF2 | neutrophil cytosolic factor 2 | 4688 | −1.34905 | 0.01953 | 0.099726 |
| 204122_at | TYROBP | TYRO protein tyrosine kinase binding protein | 7305 | −1.58727 | 0.019681 | 0.100052 |
| 201811_x_at | SH3BP5 | SH3-domain binding protein 5 (BTK-associated) | 9467 | −1.02097 | 0.020101 | 0.101165 |
| 214469_at | HIST1H2AE | histone cluster 1, H2ae | 3012 | −1.04742 | 0.020232 | 0.101492 |
| 200999_s_at | CKAP4 | cytoskeleton-associated protein 4 | 10970 | −1.1494 | 0.020405 | 0.101743 |
| 204319_s_at | RGS10 | regulator of G-protein signaling 10 | 6001 | −1.05791 | 0.020642 | 0.102328 |
| 37966_at | PARVB | parvin, beta | 29780 | −1.18316 | 0.020871 | 0.102995 |
| AFFX-HUMISGF3A/M97935_3_at | STAT1 | signal transducer and activator of transcription 1, 91 kDa | 6772 | −1.13562 | 0.022192 | 0.106109 |
| 208546_x_at | HIST1H2BH | histone cluster 1, H2bh | 8345 | −1.03067 | 0.022452 | 0.106776 |
| 204834_at | FGL2 | fibrinogen-like 2 | 10875 | −1.4682 | 0.022775 | 0.107256 |
| 216442_x_at | FN1 | fibronectin 1 | 2335 | −1.90726 | 0.023141 | 0.108166 |
| 204103_at | CCL4 | chemokine (C-C motif) ligand 4 | 6351 | −1.0683 | 0.02465 | 0.111906 |
| 221269_s_at | SH3BGRL3 | SH3 domain binding glutamic acid-rich protein like 3 | 83442 | −1.17357 | 0.024677 | 0.111906 |
| 201842_s_at | EFEMP1 | EGF containing fibulin-like extracellular matrix protein 1 | 2202 | −1.50062 | 0.024795 | 0.112138 |
| 208450_at | LGALS2 | lectin, galactoside-binding, soluble, 2 | 3957 | −1.55709 | 0.025744 | 0.114214 |
| 212464_s_at | FN1 | fibronectin 1 | 2335 | −1.96353 | 0.025831 | 0.114387 |
| 204971_at | CSTA | cystatin A (stefin A) | 1475 | −1.4559 | 0.026275 | 0.115382 |
| 211719_x_at | FN1 | fibronectin 1 | 2335 | −2.20582 | 0.026796 | 0.116477 |
| 210495_x_at | FN1 | fibronectin 1 | 2335 | −1.90768 | 0.026965 | 0.116845 |
| 216248_s_at | NR4A2 | nuclear receptor subfamily 4, group A, member 2 | 4929 | −1.17499 | 0.028238 | 0.119726 |
| 204912_at | IL10RA | interleukin 10 receptor, alpha | 3587 | −1.05258 | 0.02903 | 0.121428 |
| 211699_x_at | HBA1 | hemoglobin, alpha 1 | 3039 | −1.60002 | 0.029162 | 0.121623 |
| AFFX-HSAC07/X00351_5_at | ACTB | actin, beta | 60 | −1.04373 | 0.029941 | 0.123368 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 218280_x_at | HIST2H2AA4 | histone cluster 2, H2aa4 | 723790 | −1.035 | 0.029948 | 0.123368 |
| 215240_at | ITGB3 | integrin, beta 3 (platelet glycoprotein IIIa, antigen CD61) | 3690 | −1.18589 | 0.030708 | 0.124841 |
| 219630_at | PDZK1IP1 | PDZK1 interacting protein 1 | 10158 | −1.16143 | 0.031505 | 0.126922 |
| 56256_at | SIDT2 | SID1 transmembrane family, member 2 | 51092 | −1.06356 | 0.03192 | 0.127917 |
| 214146_s_at | PPBP | pro-platelet basic protein (chemokine (C-X-C motif) ligand 7) | 5473 | −2.2804 | 0.032189 | 0.128506 |
| 217683_at | HBE1 | hemoglobin, epsilon 1 | 3046 | −1.01632 | 0.03275 | 0.12959 |
| 202627_s_at | SERPINE1 | serpin peptidase inhibitor, clade E (nexin, plasminogen activator inhibitor type 1), member 1 | 5054 | −1.24155 | 0.035257 | 0.134957 |
| 218223_s_at | PLEKHO1 | pleckstrin homology domain containing, family O member 1 | 51177 | −1.02949 | 0.035417 | 0.13521 |
| 203394_s_at | HES1 | hairy and enhancer of split 1, (Drosophila) | 3280 | −1.19137 | 0.036252 | 0.137146 |
| 214511_x_at | FCGR1B | Fc fragment of IgG, high affinity Ib, receptor (CD64) | 2210 | −1.00332 | 0.036916 | 0.1385 |
| 211980_at | COL4A1 | collagen, type IV, alpha 1 | 1282 | −1.2568 | 0.037235 | 0.139094 |
| 215076_s_at | COL3A1 | collagen, type III, alpha 1 | 1281 | −1.43307 | 0.038584 | 0.141774 |
| 218723_s_at | RGCC | regulator of cell cycle | 28984 | −1.35285 | 0.038884 | 0.142295 |
| 201465_s_at | JUN | jun proto-oncogene | 3725 | −1.23554 | 0.039397 | 0.143388 |
| 206493_at | ITGA2B | integrin, alpha 2b (platelet glycoprotein IIb of IIb/IIIa complex, antigen CD41) | 3674 | −1.40259 | 0.040966 | 0.146453 |
| 209651_at | TGFB1I1 | transforming growth factor beta 1 induced transcript 1 | 7041 | −1.18925 | 0.043241 | 0.150602 |
| 202403_s_at | COL1A2 | collagen, type I, alpha 2 | 1278 | −1.44055 | 0.046503 | 0.156448 |
| 213975_s_at | LYZ | lysozyme | 4069 | −1.35445 | 0.046533 | 0.156457 |
| 202391_at | BASP1 | brain abundant, membrane attached signal protein 1 | 10409 | −1.21789 | 0.050925 | 0.164058 |
| 200897_s_at | PALLD | palladin, cytoskeletal associated protein | 23022 | −1.19733 | 0.054484 | 0.169794 |
| 207206_s_at | ALOX12 | arachidonate 12-lipoxygenase | 239 | −1.13633 | 0.054626 | 0.170045 |
| 202404_s_at | COL1A2 | collagen, type I, alpha 2 | 1278 | −1.71166 | 0.056539 | 0.173313 |
| 210809_s_at | POSTN | periostin, osteoblast specific factor | 10631 | −1.70047 | 0.059219 | 0.177986 |
| 217572_at | — | — | | −1.0617 | 0.061496 | 0.181515 |
| 204351_at | S100P | S100 calcium binding protein P | 6286 | −1.10416 | 0.061934 | 0.182039 |
| 202953_at | C1QB | complement component 1, q subcomponent, B chain | 713 | −1.04337 | 0.061996 | 0.182121 |
| 36711_at | MAFF | v-maf musculoaponeurotic fibrosarcoma oncogene homolog F (avian) | 23764 | −2.07111 | 0.062874 | 0.183657 |
| 214290_s_at | HIST2H2AA4 | histone cluster 2, H2aa4 | 723790 | −1.00017 | 0.063196 | 0.184141 |
| 220496_at | CLEC1B | C-type lectin domain family 1, member B | 51266 | −1.26133 | 0.068125 | 0.192398 |
| 202628_s_at | SERPINE1 | serpin peptidase inhibitor, clade E (nexin, plasminogen activator inhibitor type 1), member 1 | 5054 | −1.0038 | 0.068895 | 0.193543 |
| 201852_x_at | COL3A1 | collagen, type III, alpha 1 | 1281 | −1.06074 | 0.069846 | 0.19499 |
| 209210_s_at | FERMT2 | fermitin family member 2 | 10979 | −1.18848 | 0.071118 | 0.197 |
| 208937_s_at | ID1 | inhibitor of DNA binding 1, dominant negative helix-loop-helix protein | 3397 | −1.06464 | 0.076912 | 0.204982 |
| 202644_s_at | TNFAIP3 | tumor necrosis factor, alpha-induced protein 3 | 7128 | −1.11193 | 0.077731 | 0.206126 |
| 202555_s_at | MYLK | myosin light chain kinase | 4638 | −1.20646 | 0.078352 | 0.206861 |
| 207808_s_at | PROS1 | protein S (alpha) | 5627 | −1.05757 | 0.080762 | 0.210082 |
| 202237_at | NNMT | nicotinamide N-methyltransferase | 4837 | −1.16906 | 0.084988 | 0.216541 |
| 204959_at | MNDA | myeloid cell nuclear differentiation antigen | 4332 | −1.11553 | 0.099265 | 0.237052 |
| 206390_x_at | PF4 | platelet factor 4 | 5196 | −1.56272 | 0.105914 | 0.246063 |
| 207076_at | ASS1 | argininosuccinate synthase 1 | 445 | −1.01934 | 0.110808 | 0.252682 |
| 206494_s_at | ITGA2B | integrin, alpha 2b (platelet glycoprotein IIb of IIb/IIIa complex, antigen CD41) | 3674 | −1.21162 | 0.118492 | 0.262217 |
| 207140_at | ALPI | alkaline phosphatase, intestinal | 248 | −1.14253 | 0.12301 | 0.267727 |
| 216834_at | RGS1 | regulator of G-protein signaling 1 | 5996 | −1.34806 | 0.15206 | 0.303847 |
| 202988_s_at | RGS1 | regulator of G-protein signaling 1 | 5996 | −1.08916 | 0.188906 | 0.346892 |
| 213515_x_at | HBG1 | hemoglobin, gamma A | 3047 | −1.06377 | 0.246664 | 0.407885 |
| 212671_s_at | HLA-DQA1 | major histocompatibility complex, class II, DQ alpha 1 | 3117 | 1.097239 | 0.126891 | 0.272796 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 211734_s_at | FCER1A | Fc fragment of IgE, high affinity I, receptor for; alpha polypeptide | 2205 | 1.009251 | 0.078698 | 0.207233 |
| 210982_s_at | HLA-DRA | major histocompatibility complex, class II, DR alpha | 3122 | 1.194665 | 0.07091 | 0.196595 |
| 202016_at | MEST | mesoderm specific transcript | 4232 | 1.10616 | 0.05007 | 0.162642 |
| 209773_s_at | RRM2 | ribonucleotide reductase M2 | 6241 | 1.272153 | 0.049561 | 0.161602 |
| 202946_s_at | BTBD3 | BTB (POZ) domain containing 3 | 22903 | 1.045621 | 0.04313 | 0.150497 |
| 208894_at | HLA-DRA | major histocompatibility complex, class II, DR alpha | 3122 | 1.34853 | 0.028179 | 0.119545 |
| 213376_at | ZBTB1 | zinc finger and BTB domain containing 1 | 22890 | 1.088786 | 0.026552 | 0.116003 |
| 206310_at | SPINK2 | serine peptidase inhibitor, Kazal type 2 (acrosin-trypsin inhibitor) | 6691 | 1.055612 | 0.024944 | 0.112515 |
| 203817_at | GUCY1B3 | guanylate cyclase 1, soluble, beta 3 | 2983 | 1.163996 | 0.024688 | 0.111906 |
| 209392_at | ENPP2 | ectonucleotide pyrophosphatase/phosphodiesterase 2 | 5168 | 1.030545 | 0.023369 | 0.108718 |
| 216640_s_at | PDIA6 | protein disulfide isomerase family A, member 6 | 10130 | 1.19128 | 0.020388 | 0.10174 |
| 212588_at | PTPRC | protein tyrosine phosphatase, receptor type, C | 5788 | 1.226601 | 0.019819 | 0.100488 |
| 209894_at | LEPR | leptin receptor | 3953 | 1.184929 | 0.018148 | 0.09595 |
| 218039_at | NUSAP1 | nucleolar and spindle associated protein 1 | 51203 | 1.157405 | 0.017634 | 0.094469 |
| 213129_s_at | GCSHP5 | glycine cleavage system protein H pseudogene 5 | 100329108 | 1.10714 | 0.01585 | 0.088615 |
| 201577_at | NME1 | NME/NM23 nucleoside diphosphate kinase 1 | 4830 | 1.034901 | 0.015518 | 0.087753 |
| 214741_at | ZNF131 | zinc finger protein 131 | 7690 | 1.072298 | 0.015265 | 0.086843 |
| 212498_at | — | — |  | 1.007129 | 0.014477 | 0.084233 |
| 200953_s_at | CCND2 | cyclin D2 | 894 | 1.083456 | 0.014299 | 0.083701 |
| 207668_x_at | PDIA6 | protein disulfide isomerase family A, member 6 | 10130 | 1.075588 | 0.014187 | 0.083288 |
| 208639_x_at | PDIA6 | protein disulfide isomerase family A, member 6 | 10130 | 1.148925 | 0.013925 | 0.082576 |
| 212749_s_at | RCHY1 | ring finger and CHY zinc finger domain containing 1, E3 ubiquitin protein ligase | 25898 | 1.154346 | 0.013753 | 0.081884 |
| 213599_at | OIP5 | Opa interacting protein 5 | 11339 | 1.034915 | 0.013279 | 0.080287 |
| 218477_at | TMEM14A | transmembrane protein 14A | 28978 | 1.038055 | 0.01243 | 0.077084 |
| 209160_at | AKR1C3 | aldo-keto reductase family 1, member C3 | 8644 | 1.050868 | 0.012306 | 0.076764 |
| 207165_at | HMMR | hyaluronan-mediated motility receptor (RHAMM) | 3161 | 1.12524 | 0.012278 | 0.076763 |
| 200750_s_at | RAN | RAN, member RAS oncogene family | 5901 | 1.196145 | 0.012173 | 0.076447 |
| 200853_at | H2AFZ | H2A histone family, member Z | 3015 | 1.133212 | 0.012107 | 0.076162 |
| 211762_s_at | KPNA2 | karyopherin alpha 2 (RAG cohort 1, importin alpha 1) | 3838 | 1.122517 | 0.011697 | 0.074903 |
| 202591_s_at | SSBP1 | single-stranded DNA binding protein 1, mitochondrial | 6742 | 1.079587 | 0.011546 | 0.074317 |
| 212224_at | ALDH1A1 | aldehyde dehydrogenase 1 family, member A1 | 216 | 1.532805 | 0.011256 | 0.073081 |
| 202157_s_at | CELF2 | CUGBP, Elav-like family member 2 | 10659 | 1.345852 | 0.011153 | 0.072851 |
| 201018_at | EIF1AX | eukaryotic translation initiation factor 1A, X-linked | 1964 | 1.07069 | 0.011072 | 0.072653 |
| 214359_s_at | HSP90AB1 | heat shock protein 90 kDa alpha (cytosolic), class B member 1 | 3326 | 1.611725 | 0.010493 | 0.070756 |
| 202266_at | TDP2 | tyrosyl-DNA phosphodiesterase 2 | 51567 | 1.168396 | 0.009941 | 0.068453 |
| 204023_at | RFC4 | replication factor C (activator 1) 4, 37 kDa | 5984 | 1.161476 | 0.009896 | 0.068217 |
| 208852_at | CANX | calnexin | 821 | 1.147782 | 0.009836 | 0.067995 |
| 208990_s_at | HNRNPH3 | heterogeneous nuclear ribonucleoprotein H3 (2H9) | 3189 | 1.022691 | 0.009773 | 0.067735 |
| 201193_at | IDH1 | isocitrate dehydrogenase 1 (NADP+), soluble | 3417 | 1.109705 | 0.009675 | 0.067345 |
| 204444_at | KIF11 | kinesin family member 11 | 3832 | 1.052307 | 0.009568 | 0.06712 |
| 202899_s_at | SRSF3 | serine/arginine-rich splicing factor 3 | 6428 | 1.121111 | 0.009554 | 0.067103 |
| 206834_at | HBD | hemoglobin, delta | 3045 | 1.603183 | 0.009504 | 0.066927 |
| 213241_at | PLXNC1 | plexin C1 | 10154 | 1.098497 | 0.009355 | 0.066441 |
| 208783_s_at | CD46 | CD46 molecule, complement regulatory protein | 4179 | 1.009037 | 0.009253 | 0.066184 |
| 204905_s_at | EEF1E1 | eukaryotic translation elongation factor 1 epsilon 1 | 9521 | 1.018486 | 0.009203 | 0.06606 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 203755_at | BUB1B | BUB1 mitotic checkpoint serine/threonine kinase B | 701 | 1.106693 | 0.009061 | 0.065504 |
| 201462_at | SCRN1 | secernin 1 | 9805 | 1.089176 | 0.008825 | 0.064512 |
| 207238_s_at | PTPRC | protein tyrosine phosphatase, receptor type, C | 5788 | 1.002292 | 0.00794 | 0.060948 |
| 202469_s_at | CPSF6 | cleavage and polyadenylation specific factor 6, 68 kDa | 11052 | 1.017757 | 0.007655 | 0.05992 |
| 218350_s_at | GMNN | geminin, DNA replication inhibitor | 51053 | 1.289682 | 0.007592 | 0.059577 |
| 201653_at | CNIH | cornichon homolog (*Drosophila*) | 10175 | 1.024747 | 0.007566 | 0.059412 |
| 210759_s_at | PSMA1 | proteasome (prosome, macropain) subunit, alpha type, 1 | 5682 | 1.025107 | 0.007534 | 0.05925 |
| 218984_at | PUS7 | pseudouridylate synthase 7 homolog (*S. cerevisiae*) | 54517 | 1.092719 | 0.007372 | 0.058683 |
| 213541_s_at | ERG | v-ets erythroblastosis virus E26 oncogene homolog (avian) | 2078 | 1.268671 | 0.007213 | 0.058222 |
| 214214_s_at | C1QBP | complement component 1, q subcomponent binding protein | 708 | 1.081512 | 0.006939 | 0.057298 |
| 218883_s_at | MLF1IP | MLF1 interacting protein | 79682 | 1.002951 | 0.006546 | 0.05522 |
| 204798_at | MYB | v-myb myeloblastosis viral oncogene homolog (avian) | 4602 | 1.33907 | 0.006372 | 0.054414 |
| 214710_s_at | CCNB1 | cyclin B1 | 891 | 1.30622 | 0.006365 | 0.05438 |
| 200892_s_at | TRA2B | transformer 2 beta homolog (*Drosophila*) | 6434 | 1.059953 | 0.006225 | 0.053824 |
| 201084_s_at | BCLAF1 | BCL2-associated transcription factor 1 | 9774 | 1.042614 | 0.006038 | 0.053075 |
| 219306_at | KIF15 | kinesin family member 15 | 56992 | 1.005174 | 0.005933 | 0.052485 |
| 209180_at | RABGGTB | Rab geranylgeranyltransferase, beta subunit | 5876 | 1.030791 | 0.00587 | 0.05217 |
| 201829_at | NET1 | neuroepithelial cell transforming 1 | 10276 | 1.16411 | 0.005759 | 0.051649 |
| 213047_x_at | SET | SET nuclear oncogene | 6418 | 1.072575 | 0.005512 | 0.05039 |
| 201241_at | DDX1 | DEAD (Asp-Glu-Ala-Asp) box helicase 1 | 1653 | 1.20415 | 0.005509 | 0.05039 |
| 209728_at | HLA-DRB4 | major histocompatibility complex, class II, DR beta 4 | 3126 | 2.396871 | 0.005479 | 0.050353 |
| 201890_at | RRM2 | ribonucleotide reductase M2 | 6241 | 1.743456 | 0.005295 | 0.049397 |
| 201477_s_at | RRM1 | ribonucleotide reductase M1 | 6240 | 1.259059 | 0.005293 | 0.049397 |
| 200728_at | ACTR2 | ARP2 actin-related protein 2 homolog (yeast) | 10097 | 1.079756 | 0.005255 | 0.049248 |
| 212250_at | MTDH | metadherin | 92140 | 1.112188 | 0.005254 | 0.049248 |
| 200996_at | ACTR3 | ARP3 actin-related protein 3 homolog (yeast) | 10096 | 1.167525 | 0.005078 | 0.048328 |
| 203405_at | PSMG1 | proteasome (prosome, macropain) assembly chaperone 1 | 8624 | 1.002781 | 0.005039 | 0.048111 |
| 200877_at | CCT4 | chaperonin containing TCP1, subunit 4 (delta) | 10575 | 1.134112 | 0.004843 | 0.047046 |
| 210438_x_at | TROVE2 | TROVE domain family, member 2 | 6738 | 1.075252 | 0.004643 | 0.046201 |
| 201417_at | SOX4 | SRY (sex determining region Y)-box 4 | 6659 | 1.240673 | 0.004546 | 0.045582 |
| 201014_s_at | PAICS | phosphoribosylaminoimidazole carboxylase, phosphoribosylaminoimidazole succinocarboxamide synthetase | 10606 | 1.325476 | 0.004523 | 0.045413 |
| 200064_at | HSP90AB1 | heat shock protein 90 kDa alpha (cytosolic), class B member 1 | 3326 | 1.128671 | 0.004413 | 0.044877 |
| 202268_s_at | NAE1 | NEDD8 activating enzyme E1 subunit 1 | 8883 | 1.117633 | 0.004311 | 0.044378 |
| 211137_s_at | ATP2C1 | ATPase, Ca++ transporting, type 2C, member 1 | 27032 | 1.024207 | 0.004133 | 0.04339 |
| 218694_at | ARMCX1 | armadillo repeat containing, X-linked 1 | 51309 | 1.240431 | 0.004091 | 0.043202 |
| 201676_x_at | PSMA1 | proteasome (prosome, macropain) subunit, alpha type, 1 | 5682 | 1.034639 | 0.00406 | 0.043079 |
| 217987_at | ASNSD1 | asparagine synthetase domain containing 1 | 54529 | 1.242982 | 0.004059 | 0.043079 |
| 219563_at | LINC00341 | long intergenic non-protein coding RNA 341 | 79686 | 1.115324 | 0.004051 | 0.043037 |
| 201240_s_at | LOC653566 | signal peptidase complex subunit 2 homolog (*S. cerevisiae*) pseudogene | 653566 | 1.053758 | 0.004022 | 0.042778 |
| 204146_at | RAD51AP1 | RAD51 associated protein 1 | 10635 | 1.156331 | 0.004016 | 0.042729 |
| 209757_s_at | MYCN | v-myc myelocytomatosis viral related oncogene, neuroblastoma derived (avian) | 4613 | 1.210293 | 0.003996 | 0.042614 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 209095_at | DLD | dihydrolipoamide dehydrogenase | 1738 | 1.319642 | 0.003935 | 0.042191 |
| 211971_s_at | LRPPRC | leucine-rich pentatricopeptide repeat containing | 10128 | 1.113512 | 0.003889 | 0.041998 |
| 211746_x_at | PSMA1 | proteasome (prosome, macropain) subunit, alpha type, 1 | 5682 | 1.018568 | 0.003854 | 0.041914 |
| 200052_s_at | ILF2 | interleukin enhancer binding factor 2 | 3608 | 1.0667 | 0.003851 | 0.041914 |
| 212640_at | PTPLB | protein tyrosine phosphatase-like (proline instead of catalytic arginine), member b | 201562 | 1.131425 | 0.003826 | 0.041838 |
| 200774_at | FAM120A | family with sequence similarity 120A | 23196 | 1.114974 | 0.003738 | 0.04145 |
| 209318_x_at | PLAGL1 | pleiomorphic adenoma gene-like 1 | 5325 | 1.23893 | 0.003682 | 0.04125 |
| 201180_s_at | GNAI3 | guanine nucleotide binding protein (G protein), alpha inhibiting activity polypeptide 3 | 2773 | 1.037392 | 0.003621 | 0.040838 |
| 215933_s_at | HHEX | hematopoietically expressed homeobox | 3087 | 1.279779 | 0.003597 | 0.040702 |
| 200807_s_at | HSPD1 | heat shock 60 kDa protein 1 (chaperonin) | 3329 | 1.015247 | 0.00358 | 0.040641 |
| 202539_s_at | HMGCR | 3-hydroxy-3-methylglutaryl-CoA reductase | 3156 | 1.103166 | 0.003517 | 0.040158 |
| 200072_s_at | HNRNPM | heterogeneous nuclear ribonucleoprotein M | 4670 | 1.402849 | 0.00349 | 0.040028 |
| 204373_s_at | CEP350 | centrosomal protein 350 kDa | 9857 | 1.185706 | 0.003481 | 0.040028 |
| 203209_at | RFC5 | replication factor C (activator 1) 5, 36.5 kDa | 5985 | 1.113492 | 0.00338 | 0.039333 |
| 211935_at | ARL6IP1 | ADP-ribosylation factor-like 6 interacting protein 1 | 23204 | 1.159268 | 0.003341 | 0.039 |
| 203566_s_at | AGL | amylo-alpha-1,6-glucosidase, 4-alpha-glucanotransferase | 178 | 1.046125 | 0.003305 | 0.038871 |
| 201549_x_at | KDM5B | lysine (K)-specific demethylase 5B | 10765 | 1.065448 | 0.003285 | 0.038786 |
| 208029_s_at | LAPTM4B | lysosomal protein transmembrane 4 beta | 55353 | 1.253963 | 0.003231 | 0.038501 |
| 218585_s_at | DTL | denticleless E3 ubiquitin protein ligase homolog (*Drosophila*) | 51514 | 1.350603 | 0.003194 | 0.03822 |
| 212893_at | ZZZ3 | zinc finger, ZZ-type containing 3 | 26009 | 1.08034 | 0.003179 | 0.038151 |
| 215440_s_at | BEX4 | brain expressed, X-linked 4 | 56271 | 1.274266 | 0.00308 | 0.037537 |
| 200020_at | TARDBP | TAR DNA binding protein | 23435 | 1.100346 | 0.002966 | 0.036705 |
| 213293_s_at | TRIM22 | tripartite motif containing 22 | 10346 | 1.403817 | 0.00295 | 0.036579 |
| 205612_at | MMRN1 | multimerin 1 | 22915 | 1.21464 | 0.002937 | 0.036484 |
| 201930_at | MCM6 | minichromosome maintenance complex component 6 | 4175 | 1.051838 | 0.002935 | 0.036484 |
| 208910_s_at | C1QBP | complement component 1, q subcomponent binding protein | 708 | 1.40182 | 0.00291 | 0.036295 |
| 218870_at | ARHGAP15 | Rho GTPase activating protein 15 | 55843 | 1.442188 | 0.002874 | 0.036047 |
| 204236_at | FLI1 | Friend leukemia virus integration 1 | 2313 | 1.290793 | 0.002863 | 0.036016 |
| 211784_s_at | SRSF1 | serine/arginine-rich splicing factor 1 | 6426 | 1.027483 | 0.002853 | 0.035922 |
| 212215_at | PREPL | prolyl endopeptidase-like | 9581 | 1.016567 | 0.002832 | 0.03582 |
| 201713_s_at | RANBP2 | RAN binding protein 2 | 5903 | 1.15906 | 0.002829 | 0.035812 |
| 201589_at | SMC1A | structural maintenance of chromosomes 1A | 8243 | 1.429532 | 0.002826 | 0.035794 |
| 201327_s_at | CCT6A | chaperonin containing TCP1, subunit 6A (zeta 1) | 908 | 1.110939 | 0.002792 | 0.035561 |
| 214949_at | — | — | | 1.096897 | 0.002708 | 0.034908 |
| 213222_at | PLCB1 | phospholipase C, beta 1 (phosphoinositide-specific) | 23236 | 1.045277 | 0.002634 | 0.03437 |
| 205051_s_at | KIT | v-kit Hardy-Zuckerman 4 feline sarcoma viral oncogene homolog | 3815 | 1.349599 | 0.002631 | 0.034353 |
| 201652_at | COPS5 | COP9 constitutive photomorphogenic homolog subunit 5 (*Arabidopsis*) | 10987 | 1.133169 | 0.002622 | 0.034334 |
| 208767_s_at | LAPTM4B | lysosomal protein transmembrane 4 beta | 55353 | 1.125608 | 0.002597 | 0.034178 |
| 204026_s_at | ZWINT | ZW10 interactor, kinetochore protein | 11130 | 1.36409 | 0.002574 | 0.033989 |
| 211615_s_at | LRPPRC | leucine-rich pentatricopeptide repeat containing | 10128 | 1.077666 | 0.002524 | 0.03353 |
| 206332_s_at | IFI16 | interferon, gamma-inducible protein 16 | 3428 | 1.04713 | 0.002479 | 0.033114 |
| 213605_s_at | — | — | | 1.301604 | 0.002445 | 0.032816 |
| 219054_at | NPR3 | natriuretic peptide receptor C/guanylate cyclase C (atrionatriuretic peptide receptor C) | 4883 | 1.079574 | 0.002372 | 0.032376 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 212867_at | NCOA2 | nuclear receptor coactivator 2 | 10499 | 1.169646 | 0.002371 | 0.032376 |
| 208828_at | POLE3 | polymerase (DNA directed), epsilon 3, accessory subunit | 54107 | 1.189315 | 0.002289 | 0.031795 |
| 204127_at | RFC3 | replication factor C (activator 1) 3, 38 kDa | 5983 | 1.217624 | 0.002267 | 0.031632 |
| 202599_s_at | NRIP1 | nuclear receptor interacting protein 1 | 8204 | 1.485341 | 0.002258 | 0.03152 |
| 212557_at | ZNF451 | zinc finger protein 451 | 26036 | 1.087217 | 0.002254 | 0.031489 |
| 210766_s_at | CSE1L | CSE1 chromosome segregation 1-like (yeast) | 1434 | 1.038634 | 0.002233 | 0.031297 |
| 211922_s_at | CAT | catalase | 847 | 1.262699 | 0.002221 | 0.031297 |
| 205345_at | BARD1 | BRCA1 associated RING domain 1 | 580 | 1.097185 | 0.002218 | 0.031297 |
| 201197_at | AMD1 | adenosylmethionine decarboxylase 1 | 262 | 1.147451 | 0.002213 | 0.031264 |
| 204689_at | HHEX | hematopoietically expressed homeobox | 3087 | 1.069023 | 0.002165 | 0.030957 |
| 201624_at | DARS | aspartyl-tRNA synthetase | 1615 | 1.026982 | 0.002159 | 0.030955 |
| 212766_s_at | ISG20L2 | interferon stimulated exonuclease gene 20 kDa-like 2 | 81875 | 1.137911 | 0.002146 | 0.030863 |
| 201112_s_at | CSE1L | CSE1 chromosome segregation 1-like (yeast) | 1434 | 1.11844 | 0.002142 | 0.030838 |
| 212038_s_at | VDAC1 | voltage-dependent anion channel 1 | 7416 | 1.422303 | 0.002135 | 0.030796 |
| 211953_s_at | IPO5 | importin 5 | 3843 | 1.242501 | 0.002132 | 0.030796 |
| 212612_at | RCOR1 | REST corepressor 1 | 23186 | 1.102759 | 0.002126 | 0.030796 |
| 218715_at | UTP6 | UTP6, small subunit (SSU) processome component, homolog (yeast) | 55813 | 1.287375 | 0.002119 | 0.030758 |
| 217957_at | C16orf80 | chromosome 16 open reading frame 80 | 29105 | 1.235392 | 0.002104 | 0.030707 |
| 208666_s_at | ST13 | suppression of tumorigenicity 13 (colon carcinoma) (Hsp70 interacting protein) | 6767 | 1.060002 | 0.00206 | 0.030421 |
| 201054_at | HNRNPA0 | heterogeneous nuclear ribonucleoprotein A0 | 10949 | 1.042824 | 0.002053 | 0.030384 |
| 208863_s_at | SRSF1 | serine/arginine-rich splicing factor 1 | 6426 | 1.155243 | 0.002024 | 0.03021 |
| 221942_s_at | GUCY1A3 | guanylate cyclase 1, soluble, alpha 3 | 2982 | 1.274671 | 0.002022 | 0.030194 |
| 203380_x_at | SRSF5 | serine/arginine-rich splicing factor 5 | 6430 | 1.094125 | 0.002013 | 0.030181 |
| 204439_at | IFI44L | interferon-induced protein 44-like | 10964 | 1.917025 | 0.002005 | 0.030152 |
| 202119_s_at | CPNE3 | copine III | 8895 | 1.240924 | 0.001996 | 0.030069 |
| 202491_s_at | IKBKAP | inhibitor of kappa light polypeptide gene enhancer in B-cells, kinase complex-associated protein | 8518 | 1.162396 | 0.001995 | 0.030069 |
| 200816_s_at | PAFAH1B1 | platelet-activating factor acetylhydrolase 1b, regulatory subunit 1 (45 kDa) | 5048 | 1.041005 | 0.001981 | 0.029948 |
| 203011_at | IMPA1 | inositol(myo)-1(or 4)-monophosphatase 1 | 3612 | 1.283329 | 0.001971 | 0.029877 |
| 202613_at | CTPS1 | CTP synthase 1 | 1503 | 1.114581 | 0.001955 | 0.0297 |
| 206937_at | SPTA1 | spectrin, alpha, erythrocytic 1 (elliptocytosis 2) | 6708 | 1.151575 | 0.001936 | 0.029531 |
| 212037_at | PNN | pinin, desmosome associated protein | 5411 | 1.494883 | 0.001917 | 0.029474 |
| 206052_s_at | SLBP | stem-loop binding protein | 7884 | 1.082828 | 0.001906 | 0.029434 |
| 201013_s_at | PAICS | phosphoribosylaminoimidazole carboxylase, phosphoribosylaminoimidazole succinocarboxamide synthetase | 10606 | 1.121467 | 0.00186 | 0.029062 |
| 209642_at | BUB1 | BUB1 mitotic checkpoint serine/threonine kinase | 699 | 1.034101 | 0.001808 | 0.028585 |
| 210425_x_at | GOLGA8B | golgin A8 family, member B | 440270 | 1.211965 | 0.001808 | 0.028585 |
| 209861_s_at | METAP2 | methionyl aminopeptidase 2 | 10988 | 1.173435 | 0.001784 | 0.0285 |
| 221547_at | PRPF18 | PRP18 pre-mRNA processing factor 18 homolog (S. cerevisiae) | 8559 | 1.010609 | 0.001784 | 0.0285 |
| 203138_at | HAT1 | histone acetyltransferase 1 | 8520 | 1.697742 | 0.001772 | 0.028447 |
| 209630_s_at | FBXW2 | F-box and WD repeat domain containing 2 | 26190 | 1.00777 | 0.001755 | 0.028286 |
| 201330_at | RARS | arginyl-tRNA synthetase | 5917 | 1.048926 | 0.001753 | 0.028265 |
| 211727_s_at | COX11 | cytochrome c oxidase assembly homolog 11 (yeast) | 1353 | 1.104041 | 0.001747 | 0.028216 |
| 212287_at | SUZ12 | suppressor of zeste 12 homolog (Drosophila) | 23512 | 1.060589 | 0.001742 | 0.028189 |
| 208802_at | SRP72 | signal recognition particle 72 kDa | 6731 | 1.080033 | 0.001713 | 0.028028 |
| 200978_at | MDH1 | malate dehydrogenase 1, NAD (soluble) | 4190 | 1.102564 | 0.001677 | 0.027682 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 203373_at | SOCS2 | suppressor of cytokine signaling 2 | 8835 | 1.193044 | 0.001676 | 0.027682 |
| 218263_s_at | ZBED5 | zinc finger, BED-type containing 5 | 58486 | 1.068226 | 0.001674 | 0.027682 |
| 202303_x_at | SMARCA5 | SWI/SNF related, matrix associated, actin dependent regulator of chromatin, subfamily a, member 5 | 8467 | 1.013631 | 0.001653 | 0.02757 |
| 201472_at | VBP1 | von Hippel-Lindau binding protein 1 | 7411 | 1.093136 | 0.001639 | 0.027452 |
| 212825_at | PAXIP1 | PAX interacting (with transcription-activation domain) protein 1 | 22976 | 1.152279 | 0.001534 | 0.026427 |
| 217993_s_at | MAT2B | methionine adenosyltransferase II, beta | 27430 | 1.083589 | 0.001528 | 0.02639 |
| 202113_s_at | SNX2 | sorting nexin 2 | 6643 | 1.270036 | 0.001506 | 0.02616 |
| 209330_s_at | HNRNPD | heterogeneous nuclear ribonucleoprotein D (AU-rich element RNA binding protein 1, 37 kDa) | 3184 | 1.161084 | 0.001504 | 0.02616 |
| 206958_s_at | UPF3A | UPF3 regulator of nonsense transcripts homolog A (yeast) | 65110 | 1.374126 | 0.001456 | 0.025618 |
| 201478_s_at | DKC1 | dyskeratosis congenita 1, dyskerin | 1736 | 1.420645 | 0.00145 | 0.025591 |
| 210260_s_at | TNFAIP8 | tumor necrosis factor, alpha-induced protein 8 | 25816 | 1.079476 | 0.001424 | 0.025305 |
| 205394_at | CHEK1 | checkpoint kinase 1 | 1111 | 1.025967 | 0.001414 | 0.025236 |
| 208966_x_at | IFI16 | interferon, gamma-inducible protein 16 | 3428 | 1.261519 | 0.001413 | 0.025236 |
| 202227_s_at | BRD8 | bromodomain containing 8 | 10902 | 1.211398 | 0.001397 | 0.025152 |
| 202983_at | HLTF | helicase-like transcription factor | 6596 | 1.292442 | 0.001395 | 0.025148 |
| 218966_at | MYO5C | myosin VC | 55930 | 1.153543 | 0.001385 | 0.025003 |
| 208787_at | MRPL3 | mitochondrial ribosomal protein L3 | 11222 | 1.176304 | 0.001376 | 0.02497 |
| 203427_at | ASF1A | ASF1 anti-silencing function 1 homolog A (S. cerevisiae) | 25842 | 1.059991 | 0.001373 | 0.02497 |
| 201260_s_at | SYPL1 | synaptophysin-like 1 | 6856 | 1.204425 | 0.001372 | 0.02497 |
| 212652_s_at | SNX4 | sorting nexin 4 | 8723 | 1.052201 | 0.001368 | 0.024963 |
| 217850_at | GNL3 | guanine nucleotide binding protein-like 3 (nucleolar) | 26354 | 1.41406 | 0.00135 | 0.024754 |
| 212435_at | TRIM33 | tripartite motif containing 33 | 51592 | 1.036739 | 0.001348 | 0.024743 |
| 210983_s_at | MCM7 | minichromosome maintenance complex component 7 | 4176 | 1.380913 | 0.001341 | 0.024732 |
| 204510_at | CDC7 | cell division cycle 7 | 8317 | 1.373466 | 0.001299 | 0.024412 |
| 201970_s_at | NASP | nuclear autoantigenic sperm protein (histone-binding) | 4678 | 1.246396 | 0.00128 | 0.024202 |
| 214043_at | PTPRD | protein tyrosine phosphatase, receptor type, D | 5789 | 1.253071 | 0.001271 | 0.02415 |
| 209572_s_at | EED | embryonic ectoderm development | 8726 | 1.058266 | 0.00127 | 0.02415 |
| 202890_at | MAP7 | microtubule-associated protein 7 | 9053 | 1.299804 | 0.001265 | 0.02408 |
| 201129_at | SRSF7 | serine/arginine-rich splicing factor 7 | 6432 | 1.119633 | 0.001254 | 0.023956 |
| 201699_at | PSMC6 | proteasome (prosome, macropain) 26S subunit, ATPase, 6 | 5706 | 1.503145 | 0.00122 | 0.023629 |
| 212266_s_at | SRSF5 | serine/arginine-rich splicing factor 5 | 6430 | 1.41576 | 0.001217 | 0.023629 |
| 206544_x_at | SMARCA2 | SWI/SNF related, matrix associated, actin dependent regulator of chromatin, subfamily a, member 2 | 6595 | 1.067396 | 0.001209 | 0.023601 |
| 209049_s_at | ZMYND8 | zinc finger, MYND-type containing 8 | 23613 | 1.006778 | 0.001203 | 0.023563 |
| 213313_at | RABGAP1 | RAB GTPase activating protein 1 | 23637 | 1.398753 | 0.001197 | 0.0235 |
| 222204_s_at | RRN3 | RRN3 RNA polymerase I transcription factor homolog (S. cerevisiae) | 54700 | 1.07798 | 0.001196 | 0.0235 |
| 203362_s_at | MAD2L1 | MAD2 mitotic arrest deficient-like 1 (yeast) | 4085 | 1.334952 | 0.001171 | 0.02321 |
| 221264_s_at | TARDBP | TAR DNA binding protein | 23435 | 1.148261 | 0.00117 | 0.02321 |
| 204009_s_at | KRAS | v-Ki-ras2 Kirsten rat sarcoma viral oncogene homolog | 3845 | 1.15051 | 0.001169 | 0.02321 |
| 213416_at | ITGA4 | integrin, alpha 4 (antigen CD49D, alpha 4 subunit of VLA-4 receptor) | 3676 | 1.585393 | 0.00116 | 0.023183 |
| 200993_at | IPO7 | importin 7 | 10527 | 1.052977 | 0.001144 | 0.023074 |
| 202911_at | MSH6 | mutS homolog 6 (E. coli) | 2956 | 1.406267 | 0.00114 | 0.023016 |
| 201619_at | PRDX3 | peroxiredoxin 3 | 10935 | 1.166794 | 0.001136 | 0.02301 |
| 203743_s_at | TDG | thymine-DNA glycosylase | 6996 | 1.30963 | 0.00113 | 0.022997 |
| 212199_at | MRFAP1L1 | Morf4 family associated protein 1-like 1 | 114932 | 1.630757 | 0.001123 | 0.022952 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 202164_s_at | CNOT8 | CCR4-NOT transcription complex, subunit 8 | 9337 | 1.199704 | 0.001118 | 0.022906 |
| 204809_at | CLPX | ClpX caseinolytic peptidase X homolog (E. coli) | 10845 | 1.04299 | 0.001099 | 0.02276 |
| 206542_s_at | SMARCA2 | SWI/SNF related, matrix associated, actin dependent regulator of chromatin, subfamily a, member 2 | 6595 | 1.42069 | 0.001047 | 0.022288 |
| 203948_s_at | MPO | myeloperoxidase | 4353 | 1.629289 | 0.001047 | 0.022288 |
| 200927_s_at | RAB14 | RAB14, member RAS oncogene family | 51552 | 1.113603 | 0.001045 | 0.022285 |
| 205961_s_at | PSIP1 | PC4 and SFRS1 interacting protein 1 | 11168 | 1.119456 | 0.001035 | 0.022115 |
| 203139_at | DAPK1 | death-associated protein kinase 1 | 1612 | 1.135088 | 0.001004 | 0.021669 |
| 219485_s_at | PSMD10 | proteasome (prosome, macropain) 26S subunit, non-ATPase, 10 | 5716 | 1.237831 | 0.000994 | 0.021584 |
| 202169_s_at | AASDHPPT | aminoadipate-semialdehyde dehydrogenase-phosphopantetheinyl transferase | 60496 | 1.491517 | 0.000983 | 0.021447 |
| 213761_at | MDM1 | Mdm1 nuclear protein homolog (mouse) | 56890 | 1.12881 | 0.000976 | 0.02135 |
| 212544_at | ZNHIT3 | zinc finger, HIT-type containing 3 | 9326 | 1.294137 | 0.000971 | 0.0213 |
| 201368_at | ZFP36L2 | ZFP36 ring finger protein-like 2 | 678 | 1.289879 | 0.000961 | 0.021237 |
| 218882_s_at | WDR3 | WD repeat domain 3 | 10885 | 1.059399 | 0.000955 | 0.021168 |
| 202431_s_at | MYC | v-myc myelocytomatosis viral oncogene homolog (avian) | 4609 | 1.493528 | 0.000946 | 0.02101 |
| 217828_at | SLTM | SAFB-like, transcription modulator | 79811 | 1.118355 | 0.000938 | 0.020912 |
| 201111_at | CSE1L | CSE1 chromosome segregation 1-like (yeast) | 1434 | 1.623491 | 0.000932 | 0.020833 |
| 203474_at | IQGAP2 | IQ motif containing GTPase activating protein 2 | 10788 | 1.614975 | 0.000922 | 0.020814 |
| 217906_at | KLHDC2 | kelch domain containing 2 | 23588 | 1.142864 | 0.00092 | 0.020814 |
| 203531_at | CUL5 | cullin 5 | 8065 | 1.096581 | 0.000891 | 0.020435 |
| 202746_at | ITM2A | integral membrane protein 2A | 9452 | 1.664011 | 0.000885 | 0.020363 |
| 209421_at | MSH2 | mutS homolog 2, colon cancer, nonpolyposis type 1 (E. coli) | 4436 | 1.490121 | 0.00088 | 0.020343 |
| 213698_at | ZMYM6NB | ZMYM6 neighbor | 100506144 | 1.042591 | 0.00087 | 0.020236 |
| 218605_at | TFB2M | transcription factor B2, mitochondrial | 64216 | 1.183958 | 0.000854 | 0.02007 |
| 201947_s_at | CCT2 | chaperonin containing TCP1, subunit 2 (beta) | 10576 | 1.143067 | 0.000853 | 0.02007 |
| 202602_s_at | HTATSF1 | HIV-1 Tat specific factor 1 | 27336 | 1.187599 | 0.000849 | 0.020015 |
| 202930_s_at | SUCLA2 | succinate-CoA ligase, ADP-forming, beta subunit | 8803 | 1.176902 | 0.000838 | 0.019818 |
| 201277_s_at | HNRNPAB | heterogeneous nuclear ribonucleoprotein A/B | 3182 | 1.014906 | 0.000822 | 0.019567 |
| 208798_x_at | GOLGA8A | golgin A8 family, member A | 23015 | 1.082102 | 0.000821 | 0.019567 |
| 202413_s_at | USP1 | ubiquitin specific peptidase 1 | 7398 | 1.360578 | 0.000801 | 0.01926 |
| 201742_x_at | SRSF1 | serine/arginine-rich splicing factor 1 | 6426 | 1.198562 | 0.000799 | 0.01924 |
| 218014_at | NUP85 | nucleoporin 85 kDa | 79902 | 1.180004 | 0.000796 | 0.019229 |
| 204240_s_at | SMC2 | structural maintenance of chromosomes 2 | 10592 | 1.406601 | 0.000787 | 0.01907 |
| 209337_at | PSIP1 | PC4 and SFRS1 interacting protein 1 | 11168 | 1.241851 | 0.000784 | 0.019026 |
| 201273_s_at | SRP9 | signal recognition particle 9 kDa | 6726 | 1.202073 | 0.000784 | 0.019026 |
| 222303_at | — | — | | 1.254922 | 0.000781 | 0.019002 |
| 212330_at | TFDP1 | transcription factor Dp-1 | 7027 | 1.341814 | 0.00078 | 0.019002 |
| 203432_at | TMPO | thymopoietin | 7112 | 1.068195 | 0.000768 | 0.01881 |
| 203493_s_at | CEP57 | centrosomal protein 57 kDa | 9702 | 1.03691 | 0.000766 | 0.018788 |
| 202330_s_at | UNG | uracil-DNA glycosylase | 7374 | 1.326002 | 0.000761 | 0.018729 |
| 209814_at | ZNF330 | zinc finger protein 330 | 27309 | 1.444996 | 0.000758 | 0.018729 |
| 203560_at | GGH | gamma-glutamyl hydrolase (conjugase, folylpolygammaglutamyl hydrolase) | 8836 | 1.446967 | 0.00075 | 0.018617 |
| 209112_at | CDKN1B | cyclin-dependent kinase inhibitor 1B (p27, Kip1) | 1027 | 1.181993 | 0.000749 | 0.018617 |
| 35974_at | LRMP | lymphoid-restricted membrane protein | 4033 | 1.001783 | 0.000732 | 0.018537 |
| 208643_s_at | XRCC5 | X-ray repair complementing defective repair in Chinese hamster cells 5 (double-strand-break rejoining) | 7520 | 1.057033 | 0.000731 | 0.018525 |
| 214651_s_at | HOXA9 | homeobox A9 | 3205 | 1.466349 | 0.000687 | 0.017825 |
| 204767_s_at | FEN1 | flap structure-specific endonuclease 1 | 2237 | 1.47296 | 0.000685 | 0.017799 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 202658_at | PEX11B | peroxisomal biogenesis factor 11 beta | 8799 | 1.013624 | 0.000684 | 0.017799 |
| 218989_x_at | SLC30A5 | solute carrier family 30 (zinc transporter), member 5 | 64924 | 1.011398 | 0.000683 | 0.017799 |
| 212740_at | PIK3R4 | phosphoinositide-3-kinase, regulatory subunit 4 | 30849 | 1.016978 | 0.000678 | 0.017687 |
| 212378_at | GART | phosphoribosylglycinamide formyltransferase, phosphoribosylglycinamide synthetase, phosphoribosylaminoimidazole synthetase | 2618 | 1.210756 | 0.000671 | 0.017573 |
| 221931_s_at | SEH1L | SEH1-like (S. cerevisiae) | 81929 | 1.151366 | 0.000671 | 0.017573 |
| 201830_s_at | NET1 | neuroepithelial cell transforming 1 | 10276 | 1.193353 | 0.000654 | 0.017314 |
| 202174_s_at | PCM1 | pericentriolar material 1 | 5108 | 1.195075 | 0.000641 | 0.017181 |
| 202717_s_at | CDC16 | cell division cycle 16 | 8881 | 1.000687 | 0.000632 | 0.017087 |
| 204720_s_at | DNAJC6 | DnaJ (Hsp40) homolog, subfamily C, member 6 | 9829 | 1.165169 | 0.00063 | 0.017071 |
| 202503_s_at | KIAA0101 | KIAA0101 | 9768 | 1.410664 | 0.000627 | 0.01707 |
| 212513_s_at | USP33 | ubiquitin specific peptidase 33 | 23032 | 1.349055 | 0.000623 | 0.01703 |
| 203583_at | UNC50 | unc-50 homolog (C. elegans) | 25972 | 1.021413 | 0.000607 | 0.016773 |
| 209199_s_at | MEF2C | myocyte enhancer factor 2C | 4208 | 1.384786 | 0.000605 | 0.016755 |
| 203949_at | MPO | myeloperoxidase | 4353 | 2.09466 | 0.0006 | 0.016728 |
| 213088_s_at | DNAJC9 | DnaJ (Hsp40) homolog, subfamily C, member 9 | 23234 | 1.165365 | 0.0006 | 0.016728 |
| 201873_s_at | ABCE1 | ATP-binding cassette, sub-family E (OABP), member 1 | 6059 | 1.123959 | 0.000598 | 0.016728 |
| 201518_at | CBX1 | chromobox homolog 1 | 10951 | 1.118253 | 0.000591 | 0.016699 |
| 221771_s_at | MPHOSPH8 | M-phase phosphoprotein 8 | 54737 | 1.003732 | 0.000588 | 0.016642 |
| 218236_s_at | PRKD3 | protein kinase D3 | 23683 | 1.039419 | 0.00058 | 0.016542 |
| 218979_at | RMI1 | RMI1, RecQ mediated genome instability 1, homolog (S. cerevisiae) | 80010 | 1.012559 | 0.000577 | 0.016542 |
| 201532_at | PSMA3 | proteasome (prosome, macropain) subunit, alpha type, 3 | 5684 | 1.445319 | 0.000575 | 0.016531 |
| 212653_s_at | EHBP1 | EH domain binding protein 1 | 23301 | 1.032735 | 0.000566 | 0.016422 |
| 210338_s_at | HSPA8 | heat shock 70 kDa protein 8 | 3312 | 1.574514 | 0.000564 | 0.016422 |
| 218642_s_at | CHCHD7 | coiled-coil-helix-coiled-coil-helix domain containing 7 | 79145 | 1.029917 | 0.000561 | 0.016422 |
| 221970_s_at | NOL11 | nucleolar protein 11 | 25926 | 1.054307 | 0.00056 | 0.016422 |
| 202741_at | PRKACB | protein kinase, cAMP-dependent, catalytic, beta | 5567 | 1.048386 | 0.000557 | 0.016422 |
| 209905_at | HOXA9 | homeobox A9 | 3205 | 1.24736 | 0.000554 | 0.016422 |
| 202589_at | TYMS | thymidylate synthetase | 7298 | 1.65426 | 0.000548 | 0.01628 |
| 200071_at | SMNDC1 | survival motor neuron domain containing 1 | 10285 | 1.034914 | 0.000544 | 0.016265 |
| 201303_at | EIF4A3 | eukaryotic translation initiation factor 4A3 | 9775 | 1.17097 | 0.000539 | 0.016206 |
| 205632_s_at | PIP5K1B | phosphatidylinositol-4-phosphate 5-kinase, type I, beta | 8395 | 1.175229 | 0.000533 | 0.016113 |
| 215380_s_at | GGCT | gamma-glutamylcyclotransferase | 79017 | 1.189841 | 0.000531 | 0.016099 |
| 203765_at | GCA | grancalcin, EF-hand calcium binding protein | 25801 | 1.046003 | 0.00053 | 0.016099 |
| 220865_s_at | PDSS1 | prenyl (decaprenyl) diphosphate synthase, subunit 1 | 23590 | 1.074485 | 0.000525 | 0.016054 |
| 202446_s_at | PLSCR1 | phospholipid scramblase 1 | 5359 | 1.327281 | 0.000524 | 0.01605 |
| 200970_s_at | SERP1 | stress-associated endoplasmic reticulum protein 1 | 27230 | 1.075633 | 0.000512 | 0.015879 |
| 216920_s_at | TARP | TCR gamma alternate reading frame protein | 445347 | 1.485156 | 0.000485 | 0.015374 |
| 212693_at | MDN1 | MDN1, midasin homolog (yeast) | 23195 | 1.087501 | 0.000484 | 0.015374 |
| 213359_at | HNRNPD | heterogeneous nuclear ribonucleoprotein D (AU-rich element RNA binding protein 1, 37 kDa) | 3184 | 1.09076 | 0.000478 | 0.015321 |
| 206102_at | GINS1 | GINS complex subunit 1 (Psf1 homolog) | 9837 | 1.575105 | 0.000474 | 0.015221 |
| 202950_at | CRYZ | crystallin, zeta (quinone reductase) | 1429 | 1.315997 | 0.000472 | 0.015221 |
| 202395_at | NSF | N-ethylmaleimide-sensitive factor | 4905 | 1.021689 | 0.000471 | 0.015221 |
| 220615_s_at | FAR2 | fatty acyl CoA reductase 2 | 55711 | 1.050613 | 0.000469 | 0.015212 |
| 211700_s_at | TRO | trophinin | 7216 | 1.068948 | 0.000465 | 0.015212 |
| 206095_s_at | SRSF10 | serine/arginine-rich splicing factor 10 | 10772 | 1.179453 | 0.000464 | 0.015212 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 208694_at | PRKDC | protein kinase, DNA-activated, catalytic polypeptide | 5591 | 1.097773 | 0.000458 | 0.015075 |
| 214141_x_at | SRSF7 | serine/arginine-rich splicing factor 7 | 6432 | 1.331333 | 0.000439 | 0.014608 |
| 203517_at | MTX2 | metaxin 2 | 10651 | 1.225852 | 0.000439 | 0.014608 |
| 205857_at | SLC18A2 | solute carrier family 18 (vesicular monoamine), member 2 | 6571 | 1.065076 | 0.000431 | 0.014432 |
| 203856_at | VRK1 | vaccinia related kinase 1 | 7443 | 1.237886 | 0.00043 | 0.014432 |
| 203372_s_at | SOCS2 | suppressor of cytokine signaling 2 | 8835 | 1.09312 | 0.00042 | 0.014308 |
| 221652_s_at | ASUN | asunder, spermatogenesis regulator | 55726 | 1.363988 | 0.000412 | 0.014181 |
| 212690_at | DDHD2 | DDHD domain containing 2 | 23259 | 1.236377 | 0.000412 | 0.014181 |
| 208808_s_at | HMGB2 | high mobility group box 2 | 3148 | 1.445021 | 0.000402 | 0.014069 |
| 212896_at | SKIV2L2 | superkiller viralicidic activity 2-like 2 (S. cerevisiae) | 23517 | 1.098253 | 0.000395 | 0.013905 |
| 221622_s_at | TMEM126B | transmembrane protein 126B | 55863 | 1.103945 | 0.000394 | 0.013871 |
| 218303_x_at | KRCC1 | lysine-rich coiled-coil 1 | 51315 | 1.054683 | 0.000393 | 0.013857 |
| 201479_at | DKC1 | dyskeratosis congenita 1, dyskerin | 1736 | 1.261576 | 0.00039 | 0.013806 |
| 203156_at | AKAP11 | A kinase (PRKA) anchor protein 11 | 11215 | 1.181561 | 0.000384 | 0.013683 |
| 201756_at | RPA2 | replication protein A2, 32 kDa | 6118 | 1.039715 | 0.000379 | 0.013533 |
| 209903_s_at | ATR | ataxia telangiectasia and Rad3 related | 545 | 1.074716 | 0.000376 | 0.013488 |
| 206976_s_at | HSPH1 | heat shock 105 kDa/110 kDa protein 1 | 10808 | 1.254331 | 0.000376 | 0.013488 |
| 219454_at | EGFL6 | EGF-like-domain, multiple 6 | 25975 | 1.30877 | 0.000367 | 0.013369 |
| 211144_x_at | TARP | TCR gamma alternate reading frame protein | 445347 | 1.365625 | 0.000366 | 0.013369 |
| 205133_s_at | HSPE1 | heat shock 10 kDa protein 1 (chaperonin 10) | 3336 | 1.081382 | 0.000365 | 0.013369 |
| 202429_s_at | PPP3CA | protein phosphatase 3, catalytic subunit, alpha isozyme | 5530 | 1.056462 | 0.000363 | 0.013369 |
| 210038_at | PRKCQ | protein kinase C, theta | 5588 | 1.046788 | 0.000358 | 0.013295 |
| 205668_at | LY75 | lymphocyte antigen 75 | 4065 | 1.075449 | 0.000357 | 0.013295 |
| 201515_s_at | TSN | translin | 7247 | 1.30897 | 0.000349 | 0.01317 |
| 221825_at | ANGEL2 | angel homolog 2 (Drosophila) | 90806 | 1.010739 | 0.000347 | 0.013115 |
| 212168_at | RBM12 | RNA binding motif protein 12 | 10137 | 1.209363 | 0.000346 | 0.013115 |
| 201555_at | MCM3 | minichromosome maintenance complex component 3 | 4172 | 1.057831 | 0.000343 | 0.013089 |
| 208766_s_at | HNRNPR | heterogeneous nuclear ribonucleoprotein R | 10236 | 1.04567 | 0.000341 | 0.013032 |
| 213294_at | EIF2AK2 | eukaryotic translation initiation factor 2-alpha kinase 2 | 5610 | 1.224521 | 0.000339 | 0.012995 |
| 217956_s_at | ENOPH1 | enolase-phosphatase 1 | 58478 | 1.13057 | 0.000325 | 0.012646 |
| 212211_at | ANKRD17 | ankyrin repeat domain 17 | 26057 | 1.06166 | 0.000321 | 0.012541 |
| 218396_at | VPS13C | vacuolar protein sorting 13 homolog C (S. cerevisiae) | 54832 | 1.169643 | 0.000315 | 0.012391 |
| 202020_s_at | LANCL1 | LanC lantibiotic synthetase component C-like 1 (bacterial) | 10314 | 1.265915 | 0.000314 | 0.012374 |
| 213304_at | FAM179B | family with sequence similarity 179, member B | 23116 | 1.05681 | 0.000311 | 0.01229 |
| 214093_s_at | FUBP1 | far upstream element (FUSE) binding protein 1 | 8880 | 1.19343 | 0.000311 | 0.01229 |
| 221761_at | ADSS | adenylosuccinate synthase | 159 | 1.010834 | 0.000308 | 0.012252 |
| 201386_s_at | DHX15 | DEAH (Asp-Glu-Ala-His) box polypeptide 15 | 1665 | 1.650845 | 0.000306 | 0.012244 |
| 221505_at | ANP32E | acidic (leucine-rich) nuclear phosphoprotein 32 family, member E | 81611 | 1.183054 | 0.000303 | 0.012139 |
| 218127_at | NFYB | nuclear transcription factor Y, beta | 4801 | 1.104339 | 0.00029 | 0.011904 |
| 219303_at | RNF219 | ring finger protein 219 | 79596 | 1.119496 | 0.000279 | 0.011636 |
| 218133_s_at | NIF3L1 | NIF3 NGG1 interacting factor 3-like 1 (S. cerevisiae) | 60491 | 1.192936 | 0.000269 | 0.011358 |
| 203428_s_at | ASF1A | ASF1 anti-silencing function 1 homolog A (S. cerevisiae) | 25842 | 1.128273 | 0.000268 | 0.011351 |
| 219037_at | RRP15 | ribosomal RNA processing 15 homolog (S. cerevisiae) | 51018 | 1.057006 | 0.000267 | 0.011351 |
| 218889_at | NOC3L | nucleolar complex associated 3 homolog (S. cerevisiae) | 64318 | 1.366019 | 0.000262 | 0.011306 |
| 201413_at | HSD17B4 | hydroxysteroid (17-beta) dehydrogenase 4 | 3295 | 1.140766 | 0.000255 | 0.011131 |
| 212526_at | SPG20 | spastic paraplegia 20 (Troyer syndrome) | 23111 | 1.026783 | 0.000251 | 0.01101 |
| 208021_s_at | RFC1 | replication factor C (activator 1) 1, 145 kDa | 5981 | 1.039138 | 0.00025 | 0.010974 |
| 213253_at | SMC2 | structural maintenance of chromosomes 2 | 10592 | 1.034612 | 0.000246 | 0.010839 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 218713_at | NARG2 | NMDA receptor regulated 2 | 79664 | 1.010022 | 0.000244 | 0.010824 |
| 209092_s_at | GLOD4 | glyoxalase domain containing 4 | 51031 | 1.452265 | 0.000233 | 0.010534 |
| 208634_s_at | MACF1 | microtubule-actin crosslinking factor 1 | 23499 | 1.053724 | 0.000229 | 0.010503 |
| 202854_at | HPRT1 | hypoxanthine phosphoribosyltransferase 1 | 3251 | 1.377438 | 0.000227 | 0.010458 |
| 202345_s_at | FABP5 | fatty acid binding protein 5 (psoriasis-associated) | 2171 | 1.412774 | 0.000223 | 0.010332 |
| 217832_at | SYNCRIP | synaptotagmin binding, cytoplasmic RNA interacting protein | 10492 | 1.449861 | 0.000222 | 0.010305 |
| 220742_s_at | NGLY1 | N-glycanase 1 | 55768 | 1.055086 | 0.00022 | 0.010287 |
| 202318_s_at | SENP6 | SUMO1/sentrin specific peptidase 6 | 26054 | 1.021802 | 0.000214 | 0.010126 |
| 202892_at | CDC23 | cell division cycle 23 | 8697 | 1.142138 | 0.000212 | 0.010103 |
| 201964_at | SETX | senataxin | 23064 | 1.253372 | 0.000211 | 0.010103 |
| 209056_s_at | CDC5L | cell division cycle 5-like | 988 | 1.214199 | 0.000208 | 0.010028 |
| 214047_s_at | MBD4 | methyl-CpG binding domain protein 4 | 8930 | 1.011612 | 0.000208 | 0.010028 |
| 201603_at | PPP1R12A | protein phosphatase 1, regulatory subunit 12A | 4659 | 1.089584 | 0.000204 | 0.00993 |
| 208716_s_at | TMCO1 | transmembrane and coiled-coil domains 1 | 54499 | 1.113356 | 0.000202 | 0.009867 |
| 218710_at | TTC27 | tetratricopeptide repeat domain 27 | 55622 | 1.090229 | 0.000201 | 0.009867 |
| 216221_s_at | PUM2 | pumilio homolog 2 (Drosophila) | 23369 | 1.105518 | 0.000201 | 0.009867 |
| 202107_s_at | MCM2 | minichromosome maintenance complex component 2 | 4171 | 1.506995 | 0.000201 | 0.009867 |
| 214453_s_at | IFI44 | interferon-induced protein 44 | 10561 | 1.719005 | 0.0002 | 0.009867 |
| 208775_at | XPO1 | exportin 1 (CRM1 homolog, yeast) | 7514 | 1.473631 | 0.000198 | 0.009851 |
| 211929_at | HNRNPA3 | heterogeneous nuclear ribonucleoprotein A3 | 220988 | 1.257569 | 0.000198 | 0.009839 |
| 212406_s_at | PCMTD2 | protein-L-isoaspartate (D-aspartate) O-methyltransferase domain containing 2 | 55251 | 1.452466 | 0.000196 | 0.009776 |
| 204354_at | POT1 | protection of telomeres 1 | 25913 | 1.126965 | 0.000194 | 0.009746 |
| 218323_at | RHOT1 | ras homolog family member T1 | 55288 | 1.007825 | 0.000186 | 0.009582 |
| 200994_at | IPO7 | importin 7 | 10527 | 1.001576 | 0.000186 | 0.009582 |
| 201773_at | ADNP | activity-dependent neuroprotector homeobox | 23394 | 1.388566 | 0.000183 | 0.009532 |
| 202060_at | CTR9 | Ctr9, Paf1/RNA polymerase II complex component, homolog (S. cerevisiae) | 9646 | 1.453326 | 0.00018 | 0.00945 |
| 209218_at | SQLE | squalene epoxidase | 6713 | 1.758399 | 0.000177 | 0.009364 |
| 209580_s_at | MBD4 | methyl-CpG binding domain protein 4 | 8930 | 1.160508 | 0.000174 | 0.009336 |
| 202633_at | TOPBP1 | topoisomerase (DNA) II binding protein 1 | 11073 | 1.197566 | 0.000173 | 0.009336 |
| 213106_at | ATP8A1 | ATPase, aminophospholipid transporter (APLT), class I, type 8A, member 1 | 10396 | 1.20933 | 0.000168 | 0.009246 |
| 212058_at | U2SURP | U2 snRNP-associated SURP domain containing | 23350 | 1.398897 | 0.000168 | 0.009246 |
| 212408_at | TOR1AIP1 | torsin A interacting protein 1 | 26092 | 1.153349 | 0.000163 | 0.009063 |
| 203067_at | PDHX | pyruvate dehydrogenase complex, component X | 8050 | 1.024437 | 0.00016 | 0.009007 |
| 202184_s_at | NUP133 | nucleoporin 133 kDa | 55746 | 1.163427 | 0.000156 | 0.008893 |
| 204749_at | NAP1L3 | nucleosome assembly protein 1-like 3 | 4675 | 1.756608 | 0.000149 | 0.008702 |
| 212621_at | TMEM194A | transmembrane protein 194A | 23306 | 1.117235 | 0.000148 | 0.008702 |
| 200723_s_at | CAPRIN1 | cell cycle associated protein 1 | 4076 | 1.360735 | 0.000145 | 0.008669 |
| 219008_at | C2orf43 | chromosome 2 open reading frame 43 | 60526 | 1.160627 | 0.000144 | 0.008657 |
| 202220_at | KIAA0907 | KIAA0907 | 22889 | 1.542705 | 0.000144 | 0.008657 |
| 211987_at | TOP2B | topoisomerase (DNA) II beta 180 kDa | 7155 | 1.023919 | 0.000143 | 0.008633 |
| 202441_at | ERLIN1 | ER lipid raft associated 1 | 10613 | 1.221226 | 0.000141 | 0.008533 |
| 218171_at | VPS4B | vacuolar protein sorting 4 homolog B (S. cerevisiae) | 9525 | 1.099892 | 0.000138 | 0.008402 |
| 209974_s_at | BUB3 | BUB3 mitotic checkpoint protein | 9184 | 1.177194 | 0.000136 | 0.008296 |
| 219412_at | RAB38 | RAB38, member RAS oncogene family | 23682 | 1.455958 | 0.000133 | 0.008144 |
| 205474_at | CRLF3 | cytokine receptor-like factor 3 | 51379 | 1.012784 | 0.000132 | 0.008144 |
| 222201_s_at | CASP8AP2 | caspase 8 associated protein 2 | 9994 | 1.164562 | 0.00013 | 0.008097 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 208838_at | CAND1 | cullin-associated and neddylation-dissociated 1 | 55832 | 1.071114 | 0.000128 | 0.007998 |
| 204521_at | FAM216A | family with sequence similarity 216, member A | 29902 | 1.272748 | 0.000124 | 0.007921 |
| 213506_at | F2RL1 | coagulation factor II (thrombin) receptor-like 1 | 2150 | 1.465639 | 0.000123 | 0.007906 |
| 214988_s_at | SON | SON DNA binding protein | 6651 | 1.293714 | 0.00012 | 0.007803 |
| 218005_at | ZNF22 | zinc finger protein 22 | 7570 | 1.363822 | 0.000117 | 0.007673 |
| 202798_at | SEC24B | SEC24 family, member B (S. cerevisiae) | 10427 | 1.217371 | 0.000115 | 0.007613 |
| 203519_s_at | UPF2 | UPF2 regulator of nonsense transcripts homolog (yeast) | 26019 | 1.021857 | 0.000114 | 0.007613 |
| 213227_at | PGRMC2 | progesterone receptor membrane component 2 | 10424 | 1.088092 | 0.000114 | 0.007613 |
| 212918_at | RECQL | RecQ protein-like (DNA helicase Q1-like) | 5965 | 1.204724 | 0.000111 | 0.007613 |
| 218842_at | RPAP3 | RNA polymerase II associated protein 3 | 79657 | 1.007012 | 0.000109 | 0.007613 |
| 218370_s_at | S100PBP | S100P binding protein | 64766 | 1.040583 | 0.000107 | 0.007601 |
| 209043_at | PAPSS1 | 3'-phosphoadenosine 5'-phosphosulfate synthase 1 | 9061 | 1.266585 | 0.000106 | 0.007558 |
| 213374_x_at | HIBCH | 3-hydroxyisobutyryl-CoA hydrolase | 26275 | 1.37257 | 0.000104 | 0.00745 |
| 201202_at | PCNA | proliferating cell nuclear antigen | 5111 | 1.874541 | 0.000102 | 0.00739 |
| 208925_at | CLDND1 | claudin domain containing 1 | 56650 | 1.035219 | 0.000101 | 0.007343 |
| 208986_at | TCF12 | transcription factor 12 | 6938 | 1.13518 | 9.80E−05 | 0.00719 |
| 202706_s_at | UMPS | uridine monophosphate synthetase | 7372 | 1.021819 | 9.71E−05 | 0.007147 |
| 222209_s_at | TMEM135 | transmembrane protein 135 | 65084 | 1.139737 | 9.39E−05 | 0.007017 |
| 202956_at | ARFGEF1 | ADP-ribosylation factor guanine nucleotide-exchange factor 1 (brefeldin A-inhibited) | 10565 | 1.048197 | 9.25E−05 | 0.006996 |
| 208877_at | PAK2 | p21 protein (Cdc42/Rac)-activated kinase 2 | 5062 | 1.095691 | 9.02E−05 | 0.006891 |
| 212454_x_at | HNRPDL | heterogeneous nuclear ribonucleoprotein D-like | 9987 | 1.012227 | 8.99E−05 | 0.006891 |
| 201832_s_at | USO1 | USO1 vesicle transport factor | 8615 | 1.196724 | 8.58E−05 | 0.006807 |
| 218104_at | TEX10 | testis expressed 10 | 54881 | 1.063963 | 8.48E−05 | 0.006794 |
| 209585_s_at | MINPP1 | multiple inositol-polyphosphate phosphatase 1 | 9562 | 1.5483 | 8.34E−05 | 0.006749 |
| 204160_s_at | ENPP4 | ectonucleotide pyrophosphatase/phosphodiesterase 4 (putative) | 22875 | 1.023317 | 8.15E−05 | 0.006724 |
| 201872_s_at | ABCE1 | ATP-binding cassette, sub-family E (OABP), member 1 | 6059 | 1.056302 | 7.77E−05 | 0.006497 |
| 203608_at | ALDH5A1 | aldehyde dehydrogenase 5 family, member A1 | 7915 | 1.567849 | 7.76E−05 | 0.006497 |
| 201177_s_at | UBA2 | ubiquitin-like modifier activating enzyme 2 | 10054 | 1.011771 | 7.72E−05 | 0.006497 |
| 201663_s_at | SMC4 | structural maintenance of chromosomes 4 | 10051 | 1.397017 | 7.58E−05 | 0.006462 |
| 206478_at | KIAA0125 | KIAA0125 | 9834 | 1.699586 | 7.39E−05 | 0.006369 |
| 209259_s_at | SMC3 | structural maintenance of chromosomes 3 | 9126 | 1.536331 | 7.36E−05 | 0.006369 |
| 201491_at | AHSA1 | AHA1, activator of heat shock 90 kDa protein ATPase homolog 1 (yeast) | 10598 | 1.017409 | 7.09E−05 | 0.006348 |
| 200050_at | ZNF146 | zinc finger protein 146 | 7705 | 1.112747 | 6.82E−05 | 0.006137 |
| 212798_s_at | ANKMY2 | ankyrin repeat and MYND domain containing 2 | 57037 | 1.282009 | 6.82E−05 | 0.006137 |
| 200597_at | EIF3A | eukaryotic translation initiation factor 3, subunit A | 8661 | 1.15333 | 6.58E−05 | 0.006137 |
| 220416_at | ATP8B4 | ATPase, class I, type 8B, member 4 | 79895 | 1.319886 | 6.56E−05 | 0.006137 |
| 218352_at | RCBTB1 | regulator of chromosome condensation (RCC1) and BTB (POZ) domain containing protein 1 | 55213 | 1.401043 | 6.56E−05 | 0.006137 |
| 208954_s_at | LARP4B | La ribonucleoprotein domain family, member 4B | 23185 | 1.035215 | 6.55E−05 | 0.006137 |
| 200754_x_at | SRSF2 | serine/arginine-rich splicing factor 2 | 6427 | 1.189498 | 6.53E−05 | 0.006137 |
| 213094_at | GPR126 | G protein-coupled receptor 126 | 57211 | 1.723615 | 6.36E−05 | 0.006137 |
| 201726_at | ELAVL1 | ELAV (embryonic lethal, abnormal vision, Drosophila)-like 1 (Hu antigen R) | 1994 | 1.210067 | 6.33E−05 | 0.006137 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 202797_at | SACM1L | SAC1 suppressor of actin mutations 1-like (yeast) | 22908 | 1.068996 | 6.19E−05 | 0.006092 |
| 218932_at | ZNHIT6 | zinc finger, HIT-type containing 6 | 54680 | 1.533903 | 6.11E−05 | 0.006036 |
| 205909_at | POLE2 | polymerase (DNA directed), epsilon 2, accessory subunit | 5427 | 1.13581 | 6.10E−05 | 0.006036 |
| 201493_s_at | PUM2 | pumilio homolog 2 (Drosophila) | 23369 | 1.045091 | 6.09E−05 | 0.006036 |
| 203605_at | SRP54 | signal recognition particle 54 kDa | 6729 | 1.336501 | 6.08E−05 | 0.006036 |
| 213737_x_at | GOLGA8H | golgin A8 family, member H | 728498 | 1.276782 | 5.98E−05 | 0.006036 |
| 205848_at | GAS2 | growth arrest-specific 2 | 2620 | 1.882946 | 5.69E−05 | 0.005965 |
| 207483_s_at | CAND1 | cullin-associated and neddylation-dissociated 1 | 55832 | 1.101083 | 5.60E−05 | 0.005911 |
| 219497_s_at | BCL11A | B-cell CLL/lymphoma 11A (zinc finger protein) | 53335 | 1.051534 | 5.48E−05 | 0.00586 |
| 201664_at | SMC4 | structural maintenance of chromosomes 4 | 10051 | 1.810802 | 5.39E−05 | 0.005828 |
| 209362_at | MED21 | mediator complex subunit 21 | 9412 | 1.351739 | 5.36E−05 | 0.005828 |
| 201458_s_at | BUB3 | BUB3 mitotic checkpoint protein | 9184 | 1.194027 | 5.30E−05 | 0.005828 |
| 203804_s_at | LUC7L3 | LUC7-like 3 (S. cerevisiae) | 51747 | 1.117694 | 5.28E−05 | 0.005828 |
| 206316_s_at | KNTC1 | kinetochore associated 1 | 9735 | 1.132251 | 5.10E−05 | 0.00579 |
| 204030_s_at | IQCJ-SCHIP1 | IQCJ-SCHIP1 readthrough | 100505385 | 1.123787 | 5.04E−05 | 0.005746 |
| 218437_s_at | LZTFL1 | leucine zipper transcription factor-like 1 | 54585 | 1.226372 | 4.98E−05 | 0.005732 |
| 202502_at | ACADM | acyl-CoA dehydrogenase, C-4 to C-12 straight chain | 34 | 1.024159 | 4.94E−05 | 0.005732 |
| 204256_at | ELOVL6 | ELOVL fatty acid elongase 6 | 79071 | 1.533869 | 4.93E−05 | 0.005732 |
| 215165_x_at | UMPS | uridine monophosphate synthetase | 7372 | 1.104322 | 4.89E−05 | 0.005732 |
| 217814_at | CCDC47 | coiled-coil domain containing 47 | 57003 | 1.430862 | 4.63E−05 | 0.005622 |
| 212944_at | SLC5A3 | solute carrier family 5 (sodium/myo-inositol cotransporter), member 3 | 6526 | 1.422266 | 4.48E−05 | 0.005619 |
| 208861_s_at | ATRX | alpha thalassemia/mental retardation syndrome X-linked | 546 | 1.174112 | 4.47E−05 | 0.005619 |
| 208848_at | ADH5 | alcohol dehydrogenase 5 (class III), chi polypeptide | 128 | 1.350061 | 4.32E−05 | 0.005587 |
| 209813_x_at | TARP | TCR gamma alternate reading frame protein | 445347 | 1.675539 | 4.27E−05 | 0.005556 |
| 208860_s_at | ATRX | alpha thalassemia/mental retardation syndrome X-linked | 546 | 1.385939 | 4.22E−05 | 0.005556 |
| 216199_s_at | MAP3K4 | mitogen-activated protein kinase kinase kinase 4 | 4216 | 1.101219 | 4.03E−05 | 0.005398 |
| 218577_at | LRRC40 | leucine rich repeat containing 40 | 55631 | 1.237191 | 3.99E−05 | 0.005382 |
| 208955_at | DUT | deoxyuridine triphosphatase | 1854 | 1.439155 | 3.92E−05 | 0.005311 |
| 203614_at | UTP14C | UTP14, U3 small nucleolar ribonucleoprotein, homolog C (yeast) | 9724 | 1.05731 | 3.86E−05 | 0.005287 |
| 202540_s_at | HMGCR | 3-hydroxy-3-mehylglutaryl-CoA reductase | 3156 | 1.149998 | 3.83E−05 | 0.005286 |
| 209025_s_at | SYNCRIP | synaptotagmin binding, cytoplasmic RNA interacting protein | 10492 | 1.11864 | 3.81E−05 | 0.005286 |
| 221884_at | MECOM | MDS1 and EVI1 complex locus | 2122 | 1.313552 | 3.58E−05 | 0.005097 |
| 213677_s_at | PMS1 | PMS1 postmeiotic segregation increased 1 (S. cervisiae) | 5378 | 1.319836 | 3.48E−05 | 0.004995 |
| 203482_at | FAM178A | family with sequence similarity 178, member A | 55719 | 1.006684 | 3.46E−05 | 0.004994 |
| 205395_s_at | MRE11A | MRE11 meiotic recombination 11 homolog A (S. cerevisiae) | 4361 | 1.047297 | 3.44E−05 | 0.004994 |
| 205541_s_at | GSPT2 | G1 to S phase transition 2 | 23708 | 1.302983 | 3.23E−05 | 0.004813 |
| 213111_at | PIKFYVE | phosphoinositide kinase, FYVE finger containing | 200576 | 1.505014 | 3.21E−05 | 0.004813 |
| 203406_at | MFAP1 | microfibrillar-associated protein 1 | 4236 | 1.105243 | 2.95E−05 | 0.004627 |
| 212648_at | DHX29 | DEAH (Asp-Glu-Ala-His) box polypeptide 29 | 54505 | 1.181102 | 2.90E−05 | 0.004616 |
| 212905_at | CSTF2T | cleavage stimulation factor, 3' pre-RNA, submit 2, 64 kDa, tau variant | 23283 | 1.012536 | 2.79E−05 | 0.004519 |
| 203102_s_at | MGAT2 | mannosyl (alpha-1,6-)-glycoprotein beta-1,2-N-acetylglucosaminyltransferase | 4247 | 1.02975 | 2.78E−05 | 0.004519 |
| 212407_at | METTL13 | methyltransferase like 13 | 51603 | 1.183202 | 2.73E−05 | 0.004519 |
| 212584_at | AQR | aquarius homolog (mouse) | 9716 | 1.131181 | 2.71E−05 | 0.004519 |
| 221522_at | ANKRD27 | ankyrin repeat domain 27 (VPS9 domain) | 84079 | 1.408053 | 2.46E−05 | 0.004336 |
| 215143_at | DPY19L2P2 | dpy-19-like 2 pseudogene 2 (C. elegans) | 349152 | 1.163809 | 2.42E−05 | 0.004298 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 212402_at | AC3H13 | zinc finger CCCH-type containing 13 | 23091 | 1.411241 | 2.40E-05 | 0.004298 |
| 213005_s_at | KANK1 | KN motif and ankyrin repeat domains 1 | 23189 | 1.420285 | 2.37E-05 | 0.004281 |
| 201086_x_at | SON | SON DNA binding protein | 6651 | 1.303827 | 2.37E-05 | 0.004281 |
| 205885_s_at | ITGA4 | integrin, alpha 4 (antigen CD49D, alpha 4 subunit of VLA-4 receptor) | 3676 | 1.152728 | 2.32E-05 | 0.004281 |
| 218957_s_at | PAAF1 | proteasomal ATPase-associated factor 1 | 80227 | 1.082321 | 2.32E-05 | 0.004281 |
| 209409_at | GRB10 | growth factor receptor-bound protein 10 | 2887 | 1.411903 | 2.31E-05 | 0.004281 |
| 218428_s_at | REV1 | REV1, polymerase (DNA directed) | 51455 | 1.014141 | 2.30E-05 | 0.004281 |
| 212982_at | ZDHHC17 | zinc finger, DHHC-type containing 17 | 23390 | 1.24448 | 2.23E-05 | 0.004281 |
| 206854_s_at | MAP3K7 | mitogen-activated protein kinase kinase kinase 7 | 6885 | 1.362632 | 2.14E-05 | 0.004215 |
| 213164_at | SLC5A3 | solute carrier family 5 (sodium/myo-inositol cotransporter), member 3 | 6526 | 1.12656 | 2.14E-05 | 0.004215 |
| 209662_at | CETN3 | centrin, EF-hand protein, 3 | 1070 | 1.780447 | 2.13E-05 | 0.004215 |
| 213092_x_at | DNAJC9 | DnaJ (Hsp40) homolog, subfamily C, member 9 | 23234 | 1.281922 | 2.11E-05 | 0.004215 |
| 219130_at | TRMT13 | tRNA methyltransferase 13 homolog (S. cerevisiae) | 54482 | 1.054729 | 2.09E-05 | 0.004215 |
| 218096_at | AGPAT5 | 1-acylglycerol-3-phosphate O-acyltransferase 5 | 55326 | 1.046759 | 2.05E-05 | 0.004215 |
| 200783_s_at | STMN1 | stathmin 1 | 3925 | 1.021197 | 1.99E-05 | 0.004183 |
| 202763_at | CASP3 | caspase 3, apoptosis-related cysteine peptidase | 836 | 1.113632 | 1.97E-05 | 0.004167 |
| 206874_s_at | SLK | STE20-like kinase | 9748 | 1.508576 | 1.95E-05 | 0.004162 |
| 215806_x_at | TARP | TCR gamma alternate reading frame protein | 445347 | 1.699601 | 1.94E-05 | 0.004162 |
| 218139_s_at | AP5M1 | adaptor-related protein complex 5, mu 1 subunit | 55745 | 1.213838 | 1.93E-05 | 0.004162 |
| 212731_at | ANKRD46 | ankyrin repeat domain 46 | 157567 | 1.139853 | 1.87E-05 | 0.004117 |
| 217317_s_at | HERC2P2 | hect domain and RLD 2 pseudogene 2 | 400322 | 1.063595 | 1.62E-05 | 0.003764 |
| 212176_at | PNISR | PNN-interacting serine/arginine-rich protein | 25957 | 1.0103 | 1.62E-05 | 0.003764 |
| 218313_s_at | GALNT7 | UDP-N-acetyl-alpha-D-galactosamine:polypeptide N-acetylgalactosaminyltransferase 7 (GalNAc-T7) | 51809 | 1.507414 | 1.62E-05 | 0.003764 |
| 219083_at | SHQ1 | SHQ1, H/ACA ribonucleoprotein assembly factor | 55164 | 1.675814 | 1.53E-05 | 0.003721 |
| 203302_at | DCK | deoxycytidine kinase | 1633 | 1.276653 | 1.43E-05 | 0.003616 |
| 218515_at | PAXBP1 | PAX3 and PAX7 binding protein 1 | 94104 | 1.243818 | 1.43E-05 | 0.003616 |
| 213391_at | DPY19L4 | dpy-19-like 4 (C. elegans) | 286148 | 1.187053 | 1.29E-05 | 0.003444 |
| 202907_s_at | NBN | nibrin | 4683 | 1.588244 | 1.26E-05 | 0.003444 |
| 217886_at | EPS15 | epidermal growth factor receptor pathway substrate 15 | 2060 | 1.345925 | 1.23E-05 | 0.003411 |
| 218622_at | NUP37 | nucleoporin 37 kDa | 79023 | 1.261215 | 1.22E-05 | 0.003411 |
| 208654_s_at | CD164 | CD164 molecule, sialomucin | 8763 | 1.456204 | 1.21E-05 | 0.003411 |
| 219035_s_at | RNF34 | ring finger protein 34, E3 ubiquitin protein ligase | 80196 | 1.187459 | 1.15E-05 | 0.003369 |
| 220044_x_at | LUC7L3 | LUC7-like 3 (S. cerevisiae) | 51747 | 1.199028 | 1.15E-05 | 0.003369 |
| 218768_at | NUP107 | nucleoporin 107 kDa | 57122 | 1.457543 | 1.14E-05 | 0.003369 |
| 208405_s_at | CD164 | CD164 molecule, sialomucin | 8763 | 1.103873 | 1.11E-05 | 0.003369 |
| 212675_s_at | CEP68 | centrosomal protein 68 kDa | 23177 | 1.33608 | 1.11E-05 | 0.003369 |
| 209200_at | MEF2C | myocyte enhancer factor 2C | 4208 | 1.964319 | 1.10E-05 | 0.003369 |
| 209476_at | TMX1 | thioredoxin-related transmembrane protein 1 | 81542 | 1.209672 | 1.07E-05 | 0.003369 |
| 212474_at | AVL9 | AVL9 homolog (S. cerevisiae) | 23080 | 1.128401 | 9.17E-06 | 0.003236 |
| 203306_s_at | SLC35A1 | solute carrier family 35 (CMP-sialic acid transporter), member A1 | 10559 | 1.184632 | 9.10E-06 | 0.003236 |
| 219405_at | TRIM68 | tripartite motif containing 68 | 55128 | 1.092848 | 8.27E-06 | 0.003067 |
| 217954_s_at | PHF3 | PHD finger protein 3 | 23469 | 1.096771 | 8.00E-06 | 0.003017 |
| 201448_at | TIA1 | TIA1 cytotoxic granule-associated RNA binding protein | 7072 | 1.364827 | 7.61E-06 | 0.002919 |
| 202918_s_at | MOB4 | MOB family member 4, phocein | 25843 | 1.281577 | 7.60E-06 | 0.002919 |
| 201503_at | G3BP1 | GTPase activating protein (SH3 domain) binding protein 1 | 10146 | 1.400871 | 7.40E-06 | 0.002919 |
| 221606_s_at | HMGN5 | high mobility group nucleosome binding domain 5 | 79366 | 1.041186 | 7.16E-06 | 0.002919 |

TABLE 8-continued

Genes Differently Regulated in the Indolent Group as Compared to the Controls

| ProbesetID | Symbol (Na32 consensus Mar13) | Gene Title (Na32 consensus Mar13) | Entrez GeneID (consensus Mar-13) | Log2(FC) | P-Value | Adjusted P-Value |
|---|---|---|---|---|---|---|
| 212179_at | PNISR | PNN-interacting serine/arginine-rich protein | 25957 | 1.659487 | 7.06E−06 | 0.002919 |
| 207943_x_at | PLAGL1 | pleiomorphic adenoma gene-like 1 | 5325 | 1.02225 | 6.80E−06 | 0.002919 |
| 219002_at | FASTKD1 | FAST kinase domains 1 | 79675 | 1.139996 | 6.78E−06 | 0.002919 |
| 219649_at | ALG6 | ALG6, alpha-1,3-glucosyltransferase | 29929 | 1.318705 | 6.36E−06 | 0.002919 |
| 218593_at | RBM28 | RNA binding motif protein 28 | 55131 | 1.095331 | 6.00E−06 | 0.002867 |
| 218152_at | HMG20A | high mobility group 20A | 10363 | 1.329726 | 5.52E−06 | 0.002834 |
| 218108_at | UBR7 | ubiquitin protein ligase E3 component n-recognin 7 (putative) | 55148 | 1.468044 | 4.88E−06 | 0.002649 |
| 212959_s_at | GNPTAB | N-acetylglucosamine-1-phosphate transferase, alpha and beta subunits | 79158 | 1.108946 | 4.43E−06 | 0.002528 |
| 213653_at | METTL3 | methyltransferase like 3 | 56339 | 1.135123 | 4.23E−06 | 0.002528 |
| 201218_at | CTBP2 | C-terminal binding protein 2 | 1488 | 1.622964 | 4.00E−06 | 0.002528 |
| 202520_s_at | MLH1 | mutL homolog 1, colon cancer, nonpolyposis type 2 (E. coli) | 4292 | 1.112927 | 3.95E−06 | 0.002528 |
| 209022_at | STAG2 | stromal antigen 2 | 10735 | 1.149995 | 3.82E−06 | 0.002528 |
| 218343_s_at | GTF3C3 | general transcription factor IIIC, polypeptide 3, 102 kDa | 9330 | 1.144191 | 3.71E−06 | 0.002528 |
| 219960_s_at | UCHL5 | ubiquitin carboxyl-terminal hydrolase L5 | 51377 | 1.108112 | 3.64E−06 | 0.002528 |
| 209175_at | SEC23IP | SEC23 interacting protein | 11196 | 1.255797 | 3.63E−06 | 0.002528 |
| 218170_at | ISOC1 | isochorismatase domain containing 1 | 51015 | 1.24304 | 3.49E−06 | 0.002528 |
| 209265_s_at | METTL3 | methyltransferase like 3 | 56339 | 1.227046 | 3.29E−06 | 0.002528 |
| 222127_s_at | EXOC1 | exocyst complex component 1 | 55763 | 1.394408 | 2.86E−06 | 0.002528 |
| 207002_s_at | PLAGL1 | pleiomorphic adenoma gene-like 1 | 5325 | 1.171723 | 2.49E−06 | 0.002309 |
| 204168_at | MGST2 | microsomal glutathione S-transferase 2 | 4258 | 1.037395 | 1.79E−06 | 0.001991 |
| 205609_at | ANGPT1 | angiopoietin 1 | 284 | 1.547029 | 1.71E−06 | 0.001991 |
| 209537_at | EXTL2 | exostosin-like glycosyltransferase 2 | 2135 | 1.05732 | 7.39E−07 | 0.001096 |
| 209748_at | SPAST | spastin | 6683 | 1.096487 | 6.60E−07 | 0.001049 |
| 218397_at | FANCL | Fanconi anemia, complementation group L | 55120 | 1.889757 | 4.53E−07 | 0.000871 |
| 210621_s_at | RASA1 | RAS p21 protein activator (GTPase activating protein) 1 | 5921 | 1.39113 | 3.67E−07 | 0.000871 |
| 201687_s_at | API5 | apoptosis inhibitor 5 | 8539 | 1.055434 | 1.84E−07 | 0.000682 |
| 212828_at | SYNJ2 | synaptojanin 2 | 8871 | 1.111098 | 1.84E−07 | 0.000682 |
| 209007_s_at | C1orf63 | chromosome 1 open reading frame 63 | 57035 | 1.046263 | 8.11E−08 | 0.000601 |
| 218361_at | GOLPH3L | golgi phosphoprotein 3-like | 55204 | 1.174016 | 5.59E−08 | 0.000601 |
| 219913_s_at | CRNKL1 | crooked neck pre-mRNA splicing factor-like 1 (Drosophila) | 51340 | 1.468407 | 2.17E−08 | 0.000482 |

TABLE 9

Genes Differently Regulated in the Aggressive Group as Compared to the Controls

| Probeset ID | Symbol (Na32 consensus Mar13) | Gene Title (Na32 consensus Mar13) | Entrez GeneID (consensus Mar-13) | Log2 (FC) | P-Value | Adjusted P-Value |
|---|---|---|---|---|---|---|
| 209763_at | CHRDL1 | chordin-like 1 | 91851 | −1.17606 | 5.21E−09 | 6.67E−05 |
| 210487_at | DNTT | deoxynucleotidyltransferase, terminal | 1791 | −1.91383 | 6.00E−09 | 6.67E−05 |
| 205933_at | SETBP1 | SET binding protein 1 | 26040 | −1.1773 | 1.51E−08 | 0.000112 |
| 202723_s_at | FOXO1 | forkhead box O1 | 2308 | −1.10201 | 4.34E−06 | 0.024108 |
| 201324_at | EMP1 | epithelial membrane protein 1 | 2012 | −1.73635 | 6.04E−06 | 0.026802 |
| 201325_s_at | EMP1 | epithelial membrane protein 1 | 2012 | −1.00997 | 1.48E−05 | 0.029925 |
| 209398_at | HIST1H1C | histone cluster 1, H1c | 3006 | −2.26773 | 3.33E−05 | 0.061697 |
| 212827_at | IGHM | immunoglobulin heavy constant mu | 3507 | −1.62695 | 0.000114 | 0.134692 |
| 206385_s_at | ANK3 | ankyrin 3, node of Ranvier (ankyrin G) | 288 | −1.01371 | 0.000117 | 0.134692 |
| 209183_s_at | C10orf10 | chromosome 10 open reading frame 10 | 11067 | −1.07496 | 0.000131 | 0.139056 |
| 209374_s_at | IGHM | immunoglobulin heavy constant mu | 3507 | −1.78678 | 0.000238 | 0.21202 |
| 204430_s_at | SLC2A5 | solute carrier family 2 (facilitated glucose/fructose transporter), member 5 | 6518 | −1.13053 | 0.00026 | 0.213741 |
| 200872_at | S100A10 | S100 calcium binding protein A10 | 6281 | −1.47658 | 0.000279 | 0.215629 |
| 209069_s_at | H3F3B | H3 histone, family 3B (H3.3B) | 3021 | −1.18661 | 0.000318 | 0.221129 |
| 210592_s_at | SAT1 | spermidine/spermine N1-acetyltransferase 1 | 6303 | −1.08035 | 0.000376 | 0.227751 |
| 207111_at | EMR1 | egf-like module containing, mucin-like, hormone receptor-like 1 | 2015 | −1.08619 | 0.000401 | 0.227751 |

TABLE 9-continued

Genes Differently Regulated in the Aggressive Group as Compared to the Controls

| Probeset ID | Symbol (Na32 consensus Mar13) | Gene Title (Na32 consensus Mar13) | Entrez GeneID (consensus Mar-13) | Log2 (FC) | P-Value | Adjusted P-Value |
|---|---|---|---|---|---|---|
| 204304_s_at | PROM1 | prominin 1 | 8842 | −1.82999 | 0.00042 | 0.227751 |
| 205984_at | CRHBP | corticotropin releasing hormone binding protein | 1393 | −1.68559 | 0.000482 | 0.239161 |
| 218280_x_at | HIST2H2AA4 | histone cluster 2, H2aa4 | 723790 | −2.04755 | 0.000661 | 0.271413 |
| 211997_x_at | H3F3B | H3 histone, family 3B (H3.3B) | 3021 | −1.22595 | 0.000753 | 0.293064 |
| 211998_at | H3F3B | H3 histone, family 3B (H3.3B) | 3021 | −1.37161 | 0.001101 | 0.376554 |
| 214290_s_at | HIST2H2AA4 | histone cluster 2, H2aa4 | 723790 | −2.10063 | 0.001825 | 0.399532 |
| 202888_s_at | ANPEP | alanyl (membrane) aminopeptidase | 290 | −1.09433 | 0.001827 | 0.399532 |
| 210785_s_at | THEMIS2 | thymocyte selection associated family member 2 | 9473 | −1.40909 | 0.001958 | 0.412534 |
| 205402_x_at | PRSS2 | protease, serine, 2 (trypsin 2) | 5645 | −1.05383 | 0.002001 | 0.412534 |
| 220990_s_at | MIR21 | microRNA 21 | 406991 | −1.16662 | 0.002023 | 0.412534 |
| 201369_s_at | ZFP36L2 | ZFP36 ring finger protein-like 2 | 678 | −1.42932 | 0.002729 | 0.450281 |
| 207571_x_at | THEMIS2 | thymocyte selection associated family member 2 | 9473 | −1.3478 | 0.0028 | 0.450281 |
| 212543_at | AIM1 | absent in melanoma 1 | 202 | −1.12719 | 0.002817 | 0.450281 |
| 204698_at | ISG20 | interferon stimulated exonuclease gene 20 kDa | 3669 | −1.19993 | 0.002841 | 0.450281 |
| 204872_at | TLE4 | transducin-like enhancer of split 4 (E(sp1) homolog, Drosophila) | 7091 | −1.08661 | 0.004743 | 0.516178 |
| 211597_s_at | HOPX | HOP homeobox | 84525 | −1.35699 | 0.004787 | 0.516178 |
| 220377_at | KIAA0125 | KIAA0125 | 9834 | −1.15785 | 0.004957 | 0.516178 |
| 202708_s_at | HIST2H2BE | histone cluster 2, H2be | 8349 | −1.73994 | 0.00501 | 0.516178 |
| 222258_s_at | SH3BP4 | SH3-domain binding protein 4 | 23677 | −1.25738 | 0.006817 | 0.549162 |
| 202748_at | GBP2 | guanylate binding protein 2, interferon-inducible | 2634 | −1.47788 | 0.007224 | 0.557788 |
| 222067_x_at | HIST1H2BD | histone cluster 1, H2bd | 3017 | −1.3732 | 0.007682 | 0.562835 |
| 204805_s_at | H1FX | H1 histone family, member X | 8971 | −1.45025 | 0.012357 | 0.587079 |
| 214472_at | HIST1H2AD | histone cluster 1, H2ad | 3013 | −1.33457 | 0.016968 | 0.609599 |
| 215071_s_at | HIST1H2AC | histone cluster 1, H2ac | 8334 | −1.59794 | 0.020339 | 0.631601 |
| 204057_at | IRF8 | interferon regulatory factor 8 | 3394 | −1.01328 | 0.021285 | 0.631601 |
| 221760_at | MAN1A1 | mannosidase, alpha, class 1A, member 1 | 4121 | −1.18372 | 0.02233 | 0.632753 |
| 208490_x_at | HIST1H2BF | histone cluster 1, H2bf | 8343 | −1.14111 | 0.027318 | 0.639545 |
| 221556_at | CDC14B | cell division cycle 14B | 8555 | −1.26289 | 0.028048 | 0.64494 |
| 210387_at | HIST1H2BG | histone cluster 1, H2bg | 8339 | −1.14146 | 0.02951 | 0.651733 |
| 201416_at | SOX4 | SRY (sex determining region Y)-box 4 | 6659 | −1.05187 | 0.032258 | 0.65293 |
| 208579_x_at | H2BFS | H2B histone family, member S (pseudogene) | 54145 | −1.30549 | 0.035551 | 0.658786 |
| 208527_x_at | HIST1H2BE | histone cluster 1, H2be | 8344 | −1.05374 | 0.035992 | 0.658786 |
| 203708_at | PDE4B | phosphodiesterase 4B, cAMP-specific | 5142 | −1.26501 | 0.039076 | 0.662929 |
| 212488_at | COL5A1 | collagen, type V, alpha 1 | 1289 | −1.01422 | 0.041826 | 0.666611 |
| 203140_at | BCL6 | B-cell CLL/lymphoma 6 | 604 | −1.00963 | 0.04395 | 0.666724 |
| 208546_x_at | HIST1H2BH | histone cluster 1, H2bh | 8345 | −1.02623 | 0.048771 | 0.677506 |
| 214455_at | HIST1H2BC | histone cluster 1, H2bc | 8347 | −1.16847 | 0.051456 | 0.680853 |
| 218999_at | TMEM140 | transmembrane protein 140 | 55281 | −1.01862 | 0.053069 | 0.682752 |
| 208018_s_at | HCK | hemopoietic cell kinase | 3055 | −1.13981 | 0.05449 | 0.684183 |
| 204897_at | PTGER4 | prostaglandin E receptor 4 (subtype EP4) | 5734 | −1.13843 | 0.058834 | 0.692792 |
| 201565_s_at | ID2 | inhibitor of DNA binding 2, dominant negative helix-loop-helix protein | 3398 | −1.33513 | 0.06594 | 0.694022 |
| 212587_s_at | PTPRC | protein tyrosine phosphatase, receptor type, C | 5788 | −1.10126 | 0.080672 | 0.719636 |
| 200897_s_at | PALLD | palladin, cytoskeletal associated protein | 23022 | −1.24085 | 0.085951 | 0.722194 |
| 208891_at | DUSP6 | dual specificity phosphatase 6 | 1848 | −1.07107 | 0.098612 | 0.730122 |
| 202391_at | BASP1 | brain abundant, membrane attached signal protein 1 | 10409 | −1.1892 | 0.099272 | 0.730445 |
| 201743_at | CD14 | CD14 molecule | 929 | −1.11579 | 0.106127 | 0.731069 |
| 221841_s_at | KLF4 | Kruppel-like factor 4 (gut) | 9314 | −1.20574 | 0.106845 | 0.731355 |
| 206110_at | HIST1H3H | histone cluster 1, H3h | 8357 | −1.19698 | 0.116318 | 0.738259 |
| 213975_s_at | LYZ | lysozyme | 4069 | −1.22513 | 0.117821 | 0.738667 |
| 218723_s_at | RGCC | regulator of cell cycle | 28984 | −1.01755 | 0.173123 | 0.764957 |
| 202917_s_at | S100A8 | S100 calcium binding protein A8 | 6279 | −1.01114 | 0.365329 | 0.843162 |
| 209774_x_at | CXCL2 | chemokine (C—X—C motif) ligand 2 | 2920 | 1.127083 | 0.184971 | 0.770504 |
| 206488_s_at | CD36 | CD36 molecule (thrombospondin receptor) | 948 | 1.062242 | 0.179158 | 0.767834 |
| 206049_at | SELP | selectin P (granule membrane protein 140 kDa, antigen CD62) | 6403 | 1.027039 | 0.142209 | 0.749649 |
| 202581_at | HSPA1A | heat shock 70 kDa protein 1A | 3303 | 1.07338 | 0.141805 | 0.749649 |
| 212671_s_at | HLA-DQA1 | major histocompatibility complex, class II, DQ alpha 1 | 3117 | 1.256994 | 0.134567 | 0.747232 |
| 207808_s_at | PROS1 | protein S (alpha) | 5627 | 1.076302 | 0.125868 | 0.743062 |
| 204419_x_at | HBG1 | hemoglobin, gamma A | 3047 | 1.666375 | 0.091429 | 0.723603 |
| 204848_x_at | HBG1 | hemoglobin, gamma A | 3047 | 1.565419 | 0.086123 | 0.722194 |

TABLE 9-continued

Genes Differently Regulated in the Aggressive Group as Compared to the Controls

| Probeset ID | Symbol (Na32 consensus Mar13) | Gene Title (Na32 consensus Mar13) | Entrez GeneID (consensus Mar-13) | Log2 (FC) | P-Value | Adjusted P-Value |
|---|---|---|---|---|---|---|
| 209839_at | DNM3 | dynamin 3 | 26052 | 1.130837 | 0.075473 | 0.711904 |
| 217388_s_at | KYNU | kynureninase | 8942 | 1.468314 | 0.069766 | 0.703289 |
| 214710_s_at | CCNB1 | cyclin B1 | 891 | 1.019442 | 0.057837 | 0.692792 |
| 202729_s_at | LTBP1 | latent transforming growth factor beta binding protein 1 | 4052 | 1.205454 | 0.056194 | 0.689409 |
| 205950_s_at | CA1 | carbonic anhydrase I | 759 | 1.154113 | 0.05527 | 0.686498 |
| 201014_s_at | PAICS | phosphoribosylaminoimidazole carboxylase, phosphoribosylaminoimidazole succinocarboxamide synthetase | 10606 | 1.001269 | 0.054655 | 0.684183 |
| 215813_s_at | PTGS1 | prostaglandin-endoperoxide synthase 1 (prostaglandin G/H synthase and cyclooxygenase) | 5742 | 1.093699 | 0.054246 | 0.684183 |
| 216063_at | HBBP1 | hemoglobin, beta pseudogene 1 | 3044 | 1.237304 | 0.051626 | 0.680853 |
| 209290_s_at | NFIB | nuclear factor I/B | 4781 | 1.089323 | 0.047583 | 0.675495 |
| 212224_at | ALDH1A1 | aldehyde dehydrogenase 1 family, member A1 | 216 | 1.365131 | 0.047481 | 0.675495 |
| 207165_at | HMMR | hyaluronan-mediated motility receptor (RHAMM) | 3161 | 1.035451 | 0.04372 | 0.666724 |
| 207668_x_at | PDIA6 | protein disulfide isomerase family A, member 6 | 10130 | 1.01888 | 0.042673 | 0.666611 |
| 208639_x_at | PDIA6 | protein disulfide isomerase family A, member 6 | 10130 | 1.087019 | 0.04232 | 0.666611 |
| 201202_at | PCNA | proliferating cell nuclear antigen | 5111 | 1.025175 | 0.040518 | 0.664974 |
| 202705_at | CCNB2 | cyclin B2 | 9133 | 1.000457 | 0.037459 | 0.658786 |
| 202870_s_at | CDC20 | cell division cycle 20 | 991 | 1.339489 | 0.036577 | 0.658786 |
| 217232_x_at | HBB | hemoglobin, beta | 3043 | 1.819046 | 0.034587 | 0.658786 |
| 218009_s_at | PRC1 | protein regulator of cytokinesis 1 | 9055 | 1.316131 | 0.032297 | 0.65293 |
| 213515_x_at | HBG1 | hemoglobin, gamma A | 3047 | 2.417287 | 0.029879 | 0.651733 |
| 218350_s_at | GMNN | geminin, DNA replication inhibitor | 51053 | 1.197599 | 0.02966 | 0.651733 |
| 209728_at | HLA-DRB4 | major histocompatibility complex, class II, DR beta 4 | 3126 | 2.147596 | 0.028176 | 0.645955 |
| 204023_at | RFC4 | replication factor C (activator 1) 4, 37 kDa | 5984 | 1.139793 | 0.027395 | 0.640611 |
| 203755_at | BUB1B | BUB1 mitotic checkpoint serine/threonine kinase B | 701 | 1.078262 | 0.026537 | 0.639024 |
| 202760_s_at | AKAP2 | A kinase (PRKA) anchor protein 2 | 11217 | 1.132676 | 0.023696 | 0.635738 |
| 201477_s_at | RRM1 | ribonucleotide reductase M1 | 6240 | 1.170464 | 0.02268 | 0.635738 |
| 218039_at | NUSAP1 | nucleolar and spindle associated protein 1 | 51203 | 1.296022 | 0.022485 | 0.634539 |
| 209773_s_at | RRM2 | ribonucleotide reductase M2 | 6241 | 1.767338 | 0.021614 | 0.631601 |
| 206632_s_at | APOBEC3B | apolipoprotein B mRNA editing enzyme, catalytic polypeptide-like 3B | 9582 | 1.217919 | 0.021271 | 0.631601 |
| 201563_at | SORD | sorbitol dehydrogenase | 6652 | 1.003384 | 0.021071 | 0.631601 |
| 211696_x_at | HBB | hemoglobin, beta | 3043 | 1.960803 | 0.020716 | 0.631601 |
| 201490_s_at | PPIF | peptidylprolyl isomerase F | 10105 | 1.068584 | 0.02005 | 0.62633 |
| 209969_s_at | STAT1 | signal transducer and activator of transcription 1, 91 kDa | 6772 | 1.033433 | 0.018323 | 0.612297 |
| 202112_at | VWF | von Willebrand factor | 7450 | 1.065252 | 0.017067 | 0.610194 |
| 211005_at | LAT | linker for activation of T cells | 27040 | 1.441264 | 0.016468 | 0.605865 |
| 206102_at | GINS1 | GINS complex subunit 1 (Psf1 homolog) | 9837 | 1.19856 | 0.014854 | 0.595174 |
| 206698_at | XK | X-linked Kx blood group (McLeod syndrome) | 7504 | 1.473769 | 0.014747 | 0.595174 |
| 201761_at | MTHFD2 | methylenetetrahydrofolate dehydrogenase (NADP+ dependent) 2, methenyltetrahydrofolate cyclohydrolase | 10797 | 1.176486 | 0.01448 | 0.595174 |
| 202589_at | TYMS | thymidylate synthetase | 7298 | 1.284352 | 0.014339 | 0.594132 |
| 203362_s_at | MAD2L1 | MAD2 mitotic arrest deficient-like 1 (yeast) | 4085 | 1.12377 | 0.014136 | 0.591776 |
| 204146_at | RAD51AP1 | RAD51 associated protein 1 | 10635 | 1.138009 | 0.013242 | 0.587079 |
| 202814_s_at | HEXIM1 | hexamethylene bis-acetamide inducible 1 | 10614 | 1.018846 | 0.011855 | 0.587079 |
| 211953_s_at | IPO5 | importin 5 | 3843 | 1.1663 | 0.010926 | 0.587079 |
| 212589_at | RRAS2 | related RAS viral (r-ras) oncogene homolog 2 | 22800 | 1.248922 | 0.010896 | 0.587079 |
| 201897_s_at | CKS1B | CDC28 protein kinase regulatory subunit 1B | 1163 | 1.237742 | 0.010699 | 0.587079 |
| 201829_at | NET1 | neuroepithelial cell transforming 1 | 10276 | 1.249173 | 0.010403 | 0.58573 |
| 212459_x_at | SUCLG2 | succinate-CoA ligase, GDP-forming, beta subunit | 8801 | 1.16554 | 0.009868 | 0.58573 |
| 201930_at | MCM6 | minichromosome maintenance complex component 6 | 4175 | 1.046236 | 0.009628 | 0.582356 |
| 209116_x_at | HBB | hemoglobin, beta | 3043 | 2.529691 | 0.008816 | 0.568066 |

TABLE 9-continued

Genes Differently Regulated in the Aggressive Group as Compared to the Controls

| Probeset ID | Symbol (Na32 consensus Mar13) | Gene Title (Na32 consensus Mar13) | Entrez GeneID (consensus Mar-13) | Log2 (FC) | P-Value | Adjusted P-Value |
|---|---|---|---|---|---|---|
| 218585_s_at | DTL | denticleless E3 ubiquitin protein ligase homolog (Drosophila) | 51514 | 1.376897 | 0.008767 | 0.568066 |
| 206937_at | SPTA1 | spectrin, alpha, erythrocytic 1 (elliptocytosis 2) | 6708 | 1.114075 | 0.008321 | 0.566014 |
| 218883_s_at | MLF1IP | MLF1 interacting protein | 79682 | 1.136186 | 0.008177 | 0.566014 |
| 215772_x_at | SUCLG2 | succinate-CoA ligase, GDP-forming, beta subunit | 8801 | 1.175819 | 0.008054 | 0.566014 |
| 213088_s_at | DNAJC9 | DnaJ (Hsp40) homolog, subfamily C, member 9 | 23234 | 1.00079 | 0.007957 | 0.565327 |
| 206145_at | RHAG | Rh-associated glycoprotein | 6005 | 1.393541 | 0.006392 | 0.547427 |
| 204695_at | CDC25A | cell division cycle 25A | 993 | 1.084134 | 0.006299 | 0.547427 |
| 204240_s_at | SMC2 | structural maintenance of chromosomes 2 | 10592 | 1.294656 | 0.005936 | 0.540991 |
| 202107_s_at | MCM2 | minichromosome maintenance complex component 2 | 4171 | 1.222252 | 0.005761 | 0.536001 |
| 222204_s_at | RRN3 | RRN3 RNA polymerase I transcription factor homolog (S. cerevisiae) | 54700 | 1.042118 | 0.005729 | 0.536001 |
| 203560_at | GGH | gamma-glutamyl hydrolase (conjugase, folylpolygammaglutamyl hydrolase) | 8836 | 1.340214 | 0.00547 | 0.526569 |
| 202613_at | CTPS1 | CTP synthase 1 | 1503 | 1.14984 | 0.005331 | 0.526569 |
| 208955_at | DUT | deoxyuridine triphosphatase | 1854 | 1.03421 | 0.005157 | 0.523702 |
| 212282_at | TMEM97 | transmembrane protein 97 | 27346 | 1.011374 | 0.004822 | 0.516178 |
| 219412_at | RAB38 | RAB38, member RAS oncogene family | 23682 | 1.168702 | 0.004753 | 0.516178 |
| 202503_s_at | KIAA0101 | KIAA0101 | 9768 | 1.309228 | 0.00471 | 0.516178 |
| 204767_s_at | FEN1 | flap structure-specific endonuclease 1 | 2237 | 1.381621 | 0.004647 | 0.516178 |
| 205394_at | CHEK1 | checkpoint kinase 1 | 1111 | 1.045411 | 0.004442 | 0.516178 |
| 201489_at | PPIF | peptidylprolyl isomerase F | 10105 | 1.118185 | 0.004062 | 0.507454 |
| 201890_at | RRM2 | ribonucleotide reductase M2 | 6241 | 2.141038 | 0.00366 | 0.47601 |
| 219306_at | KIF15 | kinesin family member 15 | 56992 | 1.266139 | 0.003389 | 0.461859 |
| 211144_x_at | TARP | TCR gamma alternate reading frame protein | 445347 | 1.260002 | 0.003285 | 0.456931 |
| 206834_at | HBD | hemoglobin, delta | 3045 | 2.172202 | 0.003266 | 0.456931 |
| 203476_at | TPBG | trophoblast glycoprotein | 7162 | 1.132385 | 0.002991 | 0.450281 |
| 212281_s_at | TMEM97 | transmembrane protein 97 | 27346 | 1.2802 | 0.002875 | 0.450281 |
| 206067_s_at | WT1 | Wilms tumor 1 | 7490 | 1.247746 | 0.002812 | 0.450281 |
| 208694_at | PRKDC | protein kinase, DNA-activated, catalytic polypeptide | 5591 | 1.067872 | 0.002544 | 0.438543 |
| 206118_at | STAT4 | signal transducer and activator of transcription 4 | 6775 | 1.012186 | 0.002506 | 0.438543 |
| 216920_s_at | TARP | TCR gamma alternate reading frame protein | 445347 | 1.474096 | 0.002252 | 0.428068 |
| 202949_s_at | FHL2 | four and a half LIM domains 2 | 2274 | 1.107316 | 0.002224 | 0.428068 |
| 222201_s_at | CASP8AP2 | caspase 8 associated protein 2 | 9994 | 1.054149 | 0.001764 | 0.399532 |
| 204026_s_at | ZWINT | ZW10 interactor, kinetochore protein | 11130 | 1.720113 | 0.001341 | 0.397293 |
| 209894_at | LEPR | leptin receptor | 3953 | 2.015714 | 0.001141 | 0.380525 |
| 213092_x_at | DNAJC9 | DnaJ (Hsp40) homolog, subfamily C, member 9 | 23234 | 1.090583 | 0.000823 | 0.310206 |
| 219454_at | EGFL6 | EGF-like-domain, multiple 6 | 25975 | 1.45589 | 0.000616 | 0.258418 |
| 213262_at | SACS | spastic ataxia of Charlevoix-Saguenay (sacsin) | 26278 | 1.042232 | 0.00059 | 0.252396 |
| 204256_at | ELOVL6 | ELOVL fatty acid elongase 6 | 79071 | 1.448618 | 0.000559 | 0.252191 |
| 215806_x_at | TARP | TCR gamma alternate reading frame protein | 445347 | 1.534041 | 0.000427 | 0.227751 |
| 209813_x_at | TARP | TCR gamma alternate reading frame protein | 445347 | 1.665423 | 0.000291 | 0.215629 |
| 201830_s_at | NET1 | neuroepithelial cell transforming 1 | 10276 | 1.530152 | 0.000251 | 0.213741 |
| 219615_s_at | KCNK5 | potassium channel, subfamily K, member 5 | 8645 | 1.04543 | 0.000225 | 0.21202 |
| 219602_s_at | PIEZO2 | piezo-type mechanosensitive ion channel component 2 | 63895 | 1.504577 | 7.50E−05 | 0.117928 |
| 219000_s_at | DSCC1 | defective in sister chromatid cohesion 1 homolog (S. cerevisiae) | 79075 | 1.081581 | 4.67E−05 | 0.079813 |
| 205848_at | GAS2 | growth arrest-specific 2 | 2620 | 2.492596 | 1.11E−05 | 0.02744 |

TABLE 10

Gene Expression in the Aggressive Group of the Core 102 Genes

| Probeset ID | Symbol (Na32 consesus Mar13) | Gene Title (Na32 consensus Mar13) | GeneID (NCBI Mar) | Log2 (FC) | P-Value | Adjusted p-Value |
|---|---|---|---|---|---|---|
| 209763_at | CHRDL1 | chordin-like 1 | 91851 | -1.1760592 | 5.21E-09 | 6.67E-05 |
| 210487_at | DNTT | deoxynucleotidyltransferase, terminal | 1791 | -1.91383418 | 6.00E-09 | 6.67E-05 |
| 205933_at | SETBP1 | SET binding protein 1 | 26040 | -1.17729694 | 1.51E-08 | 0.0001121 |
| 201324_at | EMP1 | epithelial membrane protein 1 | 2012 | -1.73634604 | 6.04E-06 | 0.0268018 |
| 209183_s_at | C10orf10 | chromosome 10 open reading frame 10 | 11067 | -1.07496461 | 0.000131314 | 0.1390556 |
| 209374_s_at | IGHM | immunoglobulin heavy constant mu | 3507 | -1.78677828 | 0.000238354 | 0.2120204 |
| 204430_s_at | SLC2A5 | solute carrier family 2 (facilitated glucose/fructose transporter), member 5 | 6518 | -1.13053427 | 0.000259511 | 0.2137408 |
| 209069_s_at | H3F3B | H3 histone, family 3B (H3.3B) | 3021 | -1.18660722 | 0.0003182 | 0.221129 |
| 219777_at | GIMAP6 | GTPase, IMAP family member 6 | 474344 | -0.96412142 | 0.000351795 | 0.2277507 |
| 204304_s_at | PROM1 | prominin 1 | 8842 | -1.82998841 | 0.000419599 | 0.2277507 |
| 205984_at | CRHBP | corticotropin releasing hormone binding protein | 1393 | -1.68558627 | 0.000481558 | 0.2391606 |
| 211998_at | H3F3B | H3 histone, family 3B (H3.3B) | 3021 | -1.37160868 | 0.00110064 | 0.3765544 |
| 220990_s_at | MIR21 | microRNA 21 | 406991 | -1.1666179 | 0.002023122 | 0.4125343 |
| 201369_s_at | ZFP36L2 | ZFP36 ring finger protein-like 2 | 678 | -1.42931862 | 0.002728865 | 0.4502813 |
| 204872_at | TLE4 | transducin-like enhancer of split 4 (E(sp1) homolog, Drosophila) | 7091 | -1.08661045 | 0.004743456 | 0.5161776 |
| 211597_s_at | HOPX | HOP homeobox | 84525 | -1.35969251 | 0.004786898 | 0.5161776 |
| 220377_at | KIAA0125 | KIAA0125 | 9834 | -1.15784914 | 0.004956965 | 0.5161776 |
| 219304_s_at | PDGFD | platelet derived growth factor D | 80310 | -0.94059913 | 0.005103212 | 0.5229734 |
| 208960_s_at | KLF6 | Kruppel-like factor 6 | 1316 | -0.94664654 | 0.010221625 | 0.5857297 |
| 203787_at | SSBP2 | single-stranded DNA binding protein 2 | 23635 | -0.79229496 | 0.013428932 | 0.5870789 |
| 204755_x_at | HLF | hepatic leukemia factor | 3131 | -0.61251884 | 0.013936253 | 0.5899467 |
| 209576_at | GNAI1 | guanine nucleotide binding protein (G protein), alpha inhibiting activity polypeptide 1 | 2770 | -0.63080373 | 0.015529376 | 0.6015332 |
| 204753_s_at | HLF | hepatic leukemia factor | 3131 | -0.70807109 | 0.021022562 | 0.6316009 |
| 221760_at | MAN1A1 | mannosidase, alpha, class 1A, member 1 | 4121 | -1.18371513 | 0.022329984 | 0.6327526 |
| 206478_at | KIAA0125 | KIAA0125 | 9834 | -0.99597623 | 0.02539777 | 0.6372958 |
| 221556_at | CDC14B | cell division cycle 14B | 8555 | -1.26288843 | 0.028047825 | 0.6449399 |
| 214805_at | EIF4A1 | eukaryotic translation initiation factor 4A1 | 1973 | -0.67982725 | 0.028070099 | 0.6449399 |
| 220416_at | ATP8B4 | ATPase, class I, type 8B, member 4 | 79895 | -0.73256572 | 0.031829237 | 0.6529304 |
| 208835_s_at | LUC7L3 | LUC7-like 3 (S. cerevisiae) | 51747 | -0.90441159 | 0.042521869 | 0.666611 |
| 204030_s_at | IQCJ-SCHIP1 | IQCJ-SCHIP1 readthrough | 100505385 | -0.57342 | 0.042715691 | 0.666611 |
| 204897_at | PTGER4 | prostaglandin E receptor 4 (subtype EP4) | 5734 | -1.13842542 | 0.058834073 | 0.6927923 |
| 208949_s_at | LGALS3 | lectin, galactoside-binding, soluble, 3 | 3958 | -0.78834036 | 0.075957894 | 0.7119044 |
| 208961_s_at | KLF6 | Kruppel-like factor 6 | 1316 | -0.79400193 | 0.078101123 | 0.7129149 |
| 209112_at | CDKN1B | cyclin-dependent kinase inhibitor 1B (p27, Kip1) | 1027 | -0.57998283 | 0.119332543 | 0.7386668 |
| 204563_at | SELL | selectin L | 6402 | -0.97868544 | 0.120606528 | 0.7393127 |
| 214651_s_at | HOXA9 | homeobox A9 | 3205 | -0.56461825 | 0.211940371 | 0.7838234 |
| 208892_s_at | DUSP6 | dual specificity phosphatase 6 | 1848 | -0.85096752 | 0.235607663 | 0.7928467 |
| 213524_s_at | G0S2 | G0/G1 switch 2 | 50486 | -0.82501945 | 0.239215682 | 0.7948695 |
| 203535_at | S100A9 | S100 calcium binding protein A9 | 6280 | -0.80627992 | 0.254346668 | 0.8015736 |
| 213668_s_at | SOX4 | SRY (sex determining region Y)-box 4 | 6659 | -0.82323589 | 0.260556623 | 0.802741 |
| 222044_at | PCIF1 | PDX1 C-terminal inhibiting factor 1 | 63935 | -0.49806168 | 0.282560332 | 0.8109941 |
| 213593_s_at | TRA2A | transformer 2 alpha homolog (Drosophila) | 29896 | -0.60971572 | 0.344365936 | 0.8383152 |
| 214041_x_at | RPL37A | ribosomal protein L37a | 6168 | -0.39653673 | 0.407444152 | 0.8568069 |
| 205442_at | MFAP3L | microfibrillar-associated protein 3-like | 9848 | -0.51285589 | 0.449796577 | 0.8725199 |
| 214974_x_at | CXCL5 | chemokine (C—X—C motif) ligand 5 | 6374 | -0.41826978 | 0.551543186 | 0.9009074 |
| 213979_s_at | — | — |  | -0.35065846 | 0.599848748 | 0.9149341 |
| 214911_s_at | BRD2 | bromodomain containing 2 | 6046 | -0.27608523 | 0.611740131 | 0.9174215 |
| 211074_at | FOLR1 | folate receptor 1 (adult) | 2348 | -0.45112625 | 0.632000886 | 0.9246948 |
| 208180_s_at | HIST1H4H | histone cluster 1, H4h | 8365 | -0.2778544 | 0.639528185 | 0.9257406 |
| 207815_at | PF4V1 | platelet factor 4 variant 1 | 5197 | -0.30911148 | 0.651979155 | 0.9286903 |
| 205547_s_at | TAGLN | transgelin | 6876 | -0.28088743 | 0.708017145 | 0.9439304 |

TABLE 10-continued

Gene Expression in the Aggressive Group of the Core 102 Genes

| Probeset ID | Symbol (Na32 consesus Mar13) | Gene Title (Na32 consensus Mar13) | GeneID (NCBI Mar) | Log2 (FC) | P-Value | Adjusted p-Value |
|---|---|---|---|---|---|---|
| 205237_at | FCN1 | ficolin (collagen/fibrinogen domain containing) 1 | 2219 | −0.32136788 | 0.711156716 | 0.944669 |
| 219922_s_at | LTBP3 | latent transforming growth factor beta binding protein 3 | 4054 | −0.18060244 | 0.723881126 | 0.9484945 |
| 204141_at | TUBB2A | tubulin, beta 2A class IIa | 7280 | −0.29534658 | 0.735081772 | 0.9498889 |
| 212952_at | LOC100507328 | hypothetical LOC100507328 | 100507328 | −0.22415499 | 0.743954062 | 0.9528039 |
| 209803_s_at | PHLDA2 | pleckstrin homology-like domain, family A, member 2 | 7262 | −0.19751659 | 0.762353226 | 0.9568355 |
| 204834_at | FGL2 | fibrinogen-like 2 | 10875 | −0.20803456 | 0.771018008 | 0.9582727 |
| 213350_at | RPS11 | ribosomal protein S11 | 6205 | −0.21555457 | 0.772923808 | 0.9589509 |
| 211964_at | COL4A2 | collagen, type IV, alpha 2 | 1284 | −0.15879898 | 0.78084214 | 0.9613311 |
| 205114_s_at | CCL3L3 | chemokine (C-C motif) ligand 3-like 3 | 414062 | −0.20519345 | 0.793565216 | 0.9626063 |
| 202310_s_at | COL1A1 | collagen, type I, alpha 1 | 1277 | −0.22272495 | 0.796823974 | 0.9633788 |
| 217683_at | HBE1 | hemoglobin, epsilon 1 | 3046 | −0.12978731 | 0.806948287 | 0.964919 |
| 201842_s_at | EFEMP1 | EGF containing fibulin-like extracellular matrix protein 1 | 2202 | −0.17500966 | 0.813572867 | 0.9663992 |
| 201631_s_at | IER3 | immediate early response 3 | 8870 | −0.12662907 | 0.836432308 | 0.9684535 |
| 201798_s_at | MYOF | myoferlin | 26509 | −0.12987194 | 0.839316831 | 0.9692311 |
| 1405_i_at | CCL5 | chemokine (C-C motif) ligand 5 | 6352 | −0.16353025 | 0.840439597 | 0.9695199 |
| 201058_s_at | MYL9 | myosin, light chain 9, regulatory | 10398 | −0.11665284 | 0.854796069 | 0.9731863 |
| 215076_s_at | COL3A1 | collagen, type III, alpha 1 | 1281 | −0.11954993 | 0.877410108 | 0.9785103 |
| 202403_s_at | COL1A2 | collagen, type I, alpha 2 | 1278 | −0.11102553 | 0.891268391 | 0.9806744 |
| 210809_s_at | POSTN | periostin, osteoblast specific factor | 10631 | −0.1111146 | 0.912911705 | 0.9851423 |
| 212531_at | LCN2 | lipocalin 2 | 3934 | −0.02914052 | 0.962852347 | 0.9923439 |
| 210873_x_at | APOBEC3A | apolipoprotein B mRNA editing enzyme, catalytic polypeptide-like 3A | 200315 | −0.02534114 | 0.967184016 | 0.9940037 |
| 211980_at | COL4A1 | collagen, type IV, alpha 1 | 1282 | −0.01874739 | 0.977820792 | 0.9959916 |
| 201438_at | COL6A3 | collagen, type VI, alpha 3 | 1293 | 0.009703779 | 0.9863171 | 0.9970689 |
| 74694_s_at | RABEP2 | rabaptin, RAB GTPase binding effector protein 2 | 79874 | 0.011843173 | 0.981583585 | 0.9961445 |
| 211719_x_at | FN1 | fibronectin 1 | 2335 | 0.037210894 | 0.973177363 | 0.9950096 |
| 202404_s_at | COL1A2 | collagen, type I, alpha 2 | 1278 | 0.034227062 | 0.972988883 | 0.9950096 |
| 204655_at | CCL5 | chemokine (C-C motif) ligand 5 | 6352 | 0.038628831 | 0.965309914 | 0.9935003 |
| 216442_x_at | FN1 | fibronectin 1 | 2335 | 0.054191701 | 0.95355946 | 0.9912349 |
| 210495_x_at | FN1 | fibronectin 1 | 2335 | 0.058226728 | 0.951550365 | 0.9910374 |
| 212464_s_at | FN1 | fibronectin 1 | 2335 | 0.081392657 | 0.933688332 | 0.988994 |
| 211161_s_at | COL3A1 | collagen, type III, alpha 1 | 1281 | 0.056146834 | 0.930500411 | 0.9881951 |
| 212667_at | SPARC | secreted protein, acidic, cysteine-rich (osteonectin) | 6678 | 0.058151732 | 0.926810399 | 0.9875364 |
| 202627_s_at | SERPINE1 | serpin peptidase inhibitor, clade E (nexin, plasminogen activator inhibitor type 1), member 1 | 5054 | 0.130825837 | 0.842575178 | 0.9702264 |
| 213757_at | EIF5A | eukaryotic translation initiation factor 5A | 1984 | 0.138314467 | 0.836269539 | 0.9684535 |
| 202600_s_at | NRIP1 | nuclear receptor interacting protein 1 | 8204 | 0.146667606 | 0.81125437 | 0.9660204 |
| 202237_at | NNMT | nicotinamide N-methyltransferase | 4837 | 0.357137196 | 0.643404225 | 0.9262055 |
| 201666_at | TIMP1 | TIMP metallopeptidase inhibitor 1 | 7076 | 0.178832267 | 0.632222051 | 0.9248966 |
| 204018_x_at | HBA1 | hemoglobin, alpha 1 | 3039 | 0.503353692 | 0.544752592 | 0.8986814 |
| 200999_s_at | CKAP4 | cytoskeleton-associated protein 4 | 10970 | 0.335798499 | 0.541539556 | 0.8965721 |
| 204622_x_at | NR4A2 | nuclear receptor subfamily 4, group A, member 2 | 4929 | 0.334447219 | 0.497538974 | 0.8848345 |
| 203394_s_at | HES1 | hairy and enhancer of split 1, (*Drosophila*) | 3280 | 0.443814733 | 0.487186309 | 0.8828267 |
| 206157_at | PTX3 | pentraxin 3, long | 5806 | 0.494269798 | 0.426649316 | 0.8638802 |
| 205382_s_at | CFD | complement factor D (adipsin) | 1675 | 0.493713983 | 0.395763648 | 0.8528093 |
| 217414_x_at | HBA1 | hemoglobin, alpha 1 | 3039 | 0.792680859 | 0.377115905 | 0.8469171 |
| 211745_x_at | HBA1 | hemoglobin, alpha 1 | 3039 | 0.872403284 | 0.371311295 | 0.8441546 |
| 214414_x_at | HBA1 | hemoglobin, alpha 1 | 3039 | 0.997898457 | 0.369791698 | 0.8441546 |
| 211699_x_at | HBA1 | hemoglobin, alpha 1 | 3039 | 0.740693292 | 0.368184583 | 0.844099 |
| 209458_x_at | HBA1 | hemoglobin, alpha 1 | 3039 | 0.850433299 | 0.356237193 | 0.8404624 |
| 212077_at | CALD1 | caldesmon 1 | 800 | 0.588320285 | 0.348578502 | 0.8401911 |
| 216248_s_at | NR4A2 | nuclear receptor subfamily 4, group A, member 2 | 4929 | 0.570789503 | 0.342393968 | 0.8375489 |
| 219403_s_at | HPSE | heparanase | 10855 | 0.691038194 | 0.269546864 | 0.8062958 |
| 201110_s_at | THBS1 | thrombospondin 1 | 7057 | 0.670401219 | 0.251133297 | 0.8008466 |
| 203395_s_at | HES1 | hairy and enhancer of split 1, (*Drosophila*) | 3280 | 0.85070808 | 0.193692 | 0.7743035 |
| 200629_at | WARS | tryptophanyl-tRNA synthetase | 7453 | 0.666045516 | 0.186006457 | 0.7721508 |

TABLE 10-continued

Gene Expression in the Aggressive Group of the Core 102 Genes

| Probeset ID | Symbol (Na32 consesus Mar13) | Gene Title (Na32 consensus Mar13) | GeneID (NCBI Mar) | Log2 (FC) | P-Value | Adjusted p-Value |
|---|---|---|---|---|---|---|
| 201669_s_at | MARCKS | myristoylated alanine-rich protein kinase C substrate | 4082 | 0.759568605 | 0.132720593 | 0.7472316 |
| 201195_s_at | SLC7A5 | solute carrier family 7 (amino acid transporter light chain, L system), member 5 | 8140 | 0.824741527 | 0.116329142 | 0.7382591 |
| 204419_x_at | HBG1 | hemoglobin, gamma A | 3047 | 1.666375122 | 0.09142905 | 0.723603 |
| 204848_x_at | HBG1 | hemoglobin, gamma A | 3047 | 1.565419124 | 0.086123226 | 0.7221941 |
| 219410_at | TMEM45A | transmembrane protein 45A | 55076 | 0.991276475 | 0.082130669 | 0.7221941 |
| 217388_s_at | KYNU | kynureninase | 8942 | 1.468313974 | 0.069766007 | 0.7032894 |
| 209290_s_at | NFIB | nuclear factor I/B | 4781 | 1.089323355 | 0.04758335 | 0.6754948 |
| 202870_s_at | CDC20 | cell division cycle 20 | 991 | 1.339488946 | 0.036576735 | 0.658786 |
| 217232_x_at | HBB | hemoglobin, beta | 3043 | 1.819045943 | 0.03458682 | 0.658786 |
| 213515_x_at | HBG1 | hemoglobin, gamma A | 3047 | 2.417286959 | 0.029878597 | 0.651733 |
| 209773_s_at | RRM2 | ribonucleotide reductase M2 | 6241 | 1.767337745 | 0.021613828 | 0.6316009 |
| 211696_x_at | HBB | hemoglobin, beta | 3043 | 1.960802898 | 0.020715624 | 0.6316009 |
| 206698_at | XK | X-linked Kx blood group (McLeod syndrome) | 7504 | 1.473769082 | 0.01474655 | 0.5951742 |
| 212589_at | RRAS2 | related RAS viral (r-ras) oncogene homolog 2 | 22800 | 1.248921748 | 0.010895573 | 0.5870789 |
| 209116_x_at | HBB | hemoglobin, beta | 3043 | 2.529691269 | 0.008815809 | 0.5680662 |
| 215772_x_at | SUCLG2 | succinate-CoA ligase, GDP-forming, beta subunit | 8801 | 1.175819449 | 0.008054348 | 0.5660139 |
| 201890_at | RRM2 | ribonucleotide reductase M2 | 6241 | 2.141037934 | 0.003660296 | 0.4760098 |
| 209894_at | LEPR | leptin receptor | 3953 | 2.015713837 | 0.00114085 | 0.3805249 |
| 219602_s_at | PIEZO2 | piezo-type mechanosensitive ion channel component 2 | 63895 | 1.504577032 | 7.50E-05 | 0.1179278 |
| 205848_at | GAS2 | growth arrest-specific 2 | 2620 | 2.492595762 | 1.11E-05 | 0.0274403 |

TABLE 11

Gene Expression in the Indolent Group of the Core 102 Genes

| Probeset ID | Symbol (Na32 consensus Mar13) | Gene Title (Na32 consensus Mar13) | GeneID (consensus1 Mar-13) | Log2 (FC) | P-Value | Adjusted p-Value |
|---|---|---|---|---|---|---|
| 208949_s_at | LGALS3 | lectin, galactoside-binding, soluble, 3 | 3958 | -2.46115508 | 4.71E-07 | 0.0008705 |
| 201666_at | TIMP1 | TIMP metallopeptidase inhibitor 1 | 7076 | -1.63941887 | 2.35E-05 | 0.0042807 |
| 201058_s_at | MYL9 | myosin, light chain 9, regulatory | 10398 | -2.74636917 | 3.07E-05 | 0.0046717 |
| 207815_at | PF4V1 | platelet factor 4 variant 1 | 5197 | -2.82238801 | 5.35E-05 | 0.0058277 |
| 1405_i_at | CCL5 | chemokine (C-C motif) ligand 5 | 6352 | -3.32636522 | 5.85E-05 | 0.0060359 |
| 213524_s_at | G0S2 | G0/G1switch 2 | 50486 | -2.65614662 | 0.0001262 | 0.007998 |
| 201631_s_at | IER3 | immediate early response 3 | 8870 | -2.29780898 | 0.000169 | 0.009257 |
| 204655_at | CCL5 | chemokine (C-C motif) ligand 5 | 6352 | -3.23424391 | 0.0002336 | 0.0105336 |
| 203535_at | S100A9 | S100 calcium binding protein A9 | 6280 | -2.4351969 | 0.0003703 | 0.0133722 |
| 212077_at | CALD1 | caldesmon 1 | 800 | -2.04255108 | 0.0006877 | 0.0178246 |
| 210873_x_at | APOBEC3A | apolipoprotein B mRNA editing enzyme, catalytic polypeptide-like 3A | 200315 | -1.76920321 | 0.0023357 | 0.032102 |
| 212531_at | LCN2 | lipocalin 2 | 3934 | -1.74944593 | 0.0029164 | 0.0363335 |
| 205114_s_at | CCL3L3 | chemokine (C-C motif) ligand 3-like 3 | 414062 | -2.11268057 | 0.0038941 | 0.0419976 |
| 208180_s_at | HIST1H4H | histone cluster 1, H4h | 8365 | -1.58614736 | 0.0040832 | 0.0431848 |
| 205237_at | FCN1 | ficolin (collagen/fibrinogen domain containing) 1 | 2219 | -2.31794481 | 0.0041427 | 0.0434495 |
| 214414_x_at | HBA1 | hemoglobin, alpha 1 | 3039 | -2.92561932 | 0.0044286 | 0.0449487 |
| 209803_s_at | PHLDA2 | pleckstrin homology-like domain, family A, member 2 | 7262 | -1.71861099 | 0.0046599 | 0.0462831 |
| 201438_at | COL6A3 | collagen, type VI, alpha 3 | 1293 | -1.45596175 | 0.0055357 | 0.0504893 |
| 205547_s_at | TAGLN | transgelin | 6876 | -1.89686803 | 0.0062053 | 0.0538116 |
| 211074_at | FOLR1 | folate receptor 1 (adult) | 2348 | -2.33500441 | 0.0071061 | 0.0579213 |
| 221556_at | CDC14B | cell division cycle 14B | 8555 | -1.35462909 | 0.0072261 | 0.0582223 |
| 211745_x_at | HBA1 | hemoglobin, alpha 1 | 3039 | -2.39194906 | 0.0073721 | 0.0586827 |
| 204141_at | TUBB2A | tubulin, beta 2A class IIa | 7280 | -2.13929618 | 0.0077476 | 0.0602366 |
| 204018_x_at | HBA1 | hemoglobin, alpha 1 | 3039 | -1.9801303 | 0.0092138 | 0.0661068 |
| 201798_s_at | MYOF | myoferlin | 26509 | -1.51465891 | 0.009894 | 0.0682173 |
| 209458_x_at | HBA1 | hemoglobin, alpha 1 | 3039 | -2.13257405 | 0.0108016 | 0.071832 |
| 217414_x_at | HBA1 | hemoglobin, alpha 1 | 3039 | -2.0496731 | 0.0117787 | 0.0752125 |
| 211964_at | COL4A2 | collagen, type IV, alpha 2 | 1284 | -1.30406638 | 0.0122956 | 0.0767626 |

TABLE 11-continued

Gene Expression in the Indolent Group of the Core 102 Genes

| Probeset ID | Symbol (Na32 consensus Mar13) | Gene Title (Na32 consensus Mar13) | GeneID (consensus1 Mar-13) | Log2 (FC) | P-Value | Adjusted p-Value |
|---|---|---|---|---|---|---|
| 205442_at | MFAP3L | microfibrillar-associated protein 3-like | 9848 | −1.52050559 | 0.0134371 | 0.0808545 |
| 214974_x_at | CXCL5 | chemokine (C—X—C motif) ligand 5 | 6374 | −1.55942048 | 0.0144079 | 0.083963 |
| 202310_s_at | COL1A1 | collagen, type I, alpha 1 | 1277 | −1.87618778 | 0.0168309 | 0.0918907 |
| 219403_s_at | HPSE | heparanase | 10855 | −1.31934206 | 0.0184966 | 0.0968056 |
| 212667_at | SPARC | secreted protein, acidic, cysteine-rich (osteonectin) | 6678 | −1.34731184 | 0.0188123 | 0.0976538 |
| 200999_s_at | CKAP4 | cytoskeleton-associated protein 4 | 10970 | −1.14939507 | 0.0204052 | 0.1017426 |
| 204834_at | FGL2 | fibrinogen-like 2 | 10875 | −1.46819648 | 0.0227746 | 0.1072555 |
| 216442_x_at | FN1 | fibronectin 1 | 2335 | −1.90725545 | 0.023141 | 0.1081658 |
| 201842_s_at | EFEMP1 | EGF containing fibulin-like extracellular matrix protein 1 | 2202 | −1.50062086 | 0.0247947 | 0.1121383 |
| 212464_s_at | FN1 | fibronectin 1 | 2335 | −1.96352838 | 0.0258307 | 0.1143867 |
| 211719_x_at | FN1 | fibronectin 1 | 2335 | −2.20581999 | 0.0267964 | 0.1164775 |
| 210495_x_at | FN1 | fibronectin 1 | 2335 | −1.90768224 | 0.026965 | 0.1168453 |
| 216248_s_at | NR4A2 | nuclear receptor subfamily 4, group A, member 2 | 4929 | −1.17498747 | 0.0282382 | 0.1197257 |
| 211699_x_at | HBA1 | hemoglobin, alpha 1 | 3039 | −1.60001534 | 0.0291616 | 0.1216234 |
| 217683_at | HBE1 | hemoglobin, epsilon 1 | 3046 | −1.01631722 | 0.0327501 | 0.1295902 |
| 202627_s_at | SERPINE1 | serpin peptidase inhibitor, clade E (nexin, plasminogen activator inhibitor type 1), member 1 | 5054 | −1.241552 | 0.0352569 | 0.1349566 |
| 203394_s_at | HES1 | hairy and enhancer of split 1, (Drosophila) | 3280 | −1.1913737 | 0.0362517 | 0.1371457 |
| 211980_at | COL4A1 | collagen, type IV, alpha 1 | 1282 | −1.25680354 | 0.0372348 | 0.139094 |
| 204622_x_at | NR4A2 | nuclear receptor subfamily 4, group A, member 2 | 4929 | −0.91072954 | 0.037958 | 0.1405444 |
| 215076_s_at | COL3A1 | collagen, type III, alpha 1 | 1281 | −1.43307205 | 0.0385845 | 0.1417739 |
| 202403_s_at | COL1A2 | collagen, type I, alpha 2 | 1278 | −1.44054881 | 0.0465026 | 0.1564484 |
| 202404_s_at | COL1A2 | collagen, type I, alpha 2 | 1278 | −1.71166248 | 0.0565387 | 0.1733135 |
| 210809_s_at | POSTN | periostin, osteoblast specific factor | 10631 | −1.70047318 | 0.0592192 | 0.1779858 |
| 200629_at | WARS | tryptophanyl-tRNA synthetase | 7453 | −0.81407303 | 0.0632647 | 0.1842488 |
| 205382_s_at | CFD | complement factor D (adipsin) | 1675 | −0.93430533 | 0.0674121 | 0.1911642 |
| 211161_s_at | COL3A1 | collagen, type III, alpha 1 | 1281 | −0.97790719 | 0.0849171 | 0.216434 |
| 202237_at | NNMT | nicotinamide N-methyltransferase | 4837 | −1.16905976 | 0.0849883 | 0.216541 |
| 206157_at | PTX3 | pentraxin 3, long | 5806 | −0.8886965 | 0.1017166 | 0.2401657 |
| 222044_at | PCIF1 | PDX1 C-terminal inhibiting factor 1 | 63935 | −0.59010446 | 0.1405898 | 0.2902372 |
| 203395_s_at | HES1 | hairy and enhancer of split 1, (Drosophila) | 3280 | −0.82856755 | 0.1406431 | 0.2902934 |
| 214041_x_at | RPL37A | ribosomal protein L37a | 6168 | −0.49636026 | 0.2288142 | 0.3892891 |
| 213668_s_at | SOX4 | SRY (sex determining region Y)-box 4 | 6659 | −0.74126503 | 0.2366512 | 0.397241 |
| 214911_s_at | BRD2 | bromodomain containing 2 | 6046 | −0.55589849 | 0.237402 | 0.3980366 |
| 213515_x_at | HBG1 | hemoglobin, gamma A | 3047 | −1.06377 | 0.2466641 | 0.407885 |
| 204419_x_at | HBG1 | hemoglobin, gamma A | 3047 | −0.908371 | 0.2734668 | 0.4340414 |
| 208892_s_at | DUSP6 | dual specificity phosphatase 6 | 1848 | −0.62624686 | 0.3054404 | 0.4659019 |
| 201669_s_at | MARCKS | myristoylated alanine-rich protein kinase C substrate | 4082 | −0.4343098 | 0.308411 | 0.4689854 |
| 201324_at | EMP1 | epithelial membrane protein 1 | 2012 | −0.26518451 | 0.3157697 | 0.476429 |
| 204848_x_at | HBG1 | hemoglobin, gamma A | 3047 | −0.73774161 | 0.3338994 | 0.4939304 |
| 213350_at | RPS11 | ribosomal protein S11 | 6205 | −0.59851213 | 0.3525386 | 0.5113994 |
| 213593_s_at | TRA2A | transformer 2 alpha homolog (Drosophila) | 29896 | −0.51180921 | 0.3529863 | 0.5117818 |
| 209374_s_at | IGHM | immunoglobulin heavy constant mu | 3507 | −0.31785029 | 0.3800608 | 0.5367239 |
| 213979_s_at | — | — | — | −0.40184672 | 0.4828663 | 0.6262323 |
| 201110_s_at | THBS1 | thrombospondin 1 | 7057 | −0.32862948 | 0.50663 | 0.645676 |
| 212952_at | LOC100507328 | hypothetical LOC100507328 | 100507328 | −0.3705879 | 0.5288342 | 0.6639313 |
| 213757_at | EIF5A | eukaryotic translation initiation factor 5A | 1984 | −0.30685777 | 0.5926473 | 0.7155269 |
| 201195_s_at | SLC7A5 | solute carrier family 7 (amino acid transporter light chain, L system), member 5 | 8140 | −0.21795555 | 0.6192996 | 0.7368622 |
| 217232_x_at | HBB | hemoglobin, beta | 3043 | −0.28037802 | 0.690155 | 0.7905057 |
| 206698_at | XK | X-linked Kx blood group (McLeod syndrome) | 7504 | −0.15354275 | 0.7519213 | 0.8333529 |
| 209116_x_at | HBB | hemoglobin, beta | 3043 | −0.22011194 | 0.7745612 | 0.8490507 |
| 208960_s_at | KLF6 | Kruppel-like factor 6 | 1316 | −0.0669692 | 0.8198308 | 0.8804886 |
| 211696_x_at | HBB | hemoglobin, beta | 3043 | −0.11853666 | 0.8626478 | 0.9090874 |

TABLE 11-continued

Gene Expression in the Indolent Group of the Core 102 Genes

| Probeset ID | Symbol (Na32 consensus Mar13) | Gene Title (Na32 consensus Mar13) | GeneID (consensus1 Mar-13) | Log2 (FC) | P-Value | Adjusted p-Value |
|---|---|---|---|---|---|---|
| 212589_at | RRAS2 | related RAS viral (r-ras) oncogene homolog 2 | 22800 | −0.03039679 | 0.9381282 | 0.9597619 |
| 74694_s_at | RABEP2 | rabaptin, RAB GTPase binding effector protein 2 | 79874 | −0.02974959 | 0.9459227 | 0.9655037 |
| 205933_at | SETBP1 | SET binding protein 1 | 26040 | −0.00557713 | 0.9639004 | 0.976948 |
| 219410_at | TMEM45A | transmembrane protein 45A | 55076 | −0.01300971 | 0.9780245 | 0.9864563 |
| 209183_s_at | C10orf10 | chromosome 10 open reading frame 10 | 11067 | 0.053999237 | 0.7924264 | 0.8612892 |
| 217388_s_at | KYNU | kynureninase | 8942 | 0.220147884 | 0.7422951 | 0.8265151 |
| 204872_at | TLE4 | transducin-like enhancer of split 4 (E(sp1) homolog, Drosophila) | 7091 | 0.119923227 | 0.6919854 | 0.7913794 |
| 209290_s_at | NFIB | nuclear factor I/B | 4781 | 0.179441546 | 0.6912758 | 0.7909339 |
| 209069_s_at | H3F3B | H3 histone, family 3B (H3.3B) | 3021 | 0.099846114 | 0.6841093 | 0.7862131 |
| 209763_at | CHRDL1 | chordin-like 1 | 91851 | 0.050254159 | 0.6660676 | 0.7731502 |
| 208961_s_at | KLF6 | Kruppel-like factor 6 | 1316 | 0.203610948 | 0.5862653 | 0.7103285 |
| 219922_s_at | LTBP3 | latent transforming growth factor beta binding protein 3 | 4054 | 0.265731289 | 0.5441646 | 0.676381 |
| 210487_at | DNTT | deoxynucleotidyltransferase, terminal | 1791 | 0.159844182 | 0.4049727 | 0.5588841 |
| 202600_s_at | NRIP1 | nuclear receptor interacting protein 1 | 8204 | 0.470263901 | 0.374044 | 0.5310937 |
| 211998_at | H3F3B | H3 histone, family 3B (H3.3B) | 3021 | 0.303014616 | 0.3488911 | 0.5083632 |
| 219304_s_at | PDGFD | platelet derived growth factor D | 80310 | 0.277596346 | 0.298783 | 0.4593071 |
| 204897_at | PTGER4 | prostaglandin E receptor 4 (subtype EP4) | 5734 | 0.607994686 | 0.2274529 | 0.3875045 |
| 202870_s_at | CDC20 | cell division cycle 20 | 991 | 0.762009765 | 0.1538922 | 0.3060777 |
| 220990_s_at | MIR21 | microRNA 21 | 406991 | 0.435464726 | 0.1444477 | 0.2949163 |
| 220377_at | KIAA0125 | KIAA0125 | 9834 | 0.487203922 | 0.1414233 | 0.2913494 |
| 215772_x_at | SUCLG2 | succinate-CoA ligase, GDP-forming, beta subunit | 8801 | 0.540170913 | 0.1340248 | 0.2820253 |
| 204563_at | SELL | selectin L | 6402 | 0.910468161 | 0.0926084 | 0.2277875 |
| 211597_s_at | HOPX | HOP homeobox | 84525 | 0.686080974 | 0.0787633 | 0.2073318 |
| 205984_at | CRHBP | corticotropin releasing hormone binding protein | 1393 | 0.67956433 | 0.0697279 | 0.1948001 |
| 208835_s_at | LUC7L3 | LUC7-like 3 (S. cerevisiae) | 51747 | 0.690777363 | 0.0676605 | 0.1915926 |
| 221760_at | MAN1A1 | mannosidase, alpha, class 1A, member 1 | 4121 | 0.824262339 | 0.0582629 | 0.1763029 |
| 201369_s_at | ZFP36L2 | ZFP36 ring finger protein-like 2 | 678 | 0.748937338 | 0.0520224 | 0.1657888 |
| 209773_s_at | RRM2 | ribonucleotide reductase M2 | 6241 | 1.272153164 | 0.0495607 | 0.1616025 |
| 204304_s_at | PROM1 | prominin 1 | 8842 | 0.925426909 | 0.0237482 | 0.1095213 |
| 209894_at | LEPR | leptin receptor | 3953 | 1.184929139 | 0.0181485 | 0.0959498 |
| 203787_at | SSBP2 | single-stranded DNA binding protein 2 | 23635 | 0.75811153 | 0.0063777 | 0.0544303 |
| 201890_at | RRM2 | ribonucleotide reductase M2 | 6241 | 1.743455889 | 0.0052954 | 0.0493966 |
| 219602_s_at | PIEZO2 | piezo-type mechanosensitive ion channel component 2 | 63895 | 0.949014365 | 0.0017907 | 0.0285001 |
| 204755_x_at | HLF | hepatic leukemia factor | 3131 | 0.692860181 | 0.0017806 | 0.0285001 |
| 204753_s_at | HLF | hepatic leukemia factor | 3131 | 0.867266686 | 0.0016555 | 0.0275765 |
| 209576_at | GNAI1 | guanine nucleotide binding protein (G protein), alpha inhibiting activity polypeptide 1 | 2770 | 0.736228442 | 0.0015849 | 0.0269254 |
| 214805_at | EIF4A1 | eukaryotic translation initiation factor 4A1 | 1973 | 0.894052441 | 0.001431 | 0.025337 |
| 209112_at | CDKN1B | cyclin-dependent kinase inhibitor 1B (p27, Kip1) | 1027 | 1.181992974 | 0.0007491 | 0.0186168 |
| 214651_s_at | HOXA9 | homeobox A9 | 3205 | 1.466348689 | 0.0006873 | 0.0178246 |
| 219777_at | GIMAP6 | GTPase, IMAP family member 6 | 474344 | 0.787293816 | 0.000565 | 0.016422 |
| 204430_s_at | SLC2A5 | solute carrier family 2 (facilitated glucose/fructose transporter), member 5 | 6518 | 0.916940276 | 0.0004539 | 0.0149986 |
| 206478_at | KIAA0125 | KIAA0125 | 9834 | 1.699585816 | 7.39E−05 | 0.0063689 |
| 220416_at | ATP8B4 | ATPase, class I, type 8B, member 4 | 79895 | 1.319886477 | 6.56E−05 | 0.0061373 |
| 205848_at | GAS2 | growth arrest-specific 2 | 2620 | 1.882945739 | 5.69E−05 | 0.0059648 |
| 204030_s_at | IQCJ-SCHIP1 | IQCJ-SCHIP1 readthrough | 100505385 | 1.123786747 | 5.04E−05 | 0.0057459 |

TABLE 12

Regulation of 16 PV Core Genes in Chronic Phase CML

| CML Chronic Phase | CML Blast Phase |
|---|---|
| Up Regulated Genes | Up Regulated Genes |
| HBA2 | RRAS2 |
| HBB | GAS2 |
| HBG1 | HES1 |
| COL1A1 | EMP1 |
| RRM2 | SSBP2 |
| THSB1 | LUC7L3 |
| TIMP1 | GIMAP6 |
| MARCKS | eIF5A |
| XK | SETBP1 |
| CDC20 | |
| MYOF | |
| LEPR | |
| CCL5 | |
| IER3 | |
| KYNU | |
| LGALS3 | |
| eIF5A | |
| HOXA9 | |
| FGL2 | FGL2 |
| NR4A2 | IER3 |
| CDC14B | G0S2 |
| HES1 | LGALS3 |
| NRIP1 | |
| SOX4 | |
| Down Regulated Genes | Down Regulated Genes |
| SCHIP1 | IGHM |
| HLF | SELL |
| PROM1 | EFEMP1 |
| MAN1A1 | HBA1 |
| CRHBP | FCN1 |
| KIAA1025 | LCN2 |
| DNTT | CKAP4 |
| IGHM | S100A9 |
| SELL | APOBEC3A |

TABLE 13

10 Gene Screen Probability Score: 30 Test PV Cohort

| | Aggressive (5-6/6) N = 8 | Indolent (0-4/6) N = 22 | P value |
|---|---|---|---|
| Gender (M/F) | 1/7 | 11/11 | ns |
| Median Age in Years (range) | 62 (46-76) | 65 (43-79) | ns |
| % JAK2 V617F (range) | 94 (52-100) | 81 (44-100) | ns |
| Leukocyte count | 31 | 14.5 | ns |
| Thrombosis | 6/8 | 5/22 | 0.014 |
| Hemoglobin | 10.9 | 13.1 | 0.006 |
| Median Disease Duration in years (range) | 15.5 | 7 | 0.011 |
| Platelet count | 308 | 666 | <0.019 |
| Palpable splenomegaly | 8/8 | 9/22 | 0.009 |
| Spleen size | 14 | 3.5 | 0.033 |
| Chemotherapy | 7/8 | 7/22 | 0.012 |
| Median Probability Score (range) | 5.0 (5-6) | 2.5 (0-4) | <0.001 |
| Median Clinical Score (range) | 3.0 (2-4) | 0 (0-3) | <0.001 |

TABLE 14

Ten Gene Screening Panel

| Gene Symbol | Gene Name | Context Sequence | SEQ ID No. | Target Exons |
|---|---|---|---|---|
| PCNA | proliferating cell nuclear antigen | AAAGAGGAGGAAGCTGTTACCATAG | 1 | 5 |
| TSN | translin | GCCAGTGAACTGTCGAGGCTGTCTG | 2 | 5 |
| CDKN1A | cyclin-dependent kinase inhibitor 1A (p21, Cip1) | GCAGACCAGCATGACAGATTTCTAC | 3 | 2 |
| MYL9 | myosin, light chain 9, regulatory | TGGCCTCGCTGGGTTTCATCCATGA | 4 | 2 |
| IFI30 | interferon, gamma-inducible protein 30 | CTGCCAGTTGTACCAGGGCAAGAAG | 5 | 7 |
| CTSA | cathepsin A | CAGAAGATGGAGGTGCAGCGCCGGC | 6 | 14 |
| SMC4 | structural maintenance of chromosomes4 | AAAAGAAGGAAGAATTGTATTTGCA | 7 | 21 |
| CTTN | cortactin | CTACCAGGCTGCGGGCGATGATGAG | 8 | 16 |
| SON | SON DNA binding protein | CAAACATTTTCTCTTTAGGGTATTG | 9 | 12 |
| TIA1 | TIA1 cytotoxic granule-asociated RNA binding protein | CCCGTGCAACAGCAGAATCAAATTG | 10 | 10 |

TABLE 14-continued

Ten Gene Screening Panel

| Gene Symbol | Gene Name | Context Sequence | SEQ ID No. | Target Exons |
|---|---|---|---|---|
| ACTB | Beta actin (Endogenous control) | | | 1 |

TABLE 15

Ten Gene Screening Panel NCBI Gene Accession Nos.

| Gene Symbol | NCBI Gene Accession Nos. |
|---|---|
| PCNA | NM_002592, NM_182649 |
| TSN | NM_004622 |
| CDKN1A | NM_000389, NM_001220777, NM_001220778, NM_078467 |
| MYL9 | NM_181526 |
| IFI30 | NM_006332 |
| CTSA | NM_000308, NM_001127695, NM_001167594 |
| SMC4 | NM_001002800, NM_005496 |
| CTTN | NM_001184740, NM_005231, NM_138565 |
| SON | NM_138927 |
| TIA1 | NM_022037, NM_022173 |
| ACTB | NM_001101 |

TABLE 16

Gene Expression Assay Reagents

| Gene Symbol | Primer-Probe Assay ID | Context Symbol | SEQ ID No. | Part Number |
|---|---|---|---|---|
| PCNA | Hs00952870_g1 | AAAGAGGAGGAAGCTGTTACCATAG | 11 | 4331182 |
| TSN | Hs00172824_m1 | GCCAGTGAACTGTCGAGGCTGTCTG | 12 | 4331182 |
| CDKN1A | Hs00355782_m1 | GCAGACCAGCATGACAGATTTCTAC | 13 | 4331182 |
| MYL9 | Hs00382913_m1 | TGGCCTCGCTGGGTTTCATCCATGA | 14 | 4331182 |
| IFI30 | Hs00908857_g1 | CTGCCAGTTGTACCAGGGCAAGAAG | 15 | 4351372 |
| CTSA | Hs01563956_g1 | CAGAAGATGGAGGTGCAGCGCCGGC | 16 | 4351372 |
| SMC4 | Hs00909708_g1 | AAAGAAGGAAGAATTGTATTTGCA | 17 | 4351372 |
| CTTN | Hs01124227_m1 | CTACCAGGCTGCGGGCGATGATGAG | 18 | 4351372 |
| SON | Hs01066142_g1 | CAAACATTTTCTCTTTAGGGTATTG | 19 | 4351372 |
| TIA1 | Hs01046922_m1 | CCCGTGCAACAGCAGAATCAAATTG | 20 | 4351372 |
| ACTB | N/A | N/A | | 4333762F |

TABLE 17

Algorithm for PV Patient Stratification
Ten Gene Screening Panel

For the following gene level comparisons:

If TRUE (and >2 fold difference) score 1
If FALSE (or <2 fold difference) score 0
A score of >4 out of 6 indicates an aggressive form of PV
PCNA > IFI30
TSN > CTSA
SMC4 > CDKN1A
PCNA > CTTN SON > CTTN
TIA1 > MYL9

TABLE 18

10 Gene Screening Data from Indolent PV Patients

| UPIN | Diagnosis | Dx Dur | 10 Gscore | Clin Score |
|---|---|---|---|---|
| 124 | PV | 13 | 2 | 1 |
| 124 | PV | 21 | 1 | 0 |
| 136 | PV | 11 | 2 | 1 |
| 183 | PV | 14 | 3 | 0 |
| 199 | PV/MF | 18 | 4 | 2 |
| 294 | PV | 8 | 2 | 1 |
| 326 | PV | 17 | 4 | 3 |

TABLE 18-continued

10 Gene Screening Data from Indolent PV Patients

| UPIN | Diagnosis | Dx Dur | 10 Gscore | Clin Score |
|---|---|---|---|---|
| 351 | PV | 16 | 2 | 0 |
| 355 | PV | 10 | 2 | 2 |
| 398 | PV | 6 | 3 | 1 |
| 470 | PV | 26 | 0 | 3 |
| 495 | PV | 6 | 2 | 0 |
| 564 | PV | 11 | 4 | 1 |
| 645 | PV | 11 | 2 | 1 |
| 914 | PV | 10 | 3 | 1 |
| 1045 | PV | 9 | 2 | 1 |
| 1073 | PV | 8 | 4 | 1 |
| 1092 | PV | 7 | 2 | 1 |
| 1125 | PV | 27 | 4 | 3 |
| 1191 | PV | 10 | 4 | 1 |
| 1267 | PV | 4 | 2 | 0 |
| 1308 | PV | 10 | 4 | 1 |
| 1370 | PV | 4 | 1 | 2 |
| 1418 | PV | 7 | 4 | 2 |
| 1428 | PV | 1 | 3 | 0 |
| 1428 | PV | 4 | 4 | 1 |
| 1433 | PV | 3 | 4 | 0 |
| 1438 | PV | 3 | 4 | 2 |
| 1439 | PV | 3 | 3 | 1 |
| 1459 | PV | 4 | 3 | 2 |
| 1529 | PV | 2.5 | 3 | 0 |
| 1542 | PV | 1 | 3 | 0 |
| 1542 | PV | 1 | 2 | 0 |
| 1552 | PV | 1 | 2 | 0 |
| 1552 | PV | 2 | 1 | 0 |
| 1574 | PV | 13 | 2 | 3 |
| 1574 | PV | 2 | 2 | 0 |
| 1578 | PV | 7 | 4 | 0 |
| 1585 | PV | 1.5 | 2 | 0 |
| 1591 | PV | 3 | 3 | 1 |
| 1599 | PV | 8 | 1 | 0 |
| 1635 | PV | 1.5 | 2 | 0 |
| 1127 | PV | 11 | 3 | 0 |
| Average | | | 2.651163 | 0.906977 |
| Median | | | 3 | 1 |
| Mann-Whitney U Statistic compared to PV Aggressive | | | p < 0.001 | p < 0.001 |

TABLE 19

10 Gene Screening Data from Aggressive PV Patients

| UPIN | Diagnosis | Dx Dur | 10 Gscore | Clin Score |
|---|---|---|---|---|
| 113 | PV/MF | 19 | 5 | 5 |
| 173 | PV/MF | 28 | 5 | 4 |
| 206 | PV/MF/AML | 18 | 6 | 6 |
| 249 | PV | 18 | 5 | 3 |
| 671 | PV/MF | 24 | 5 | 2 |
| 680 | PV/MF | 12 | 5 | 3 |
| 1113 | PV/MF | 7 | 5 | 5 |
| 1113 | PV/MF | 12 | 5 | 5 |
| 1235 | PV | 9 | 5 | 2 |
| 1253 | PV | 4 | 5 | 2 |
| 1463 | PV/MF | 39 | 5 | 3 |
| 1545 | PV | 11 | 5 | 1 |
| 1596 | PV/MF | 13 | 5 | 1 |
| 1639 | PV | 4 | 6 | 3 |
| 999 | PV/MF | 11 | 6 | 3 |
| 682 | PV/MF/SM | 20 | 5 | 3 |
| Mean | | | 5.1875 | 3.1875 |
| Median | | | 5 | 3 |
| Mann-Whitney U Statistic compared to PV Indolent | | | p < 0.001 | p < 0.001 |

---

The which is claimed:

1. A method for predicting the likelihood of an indolent form of Polycythemia Vera (PV) transforming to an aggressive form of PV in a subject, the method comprising:
   (a) measuring the gene products of PCNA, IFI30, TSN, CTSA, SMC4, CDKN1A, CTTN, SON, TIA1, and MYL9 in a biological sample comprising blood cells obtained from the subject, wherein the gene products are measured using the probes of SEQ ID NOS:11-20;
   (b) making the following comparisons of the gene product levels measured in (a) and recording a score of 1 for a true result and a score of 0 for a false result: PCNA>IFI30; TSN>CTSA; SMC4>CDKN1A; PCNA>CTTN; SON>CTTN; TIA1>MYL9;
   (c) adding the scores together to obtain an added score and calculating a ratio of the added score/6 to calculate a total score; and
   (d) predicting based on the total score calculated in (c) the likelihood of the indolent form of PV in the subject to transform to an aggressive form of PV, wherein a total score of 5/6 or 6/6 predicts that the indolent form of PV in a subject is likely to transform to an aggressive form of PV in the subject and wherein a total score of less than 5/6 predicts that the indolent form of PV in a subject is not likely to transform to an aggressive form of PV in the subject.

2. The method of claim 1, wherein the blood cells are white blood cells.

3. The method of claim 1, wherein the blood cells are CD34+ cells.

4. The method of claim 1, wherein the subject is mammalian.

5. The method of claim 4, wherein the subject is human.

6. The method of claim 1, wherein the expression products of PCNA, IFI30, TSN, CTSA, SMC4, CDKN1A, CTTN, SON, TIA1, and MYL9 are measured by determining mRNA expression levels.

7. The method of claim 6, wherein the mRNA expression levels are measured by using reverse transcription PCR (RT-PCR).

8. The method of claim 7, wherein the reverse transcription PCR (RT-PCR) is followed by real-time PCR (Q-PCR).

9. The method of claim 1, wherein the biological sample comprises peripheral blood or bone marrow.

10. The method of claim 1, wherein the indolent form of PV is characterized by at least one of symptom selected from the group consisting of increased production of red cells, increased production of white cells, increased production of platelets, itching, gouty arthritis, peptic ulcer disease, enlarged liver or spleen, elevated hemoglobin levels, and low erythropoietin levels in the subject.

11. The method of claim 1, wherein the aggressive form of PV is characterized by at least one symptom selected from the group consisting of thrombosis, heart attack, stroke, Budd-Chiari syndrome, myelofibrosis and acute myeloid leukemia (AML) in the subject.

12. The method of claim 1, wherein the method displays a sensitivity of at least 80% and a specificity of at least 90%.

13. The method of claim 1, further comprising informing the subject or a treating physician of the likelihood of the indolent form of Polycythemia Vera (PV) transforming to an aggressive form of PV in the subject.

14. The method of claim 1, wherein the method is used to determine if a subject should undergo therapy for PV, wherein the therapy is selected from the group consisting of bone marrow transplantation, pegylated interferon, chemotherapy, and ruxolitinib.

15. The method of claim 14, further comprising treating the patient with therapy for PV, wherein the therapy is selected from the group consisting of bone marrow transplantation, pegylated interferon, chemotherapy, and ruxolitinib.

* * * * *